(12) United States Patent
Sauer et al.

(10) Patent No.: US 11,541,105 B2
(45) Date of Patent: Jan. 3, 2023

(54) COMPOSITIONS AND METHODS FOR DISRUPTING BIOFILM FORMATION AND MAINTENANCE

(71) Applicant: The Research Foundation for the State University of new York, Binghamton, NY (US)

(72) Inventors: Karin Sauer, Binghamton, NY (US); Amber L. Doiron, Vestal, NY (US)

(73) Assignee: The Research Foundation for The State University of New York, Binghamton, NY (US)

(*) Notice: Subject to any disclaimer, the term of this patent is extended or adjusted under 35 U.S.C. 154(b) by 563 days.

(21) Appl. No.: 16/428,560

(22) Filed: May 31, 2019

(65) Prior Publication Data

US 2019/0365868 A1 Dec. 5, 2019

Related U.S. Application Data

(60) Provisional application No. 62/679,370, filed on Jun. 1, 2018.

(51) Int. Cl.
| | |
|---|---|
| *A61K 38/44* | (2006.01) |
| *A01N 37/18* | (2006.01) |
| *A61K 45/06* | (2006.01) |
| *C12R 1/38* | (2006.01) |
| *C12R 1/185* | (2006.01) |
| *C12R 1/44* | (2006.01) |
| *C12N 1/00* | (2006.01) |

(52) U.S. Cl.
CPC ............. *A61K 38/44* (2013.01); *A01N 37/18* (2013.01); *A61K 45/06* (2013.01); *C12Y 102/04001* (2013.01); *C12N 1/00* (2013.01); *C12R 2001/185* (2021.05); *C12R 2001/38* (2021.05); *C12R 2001/44* (2021.05)

(58) Field of Classification Search
CPC ............. A01N 37/18; C12Y 102/04001; A61K 31/7036; A61K 38/44; A61K 45/06; A61K 2300/00; C12R 2001/185; C12R 2001/44; C12R 2001/38; C12N 1/00
See application file for complete search history.

(56) References Cited

U.S. PATENT DOCUMENTS

| | | |
|---|---|---|
| 4,006,056 A | 2/1977 | Weber |
| 4,183,960 A | 1/1980 | Asher et al. |

(Continued)

OTHER PUBLICATIONS

Patel et al. The Pyruvate Dehydrogenase Complexes: Structure-based Function and Regulation. Journal of Biological Chemistry (2014), 289(24), 16615-16623. (Year: 2014).*

(Continued)

*Primary Examiner* — Sean C. Barron
(74) *Attorney, Agent, or Firm* — Hoffberg & Associates; Steven M. Hoffberg

(57) ABSTRACT

A method of treating a biofilm on a surface, comprising: providing a surface having a biofilm; and administering to the surface a treatment that reduces a concentration of pyruvate of the biofilm, comprising pyruvate produced by at least a portion the biofilm, under conditions effective reducing maintenance of the biofilm on the surface. A composition, comprising purified enzyme, within a particle, effective for reducing pyruvate concentration in an aqueous suspension of the composition.

18 Claims, 24 Drawing Sheets

(56) References Cited

U.S. PATENT DOCUMENTS

| | | |
|---|---|---|
| 4,257,884 A | 3/1981 | Lim |
| 4,310,554 A | 1/1982 | Olson et al. |
| 4,342,826 A | 8/1982 | Cole |
| 4,401,122 A | 8/1983 | Clark, Jr. |
| 4,418,148 A | 11/1983 | Oberhardt |
| 4,431,428 A | 2/1984 | Schmer |
| 4,458,686 A | 7/1984 | Clark, Jr. |
| 4,463,090 A | 7/1984 | Harris |
| 4,483,921 A | 11/1984 | Cole |
| 4,622,294 A | 11/1986 | Kung et al. |
| 4,666,830 A | 5/1987 | Wagner |
| 4,693,970 A | 9/1987 | O'Connell et al. |
| 4,756,844 A | 7/1988 | Walles et al. |
| 4,783,400 A | 11/1988 | Canova-Davis et al. |
| 4,861,597 A | 8/1989 | Kida et al. |
| 4,863,626 A | 9/1989 | Coyne et al. |
| 4,876,039 A | 10/1989 | Lo et al. |
| 4,898,781 A | 2/1990 | Onouchi et al. |
| 4,900,556 A | 2/1990 | Wheatley et al. |
| 4,933,185 A | 6/1990 | Wheatley et al. |
| 4,963,368 A | 10/1990 | Antrim et al. |
| 4,965,012 A | 10/1990 | Olson |
| 5,015,483 A | 5/1991 | Haynes et al. |
| 5,064,669 A | 11/1991 | Tan et al. |
| 5,068,198 A | 11/1991 | Gibbons et al. |
| 5,089,278 A | 2/1992 | Haynes et al. |
| 5,093,021 A | 3/1992 | Coyne et al. |
| 5,139,803 A | 8/1992 | Haynes et al. |
| 5,147,641 A | 9/1992 | Chang et al. |
| 5,167,854 A | 12/1992 | Deleeuw et al. |
| 5,190,762 A | 3/1993 | Yarosh |
| 5,200,236 A | 4/1993 | Lang et al. |
| 5,200,334 A | 4/1993 | Dunn et al. |
| 5,225,102 A | 7/1993 | Coyne et al. |
| 5,230,822 A | 7/1993 | Kamel et al. |
| 5,254,287 A | 10/1993 | Deleeuw et al. |
| 5,258,132 A | 11/1993 | Kamel et al. |
| 5,262,313 A | 11/1993 | Kitchell et al. |
| 5,272,079 A | 12/1993 | Yarosh |
| 5,275,154 A | 1/1994 | Von Blucher et al. |
| 5,281,355 A | 1/1994 | Tsaur et al. |
| 5,281,356 A | 1/1994 | Tsaur et al. |
| 5,281,357 A | 1/1994 | Morgan et al. |
| 5,296,231 A | 3/1994 | Yarosh |
| 5,324,436 A | 6/1994 | John et al. |
| 5,352,458 A | 10/1994 | Yarosh |
| 5,385,959 A | 1/1995 | Tsaur et al. |
| 5,413,804 A | 5/1995 | Rhodes |
| 5,434,069 A | 7/1995 | Tsaur et al. |
| 5,437,331 A | 8/1995 | Gupta et al. |
| 5,441,660 A | 8/1995 | Tsaur et al. |
| 5,492,646 A | 2/1996 | Langley et al. |
| 5,505,713 A | 4/1996 | Van Antwerp |
| 5,506,271 A | 4/1996 | Meruelo et al. |
| 5,523,232 A | 6/1996 | Sechler |
| 5,538,511 A | 7/1996 | Van Antwerp |
| 5,545,519 A | 8/1996 | Vadgama et al. |
| 5,589,370 A | 12/1996 | Ratuiste et al. |
| 5,604,186 A | 2/1997 | Hunt et al. |
| 5,665,380 A | 9/1997 | Wallach et al. |
| 5,684,144 A | 11/1997 | Romeo |
| 5,693,513 A | 12/1997 | Pope |
| 5,698,083 A | 12/1997 | Glass |
| 5,752,981 A | 5/1998 | Fornelli |
| 5,753,152 A | 5/1998 | Vasudevan |
| 5,777,078 A | 7/1998 | Bayley et al. |
| 5,788,678 A | 8/1998 | Van Antwerp |
| 5,830,663 A | 11/1998 | Embleton et al. |
| 5,846,927 A | 12/1998 | Vasudevan |
| 5,858,117 A | 1/1999 | Oakes et al. |
| 5,858,430 A | 1/1999 | Endico |
| 5,861,366 A | 1/1999 | Ihns et al. |
| 5,868,720 A | 2/1999 | Van Antwerp |
| 5,895,757 A | 4/1999 | Pope |
| 5,929,214 A | 7/1999 | Peters et al. |
| 6,017,528 A | 1/2000 | Fischetti et al. |
| 6,022,500 A | 2/2000 | John et al. |
| 6,051,541 A | 4/2000 | Neuser et al. |
| 6,086,921 A | 7/2000 | Domenico |
| 6,106,854 A | 8/2000 | Belfer et al. |
| 6,127,499 A | 10/2000 | Symes et al. |
| 6,197,739 B1 | 3/2001 | Oakes et al. |
| 6,209,646 B1 | 4/2001 | Reddy et al. |
| 6,225,372 B1 | 5/2001 | Lykke et al. |
| 6,242,405 B1 | 6/2001 | Lykke et al. |
| 6,248,371 B1 | 6/2001 | Domenico |
| 6,258,771 B1 | 7/2001 | Hsu et al. |
| 6,268,471 B1 | 7/2001 | Romeo |
| 6,280,980 B1 | 8/2001 | Waller |
| 6,287,765 B1 | 9/2001 | Cubicciotti |
| 6,303,290 B1 | 10/2001 | Liu et al. |
| 6,311,546 B1 | 11/2001 | Dickinson et al. |
| 6,313,197 B1 | 11/2001 | Symes et al. |
| 6,359,031 B1 | 3/2002 | Lykke et al. |
| 6,362,156 B1 | 3/2002 | Hsu et al. |
| 6,368,619 B1 | 4/2002 | New et al. |
| 6,369,018 B1 | 4/2002 | Hsu et al. |
| 6,395,299 B1 | 5/2002 | Babich et al. |
| 6,455,284 B1 | 9/2002 | Gokarn et al. |
| 6,495,352 B1 | 12/2002 | Brinker et al. |
| 6,500,463 B1 | 12/2002 | van Lengerich |
| 6,537,786 B2 | 3/2003 | Koffas et al. |
| 6,541,606 B2 | 4/2003 | Margolin et al. |
| 6,579,854 B1 | 6/2003 | Mitchell et al. |
| 6,608,187 B2 | 8/2003 | Nelson et al. |
| 6,630,436 B1 | 10/2003 | York et al. |
| 6,641,739 B2 | 11/2003 | Dresty, Jr. et al. |
| 6,664,239 B2 | 12/2003 | Mitchell et al. |
| 6,673,222 B1 | 1/2004 | Papavinasam et al. |
| 6,685,943 B1 | 2/2004 | Hook et al. |
| 6,692,757 B1 | 2/2004 | Day et al. |
| 6,730,212 B1 | 5/2004 | Yamagishi et al. |
| 6,730,651 B2 | 5/2004 | Hsu et al. |
| 6,756,369 B2 | 6/2004 | Mitchell et al. |
| 6,762,025 B2 | 7/2004 | Cubicciotti |
| 6,793,900 B1 | 9/2004 | Morck et al. |
| 6,818,594 B1 | 11/2004 | Freeman et al. |
| 6,833,192 B1 | 12/2004 | Caruso et al. |
| 6,863,815 B1 | 3/2005 | Smith |
| 6,884,784 B1 | 4/2005 | Mitchell et al. |
| 6,887,270 B2 | 5/2005 | Miller et al. |
| 6,908,912 B2 | 6/2005 | Rioux et al. |
| 6,927,201 B2 | 8/2005 | Hsu et al. |
| 6,943,200 B1 | 9/2005 | Corrand et al. |
| 6,955,890 B2 | 10/2005 | Schechter |
| 6,972,278 B2 | 12/2005 | Hsu et al. |
| 6,974,706 B1 | 12/2005 | Melker et al. |
| 6,979,669 B2 | 12/2005 | Raehse et al. |
| 7,001,519 B2 | 2/2006 | Linden et al. |
| 7,008,524 B2 | 3/2006 | Stanford et al. |
| 7,018,642 B2 | 3/2006 | Degenhardt et al. |
| 7,025,986 B2 | 4/2006 | Brown et al. |
| 7,033,980 B2 | 4/2006 | Waits et al. |
| 7,034,677 B2 | 4/2006 | Steinthal et al. |
| 7,052,614 B2 | 5/2006 | Barak |
| 7,052,913 B2 | 5/2006 | Babich et al. |
| 7,060,299 B2 | 6/2006 | Alavattam et al. |
| 7,087,661 B1 | 8/2006 | Alberte et al. |
| 7,128,912 B2 | 10/2006 | Hook et al. |
| 7,144,992 B2 | 12/2006 | Madhyastha |
| 7,147,888 B2 | 12/2006 | Brown et al. |
| 7,151,139 B2 | 12/2006 | Tiller et al. |
| 7,153,407 B2 | 12/2006 | Guzman |
| 7,153,515 B2 | 12/2006 | Brown et al. |
| 7,171,312 B2 | 1/2007 | Steinthal et al. |
| 7,172,682 B2 | 2/2007 | Dordick et al. |
| 7,183,100 B2 | 2/2007 | Candas et al. |
| 7,189,329 B2 | 3/2007 | Barak |
| 7,189,351 B2 | 3/2007 | Levin et al. |
| 7,195,780 B2 | 3/2007 | Dennis et al. |
| 7,198,785 B2 | 4/2007 | O'Loughlin et al. |
| 7,201,923 B1 | 4/2007 | van Lengerich |
| 7,201,925 B2 | 4/2007 | Gillis |
| 7,217,425 B2 | 5/2007 | Serhan et al. |

(56) References Cited

U.S. PATENT DOCUMENTS

| | | | |
|---|---|---|---|
| 7,241,613 B1 | 7/2007 | Willins et al. |
| 7,250,095 B2 | 7/2007 | Black et al. |
| 7,255,881 B2 | 8/2007 | Gillis et al. |
| 7,267,837 B2 | 9/2007 | Kumar et al. |
| 7,267,958 B2 | 9/2007 | Dordick et al. |
| 7,285,523 B1 | 10/2007 | Seydel et al. |
| 7,314,857 B2 | 1/2008 | Madhyastha |
| 7,329,388 B2 | 2/2008 | Guzman |
| 7,348,420 B2 | 3/2008 | Klaenhammer et al. |
| 7,351,798 B2 | 4/2008 | Margolin et al. |
| 7,375,168 B2 | 5/2008 | Zhang et al. |
| 7,399,742 B2 | 7/2008 | DiMauro et al. |
| 7,402,722 B2 | 7/2008 | Hill et al. |
| 7,413,729 B2 | 8/2008 | Apicella et al. |
| 7,419,607 B2 | 9/2008 | Downs |
| 7,427,416 B2 | 9/2008 | Gillis et al. |
| 7,427,497 B2 | 9/2008 | Dordick et al. |
| 7,446,089 B2 | 11/2008 | Singh et al. |
| 7,450,228 B2 | 11/2008 | Maier et al. |
| 7,452,345 B2 | 11/2008 | Darouiche et al. |
| 7,455,992 B2 | 11/2008 | Klaenhammer et al. |
| 7,491,699 B2 | 2/2009 | Reches et al. |
| 7,497,834 B2 | 3/2009 | Schaden et al. |
| 7,497,835 B2 | 3/2009 | Schultheiss et al. |
| 7,501,131 B2 | 3/2009 | Bakaletz et al. |
| 7,524,669 B2 | 4/2009 | Rosen et al. |
| 7,534,876 B2 | 5/2009 | Klaenhammer et al. |
| 7,538,209 B2 | 5/2009 | Klaenhammer et al. |
| 7,550,576 B2 | 6/2009 | Klaenhammer et al. |
| 7,553,653 B2 | 6/2009 | Kakkis et al. |
| 7,556,807 B2 | 7/2009 | Cvitkovitch et al. |
| 7,563,615 B2 | 7/2009 | Ponce |
| 7,601,731 B2 | 10/2009 | Raad |
| 7,604,978 B2 | 10/2009 | Eldridge |
| 7,608,419 B2 | 10/2009 | Ponce |
| 7,611,862 B2 | 11/2009 | Ponce |
| 7,612,045 B2 | 11/2009 | Eldridge |
| 7,628,929 B2 | 12/2009 | Barak |
| 7,629,141 B2 | 12/2009 | Bruce et al. |
| 7,666,404 B2 | 2/2010 | Uhich et al. |
| 7,691,267 B2 | 4/2010 | Smith et al. |
| 7,691,418 B2 | 4/2010 | Rossel |
| 7,700,104 B2 | 4/2010 | Hensel et al. |
| 7,723,056 B1 | 5/2010 | Clarke et al. |
| 7,723,087 B2 | 5/2010 | Pier et al. |
| 7,736,480 B2 | 6/2010 | Guzman |
| 7,740,821 B2 | 6/2010 | Watkins et al. |
| 7,744,555 B2 | 6/2010 | DiMauro et al. |
| 7,750,050 B2 | 7/2010 | Schuchman et al. |
| 7,750,135 B2 | 7/2010 | Zeikus et al. |
| 7,754,868 B2 | 7/2010 | Klaenhammer et al. |
| 7,760,353 B2 | 7/2010 | Maier et al. |
| 7,763,097 B2 | 7/2010 | Federspiel et al. |
| 7,771,976 B2 | 8/2010 | Gulevich et al. |
| 7,775,965 B2 | 8/2010 | McFetridge |
| 7,781,166 B2 | 8/2010 | Yu et al. |
| 7,781,396 B2 | 8/2010 | Gazit |
| 7,786,086 B2 | 8/2010 | Reches et al. |
| 7,790,947 B2 | 9/2010 | Hill et al. |
| 7,794,698 B2 | 9/2010 | Bukshpan et al. |
| 7,799,545 B2 | 9/2010 | Burgard et al. |
| 7,803,574 B2 | 9/2010 | Desai et al. |
| 7,803,589 B2 | 9/2010 | Burk et al. |
| 7,811,436 B2 | 10/2010 | Guzman |
| 7,829,305 B2 | 11/2010 | Kolari et al. |
| 7,838,502 B2 | 11/2010 | Akerley et al. |
| 7,842,290 B2 | 11/2010 | Holden |
| 7,846,747 B2 | 12/2010 | Dordick et al. |
| 7,855,060 B2 | 12/2010 | Filippov et al. |
| 7,858,561 B2 | 12/2010 | Abad et al. |
| 7,863,029 B2 | 1/2011 | Jaffe |
| 7,887,816 B2 | 2/2011 | Feldman et al. |
| 7,893,237 B2 | 2/2011 | Bakaletz et al. |
| 7,897,367 B2 | 3/2011 | Klaenhammer et al. |
| 7,897,631 B2 | 3/2011 | Melander et al. |
| 7,906,544 B2 | 3/2011 | Melander et al. |
| 7,927,496 B2 | 4/2011 | Barak |
| 7,927,629 B2 | 4/2011 | Simone et al. |
| 7,939,061 B2 | 5/2011 | Prakash et al. |
| 7,939,087 B2 | 5/2011 | Telford et al. |
| 7,942,201 B2 | 5/2011 | Ekstrand et al. |
| 7,955,600 B2 | 6/2011 | Hensel et al. |
| 7,955,604 B2 | 6/2011 | Telford et al. |
| 7,972,616 B2 | 7/2011 | Dubrow et al. |
| 7,977,084 B2 | 7/2011 | Sun et al. |
| 7,993,390 B2 | 8/2011 | Miller et al. |
| 7,998,714 B2 | 8/2011 | Gellett et al. |
| 7,998,919 B2 | 8/2011 | Rong et al. |
| 8,007,724 B2 | 8/2011 | Guzman |
| 8,007,725 B2 | 8/2011 | Guzman |
| 8,012,929 B2 | 9/2011 | Gazit |
| 8,025,890 B2 | 9/2011 | Telford et al. |
| 8,026,386 B2 | 9/2011 | Burk et al. |
| 8,030,092 B2 | 10/2011 | Guzman |
| 8,043,411 B2 | 10/2011 | Federspiel et al. |
| 8,048,661 B2 | 11/2011 | Burgard et al. |
| 8,053,554 B2 | 11/2011 | Reches et al. |
| 8,062,871 B2 | 11/2011 | Burgard et al. |
| 8,066,818 B2 | 11/2011 | Brooker et al. |
| 8,071,540 B2 | 12/2011 | Montelaro et al. |
| 8,076,117 B2 | 12/2011 | Trampuz et al. |
| 8,088,607 B2 | 1/2012 | Burgard et al. |
| 8,097,439 B2 | 1/2012 | Alibhai et al. |
| 8,101,562 B2 | 1/2012 | Classen |
| 8,105,520 B2 | 1/2012 | Miller et al. |
| 8,110,670 B2 | 2/2012 | Hu et al. |
| 8,119,385 B2 | 2/2012 | Mathur et al. |
| 8,129,154 B2 | 3/2012 | Burk et al. |
| 8,129,155 B2 | 3/2012 | Trawick et al. |
| 8,133,501 B2 | 3/2012 | Li et al. |
| 8,137,673 B2 | 3/2012 | Telford et al. |
| 8,142,764 B2 | 3/2012 | Demuth et al. |
| 8,153,119 B2 | 4/2012 | Collins et al. |
| 8,153,410 B2 | 4/2012 | Jaffe |
| 8,153,412 B2 | 4/2012 | Chang et al. |
| 8,153,597 B2 | 4/2012 | Stanton et al. |
| 8,162,924 B2 | 4/2012 | Boyden et al. |
| 8,163,526 B2 | 4/2012 | Walmsley et al. |
| 8,168,072 B2 | 5/2012 | Barak |
| 8,173,359 B2 | 5/2012 | Ponce et al. |
| 8,173,673 B2 | 5/2012 | Bringmann et al. |
| 8,178,332 B2 | 5/2012 | Gellett et al. |
| 8,182,746 B2 | 5/2012 | Guzman |
| 8,207,316 B1 | 6/2012 | Bentwich |
| 8,211,361 B2 | 7/2012 | Sun et al. |
| 8,211,432 B2 | 7/2012 | Hook et al. |
| 8,216,173 B2 | 7/2012 | Dacey, Jr. et al. |
| 8,216,814 B2 | 7/2012 | Burgard et al. |
| 8,226,996 B2 | 7/2012 | Chukwu |
| 8,227,017 B2 | 7/2012 | Leander et al. |
| 8,231,602 B2 | 7/2012 | Anderson et al. |
| 8,231,686 B2 | 7/2012 | Mangiardi |
| 8,236,281 B1 | 8/2012 | Sung et al. |
| 8,236,545 B2 | 8/2012 | Cascao-Pereira et al. |
| 8,240,936 B2 | 8/2012 | Vazquez et al. |
| 8,241,611 B2 | 8/2012 | Dashper et al. |
| 8,241,877 B2 | 8/2012 | Burgard et al. |
| 8,246,691 B2 | 8/2012 | Mangiardi |
| 8,256,233 B2 | 9/2012 | Boyden et al. |
| 8,257,827 B1 | 9/2012 | Shi et al. |
| 8,267,883 B2 | 9/2012 | DiMauro et al. |
| 8,268,247 B2 | 9/2012 | Guzman |
| 8,268,607 B2 | 9/2012 | Burgard et al. |
| 8,273,104 B2 | 9/2012 | Cohen |
| 8,278,340 B2 | 10/2012 | Melander et al. |
| 8,282,593 B2 | 10/2012 | Dacey, Jr. et al. |
| 8,282,967 B2 | 10/2012 | Schoenfisch et al. |
| 8,283,135 B2 | 10/2012 | Doyle et al. |
| 8,283,143 B2 | 10/2012 | Hu et al. |
| 8,297,959 B2 | 10/2012 | Larsen et al. |
| 8,307,894 B2 | 11/2012 | Wallace |
| 8,309,590 B2 | 11/2012 | Reid |
| 8,313,757 B2 | 11/2012 | van Lengerich |
| 8,318,156 B2 | 11/2012 | Landry et al. |

(56) References Cited

U.S. PATENT DOCUMENTS

| | | |
|---|---|---|
| 8,318,180 B2 | 11/2012 | Shirtliff et al. |
| 8,323,379 B2 | 12/2012 | Federspiel et al. |
| 8,323,950 B2 | 12/2012 | Burk et al. |
| 8,329,225 B2 | 12/2012 | Muzykantov et al. |
| 8,329,758 B2 | 12/2012 | Ali et al. |
| 8,343,086 B2 | 1/2013 | Dacey, Jr. et al. |
| 8,343,911 B2 | 1/2013 | Singh et al. |
| 8,349,368 B2 | 1/2013 | Gordon et al. |
| 8,350,004 B2 | 1/2013 | Reches et al. |
| 8,354,267 B2 | 1/2013 | Barkeloo et al. |
| 8,354,366 B2 | 1/2013 | Denome et al. |
| 8,361,239 B2 | 1/2013 | Bettiol et al. |
| 8,366,652 B2 | 2/2013 | Dacey, Jr. et al. |
| 8,367,055 B2 | 2/2013 | Talaat et al. |
| 8,367,713 B2 | 2/2013 | Melander et al. |
| 8,367,716 B2 | 2/2013 | Karaolis |
| 8,367,823 B2 | 2/2013 | Sun et al. |
| 8,372,880 B2 | 2/2013 | Gazit et al. |
| 8,377,455 B2 | 2/2013 | Ceri et al. |
| 8,377,666 B2 | 2/2013 | Haselbeck et al. |
| 8,377,680 B2 | 2/2013 | Burk et al. |
| 8,383,101 B2 | 2/2013 | Olmstead |
| 8,383,582 B2 | 2/2013 | Oh et al. |
| 8,389,021 B2 | 3/2013 | Baker |
| 8,389,679 B2 | 3/2013 | Eckert et al. |
| 8,393,395 B2 | 3/2013 | Cochet et al. |
| 8,398,705 B2 | 3/2013 | Mangiardi |
| 8,399,000 B2 | 3/2013 | Bakaletz et al. |
| 8,399,230 B2 | 3/2013 | Van Dyck et al. |
| 8,399,235 B2 | 3/2013 | Frank et al. |
| 8,399,635 B2 | 3/2013 | Baker et al. |
| 8,399,649 B2 | 3/2013 | Yu et al. |
| 8,404,469 B2 | 3/2013 | Gross et al. |
| 8,414,356 B2 | 4/2013 | Boyden et al. |
| 8,414,517 B2 | 4/2013 | Dacey, Jr. et al. |
| 8,415,159 B2 | 4/2013 | Ward et al. |
| 8,420,375 B2 | 4/2013 | Osterhout et al. |
| 8,425,880 B1 | 4/2013 | Lyczak et al. |
| 8,431,139 B2 | 4/2013 | Telford et al. |
| 8,431,151 B2 | 4/2013 | Mather et al. |
| 8,444,858 B2 | 5/2013 | Barak |
| 8,445,244 B2 | 5/2013 | Burgard et al. |
| 8,460,229 B2 | 6/2013 | Dacey, Jr. et al. |
| 8,460,907 B2 | 6/2013 | Walker et al. |
| 8,460,908 B2 | 6/2013 | Templeton |
| 8,460,916 B2 | 6/2013 | Cascao-Pereira et al. |
| 8,461,106 B2 | 6/2013 | Cohen et al. |
| 8,476,425 B1 | 7/2013 | Lai et al. |
| 8,481,138 B2 | 7/2013 | Miller et al. |
| 8,485,861 B2 | 7/2013 | Boyden et al. |
| 8,486,428 B2 | 7/2013 | Sun et al. |
| 8,501,969 B2 | 8/2013 | Meijler et al. |
| 8,507,244 B2 | 8/2013 | Shaw et al. |
| 8,513,305 B2 | 8/2013 | Davies |
| 8,513,329 B2 | 8/2013 | Lake et al. |
| 8,518,031 B2 | 8/2013 | Boyden et al. |
| 8,524,475 B1 | 9/2013 | Templeton |
| 8,535,646 B2 | 9/2013 | Sokol et al. |
| 8,541,567 B2 | 9/2013 | Schramm |
| 8,545,951 B2 | 10/2013 | Yahiaoui et al. |
| 8,546,121 B2 | 10/2013 | Aehle et al. |
| 8,546,316 B2 | 10/2013 | Perez-Prat Vinuesa et al. |
| 8,552,147 B2 | 10/2013 | Zlotkin |
| 8,552,208 B2 | 10/2013 | Lee et al. |
| 8,558,048 B2 | 10/2013 | Margolin et al. |
| 8,568,363 B2 | 10/2013 | Boyden et al. |
| 8,568,786 B2 | 10/2013 | Simone et al. |
| 8,569,449 B2 | 10/2013 | Gorr |
| 8,569,463 B2 | 10/2013 | Luk et al. |
| 8,574,660 B2 | 11/2013 | Weaver et al. |
| 8,575,083 B2 | 11/2013 | Bettiol et al. |
| 8,580,543 B2 | 11/2013 | Burk et al. |
| 8,585,627 B2 | 11/2013 | Dacey, Jr. et al. |
| 8,591,876 B2 | 11/2013 | Bauman et al. |
| 8,591,961 B2 | 11/2013 | Widgerow |
| 8,592,189 B2 | 11/2013 | Burgard et al. |
| 8,592,473 B2 | 11/2013 | Reid |
| 8,597,923 B2 | 12/2013 | Ness et al. |
| 8,603,824 B2 | 12/2013 | Ramseier et al. |
| 8,609,110 B2 | 12/2013 | Shanks et al. |
| 8,617,523 B2 | 12/2013 | Trivedi et al. |
| 8,617,542 B2 | 12/2013 | Madhyastha et al. |
| 8,617,623 B2 | 12/2013 | Shen et al. |
| 8,618,149 B2 | 12/2013 | Melander et al. |
| 8,623,340 B2 | 1/2014 | Kuhn et al. |
| 8,623,632 B2 | 1/2014 | Sabirova et al. |
| 8,632,838 B2 | 1/2014 | Roth et al. |
| 8,637,090 B2 | 1/2014 | Ohtake et al. |
| 8,637,286 B2 | 1/2014 | Burgard et al. |
| 8,641,686 B2 | 2/2014 | Stephan |
| 8,647,292 B2 | 2/2014 | Dacey, Jr. et al. |
| 8,647,857 B2 | 2/2014 | Templeton |
| 8,652,829 B2 | 2/2014 | Bellalou et al. |
| 8,653,124 B2 | 2/2014 | Melander et al. |
| 8,658,225 B2 | 2/2014 | Zinreich et al. |
| 8,663,957 B2 | 3/2014 | Osterhout et al. |
| 8,669,283 B2 | 3/2014 | Sieber et al. |
| 8,673,601 B2 | 3/2014 | Burgard et al. |
| 8,680,072 B2 | 3/2014 | Onsoyen et al. |
| 8,680,148 B2 | 3/2014 | Greenberg et al. |
| 8,684,732 B2 | 4/2014 | Jacoby |
| 8,685,171 B2 | 4/2014 | Perez-Prat Vinuesa et al. |
| 8,685,427 B2 | 4/2014 | Li et al. |
| 8,685,957 B1 | 4/2014 | Lai et al. |
| 8,691,264 B2 | 4/2014 | Li et al. |
| 8,691,553 B2 | 4/2014 | Burk et al. |
| 8,697,102 B2 | 4/2014 | Bukshpan et al. |
| 8,697,375 B2 | 4/2014 | Shirtliff et al. |
| 8,697,421 B2 | 4/2014 | Burk et al. |
| 8,702,640 B2 | 4/2014 | Dacey, Jr. et al. |
| 8,703,153 B2 | 4/2014 | Telfer et al. |
| 8,703,446 B2 | 4/2014 | Kiryukhin et al. |
| 8,706,211 B2 | 4/2014 | Dacey, Jr. et al. |
| 8,709,342 B2 | 4/2014 | Raad |
| 8,709,444 B2 | 4/2014 | Klumpp et al. |
| 8,709,487 B1 | 4/2014 | Kinnan et al. |
| 8,710,082 B2 | 4/2014 | Waters et al. |
| 8,715,733 B2 | 5/2014 | Kadiyala et al. |
| 8,715,957 B2 | 5/2014 | Osterhout et al. |
| 8,715,971 B2 | 5/2014 | Pharkya et al. |
| 8,728,467 B2 | 5/2014 | Olmstead |
| 8,734,718 B2 | 5/2014 | Dacey, Jr. et al. |
| 8,735,119 B2 | 5/2014 | Templeton |
| 8,741,855 B2 | 6/2014 | Quave et al. |
| 8,753,304 B2 | 6/2014 | Dacey, Jr. et al. |
| 8,753,692 B2 | 6/2014 | Gawande et al. |
| 8,754,039 B2 | 6/2014 | Eckert et al. |
| 8,758,781 B2 | 6/2014 | Ward et al. |
| 8,759,270 B2 | 6/2014 | Perez-Prat Vinuesa et al. |
| 8,778,370 B2 | 7/2014 | Kramer et al. |
| 8,778,387 B2 | 7/2014 | Tennican et al. |
| 8,778,889 B2 | 7/2014 | Leung |
| 8,779,023 B2 | 7/2014 | Whang et al. |
| 8,784,384 B2 | 7/2014 | Boyden et al. |
| 8,784,385 B2 | 7/2014 | Boyden et al. |
| 8,785,399 B2 | 7/2014 | Giuliani et al. |
| 8,795,727 B2 | 8/2014 | Gong et al. |
| 8,796,023 B2 | 8/2014 | Reches et al. |
| 8,796,252 B2 | 8/2014 | Rioux et al. |
| 8,798,932 B2 | 8/2014 | Boyden et al. |
| 8,798,933 B2 | 8/2014 | Boyden et al. |
| 8,802,059 B2 | 8/2014 | Fagon et al. |
| 8,802,414 B2 | 8/2014 | Frank et al. |
| 8,808,718 B2 | 8/2014 | Van Der Waal et al. |
| 8,809,031 B2 | 8/2014 | England et al. |
| 8,809,314 B1 | 8/2014 | He et al. |
| 8,810,417 B2 | 8/2014 | Hood et al. |
| 8,815,562 B2 | 8/2014 | Sherman et al. |
| 8,821,862 B2 | 9/2014 | Madhyastha et al. |
| 8,821,910 B2 | 9/2014 | Song et al. |
| 8,828,910 B2 | 9/2014 | Aksela et al. |
| 8,829,053 B2 | 9/2014 | Salamone et al. |
| 8,834,865 B2 | 9/2014 | Becker et al. |
| 8,835,644 B2 | 9/2014 | Hoffman et al. |

(56) References Cited

U.S. PATENT DOCUMENTS

| | | |
|---|---|---|
| 8,840,912 B2 | 9/2014 | Melander et al. |
| 8,845,593 B2 | 9/2014 | Anderson et al. |
| 8,846,008 B2 | 9/2014 | Tennican et al. |
| 8,846,009 B2 | 9/2014 | Tennican et al. |
| 8,846,605 B2 | 9/2014 | Ghatnekar |
| 8,849,441 B2 | 9/2014 | Boyden et al. |
| 8,852,880 B2 | 10/2014 | Godfrin |
| 8,852,912 B2 | 10/2014 | Estell et al. |
| 8,853,278 B1 | 10/2014 | Looper et al. |
| 8,858,912 B2 | 10/2014 | Boyden et al. |
| 8,865,439 B2 | 10/2014 | Burgard et al. |
| 8,865,909 B2 | 10/2014 | Srebnik et al. |
| 8,871,478 B2 | 10/2014 | Yukawa et al. |
| 8,877,506 B2 | 11/2014 | Roberts et al. |
| 8,884,022 B2 | 11/2014 | Melander et al. |
| 8,888,731 B2 | 11/2014 | Dacey, Jr. et al. |
| 8,889,196 B2 | 11/2014 | Xu |
| 8,895,019 B2 | 11/2014 | Dashper et al. |
| 8,898,069 B2 | 11/2014 | Hood et al. |
| 8,900,837 B2 | 12/2014 | Burgard et al. |
| 8,906,349 B2 | 12/2014 | Schaeffer-Korbylo et al. |
| 8,906,364 B2 | 12/2014 | Madhyastha |
| 8,906,393 B2 | 12/2014 | Kaplan et al. |
| 8,906,898 B1 | 12/2014 | Hwang et al. |
| 8,906,915 B2 | 12/2014 | De Keersmaecker et al. |
| 8,911,745 B2 | 12/2014 | Dashper et al. |
| 8,915,894 B1 | 12/2014 | Lonky et al. |
| 8,916,358 B2 | 12/2014 | Swartz |
| 8,916,542 B2 | 12/2014 | Baker et al. |
| 8,920,826 B2 | 12/2014 | Bucay-Couto |
| 8,926,951 B2 | 1/2015 | Ratcliff et al. |
| 8,927,029 B2 | 1/2015 | Melander et al. |
| 8,927,689 B2 | 1/2015 | Reches et al. |
| 8,932,578 B2 | 1/2015 | Prakash et al. |
| 8,940,911 B2 | 1/2015 | Luk et al. |
| 8,945,142 B2 | 2/2015 | Schaeffer et al. |
| 8,951,749 B2 | 2/2015 | Rylatt et al. |
| 8,951,992 B2 | 2/2015 | Nathan et al. |
| 8,952,192 B2 | 2/2015 | Sintim et al. |
| 8,956,637 B2 | 2/2015 | Dubrow et al. |
| 8,956,658 B2 | 2/2015 | Schoenfisch et al. |
| 8,956,663 B2 | 2/2015 | Gordon et al. |
| 8,956,833 B2 | 2/2015 | Swartz |
| 8,961,544 B2 | 2/2015 | Komlos et al. |
| 8,962,029 B2 | 2/2015 | Schoenfisch et al. |
| 8,962,283 B2 | 2/2015 | Cascao-Pereira et al. |
| 8,962,800 B2 | 2/2015 | Mathur et al. |
| 8,968,753 B2 | 3/2015 | Terracciano et al. |
| 8,968,765 B2 | 3/2015 | Chen et al. |
| 8,969,068 B2 | 3/2015 | Templeton |
| 8,974,802 B2 | 3/2015 | Dufour et al. |
| 8,980,252 B2 | 3/2015 | Fallon et al. |
| 8,981,139 B2 | 3/2015 | Schoenfisch et al. |
| 8,992,223 B2 | 3/2015 | Sun et al. |
| 8,992,893 B2 | 3/2015 | Sokol et al. |
| 8,992,986 B2 | 3/2015 | Finnie et al. |
| 8,993,285 B2 | 3/2015 | Burgard |
| 8,999,265 B2 | 4/2015 | Koesdjojo et al. |
| 8,999,686 B2 | 4/2015 | Hu et al. |
| 9,005,263 B2 | 4/2015 | Boyden et al. |
| 9,005,643 B2 | 4/2015 | Melander et al. |
| 9,005,928 B2 | 4/2015 | Schaffer et al. |
| 9,012,378 B2 | 4/2015 | Ekstrand et al. |
| 9,012,429 B2 | 4/2015 | Baker et al. |
| 9,017,681 B2 | 4/2015 | Levin et al. |
| 9,017,983 B2 | 4/2015 | Burgard et al. |
| 9,017,984 B2 | 4/2015 | Hu et al. |
| 9,023,636 B2 | 5/2015 | Burk et al. |
| 9,024,766 B2 | 5/2015 | Hood et al. |
| 9,028,878 B2 | 5/2015 | Baker |
| 9,029,318 B2 | 5/2015 | Zlotkin et al. |
| 9,034,346 B2 | 5/2015 | Miller et al. |
| 9,034,927 B2 | 5/2015 | Williams et al. |
| 9,040,059 B2 | 5/2015 | Curtiss, III et al. |
| 9,040,087 B2 | 5/2015 | Boyden et al. |
| 9,044,485 B2 | 6/2015 | Terracciano et al. |
| 9,045,550 B2 | 6/2015 | Zlotkin |
| 9,051,552 B2 | 6/2015 | Burk et al. |
| 9,056,050 B2 | 6/2015 | Fallon et al. |
| 9,056,899 B2 | 6/2015 | Collins et al. |
| 9,061,352 B2 | 6/2015 | Lipp et al. |
| 9,062,330 B2 | 6/2015 | Burk et al. |
| 9,068,109 B2 | 6/2015 | Rana et al. |
| 9,068,201 B2 | 6/2015 | Hu et al. |
| 9,073,884 B2 | 7/2015 | Gerwick et al. |
| 9,074,195 B1 | 7/2015 | Kinnan et al. |
| 9,078,441 B2 | 7/2015 | Raad |
| 9,084,423 B2 | 7/2015 | Melander et al. |
| 9,084,784 B2 | 7/2015 | Fallon et al. |
| 9,085,608 B2 | 7/2015 | Stensen et al. |
| 9,089,498 B2 | 7/2015 | Ortac et al. |
| 9,095,578 B2 | 8/2015 | Levin et al. |
| 9,096,703 B2 | 8/2015 | Li et al. |
| 9,102,860 B2 | 8/2015 | Cawiezel et al. |
| 9,107,419 B2 | 8/2015 | Fallon et al. |
| 9,109,189 B2 | 8/2015 | Perez-Prat Vinuesa et al. |
| 9,109,196 B2 | 8/2015 | Bazzana et al. |
| 9,109,229 B2 | 8/2015 | Ramseier et al. |
| 9,113,636 B2 | 8/2015 | von Maltzahn et al. |
| 9,121,017 B2 | 9/2015 | Walker et al. |
| 9,125,408 B2 | 9/2015 | Melander et al. |
| 9,125,853 B2 | 9/2015 | Reynolds |
| 9,125,855 B2 | 9/2015 | Pasmans et al. |
| 9,125,876 B2 | 9/2015 | Godfrin et al. |
| 9,139,622 B2 | 9/2015 | Shanks et al. |
| 9,145,395 B2 | 9/2015 | Melander et al. |
| 9,146,234 B2 | 9/2015 | Guzman |
| 9,149,648 B2 | 10/2015 | Dacey, Jr. et al. |
| 9,150,453 B1 | 10/2015 | Li et al. |
| 9,150,788 B2 | 10/2015 | Luk et al. |
| 9,156,760 B2 | 10/2015 | Zaher |
| 9,156,855 B2 | 10/2015 | Barraud et al. |
| 9,161,923 B2 | 10/2015 | Holden |
| 9,161,984 B2 | 10/2015 | Ghatnekar |
| 9,167,820 B2 | 10/2015 | Demuth et al. |
| 9,169,319 B2 | 10/2015 | Alarcon et al. |
| 9,175,234 B2 | 11/2015 | Hom et al. |
| 9,180,157 B2 | 11/2015 | Widgerow |
| 9,180,158 B2 | 11/2015 | Widgerow |
| 9,181,290 B2 | 11/2015 | Liu et al. |
| 9,181,564 B2 | 11/2015 | Leonetti et al. |
| 9,187,501 B2 | 11/2015 | Schoenfisch et al. |
| 9,187,766 B2 | 11/2015 | Prentice et al. |
| 9,198,957 B2 | 12/2015 | Ratner et al. |
| 9,200,265 B2 | 12/2015 | Landry et al. |
| 9,212,358 B2 | 12/2015 | Razavi-Shirazi et al. |
| 9,215,876 B2 | 12/2015 | Coady et al. |
| 9,220,267 B2 | 12/2015 | Williams et al. |
| 9,220,764 B2 | 12/2015 | Talaat et al. |
| 9,221,765 B2 | 12/2015 | Melander et al. |
| 9,221,875 B2 | 12/2015 | Yang et al. |
| 9,222,060 B2 | 12/2015 | Barbe et al. |
| 9,227,980 B2 | 1/2016 | Scherman et al. |
| 9,233,158 B2 | 1/2016 | Lipp et al. |
| 9,234,050 B2 | 1/2016 | Baker et al. |
| 9,242,951 B2 | 1/2016 | Meijler et al. |
| 9,247,734 B2 | 2/2016 | Sabin |
| 9,248,175 B2 | 2/2016 | Klumpp et al. |
| 9,249,128 B2 | 2/2016 | Cravatt et al. |
| 9,253,987 B2 | 2/2016 | Tennican et al. |
| 9,255,281 B2 | 2/2016 | Razavi-Shirazi et al. |
| 9,259,535 B2 | 2/2016 | Anderson et al. |
| 9,260,729 B2 | 2/2016 | Sun et al. |
| 9,265,820 B2 | 2/2016 | Shirtliff et al. |
| 9,271,493 B2 | 3/2016 | Cegelski et al. |
| 9,271,502 B2 | 3/2016 | Sabin |
| 9,271,933 B2 | 3/2016 | Devore et al. |
| 9,273,096 B2 | 3/2016 | Yang et al. |
| 9,273,305 B1 | 3/2016 | Kaehr et al. |
| 9,279,162 B2 | 3/2016 | Claverie et al. |
| 9,283,283 B2 | 3/2016 | Giammona et al. |
| 9,284,351 B2 | 3/2016 | Zlotkin |
| 9,284,562 B2 | 3/2016 | Collins et al. |
| 9,284,584 B2 | 3/2016 | Altman et al. |

(56) References Cited

U.S. PATENT DOCUMENTS

| | | |
|---|---|---|
| 9,288,995 B2 | 3/2016 | von Maltzahn et al. |
| 9,289,442 B2 | 3/2016 | Doxey et al. |
| 9,289,449 B2 | 3/2016 | Sershen et al. |
| 9,295,257 B2 | 3/2016 | Melander et al. |
| 9,295,263 B2 | 3/2016 | von Maltzahn et al. |
| 9,308,298 B2 | 4/2016 | Zhang |
| 9,309,294 B2 | 4/2016 | Bakaletz et al. |
| 9,320,740 B2 | 4/2016 | Terracciano et al. |
| 9,321,030 B2 | 4/2016 | Sukhishvili et al. |
| 9,326,511 B2 | 5/2016 | Love et al. |
| 9,326,924 B1 | 5/2016 | Fourre et al. |
| 9,326,925 B1 | 5/2016 | Fourre et al. |
| 9,333,244 B2 | 5/2016 | Li et al. |
| 9,334,466 B2 | 5/2016 | Aehle et al. |
| 9,339,525 B2 | 5/2016 | O'Neil et al. |
| 9,339,529 B2 | 5/2016 | Anderson et al. |
| 9,351,491 B2 | 5/2016 | Melander et al. |
| 9,351,492 B2 | 5/2016 | Quave et al. |
| 9,358,274 B2 | 6/2016 | Olmstead |
| 9,364,491 B2 | 6/2016 | O'Neil et al. |
| 9,370,187 B2 | 6/2016 | Reid et al. |
| 9,376,430 B2 | 6/2016 | Hoffman et al. |
| 9,376,479 B2 | 6/2016 | Govardhan et al. |
| 9,380,784 B2 | 7/2016 | Derby et al. |
| 9,382,556 B2 | 7/2016 | Burgard et al. |
| 9,387,189 B2 | 7/2016 | Glasnapp |
| 9,388,453 B2 | 7/2016 | Rey |
| 9,393,217 B2 | 7/2016 | Hammond et al. |
| 9,393,249 B2 | 7/2016 | Barrett et al. |
| 9,402,392 B2 | 8/2016 | Alper |
| 9,402,394 B2 | 8/2016 | Tang et al. |
| 9,403,851 B2 | 8/2016 | Schoenfisch et al. |
| 9,403,852 B2 | 8/2016 | Schoenfisch et al. |
| 9,408,393 B2 | 8/2016 | Baker |
| 9,408,394 B2 | 8/2016 | von Maltzahn et al. |
| 9,415,014 B2 | 8/2016 | Fallon et al. |
| 9,415,144 B2 | 8/2016 | Anzai et al. |
| 9,420,784 B2 | 8/2016 | Vanlaer et al. |
| 9,423,532 B2 | 8/2016 | Jewhurst et al. |
| 9,427,605 B2 | 8/2016 | Peters |
| 9,428,774 B2 | 8/2016 | Lee et al. |
| 9,433,527 B2 | 9/2016 | Varga et al. |
| 9,433,576 B2 | 9/2016 | Lipp et al. |
| 9,439,433 B2 | 9/2016 | Looper et al. |
| 9,439,436 B2 | 9/2016 | Melander et al. |
| 9,439,803 B2 | 9/2016 | Varga et al. |
| 9,439,925 B2 | 9/2016 | Baker et al. |
| 9,441,157 B2 | 9/2016 | Medina Perilla et al. |
| 9,441,250 B2 | 9/2016 | Bhalla et al. |
| 9,446,090 B2 | 9/2016 | Bevilacqua et al. |
| 9,452,107 B2 | 9/2016 | Bilgili et al. |
| 9,458,448 B2 | 10/2016 | Kim et al. |
| 9,458,480 B2 | 10/2016 | Burk et al. |
| 9,463,230 B2 | 10/2016 | Emery et al. |
| 9,464,368 B2 | 10/2016 | Zussman et al. |
| 9,469,584 B2 | 10/2016 | Anton et al. |
| 9,469,616 B2 | 10/2016 | Li et al. |
| 9,474,831 B2 | 10/2016 | Boyden et al. |
| 9,480,260 B2 | 11/2016 | Whang et al. |
| 9,480,541 B2 | 11/2016 | Falcone et al. |
| 9,480,696 B2 | 11/2016 | Collins et al. |
| 9,481,899 B2 | 11/2016 | Schirmer et al. |
| 9,486,486 B2 | 11/2016 | Castex-Rizzi et al. |
| 9,487,453 B2 | 11/2016 | Sabin |
| 9,492,515 B2 | 11/2016 | Fallon et al. |
| 9,492,596 B2 | 11/2016 | Herweck et al. |
| 9,499,419 B2 | 11/2016 | de Rijk |
| 9,499,594 B2 | 11/2016 | Schuch et al. |
| 9,504,688 B2 | 11/2016 | Ginsburg et al. |
| 9,504,739 B2 | 11/2016 | Berkes et al. |
| 9,505,735 B2 | 11/2016 | McLellan et al. |
| 9,511,125 B2 | 12/2016 | Fallon et al. |
| 9,517,985 B2 | 12/2016 | Basham et al. |
| 9,518,013 B2 | 12/2016 | Li et al. |
| 9,521,845 B2 | 12/2016 | Sieber et al. |
| 9,526,738 B2 | 12/2016 | Stasko et al. |
| 9,526,766 B2 | 12/2016 | Hakansson et al. |
| 9,532,572 B2 | 1/2017 | von Maltzahn et al. |
| 9,532,573 B2 | 1/2017 | von Maltzahn et al. |
| 9,533,033 B2 | 1/2017 | Bakaletz et al. |
| 9,539,233 B2 | 1/2017 | Ohtake et al. |
| 9,539,367 B2 | 1/2017 | Britigan et al. |
| 9,539,373 B2 | 1/2017 | Jones et al. |
| 9,540,471 B2 | 1/2017 | Hrabie et al. |
| 9,550,005 B2 | 1/2017 | Lin et al. |
| 9,551,013 B2 | 1/2017 | Razavi-Shirazi et al. |
| 9,554,971 B2 | 1/2017 | Xu et al. |
| 9,556,109 B1 | 1/2017 | Caran et al. |
| 9,556,223 B2 | 1/2017 | Stensen et al. |
| 9,561,168 B2 | 2/2017 | Schaeffer-Korbylo et al. |
| 9,562,085 B2 | 2/2017 | Nibbering et al. |
| 9,562,241 B2 | 2/2017 | Burk et al. |
| 9,562,251 B2 | 2/2017 | Kishore et al. |
| 9,562,254 B2 | 2/2017 | Potnis et al. |
| 9,565,857 B2 | 2/2017 | Raad et al. |
| 9,566,247 B2 | 2/2017 | Koo et al. |
| 9,566,341 B1 | 2/2017 | Stinchcomb et al. |
| 9,566,372 B2 | 2/2017 | Handa et al. |
| 9,573,908 B2 | 2/2017 | Bassler et al. |
| 9,574,185 B2 | 2/2017 | Yim et al. |
| 9,574,189 B2 | 2/2017 | Franch et al. |
| 9,580,720 B2 | 2/2017 | Schaffer et al. |
| 9,580,739 B2 | 2/2017 | Godfrin |
| 9,586,871 B2 | 3/2017 | Sabin |
| 9,587,231 B2 | 3/2017 | Hom et al. |
| 9,587,256 B2 | 3/2017 | Adams et al. |
| 9,591,852 B2 | 3/2017 | Mordas et al. |
| 9,592,299 B2 | 3/2017 | Sershen et al. |
| 9,592,324 B2 | 3/2017 | Herweck et al. |
| 9,593,095 B2 | 3/2017 | Seed et al. |
| 9,597,407 B2 | 3/2017 | Eckert et al. |
| 9,598,706 B2 | 3/2017 | Keasling et al. |
| 9,603,859 B2 | 3/2017 | Genberg et al. |
| 9,603,877 B2 | 3/2017 | Chang et al. |
| 9,603,878 B2 | 3/2017 | Berry et al. |
| 9,603,977 B2 | 3/2017 | Ghigo et al. |
| 9,603,979 B2 | 3/2017 | Ghigo et al. |
| 9,605,281 B2 | 3/2017 | Bazzana et al. |
| 9,609,861 B2 | 4/2017 | Liu et al. |
| 9,610,307 B2 | 4/2017 | Berry et al. |
| 9,611,491 B2 | 4/2017 | Sherman et al. |
| 9,612,246 B2 | 4/2017 | Bruce et al. |
| 9,617,176 B2 | 4/2017 | Cuero Rengifo et al. |
| 9,618,520 B2 | 4/2017 | Bergo |
| 9,622,476 B2 | 4/2017 | Coady et al. |
| 9,622,481 B2 | 4/2017 | Gawande et al. |
| 9,622,485 B2 | 4/2017 | von Maltzahn et al. |
| 9,624,191 B2 | 4/2017 | Fevre et al. |
| 9,631,100 B2 | 4/2017 | Reches |
| 9,631,215 B2 | 4/2017 | Houghton-Larsen et al. |
| 9,637,729 B2 | 5/2017 | Prakash et al. |
| 9,637,746 B2 | 5/2017 | Klein-Marcuschamer |
| 9,642,829 B2 | 5/2017 | Seneviratne et al. |
| 9,644,194 B2 | 5/2017 | Yim et al. |
| 9,648,876 B2 | 5/2017 | Jackson et al. |
| 9,657,132 B2 | 5/2017 | Hanson et al. |
| 9,662,372 B2 | 5/2017 | Bochner et al. |
| 9,663,759 B2 | 5/2017 | Bhalla et al. |
| 9,669,001 B2 | 6/2017 | Bowler et al. |
| 9,669,041 B2 | 6/2017 | Stasko et al. |
| 9,669,089 B2 | 6/2017 | Thess et al. |
| 9,675,077 B2 | 6/2017 | Parsons |
| 9,675,736 B2 | 6/2017 | Burgess et al. |
| 9,682,023 B2 | 6/2017 | Ratcliff et al. |
| 9,682,908 B2 | 6/2017 | Zaher |
| 9,683,197 B2 | 6/2017 | Aizenberg et al. |
| 9,687,452 B2 | 6/2017 | Fallon et al. |
| 9,687,670 B2 | 6/2017 | Dacey, Jr. et al. |
| 9,688,653 B2 | 6/2017 | Seed et al. |
| 9,688,977 B2 | 6/2017 | Blake et al. |
| 9,689,006 B2 | 6/2017 | Burk et al. |
| 9,694,114 B2 | 7/2017 | Lucchino et al. |
| 9,700,058 B2 | 7/2017 | Zlotkin |
| 9,700,519 B2 | 7/2017 | Zicari et al. |

(56) References Cited

U.S. PATENT DOCUMENTS

| | | |
|---|---|---|
| 9,700,650 B2 | 7/2017 | Gong et al. |
| 9,700,676 B2 | 7/2017 | Anderson et al. |
| 9,700,677 B2 | 7/2017 | Anderson et al. |
| 9,700,710 B2 | 7/2017 | Anderson et al. |
| 9,701,992 B2 | 7/2017 | Maertens et al. |
| 9,706,778 B2 | 7/2017 | Berkes et al. |
| 9,707,207 B2 | 7/2017 | Finegold |
| 9,707,348 B2 | 7/2017 | Anderson et al. |
| 9,707,350 B2 | 7/2017 | Anderson et al. |
| 9,708,640 B2 | 7/2017 | Wu et al. |
| 9,713,631 B2 | 7/2017 | Berkes et al. |
| 9,713,652 B2 | 7/2017 | Schoenfisch et al. |
| 9,716,287 B2 | 7/2017 | Reguera et al. |
| 9,717,251 B2 | 8/2017 | Sabin |
| 9,717,688 B2 | 8/2017 | Finnie et al. |
| 9,717,765 B2 | 8/2017 | Berkes et al. |
| 9,718,739 B2 | 8/2017 | Sabin |
| 9,723,833 B2 | 8/2017 | Kolari et al. |
| 9,723,837 B2 | 8/2017 | Melander et al. |
| 9,723,843 B2 | 8/2017 | Olson et al. |
| 9,724,353 B2 | 8/2017 | Chandorkar et al. |
| 9,732,124 B2 | 8/2017 | Zlotkin |
| 9,737,561 B2 | 8/2017 | Stasko et al. |
| 9,737,571 B2 | 8/2017 | Zlotkin et al. |
| 9,737,591 B2 | 8/2017 | Olmstead |
| 9,738,689 B2 | 8/2017 | Kwong et al. |
| 9,738,693 B2 | 8/2017 | Telford et al. |
| 9,738,870 B2 | 8/2017 | Whitlock et al. |
| 9,744,130 B2 | 8/2017 | Lipp et al. |
| 9,744,141 B2 | 8/2017 | Ortac et al. |
| 9,744,221 B2 | 8/2017 | Kaleko et al. |
| 9,744,247 B2 | 8/2017 | Ventosa Rull et al. |
| 9,744,270 B2 | 8/2017 | Boluk et al. |
| 9,751,851 B2 | 9/2017 | Bassler et al. |
| 9,752,200 B2 | 9/2017 | Rey et al. |
| 9,757,397 B2 | 9/2017 | Kougoulos et al. |
| 9,764,069 B2 | 9/2017 | Roth et al. |
| 9,765,324 B2 | 9/2017 | Corgie et al. |
| 9,770,170 B2 | 9/2017 | Shoemaker et al. |
| 9,770,418 B2 | 9/2017 | Rahimipour et al. |
| 9,771,622 B2 | 9/2017 | Rey et al. |
| 9,777,050 B2 | 10/2017 | Zlotkin et al. |
| 9,782,358 B2 | 10/2017 | Kataoka et al. |
| 9,782,388 B2 | 10/2017 | Shaw et al. |
| 9,782,423 B2 | 10/2017 | O'Neil et al. |
| 9,788,539 B2 | 10/2017 | Liu et al. |
| 9,789,005 B2 | 10/2017 | Tennican et al. |
| 9,789,194 B2 | 10/2017 | Devore et al. |
| 9,789,439 B2 | 10/2017 | Siller et al. |
| 9,790,254 B2 | 10/2017 | Marco et al. |
| 9,790,484 B2 | 10/2017 | Wackett et al. |
| 9,795,762 B2 | 10/2017 | Bouchard et al. |
| 9,801,982 B2 | 10/2017 | Herweck et al. |
| 9,808,496 B2 | 11/2017 | Luc et al. |
| 9,814,719 B2 | 11/2017 | Sun et al. |
| 9,815,794 B2 | 11/2017 | Melander et al. |
| 9,815,880 B2 | 11/2017 | Scheer et al. |
| 9,828,625 B2 | 11/2017 | Koeris et al. |
| 9,833,528 B2 | 12/2017 | Alarcon et al. |
| 9,834,744 B2 | 12/2017 | Ludwig et al. |
| 9,839,219 B2 | 12/2017 | Looper et al. |
| 9,840,533 B2 | 12/2017 | Patel et al. |
| 9,840,538 B2 | 12/2017 | Telford et al. |
| 9,845,342 B2 | 12/2017 | Thompson et al. |
| 9,845,474 B2 | 12/2017 | Silverman et al. |
| 9,848,600 B2 | 12/2017 | Mordas et al. |
| 9,849,182 B2 | 12/2017 | McInroy et al. |
| 9,850,289 B2 | 12/2017 | Thompson et al. |
| 9,850,322 B2 | 12/2017 | Schoenfisch et al. |
| 9,854,799 B2 | 1/2018 | Blank et al. |
| 9,854,807 B2 | 1/2018 | Sabin |
| 9,855,211 B2 | 1/2018 | Doxey et al. |
| 9,856,225 B2 | 1/2018 | Huigens, III et al. |
| 9,861,701 B2 | 1/2018 | Sershen et al. |
| 9,861,723 B2 | 1/2018 | Hanson et al. |
| 9,862,837 B2 | 1/2018 | Reches |
| 9,867,906 B2 | 1/2018 | Matheny |
| 9,872,491 B2 | 1/2018 | Gambogi et al. |
| 9,872,893 B2 | 1/2018 | Nelson |
| 9,872,906 B2 | 1/2018 | Terracciano et al. |
| 9,872,917 B2 | 1/2018 | Tang et al. |
| 9,877,483 B2 | 1/2018 | Neas et al. |
| 9,877,983 B2 | 1/2018 | Onsoyen et al. |
| 9,885,064 B2 | 2/2018 | Burk et al. |
| 9,889,077 B2 | 2/2018 | Schaeffer-Korbylo et al. |
| 9,890,401 B2 | 2/2018 | Hu et al. |
| 9,890,407 B2 | 2/2018 | Zimmer et al. |
| 9,895,427 B2 | 2/2018 | Fallon et al. |
| 9,895,469 B2 | 2/2018 | Schultz et al. |
| 9,907,584 B2 | 3/2018 | Mangiardi |
| 9,907,755 B2 | 3/2018 | Kabadi et al. |
| 9,909,143 B2 | 3/2018 | Schmidt-Dannert et al. |
| 9,910,040 B2 | 3/2018 | Stein et al. |
| 9,914,750 B2 | 3/2018 | Gorr |
| 9,914,947 B2 | 3/2018 | Yu et al. |
| 9,918,473 B2 | 3/2018 | Melander et al. |
| 9,919,012 B2 | 3/2018 | Berkes et al. |
| 9,919,072 B2 | 3/2018 | Stasko et al. |
| 9,919,079 B2 | 3/2018 | Matheny |
| 9,920,324 B2 | 3/2018 | Vanden-Broucke et al. |
| 9,925,253 B2 | 3/2018 | Emery et al. |
| 9,925,295 B2 | 3/2018 | McEntire et al. |
| 9,926,526 B2 | 3/2018 | Newman et al. |
| 9,931,300 B2 | 4/2018 | Bilgili et al. |
| 9,931,302 B2 | 4/2018 | Fallon et al. |
| 9,931,381 B2 | 4/2018 | Olmstead |
| 9,931,433 B2 | 4/2018 | Deschepper et al. |
| 9,932,484 B2 | 4/2018 | Aizenberg et al. |
| 9,937,104 B2 | 4/2018 | Xu et al. |
| 9,943,581 B2 | 4/2018 | Emery et al. |
| 9,944,954 B2 | 4/2018 | Bhalla et al. |
| 9,950,052 B2 | 4/2018 | Emery et al. |
| 9,951,179 B2 | 4/2018 | Fevre et al. |
| 9,951,355 B2 | 4/2018 | Burgard et al. |
| 9,956,319 B2 | 5/2018 | Mansouri et al. |
| 9,956,322 B2 | 5/2018 | Pichler-Wilhelm et al. |
| 9,957,540 B2 | 5/2018 | Mikkelsen et al. |
| 9,961,886 B2 | 5/2018 | Ala'Aldeen et al. |
| 9,962,623 B2 | 5/2018 | Zaher et al. |
| 9,968,663 B2 | 5/2018 | Godfrin et al. |
| 9,970,000 B2 | 5/2018 | Kaehr et al. |
| 9,975,857 B2 | 5/2018 | Melander et al. |
| 9,981,026 B2 | 5/2018 | Emery et al. |
| 9,987,343 B2 | 6/2018 | Bakaletz et al. |
| 9,993,533 B2 | 6/2018 | Pellico |
| 2001/0044483 A1 | 11/2001 | Symes et al. |
| 2002/0002277 A1 | 1/2002 | Maliszewski et al. |
| 2002/0034757 A1 | 3/2002 | Cubicciotti |
| 2002/0045582 A1 | 4/2002 | Margolin et al. |
| 2002/0058027 A1 | 5/2002 | Nelson et al. |
| 2002/0066702 A1 | 6/2002 | Liu |
| 2002/0094367 A1 | 7/2002 | Fuglsang et al. |
| 2002/0102697 A1 | 8/2002 | Koffas et al. |
| 2002/0106511 A1 | 8/2002 | Callisen |
| 2002/0123077 A1 | 9/2002 | O'Toole et al. |
| 2003/0045441 A1 | 3/2003 | Hsu et al. |
| 2003/0059449 A1 | 3/2003 | Hsu et al. |
| 2003/0060378 A1 | 3/2003 | Hsu et al. |
| 2003/0062263 A1 | 4/2003 | Stanford et al. |
| 2003/0065292 A1 | 4/2003 | Darouiche et al. |
| 2003/0079758 A1 | 5/2003 | Siegel et al. |
| 2003/0082238 A1 | 5/2003 | Babich et al. |
| 2003/0091641 A1 | 5/2003 | Tiller et al. |
| 2003/0099602 A1 | 5/2003 | Levin et al. |
| 2003/0103912 A1 | 6/2003 | Levin et al. |
| 2003/0105072 A1 | 6/2003 | Degenhardt et al. |
| 2003/0108564 A1 | 6/2003 | Brown et al. |
| 2003/0111420 A1 | 6/2003 | Dresty, Jr. et al. |
| 2003/0121868 A1 | 7/2003 | Barak |
| 2003/0134783 A1 | 7/2003 | Harshey et al. |
| 2003/0148494 A1 | 8/2003 | Koffas et al. |
| 2003/0158344 A1 | 8/2003 | Rodriques et al. |
| 2003/0162284 A1 | 8/2003 | Dordick et al. |
| 2003/0162293 A1 | 8/2003 | Chu et al. |

(56) References Cited

U.S. PATENT DOCUMENTS

| | | |
|---|---|---|
| 2003/0166171 A1 | 9/2003 | Koffas et al. |
| 2003/0171348 A1 | 9/2003 | Mitchell et al. |
| 2003/0175239 A1 | 9/2003 | Margolin et al. |
| 2003/0178044 A1 | 9/2003 | Brown et al. |
| 2003/0195184 A1 | 10/2003 | Mitchell et al. |
| 2003/0219491 A1 | 11/2003 | Chang et al. |
| 2004/0033549 A1 | 2/2004 | Greenberg et al. |
| 2004/0061841 A1 | 4/2004 | Black et al. |
| 2004/0076681 A1 | 4/2004 | Dennis et al. |
| 2004/0088116 A1 | 5/2004 | Khalil et al. |
| 2004/0110738 A1 | 6/2004 | Gillis et al. |
| 2004/0116371 A1 | 6/2004 | Romeo et al. |
| 2004/0116845 A1 | 6/2004 | Darouiche et al. |
| 2004/0121926 A1 | 6/2004 | Waits et al. |
| 2004/0129112 A1 | 7/2004 | Gillis et al. |
| 2004/0131698 A1 | 7/2004 | Gillis et al. |
| 2004/0135684 A1 | 7/2004 | Steinthal et al. |
| 2004/0147427 A1 | 7/2004 | Waits et al. |
| 2004/0149577 A1 | 8/2004 | Kumar et al. |
| 2004/0156883 A1 | 8/2004 | Brown et al. |
| 2004/0156884 A1 | 8/2004 | Brown et al. |
| 2004/0171020 A1 | 9/2004 | Ulrich et al. |
| 2004/0175429 A1 | 9/2004 | Alavattam et al. |
| 2004/0175731 A1 | 9/2004 | Pier et al. |
| 2004/0176312 A1 | 9/2004 | Gillis |
| 2004/0191329 A1 | 9/2004 | Burrell et al. |
| 2004/0198629 A1 | 10/2004 | Raehse et al. |
| 2004/0204915 A1 | 10/2004 | Steinthal et al. |
| 2004/0241205 A1 | 12/2004 | Babich et al. |
| 2004/0248276 A1 | 12/2004 | Candas et al. |
| 2004/0249082 A1 | 12/2004 | Zhang et al. |
| 2004/0254545 A1 | 12/2004 | Rider et al. |
| 2004/0265835 A1 | 12/2004 | Lemaster et al. |
| 2005/0003725 A1 | 1/2005 | Hill et al. |
| 2005/0013836 A1 | 1/2005 | Raad |
| 2005/0032093 A1 | 2/2005 | Romeo et al. |
| 2005/0037374 A1 | 2/2005 | Melker et al. |
| 2005/0038498 A1 | 2/2005 | Dubrow et al. |
| 2005/0049181 A1 | 3/2005 | Madhyastha |
| 2005/0053954 A1 | 3/2005 | Brennan et al. |
| 2005/0061737 A1 | 3/2005 | Linden et al. |
| 2005/0064019 A1 | 3/2005 | Hill et al. |
| 2005/0089890 A1 | 4/2005 | Cubicciotti |
| 2005/0118198 A1 | 6/2005 | Pier et al. |
| 2005/0123529 A1 | 6/2005 | O'Loughlin et al. |
| 2005/0123552 A1 | 6/2005 | Hook et al. |
| 2005/0130845 A1 | 6/2005 | Freeman et al. |
| 2005/0143286 A1 | 6/2005 | Singh et al. |
| 2005/0143386 A1 | 6/2005 | Mitchell et al. |
| 2005/0147719 A1 | 7/2005 | Hill et al. |
| 2005/0150762 A1 | 7/2005 | Butters et al. |
| 2005/0150763 A1 | 7/2005 | Butters et al. |
| 2005/0153934 A1 | 7/2005 | Schuchman et al. |
| 2005/0155861 A1 | 7/2005 | Guzman |
| 2005/0158263 A1 | 7/2005 | Rioux et al. |
| 2005/0158335 A1 | 7/2005 | Bakaletz et al. |
| 2005/0163714 A1 | 7/2005 | Sukhishvili et al. |
| 2005/0176610 A1 | 8/2005 | Hsu et al. |
| 2005/0181464 A1 | 8/2005 | Edwards et al. |
| 2005/0202424 A1 | 9/2005 | Ausubel et al. |
| 2005/0203636 A1 | 9/2005 | McFetridge |
| 2005/0221072 A1 | 10/2005 | Dubrow et al. |
| 2005/0233950 A1 | 10/2005 | Madhyastha |
| 2005/0245418 A1 | 11/2005 | Fregonese et al. |
| 2005/0245419 A1 | 11/2005 | Guzmann et al. |
| 2005/0249695 A1 | 11/2005 | Tiller et al. |
| 2005/0255543 A1 | 11/2005 | Just et al. |
| 2005/0260739 A1 | 11/2005 | Rosen et al. |
| 2006/0001865 A1 | 1/2006 | Bellalou et al. |
| 2006/0018945 A1 | 1/2006 | Britigan et al. |
| 2006/0034782 A1 | 2/2006 | Brown et al. |
| 2006/0036194 A1 | 2/2006 | Schultheiss et al. |
| 2006/0045904 A1 | 3/2006 | Aronson |
| 2006/0062775 A1 | 3/2006 | Tadros |
| 2006/0067951 A1 | 3/2006 | Cvitkovitch et al. |
| 2006/0078531 A1 | 4/2006 | Sota |
| 2006/0078532 A1 | 4/2006 | Omoigui |
| 2006/0078533 A1 | 4/2006 | Omoigui |
| 2006/0079454 A1 | 4/2006 | Reches et al. |
| 2006/0110456 A1 | 5/2006 | Teo et al. |
| 2006/0110494 A1 | 5/2006 | Dusterhoft et al. |
| 2006/0110747 A1 | 5/2006 | Ramseier et al. |
| 2006/0120916 A1 | 6/2006 | Kolari et al. |
| 2006/0134745 A1 | 6/2006 | Klaenhammer et al. |
| 2006/0138058 A1 | 6/2006 | Barak |
| 2006/0159671 A1 | 7/2006 | Fischetti |
| 2006/0160134 A1 | 7/2006 | Melker et al. |
| 2006/0162014 A1 | 7/2006 | Jaffe |
| 2006/0165648 A1 | 7/2006 | Degenhardt et al. |
| 2006/0177384 A1 | 8/2006 | Brown |
| 2006/0180552 A1 | 8/2006 | Downs |
| 2006/0199768 A1 | 9/2006 | Singleton |
| 2006/0204738 A1 | 9/2006 | Dubrow et al. |
| 2006/0224103 A1 | 10/2006 | Rontal |
| 2006/0243297 A1 | 11/2006 | Brown |
| 2006/0252719 A1 | 11/2006 | Akerley et al. |
| 2006/0257961 A1 | 11/2006 | Apicella et al. |
| 2006/0269998 A1 | 11/2006 | Buck et al. |
| 2006/0275294 A1 | 12/2006 | Omoigui |
| 2006/0275905 A1 | 12/2006 | Bae et al. |
| 2006/0280799 A1 | 12/2006 | Tirelli et al. |
| 2006/0282173 A1 | 12/2006 | McFetridge |
| 2007/0001156 A1 | 1/2007 | Toreki |
| 2007/0003607 A1 | 1/2007 | Awasthi et al. |
| 2007/0009566 A1 | 1/2007 | Balaban |
| 2007/0010856 A1 | 1/2007 | Cohen |
| 2007/0015718 A1 | 1/2007 | Mitchell et al. |
| 2007/0020309 A1 | 1/2007 | Alberte et al. |
| 2007/0048855 A1 | 3/2007 | Gamez et al. |
| 2007/0053849 A1 | 3/2007 | Doyle et al. |
| 2007/0059779 A1 | 3/2007 | Dordick et al. |
| 2007/0062884 A1 | 3/2007 | Sun et al. |
| 2007/0083156 A1 | 4/2007 | Muto et al. |
| 2007/0092533 A1 | 4/2007 | Brown et al. |
| 2007/0098651 A1 | 5/2007 | Leung |
| 2007/0098674 A1 | 5/2007 | Bukshpan et al. |
| 2007/0098745 A1 | 5/2007 | Bruno |
| 2007/0098807 A1 | 5/2007 | Babich et al. |
| 2007/0106232 A1 | 5/2007 | Rider, II et al. |
| 2007/0109535 A1 | 5/2007 | Maier et al. |
| 2007/0110748 A1 | 5/2007 | Hook et al. |
| 2007/0111329 A1 | 5/2007 | Guzman |
| 2007/0116671 A1 | 5/2007 | Prakash et al. |
| 2007/0116750 A1 | 5/2007 | Wolcott |
| 2007/0116798 A1 | 5/2007 | Brown et al. |
| 2007/0128714 A1 | 6/2007 | Guzman |
| 2007/0134649 A1 | 6/2007 | Kolari et al. |
| 2007/0134812 A1 | 6/2007 | Guzman |
| 2007/0141096 A1 | 6/2007 | Van Lengerich |
| 2007/0141217 A1 | 6/2007 | Benedict et al. |
| 2007/0148136 A1 | 6/2007 | Whitlock |
| 2007/0154466 A1 | 7/2007 | Weber et al. |
| 2007/0166285 A1 | 7/2007 | O'Loughlin et al. |
| 2007/0190090 A1 | 8/2007 | Brown |
| 2007/0202770 A1 | 8/2007 | Penalva |
| 2007/0207095 A1 | 9/2007 | Davies |
| 2007/0212311 A1 | 9/2007 | Burne et al. |
| 2007/0219269 A1 | 9/2007 | Candas et al. |
| 2007/0224161 A1 | 9/2007 | Sun et al. |
| 2007/0224273 A1 | 9/2007 | Xu et al. |
| 2007/0231406 A1 | 10/2007 | Bucalo et al. |
| 2007/0232167 A1 | 10/2007 | Hill et al. |
| 2007/0239073 A1 | 10/2007 | Schaden et al. |
| 2007/0244059 A1 | 10/2007 | Karaolis |
| 2007/0258894 A1 | 11/2007 | Melker et al. |
| 2007/0258913 A1 | 11/2007 | Rossel |
| 2007/0275894 A1 | 11/2007 | Stanton et al. |
| 2007/0282247 A1 | 12/2007 | Desai et al. |
| 2007/0296099 A1 | 12/2007 | Larsen et al. |
| 2008/0009434 A1 | 1/2008 | Reches et al. |
| 2008/0014247 A1 | 1/2008 | Lu et al. |
| 2008/0014278 A1 | 1/2008 | Lu et al. |
| 2008/0014286 A1 | 1/2008 | Gillis et al. |
| 2008/0014622 A1 | 1/2008 | Federspiel et al. |

(56) References Cited

U.S. PATENT DOCUMENTS

| | | |
|---|---|---|
| 2008/0027044 A1 | 1/2008 | Lewis et al. |
| 2008/0044491 A1 | 2/2008 | Lyczak et al. |
| 2008/0050452 A1 | 2/2008 | Chen et al. |
| 2008/0075730 A1 | 3/2008 | Storey et al. |
| 2008/0085282 A1 | 4/2008 | Yu et al. |
| 2008/0085866 A1 | 4/2008 | Greenberg et al. |
| 2008/0090276 A1 | 4/2008 | Van Dyck et al. |
| 2008/0107707 A1 | 5/2008 | Lawson et al. |
| 2008/0109017 A1 | 5/2008 | Herweck et al. |
| 2008/0113001 A1 | 5/2008 | Herweck et al. |
| 2008/0113416 A1 | 5/2008 | Filippov et al. |
| 2008/0115945 A1 | 5/2008 | Lau et al. |
| 2008/0118573 A1 | 5/2008 | Harrison et al. |
| 2008/0138634 A1 | 6/2008 | Morris et al. |
| 2008/0145477 A1 | 6/2008 | Shen et al. |
| 2008/0181923 A1 | 7/2008 | Melander et al. |
| 2008/0187487 A1 | 8/2008 | Larsen et al. |
| 2008/0201884 A1 | 8/2008 | Vazquez et al. |
| 2008/0206183 A1 | 8/2008 | Commeyras et al. |
| 2008/0206305 A1 | 8/2008 | Herweck et al. |
| 2008/0220487 A1 | 9/2008 | Zeikus et al. |
| 2008/0223722 A1 | 9/2008 | Guzman |
| 2008/0226623 A1 | 9/2008 | Margolin et al. |
| 2008/0233615 A1 | 9/2008 | Klaenhammer et al. |
| 2008/0248087 A1 | 10/2008 | Hill et al. |
| 2008/0261267 A1 | 10/2008 | Ferrer et al. |
| 2008/0264860 A1 | 10/2008 | Smith et al. |
| 2008/0268189 A1 | 10/2008 | Sun et al. |
| 2008/0274092 A1 | 11/2008 | Godfrin et al. |
| 2008/0283242 A1 | 11/2008 | Ekstrand et al. |
| 2008/0286847 A1 | 11/2008 | Jaffe |
| 2008/0293607 A1 | 11/2008 | Jones et al. |
| 2008/0300303 A1 | 12/2008 | Huse et al. |
| 2008/0302669 A1 | 12/2008 | Peters et al. |
| 2008/0311177 A1 | 12/2008 | Hammond et al. |
| 2008/0317815 A1 | 12/2008 | Davies |
| 2008/0318268 A1 | 12/2008 | Olson et al. |
| 2008/0318269 A1 | 12/2008 | Olson et al. |
| 2009/0033930 A1 | 2/2009 | Maier et al. |
| 2009/0035381 A1 | 2/2009 | Stankus et al. |
| 2009/0041774 A1 | 2/2009 | Bakaletz et al. |
| 2009/0048324 A1 | 2/2009 | Jaffe |
| 2009/0050575 A1 | 2/2009 | Barak |
| 2009/0069406 A1 | 3/2009 | Lee et al. |
| 2009/0074825 A1 | 3/2009 | Sun et al. |
| 2009/0075845 A1 | 3/2009 | Abad et al. |
| 2009/0088329 A1 | 4/2009 | Brennan et al. |
| 2009/0099529 A1 | 4/2009 | Anderson et al. |
| 2009/0099533 A1 | 4/2009 | Montelaro et al. |
| 2009/0110741 A1 | 4/2009 | Simone et al. |
| 2009/0112186 A1 | 4/2009 | Adams |
| 2009/0123553 A1 | 5/2009 | Reches et al. |
| 2009/0133810 A1 | 5/2009 | Penalva |
| 2009/0142429 A1 | 6/2009 | Belas et al. |
| 2009/0143230 A1 | 6/2009 | Melander et al. |
| 2009/0155215 A1 | 6/2009 | Collins et al. |
| 2009/0162337 A1 | 6/2009 | Gross et al. |
| 2009/0162643 A1 | 6/2009 | Dubrow et al. |
| 2009/0163964 A1 | 6/2009 | Boyden et al. |
| 2009/0163965 A1 | 6/2009 | Boyden et al. |
| 2009/0163977 A1 | 6/2009 | Boyden et al. |
| 2009/0169677 A1 | 7/2009 | Wittorff et al. |
| 2009/0171263 A1 | 7/2009 | Boyden et al. |
| 2009/0177139 A1 | 7/2009 | Boyden et al. |
| 2009/0177254 A1 | 7/2009 | Boyden et al. |
| 2009/0181106 A1 | 7/2009 | Gordon et al. |
| 2009/0181874 A1 | 7/2009 | Souter et al. |
| 2009/0186077 A1 | 7/2009 | Ying et al. |
| 2009/0202516 A1 | 8/2009 | Olmstead |
| 2009/0202836 A1 | 8/2009 | Bancroft et al. |
| 2009/0214603 A1 | 8/2009 | Demuth et al. |
| 2009/0214628 A1 | 8/2009 | de Rijk |
| 2009/0221704 A1 | 9/2009 | Aksela et al. |
| 2009/0238923 A1 | 9/2009 | Shaw et al. |
| 2009/0239266 A1 | 9/2009 | Gulevich et al. |
| 2009/0246318 A1 | 10/2009 | Johansen |
| 2009/0260632 A1 | 10/2009 | Abnousi et al. |
| 2009/0263438 A1 | 10/2009 | Melander et al. |
| 2009/0264300 A1 | 10/2009 | Franch et al. |
| 2009/0269323 A1 | 10/2009 | Luk et al. |
| 2009/0270475 A1 | 10/2009 | Melander et al. |
| 2009/0275088 A1 | 11/2009 | Templeton |
| 2009/0275122 A1 | 11/2009 | Templeton |
| 2009/0288826 A1 | 11/2009 | Gray |
| 2009/0297592 A1 | 12/2009 | Sakuraba et al. |
| 2009/0301885 A1 | 12/2009 | Guzman |
| 2009/0318382 A1 | 12/2009 | Ghigo et al. |
| 2009/0324476 A1 | 12/2009 | Watkins et al. |
| 2009/0324574 A1 | 12/2009 | Mathur et al. |
| 2009/0324638 A1 | 12/2009 | Dattwyler et al. |
| 2010/0009419 A1 | 1/2010 | Burk et al. |
| 2010/0011456 A1 | 1/2010 | Mathur et al. |
| 2010/0015245 A1 | 1/2010 | Harrison et al. |
| 2010/0015635 A1 | 1/2010 | Canters et al. |
| 2010/0016767 A1 | 1/2010 | Jones et al. |
| 2010/0021587 A1 | 1/2010 | Chang et al. |
| 2010/0028396 A1 | 2/2010 | Ward et al. |
| 2010/0034799 A1 | 2/2010 | Landry et al. |
| 2010/0048446 A1 | 2/2010 | Cascao-Pereira et al. |
| 2010/0055086 A1 | 3/2010 | Raad |
| 2010/0056415 A1 | 3/2010 | Rong et al. |
| 2010/0056474 A1 | 3/2010 | Baker et al. |
| 2010/0059433 A1 | 3/2010 | Freeman et al. |
| 2010/0063099 A1 | 3/2010 | Levin et al. |
| 2010/0064393 A1 | 3/2010 | Berka et al. |
| 2010/0074933 A1 | 3/2010 | Prakash et al. |
| 2010/0075404 A1 | 3/2010 | Templeton |
| 2010/0081849 A1 | 4/2010 | Masters et al. |
| 2010/0086983 A1 | 4/2010 | Gellett et al. |
| 2010/0096340 A1 | 4/2010 | Barak |
| 2010/0111854 A1 | 5/2010 | Boyden et al. |
| 2010/0111855 A1 | 5/2010 | Boyden et al. |
| 2010/0114348 A1 | 5/2010 | Boyden et al. |
| 2010/0119557 A1 | 5/2010 | Boyden et al. |
| 2010/0121466 A1 | 5/2010 | Boyden et al. |
| 2010/0124554 A1 | 5/2010 | Newman et al. |
| 2010/0125046 A1 | 5/2010 | Denome et al. |
| 2010/0129297 A1 | 5/2010 | Vezin |
| 2010/0129466 A1 | 5/2010 | Marques et al. |
| 2010/0130443 A1 | 5/2010 | Baker et al. |
| 2010/0130450 A1 | 5/2010 | Lewis et al. |
| 2010/0133114 A1 | 6/2010 | Bukshpan et al. |
| 2010/0136072 A1 | 6/2010 | Haidar et al. |
| 2010/0136143 A1 | 6/2010 | Bukshpan |
| 2010/0137193 A1 | 6/2010 | Baker et al. |
| 2010/0143243 A1 | 6/2010 | Boyden et al. |
| 2010/0145412 A1 | 6/2010 | Boyden et al. |
| 2010/0152101 A1 | 6/2010 | Reid |
| 2010/0152651 A1 | 6/2010 | Boyden et al. |
| 2010/0152880 A1 | 6/2010 | Boyden et al. |
| 2010/0158966 A1 | 6/2010 | Reid et al. |
| 2010/0158967 A1 | 6/2010 | Reid et al. |
| 2010/0159508 A1 | 6/2010 | Yang et al. |
| 2010/0163576 A1 | 7/2010 | Boyden et al. |
| 2010/0168203 A1 | 7/2010 | Levin et al. |
| 2010/0168900 A1 | 7/2010 | Boyden et al. |
| 2010/0173366 A1 | 7/2010 | Rhimi et al. |
| 2010/0174346 A1 | 7/2010 | Boyden et al. |
| 2010/0178268 A1 | 7/2010 | Bukshpan et al. |
| 2010/0183738 A1 | 7/2010 | Kramer et al. |
| 2010/0185174 A1 | 7/2010 | Boyden et al. |
| 2010/0187728 A1 | 7/2010 | Boyden et al. |
| 2010/0189706 A1 | 7/2010 | Chang et al. |
| 2010/0189707 A1 | 7/2010 | Barnett |
| 2010/0190724 A1 | 7/2010 | Dorian et al. |
| 2010/0192986 A1 | 8/2010 | Brooker et al. |
| 2010/0196986 A1 | 8/2010 | Laursen et al. |
| 2010/0197548 A1 | 8/2010 | Bettiol et al. |
| 2010/0197549 A1 | 8/2010 | Bettiol et al. |
| 2010/0197550 A1 | 8/2010 | Bettiol et al. |
| 2010/0197551 A1 | 8/2010 | Bettiol et al. |
| 2010/0197552 A1 | 8/2010 | Koyuncu et al. |
| 2010/0197553 A1 | 8/2010 | Barnabas et al. |
| 2010/0197554 A1 | 8/2010 | Koyuncu et al. |

(56) References Cited

U.S. PATENT DOCUMENTS

| | | |
|---|---|---|
| 2010/0197593 A1 | 8/2010 | Stanton et al. |
| 2010/0204153 A1 | 8/2010 | Bevec |
| 2010/0204161 A1 | 8/2010 | Huse et al. |
| 2010/0209362 A1 | 8/2010 | Dashper et al. |
| 2010/0209968 A1 | 8/2010 | Akers et al. |
| 2010/0210745 A1 | 8/2010 | McDaniel et al. |
| 2010/0213062 A1 | 8/2010 | Guzman |
| 2010/0221198 A1 | 9/2010 | Ratcliff et al. |
| 2010/0233101 A1 | 9/2010 | Grootveld et al. |
| 2010/0234792 A1 | 9/2010 | Dacey, Jr. et al. |
| 2010/0234793 A1 | 9/2010 | Dacey, Jr. et al. |
| 2010/0239559 A1 | 9/2010 | Freedman et al. |
| 2010/0240017 A1 | 9/2010 | Dacey, Jr. et al. |
| 2010/0240116 A1 | 9/2010 | Ostaszewski et al. |
| 2010/0241048 A1 | 9/2010 | Dacey, Jr. et al. |
| 2010/0241049 A1 | 9/2010 | Dacey, Jr. et al. |
| 2010/0241050 A1 | 9/2010 | Dacey, Jr. et al. |
| 2010/0241051 A1 | 9/2010 | Dacey, Jr. et al. |
| 2010/0241052 A1 | 9/2010 | Dacey, Jr. et al. |
| 2010/0241053 A1 | 9/2010 | Dacey, Jr. et al. |
| 2010/0241054 A1 | 9/2010 | Dacey, Jr. et al. |
| 2010/0241055 A1 | 9/2010 | Dacey, Jr. et al. |
| 2010/0247374 A1 | 9/2010 | Pellet |
| 2010/0249692 A1 | 9/2010 | Dacey, Jr. et al. |
| 2010/0254967 A1 | 10/2010 | Frank et al. |
| 2010/0255100 A1 | 10/2010 | Margolin et al. |
| 2010/0255178 A1 | 10/2010 | Leander et al. |
| 2010/0258116 A1 | 10/2010 | Federspiel et al. |
| 2010/0260857 A1 | 10/2010 | Fallon et al. |
| 2010/0261618 A1 | 10/2010 | Escaich et al. |
| 2010/0266716 A1 | 10/2010 | Olson et al. |
| 2010/0267594 A1 | 10/2010 | Rana et al. |
| 2010/0272768 A1 | 10/2010 | Bukshpan et al. |
| 2010/0273991 A1 | 10/2010 | Luk et al. |
| 2010/0279178 A1 | 11/2010 | Barkeloo et al. |
| 2010/0279349 A1 | 11/2010 | Klaenhammer et al. |
| 2010/0286198 A1 | 11/2010 | Bringmann et al. |
| 2010/0290996 A1 | 11/2010 | Nickerson et al. |
| 2010/0291162 A1 | 11/2010 | Haas |
| 2010/0291828 A1 | 11/2010 | Reches et al. |
| 2010/0292135 A1 | 11/2010 | Singleton |
| 2010/0292629 A1 | 11/2010 | Dacey, Jr. et al. |
| 2010/0297179 A1 | 11/2010 | Dashper et al. |
| 2010/0297737 A1 | 11/2010 | Barkeloo et al. |
| 2010/0298208 A1 | 11/2010 | Cohen et al. |
| 2010/0305062 A1 | 12/2010 | Onsoyen et al. |
| 2010/0307744 A1 | 12/2010 | Cochet et al. |
| 2010/0310612 A1 | 12/2010 | DuFour et al. |
| 2010/0316571 A1 | 12/2010 | Simone et al. |
| 2010/0316620 A1 | 12/2010 | Bourgeaux et al. |
| 2010/0316643 A1 | 12/2010 | Eckert et al. |
| 2010/0322903 A1 | 12/2010 | Collins et al. |
| 2011/0003001 A1 | 1/2011 | Baker |
| 2011/0008402 A1 | 1/2011 | Madhyastha et al. |
| 2011/0008786 A1 | 1/2011 | Yu et al. |
| 2011/0015088 A1 | 1/2011 | Dordick et al. |
| 2011/0020924 A1 | 1/2011 | Templeton |
| 2011/0027252 A1 | 2/2011 | Aehle et al. |
| 2011/0027384 A1 | 2/2011 | Kishen et al. |
| 2011/0029076 A1 | 2/2011 | Paletta et al. |
| 2011/0033520 A1 | 2/2011 | Mather et al. |
| 2011/0033882 A1 | 2/2011 | Aehle et al. |
| 2011/0039164 A1 | 2/2011 | Akers et al. |
| 2011/0039314 A1 | 2/2011 | Holz et al. |
| 2011/0039751 A1 | 2/2011 | Souter et al. |
| 2011/0039761 A1 | 2/2011 | Eckert et al. |
| 2011/0039762 A1 | 2/2011 | Eckert et al. |
| 2011/0039763 A1 | 2/2011 | Eckert et al. |
| 2011/0045517 A1 | 2/2011 | Derringer et al. |
| 2011/0046041 A1 | 2/2011 | Neesham-Grenon et al. |
| 2011/0046142 A1 | 2/2011 | Lewis et al. |
| 2011/0050431 A1 | 3/2011 | Hood et al. |
| 2011/0052664 A1 | 3/2011 | Tennican et al. |
| 2011/0053173 A1 | 3/2011 | Hood et al. |
| 2011/0053236 A1 | 3/2011 | Walmsley et al. |
| 2011/0053283 A1 | 3/2011 | Hood et al. |
| 2011/0054938 A1 | 3/2011 | Hood et al. |
| 2011/0056693 A1 | 3/2011 | Wallace |
| 2011/0059062 A1 | 3/2011 | Pellico |
| 2011/0070376 A1 | 3/2011 | Wales et al. |
| 2011/0077192 A1 | 3/2011 | Giuliani et al. |
| 2011/0081394 A1 | 4/2011 | Zussman et al. |
| 2011/0086101 A1 | 4/2011 | Madhyastha et al. |
| 2011/0086812 A1 | 4/2011 | Schramm |
| 2011/0098323 A1 | 4/2011 | Opperman et al. |
| 2011/0104179 A1 | 5/2011 | Reynolds et al. |
| 2011/0104766 A1 | 5/2011 | Leonetti et al. |
| 2011/0105376 A1 | 5/2011 | England et al. |
| 2011/0111425 A1 | 5/2011 | Rylatt et al. |
| 2011/0117067 A1 | 5/2011 | Esteghlalian et al. |
| 2011/0117071 A1 | 5/2011 | Barrett et al. |
| 2011/0117158 A1 | 5/2011 | Melander et al. |
| 2011/0117160 A1 | 5/2011 | Bruno |
| 2011/0117623 A1 | 5/2011 | Walker et al. |
| 2011/0119774 A1 | 5/2011 | Zlotkin et al. |
| 2011/0123462 A1 | 5/2011 | Mordas et al. |
| 2011/0124522 A1 | 5/2011 | Marrs et al. |
| 2011/0124716 A1 | 5/2011 | Passineau |
| 2011/0129454 A1 | 6/2011 | Olmstead |
| 2011/0135621 A1 | 6/2011 | Miller et al. |
| 2011/0144566 A1 | 6/2011 | Dacey, Jr. et al. |
| 2011/0150765 A1 | 6/2011 | Boyden et al. |
| 2011/0150819 A1 | 6/2011 | Melander et al. |
| 2011/0150841 A1 | 6/2011 | Mougous |
| 2011/0150889 A1 | 6/2011 | Bakaletz et al. |
| 2011/0152176 A1 | 6/2011 | Horswill |
| 2011/0152750 A1 | 6/2011 | Dacey, Jr. et al. |
| 2011/0152751 A1 | 6/2011 | Dacey, Jr. et al. |
| 2011/0152752 A1 | 6/2011 | Dacey, Jr. et al. |
| 2011/0152789 A1 | 6/2011 | Dacey, Jr. et al. |
| 2011/0152790 A1 | 6/2011 | Dacey, Jr. et al. |
| 2011/0152978 A1 | 6/2011 | Dacey, Jr. et al. |
| 2011/0160643 A1 | 6/2011 | Dacey, Jr. et al. |
| 2011/0160644 A1 | 6/2011 | Dacey, Jr. et al. |
| 2011/0160681 A1 | 6/2011 | Dacey, Jr. et al. |
| 2011/0165261 A1 | 7/2011 | Derby et al. |
| 2011/0171123 A1 | 7/2011 | Shirtliff et al. |
| 2011/0171189 A1 | 7/2011 | Olmstead |
| 2011/0171195 A1 | 7/2011 | Abraham et al. |
| 2011/0172704 A1 | 7/2011 | Bleier et al. |
| 2011/0177048 A1 | 7/2011 | Olmstead |
| 2011/0177049 A1 | 7/2011 | Olmstead |
| 2011/0177050 A1 | 7/2011 | Olmstead |
| 2011/0177111 A1 | 7/2011 | Shirtliff et al. |
| 2011/0177564 A1 | 7/2011 | Stephanopoulos |
| 2011/0177982 A1 | 7/2011 | Ekstrand et al. |
| 2011/0178182 A1 | 7/2011 | Gabbai |
| 2011/0182873 A1 | 7/2011 | Olmstead |
| 2011/0182874 A1 | 7/2011 | Olmstead |
| 2011/0183388 A1 | 7/2011 | Sabirova et al. |
| 2011/0189743 A1 | 8/2011 | Yoshikuni et al. |
| 2011/0190234 A1 | 8/2011 | Nathan et al. |
| 2011/0196027 A1 | 8/2011 | Sieber et al. |
| 2011/0201692 A1 | 8/2011 | Raad |
| 2011/0201984 A1 | 8/2011 | Dubrow et al. |
| 2011/0207816 A1 | 8/2011 | Jaffe |
| 2011/0208021 A1 | 8/2011 | Goodall et al. |
| 2011/0208023 A1 | 8/2011 | Goodall et al. |
| 2011/0208026 A1 | 8/2011 | Goodall et al. |
| 2011/0217363 A1 | 9/2011 | Chen |
| 2011/0217368 A1 | 9/2011 | Prakash et al. |
| 2011/0217544 A1 | 9/2011 | Young et al. |
| 2011/0217553 A1 | 9/2011 | Warner et al. |
| 2011/0229565 A1 | 9/2011 | Karp et al. |
| 2011/0229580 A1 | 9/2011 | Srivastava et al. |
| 2011/0229586 A1 | 9/2011 | Barak |
| 2011/0236453 A1 | 9/2011 | Stensen et al. |
| 2011/0250290 A1 | 10/2011 | Marques et al. |
| 2011/0256181 A1 | 10/2011 | Curtiss et al. |
| 2011/0256187 A1 | 10/2011 | Hortelano et al. |
| 2011/0262511 A1 | 10/2011 | Love et al. |
| 2011/0266724 A1 | 11/2011 | Hulseman et al. |
| 2011/0269029 A1 | 11/2011 | Gellett et al. |
| 2011/0274730 A1 | 11/2011 | Ceri et al. |

(56) References Cited

U.S. PATENT DOCUMENTS

| | | |
|---|---|---|
| 2011/0275518 A1 | 11/2011 | Marques et al. |
| 2011/0275912 A1 | 11/2011 | Boyden et al. |
| 2011/0280853 A1 | 11/2011 | Fallon et al. |
| 2011/0280854 A1 | 11/2011 | Fallon et al. |
| 2011/0280920 A1 | 11/2011 | Zlotkin et al. |
| 2011/0281921 A1 | 11/2011 | Srebnik et al. |
| 2011/0290799 A1 | 12/2011 | Anderson et al. |
| 2011/0294668 A1 | 12/2011 | Melander et al. |
| 2011/0295088 A1 | 12/2011 | Boyden et al. |
| 2011/0295089 A1 | 12/2011 | Boyden et al. |
| 2011/0295090 A1 | 12/2011 | Boyden et al. |
| 2011/0296543 A1 | 12/2011 | Chang et al. |
| 2011/0300201 A1 | 12/2011 | Becker et al. |
| 2011/0300623 A1 | 12/2011 | Gellett et al. |
| 2011/0301076 A1 | 12/2011 | Stensen et al. |
| 2011/0305872 A1 | 12/2011 | Li et al. |
| 2011/0305881 A1 | 12/2011 | Schultz et al. |
| 2011/0305895 A1 | 12/2011 | Roth et al. |
| 2011/0305898 A1 | 12/2011 | Zhang et al. |
| 2011/0305909 A1 | 12/2011 | Weaver et al. |
| 2011/0306699 A1 | 12/2011 | Whang et al. |
| 2011/0311499 A1 | 12/2011 | Mougous et al. |
| 2011/0311647 A1 | 12/2011 | Gawande et al. |
| 2011/0319808 A1 | 12/2011 | Bowler et al. |
| 2012/0010187 A1 | 1/2012 | Hoffman et al. |
| 2012/0010481 A1 | 1/2012 | Goodall et al. |
| 2012/0015870 A1 | 1/2012 | Zlotkin |
| 2012/0016217 A1 | 1/2012 | Srivastava et al. |
| 2012/0020896 A1 | 1/2012 | Trivedi et al. |
| 2012/0021964 A1 | 1/2012 | Barbe et al. |
| 2012/0027771 A1 | 2/2012 | Cantor |
| 2012/0027848 A1 | 2/2012 | Fallon et al. |
| 2012/0028872 A1 | 2/2012 | Perez-Prat Vinuesa et al. |
| 2012/0028873 A1 | 2/2012 | Perez-Prat Vinuesa et al. |
| 2012/0030779 A1 | 2/2012 | Benjamin et al. |
| 2012/0039945 A1 | 2/2012 | Scott et al. |
| 2012/0040030 A1 | 2/2012 | Zinreich et al. |
| 2012/0040429 A1 | 2/2012 | Federspiel et al. |
| 2012/0041285 A1 | 2/2012 | Goodall et al. |
| 2012/0041286 A1 | 2/2012 | Goodall et al. |
| 2012/0041287 A1 | 2/2012 | Goodall et al. |
| 2012/0045817 A1 | 2/2012 | Estell et al. |
| 2012/0052052 A1 | 3/2012 | Xi et al. |
| 2012/0058076 A1 | 3/2012 | Widgerow |
| 2012/0058167 A1 | 3/2012 | Widgerow |
| 2012/0058169 A1 | 3/2012 | Olson et al. |
| 2012/0058933 A1 | 3/2012 | Gorr |
| 2012/0063276 A1 | 3/2012 | Reches et al. |
| 2012/0066851 A1 | 3/2012 | Gonzales et al. |
| 2012/0071379 A1 | 3/2012 | Gonzales et al. |
| 2012/0071383 A1 | 3/2012 | Perez-Prat Vinuesa et al. |
| 2012/0077736 A1 | 3/2012 | Oh et al. |
| 2012/0087887 A1 | 4/2012 | Hen et al. |
| 2012/0088671 A1 | 4/2012 | Quave et al. |
| 2012/0093869 A1 | 4/2012 | Klumpp et al. |
| 2012/0094007 A1 | 4/2012 | Fehr et al. |
| 2012/0107258 A1 | 5/2012 | Kuhn et al. |
| 2012/0109073 A1 | 5/2012 | Anderson et al. |
| 2012/0115196 A1 | 5/2012 | Yukawa et al. |
| 2012/0121570 A1 | 5/2012 | Godfrin |
| 2012/0122729 A1 | 5/2012 | Musken et al. |
| 2012/0128599 A1 | 5/2012 | Schaeffer-Korbylo et al. |
| 2012/0129794 A1 | 5/2012 | Dowd et al. |
| 2012/0134951 A1 | 5/2012 | Stasko et al. |
| 2012/0135060 A1 | 5/2012 | Bukshpan et al. |
| 2012/0135092 A1 | 5/2012 | Singleton |
| 2012/0135925 A1 | 5/2012 | Meijler et al. |
| 2012/0136323 A1 | 5/2012 | Stasko et al. |
| 2012/0142583 A1 | 6/2012 | Singh et al. |
| 2012/0143027 A1 | 6/2012 | Phillips et al. |
| 2012/0149631 A1 | 6/2012 | Delatour et al. |
| 2012/0150119 A1 | 6/2012 | Schaeffer et al. |
| 2012/0152149 A1 | 6/2012 | Mijolovic et al. |
| 2012/0156645 A1 | 6/2012 | Jacoby |
| 2012/0157548 A1 | 6/2012 | Mijolovic et al. |
| 2012/0160779 A1 | 6/2012 | Barak |
| 2012/0171129 A1 | 7/2012 | Melander et al. |
| 2012/0178971 A1 | 7/2012 | Khan et al. |
| 2012/0189682 A1 | 7/2012 | O'Neil et al. |
| 2012/0189703 A1 | 7/2012 | Fallon et al. |
| 2012/0201869 A1 | 8/2012 | Burzell |
| 2012/0209090 A1 | 8/2012 | Goodall et al. |
| 2012/0213697 A1 | 8/2012 | Friedman et al. |
| 2012/0213835 A1 | 8/2012 | Neas et al. |
| 2012/0219638 A1 | 8/2012 | Olson et al. |
| 2012/0220025 A1 | 8/2012 | Gellett et al. |
| 2012/0225098 A1 | 9/2012 | Kaplan et al. |
| 2012/0231537 A1 | 9/2012 | Templeton et al. |
| 2012/0237987 A1 | 9/2012 | Curtiss et al. |
| 2012/0237990 A1 | 9/2012 | Burk et al. |
| 2012/0238644 A1 | 9/2012 | Gong et al. |
| 2012/0240961 A1 | 9/2012 | Denome et al. |
| 2012/0244126 A1 | 9/2012 | Collins et al. |
| 2012/0245531 A9 | 9/2012 | Anderson et al. |
| 2012/0252101 A1 | 10/2012 | Chang et al. |
| 2012/0258089 A1 | 10/2012 | Madhyastha et al. |
| 2012/0258141 A9 | 10/2012 | Scott et al. |
| 2012/0258149 A1 | 10/2012 | Fallon et al. |
| 2012/0261256 A1 | 10/2012 | Chang et al. |
| 2012/0266329 A1 | 10/2012 | Mathur et al. |
| 2012/0270271 A1 | 10/2012 | Mougous |
| 2012/0270909 A1 | 10/2012 | Sokol et al. |
| 2012/0276145 A1 | 11/2012 | Webster et al. |
| 2012/0283174 A1 | 11/2012 | Reynolds et al. |
| 2012/0283693 A1 | 11/2012 | Anderson et al. |
| 2012/0288566 A1 | 11/2012 | Friedman et al. |
| 2012/0288571 A1 | 11/2012 | Tennican et al. |
| 2012/0294842 A1 | 11/2012 | Peter Liu et al. |
| 2012/0294900 A1 | 11/2012 | Sintim et al. |
| 2012/0296284 A1 | 11/2012 | Anderson et al. |
| 2012/0301408 A1 | 11/2012 | Baker et al. |
| 2012/0301433 A1 | 11/2012 | Lu et al. |
| 2012/0308632 A1 | 12/2012 | Ghigo et al. |
| 2012/0315260 A1 | 12/2012 | Ivanova et al. |
| 2012/0318515 A1 | 12/2012 | Cawiezel et al. |
| 2012/0321566 A1 | 12/2012 | Liu et al. |
| 2012/0321601 A1 | 12/2012 | Liu et al. |
| 2012/0321647 A1 | 12/2012 | Breaker et al. |
| 2012/0321722 A1 | 12/2012 | Liu et al. |
| 2012/0322713 A1 | 12/2012 | Perez-Prat Vinuesa et al. |
| 2012/0328577 A1 | 12/2012 | Melander et al. |
| 2012/0328671 A1 | 12/2012 | O'Neil et al. |
| 2012/0328683 A1 | 12/2012 | Song et al. |
| 2012/0328684 A1 | 12/2012 | Shanks et al. |
| 2012/0328708 A1 | 12/2012 | Van Der Waal et al. |
| 2012/0328713 A1 | 12/2012 | Olson et al. |
| 2012/0329675 A1 | 12/2012 | Olson et al. |
| 2012/0329746 A1 | 12/2012 | Reid |
| 2012/0329751 A1 | 12/2012 | Baker et al. |
| 2013/0005029 A1 | 1/2013 | Cascao-Pereira et al. |
| 2013/0006194 A1 | 1/2013 | Anderson et al. |
| 2013/0011332 A1 | 1/2013 | Boyden et al. |
| 2013/0017148 A1 | 1/2013 | Larsen et al. |
| 2013/0017610 A1 | 1/2013 | Roberts et al. |
| 2013/0022578 A1 | 1/2013 | Newman et al. |
| 2013/0028847 A1 | 1/2013 | Dashper et al. |
| 2013/0028848 A1 | 1/2013 | Sokol et al. |
| 2013/0029894 A1 | 1/2013 | Bettiol et al. |
| 2013/0029895 A1 | 1/2013 | Bettiol et al. |
| 2013/0029981 A1 | 1/2013 | De Keersmaecker et al. |
| 2013/0034907 A1 | 2/2013 | Collins et al. |
| 2013/0039959 A1 | 2/2013 | Sokol et al. |
| 2013/0039978 A1 | 2/2013 | Schwarz et al. |
| 2013/0045182 A1 | 2/2013 | Gong et al. |
| 2013/0045482 A1 | 2/2013 | Claverie et al. |
| 2013/0052250 A1 | 2/2013 | Burgess et al. |
| 2013/0058983 A1 | 3/2013 | Baker |
| 2013/0059096 A1 | 3/2013 | Losick et al. |
| 2013/0059113 A1 | 3/2013 | Hatton et al. |
| 2013/0059929 A1 | 3/2013 | Koehler et al. |
| 2013/0067669 A1 | 3/2013 | Gonzales et al. |
| 2013/0071439 A1 | 3/2013 | Losick et al. |
| 2013/0084312 A1 | 4/2013 | Caputo et al. |
| 2013/0095184 A1 | 4/2013 | Lyczak et al. |

(56) References Cited

U.S. PATENT DOCUMENTS

| | | |
|---|---|---|
| 2013/0095533 A1 | 4/2013 | Sherman et al. |
| 2013/0101678 A1 | 4/2013 | Gordon et al. |
| 2013/0101963 A1 | 4/2013 | Sun |
| 2013/0102679 A1 | 4/2013 | Holden |
| 2013/0108618 A1 | 5/2013 | Zhu |
| 2013/0108708 A1 | 5/2013 | Xu |
| 2013/0108737 A1 | 5/2013 | Van Lengerich |
| 2013/0109063 A1 | 5/2013 | Kiryukhin et al. |
| 2013/0109781 A1 | 5/2013 | Lake et al. |
| 2013/0110162 A1 | 5/2013 | Cohen |
| 2013/0113129 A1 | 5/2013 | Fallon et al. |
| 2013/0123225 A1 | 5/2013 | Melander et al. |
| 2013/0123308 A1 | 5/2013 | Ghannoum et al. |
| 2013/0123309 A1 | 5/2013 | Ghannoum et al. |
| 2013/0123319 A1 | 5/2013 | Bryan |
| 2013/0129768 A1 | 5/2013 | Reynolds |
| 2013/0129795 A1 | 5/2013 | Melander et al. |
| 2013/0129800 A1 | 5/2013 | Giammona et al. |
| 2013/0130305 A1 | 5/2013 | Prusty Rao |
| 2013/0130334 A1 | 5/2013 | Reguera et al. |
| 2013/0131575 A1 | 5/2013 | Dacey, Jr. et al. |
| 2013/0131701 A1 | 5/2013 | Komlos et al. |
| 2013/0133102 A1 | 5/2013 | Kerfeld et al. |
| 2013/0136728 A1 | 5/2013 | Landry et al. |
| 2013/0136730 A1 | 5/2013 | Frank et al. |
| 2013/0136782 A1 | 5/2013 | Blackwell et al. |
| 2013/0142803 A1 | 6/2013 | Bakaletz et al. |
| 2013/0142855 A1 | 6/2013 | Gross et al. |
| 2013/0149357 A1 | 6/2013 | Remon et al. |
| 2013/0149542 A1 | 6/2013 | Chen et al. |
| 2013/0150451 A1 | 6/2013 | Salamone et al. |
| 2013/0156737 A1 | 6/2013 | Mougous et al. |
| 2013/0158127 A1 | 6/2013 | Sergere |
| 2013/0158488 A1 | 6/2013 | Weaver et al. |
| 2013/0158517 A1 | 6/2013 | Bouchard et al. |
| 2013/0158518 A1 | 6/2013 | Li et al. |
| 2013/0164228 A1 | 6/2013 | Jaracz et al. |
| 2013/0164363 A1 | 6/2013 | Raad |
| 2013/0164850 A1 | 6/2013 | Sourdive |
| 2013/0165595 A1 | 6/2013 | Reid et al. |
| 2013/0171210 A1 | 7/2013 | Baker |
| 2013/0171224 A1 | 7/2013 | Percival et al. |
| 2013/0171228 A1 | 7/2013 | Morris |
| 2013/0172187 A1 | 7/2013 | Melander et al. |
| 2013/0177504 A1 | 7/2013 | Macoviak |
| 2013/0183379 A1 | 7/2013 | Devore et al. |
| 2013/0183435 A1 | 7/2013 | Sun et al. |
| 2013/0183743 A1 | 7/2013 | Barkeloo et al. |
| 2013/0184835 A1 | 7/2013 | Ferrari et al. |
| 2013/0190227 A1 | 7/2013 | Baker et al. |
| 2013/0190699 A1 | 7/2013 | Stephan |
| 2013/0195948 A1 | 8/2013 | Laursen et al. |
| 2013/0195985 A1 | 8/2013 | Lepelletier et al. |
| 2013/0196365 A1 | 8/2013 | Reddy et al. |
| 2013/0197100 A1 | 8/2013 | Neto Pereira Cerize et al. |
| 2013/0197455 A1 | 8/2013 | Zhang |
| 2013/0202641 A1 | 8/2013 | Dashper et al. |
| 2013/0207042 A1 | 8/2013 | Joven Pineda et al. |
| 2013/0210118 A1 | 8/2013 | Templeton |
| 2013/0210708 A1 | 8/2013 | Singh et al. |
| 2013/0210761 A1 | 8/2013 | Baker et al. |
| 2013/0213398 A1 | 8/2013 | Lipp et al. |
| 2013/0216637 A1 | 8/2013 | Davies |
| 2013/0219643 A1 | 8/2013 | Gonzales et al. |
| 2013/0220331 A1 | 8/2013 | Yahiaoui et al. |
| 2013/0224172 A1 | 8/2013 | Fallon et al. |
| 2013/0224258 A1 | 8/2013 | Baker |
| 2013/0224260 A1 | 8/2013 | Ward et al. |
| 2013/0224828 A1 | 8/2013 | Finn et al. |
| 2013/0225675 A1 | 8/2013 | Kubala et al. |
| 2013/0231302 A1 | 9/2013 | Raad et al. |
| 2013/0243828 A1 | 9/2013 | Lipp et al. |
| 2013/0244301 A1 | 9/2013 | Walker et al. |
| 2013/0251786 A1 | 9/2013 | Li et al. |
| 2013/0252818 A1 | 9/2013 | Lovejoy et al. |
| 2013/0252945 A1 | 9/2013 | Lovejoy et al. |
| 2013/0266522 A1 | 10/2013 | Fagon et al. |
| 2013/0266629 A1 | 10/2013 | Arvidsson |
| 2013/0267471 A1 | 10/2013 | Ghatnekar et al. |
| 2013/0281324 A1 | 10/2013 | Gouliaev et al. |
| 2013/0281503 A1 | 10/2013 | Melander et al. |
| 2013/0284637 A1 | 10/2013 | Chou et al. |
| 2013/0287860 A1 | 10/2013 | Tennican et al. |
| 2013/0287861 A1 | 10/2013 | Tennican et al. |
| 2013/0296222 A1 | 11/2013 | Castex-Rizzi et al. |
| 2013/0302390 A1 | 11/2013 | Davies |
| 2013/0309219 A1 | 11/2013 | Ratner et al. |
| 2013/0309752 A1 | 11/2013 | Templeton |
| 2013/0310346 A1 | 11/2013 | Zurawski |
| 2013/0315874 A1 | 11/2013 | Melander et al. |
| 2013/0315967 A1 | 11/2013 | Bruno |
| 2013/0323223 A1 | 12/2013 | Fallon et al. |
| 2013/0330335 A1 | 12/2013 | Bremel et al. |
| 2013/0330386 A1 | 12/2013 | Whitten et al. |
| 2013/0330388 A1 | 12/2013 | Sekhar |
| 2013/0331424 A1 | 12/2013 | Weibel et al. |
| 2013/0337088 A1 | 12/2013 | Widgerow |
| 2013/0337518 A1 | 12/2013 | Razavi-Shirazi et al. |
| 2013/0337530 A1 | 12/2013 | Lake et al. |
| 2013/0344542 A1 | 12/2013 | Cascao-Pereira et al. |
| 2013/0345099 A1 | 12/2013 | Rana et al. |
| 2013/0345261 A1 | 12/2013 | Waters et al. |
| 2014/0004578 A1 | 1/2014 | Bond et al. |
| 2014/0005236 A1 | 1/2014 | Sokol et al. |
| 2014/0005605 A1 | 1/2014 | Samade et al. |
| 2014/0020138 A1 | 1/2014 | Ragunath et al. |
| 2014/0023691 A1 | 1/2014 | Melander et al. |
| 2014/0024064 A1 | 1/2014 | Burlew et al. |
| 2014/0027655 A1 | 1/2014 | Reches et al. |
| 2014/0037688 A1 | 2/2014 | Berkes et al. |
| 2014/0037967 A1 | 2/2014 | Roth et al. |
| 2014/0039143 A1 | 2/2014 | Vermeiren |
| 2014/0039195 A1 | 2/2014 | Luk et al. |
| 2014/0039357 A1 | 2/2014 | Boyden et al. |
| 2014/0045241 A1 | 2/2014 | Bucholz et al. |
| 2014/0046181 A1 | 2/2014 | Benchimol et al. |
| 2014/0051139 A1 | 2/2014 | Lokken |
| 2014/0056951 A1 | 2/2014 | Losick et al. |
| 2014/0056952 A1 | 2/2014 | Losick et al. |
| 2014/0056993 A1 | 2/2014 | Parsons |
| 2014/0057324 A1 | 2/2014 | Aehle et al. |
| 2014/0065200 A1 | 3/2014 | Schoenfisch et al. |
| 2014/0072525 A1 | 3/2014 | Adams, Jr. et al. |
| 2014/0073021 A1 | 3/2014 | Bazzana et al. |
| 2014/0073560 A1 | 3/2014 | Shanks et al. |
| 2014/0073690 A1 | 3/2014 | Meijler et al. |
| 2014/0073820 A1 | 3/2014 | Bazzana et al. |
| 2014/0079741 A1 | 3/2014 | Bink et al. |
| 2014/0079808 A1 | 3/2014 | Melander et al. |
| 2014/0080119 A1 | 3/2014 | Stein et al. |
| 2014/0082769 A1 | 3/2014 | Schymkowitz et al. |
| 2014/0083324 A1 | 3/2014 | Wales et al. |
| 2014/0086988 A1 | 3/2014 | Margolin et al. |
| 2014/0093888 A1 | 4/2014 | Templeton |
| 2014/0099629 A1 | 4/2014 | Liu et al. |
| 2014/0105986 A1 | 4/2014 | Doxey et al. |
| 2014/0106419 A1 | 4/2014 | Bazzana et al. |
| 2014/0106420 A1 | 4/2014 | Razavi-Shirazi et al. |
| 2014/0107071 A1 | 4/2014 | Kougoulos et al. |
| 2014/0113000 A1 | 4/2014 | Neas et al. |
| 2014/0120052 A1 | 5/2014 | Hen et al. |
| 2014/0127184 A1 | 5/2014 | Fallon et al. |
| 2014/0127273 A1 | 5/2014 | Melander et al. |
| 2014/0127305 A1 | 5/2014 | Ortac et al. |
| 2014/0127778 A1 | 5/2014 | Kim et al. |
| 2014/0128313 A1 | 5/2014 | Bishop et al. |
| 2014/0128399 A1 | 5/2014 | Abraham et al. |
| 2014/0134204 A1 | 5/2014 | Bishop et al. |
| 2014/0142028 A1 | 5/2014 | Eckert et al. |
| 2014/0147481 A1 | 5/2014 | Gerwick et al. |
| 2014/0151042 A1 | 6/2014 | Faugerstrom et al. |
| 2014/0155318 A1 | 6/2014 | Zlotkin |
| 2014/0155478 A1 | 6/2014 | Seneviratne et al. |
| 2014/0161728 A1 | 6/2014 | Bowler et al. |

(56) References Cited

U.S. PATENT DOCUMENTS

| | | |
|---|---|---|
| 2014/0161772 A1 | 6/2014 | Collins et al. |
| 2014/0161845 A1 | 6/2014 | Demuth et al. |
| 2014/0162279 A1 | 6/2014 | Ramseier et al. |
| 2014/0162325 A1 | 6/2014 | Altman et al. |
| 2014/0163094 A1 | 6/2014 | Sieber et al. |
| 2014/0170238 A1 | 6/2014 | Cliff et al. |
| 2014/0171438 A1 | 6/2014 | Pan et al. |
| 2014/0172117 A1 | 6/2014 | Anzai et al. |
| 2014/0178496 A1 | 6/2014 | Macoviak et al. |
| 2014/0186318 A1 | 7/2014 | Ghannoum et al. |
| 2014/0186911 A1 | 7/2014 | Kruckeberg et al. |
| 2014/0187666 A1 | 7/2014 | Aizenberg et al. |
| 2014/0193489 A1 | 7/2014 | Rahimipour et al. |
| 2014/0193868 A1 | 7/2014 | Sabirova et al. |
| 2014/0194594 A1 | 7/2014 | Gorr |
| 2014/0200511 A1 | 7/2014 | Boyden et al. |
| 2014/0205546 A1 | 7/2014 | Macoviak |
| 2014/0205586 A1 | 7/2014 | Xi et al. |
| 2014/0205643 A1 | 7/2014 | Onsoyen et al. |
| 2014/0212454 A1 | 7/2014 | Pasmans et al. |
| 2014/0212828 A1 | 7/2014 | Falcone et al. |
| 2014/0219980 A1 | 8/2014 | Bax et al. |
| 2014/0220152 A1 | 8/2014 | Benjamin et al. |
| 2014/0221308 A1 | 8/2014 | Baker et al. |
| 2014/0221331 A1 | 8/2014 | Barraud et al. |
| 2014/0221610 A1 | 8/2014 | Zlotkin |
| 2014/0223602 A1 | 8/2014 | Chang et al. |
| 2014/0228327 A1 | 8/2014 | Raad |
| 2014/0234369 A1 | 8/2014 | Klumpp et al. |
| 2014/0234380 A1 | 8/2014 | Rayad et al. |
| 2014/0241997 A1 | 8/2014 | McInroy et al. |
| 2014/0242023 A1 | 8/2014 | Doxey et al. |
| 2014/0243725 A1 | 8/2014 | Tennican et al. |
| 2014/0255318 A1 | 9/2014 | Stasko et al. |
| 2014/0257482 A1 | 9/2014 | Ward et al. |
| 2014/0271763 A1 | 9/2014 | Burzell |
| 2014/0271777 A1 | 9/2014 | Quave et al. |
| 2014/0273129 A1 | 9/2014 | Bhalla et al. |
| 2014/0276253 A1 | 9/2014 | Varga et al. |
| 2014/0276254 A1 | 9/2014 | Varga et al. |
| 2014/0277301 A1 | 9/2014 | Varga et al. |
| 2014/0288007 A1 | 9/2014 | Dashper et al. |
| 2014/0288171 A1 | 9/2014 | Whang et al. |
| 2014/0294907 A1 | 10/2014 | Bruno |
| 2014/0295520 A1 | 10/2014 | Schmidt-Dannert et al. |
| 2014/0295523 A1 | 10/2014 | Steer et al. |
| 2014/0302113 A1 | 10/2014 | Zhang |
| 2014/0303408 A1 | 10/2014 | Zaher |
| 2014/0308217 A1 | 10/2014 | Schaeffer-Korbylo et al. |
| 2014/0308317 A1 | 10/2014 | Fan et al. |
| 2014/0308361 A1 | 10/2014 | Rayad et al. |
| 2014/0311889 A1 | 10/2014 | Zaher et al. |
| 2014/0322351 A1 | 10/2014 | Gawande et al. |
| 2014/0322362 A1 | 10/2014 | Frim et al. |
| 2014/0323330 A1 | 10/2014 | Bergo |
| 2014/0325709 A1 | 10/2014 | Plesch et al. |
| 2014/0328801 A1 | 11/2014 | Prentice et al. |
| 2014/0328887 A1 | 11/2014 | Olson et al. |
| 2014/0328890 A1 | 11/2014 | Olson et al. |
| 2014/0328895 A1 | 11/2014 | Friedman et al. |
| 2014/0328999 A1 | 11/2014 | Aizenberg et al. |
| 2014/0335144 A1 | 11/2014 | Ward et al. |
| 2014/0335148 A1 | 11/2014 | Tong et al. |
| 2014/0342954 A1 | 11/2014 | Ingber et al. |
| 2014/0348780 A1 | 11/2014 | Glasnapp |
| 2014/0348815 A1 | 11/2014 | Jeoh-Zicari et al. |
| 2014/0349389 A1 | 11/2014 | Templeton |
| 2014/0349917 A1 | 11/2014 | Eckert et al. |
| 2014/0350017 A1 | 11/2014 | Williams et al. |
| 2014/0357592 A1 | 12/2014 | O'Neil et al. |
| 2014/0367333 A1 | 12/2014 | Razavi-Shirazi et al. |
| 2014/0370078 A1 | 12/2014 | Gurtner et al. |
| 2014/0371171 A1 | 12/2014 | Souweine |
| 2014/0371194 A1 | 12/2014 | Seed et al. |
| 2015/0004595 A1 | 1/2015 | Koeris et al. |
| 2015/0004670 A1 | 1/2015 | Mueller et al. |
| 2015/0005228 A1 | 1/2015 | Yang et al. |
| 2015/0010453 A1 | 1/2015 | Gellett et al. |
| 2015/0010984 A1 | 1/2015 | Bhalla et al. |
| 2015/0011504 A1 | 1/2015 | Gong et al. |
| 2015/0018284 A1 | 1/2015 | Ghatnekar |
| 2015/0018330 A1 | 1/2015 | Hoffman et al. |
| 2015/0018774 A1 | 1/2015 | Anderson et al. |
| 2015/0024000 A1 | 1/2015 | Shirtliff et al. |
| 2015/0024017 A1 | 1/2015 | Bukshpan et al. |
| 2015/0024052 A1 | 1/2015 | Doxey |
| 2015/0026840 A1 | 1/2015 | Kerfeld et al. |
| 2015/0030641 A1 | 1/2015 | Anderson et al. |
| 2015/0031658 A1 | 1/2015 | Seed et al. |
| 2015/0031738 A1 | 1/2015 | Li et al. |
| 2015/0038512 A1 | 2/2015 | Looper et al. |
| 2015/0038705 A1 | 2/2015 | Williams et al. |
| 2015/0044147 A1 | 2/2015 | Rayad et al. |
| 2015/0044260 A1 | 2/2015 | Birkedal et al. |
| 2015/0045515 A1 | 2/2015 | Li et al. |
| 2015/0045535 A1 | 2/2015 | Berka et al. |
| 2015/0050704 A1 | 2/2015 | Sherman et al. |
| 2015/0050717 A1 | 2/2015 | Collins et al. |
| 2015/0056411 A1 | 2/2015 | Zhang et al. |
| 2015/0071894 A1 | 3/2015 | Godfrin |
| 2015/0071904 A1 | 3/2015 | Collins et al. |
| 2015/0080289 A1 | 3/2015 | Yang et al. |
| 2015/0080290 A1 | 3/2015 | Bevilacqua et al. |
| 2015/0086521 A1 | 3/2015 | Godfrin |
| 2015/0086561 A1 | 3/2015 | Kauvar et al. |
| 2015/0086599 A1 | 3/2015 | Hammond et al. |
| 2015/0086631 A1 | 3/2015 | Kishen et al. |
| 2015/0087573 A1 | 3/2015 | Estell et al. |
| 2015/0087582 A1 | 3/2015 | LoVetri et al. |
| 2015/0093413 A1 | 4/2015 | Thess et al. |
| 2015/0098910 A1 | 4/2015 | Mordas et al. |
| 2015/0099020 A1 | 4/2015 | Genin |
| 2015/0099289 A1 | 4/2015 | Bucholz et al. |
| 2015/0104492 A1 | 4/2015 | McDermott et al. |
| 2015/0104787 A1 | 4/2015 | Rey et al. |
| 2015/0110898 A1 | 4/2015 | Gordon et al. |
| 2015/0111813 A1 | 4/2015 | Schuch et al. |
| 2015/0118219 A1 | 4/2015 | Shi et al. |
| 2015/0118262 A1 | 4/2015 | Bakaletz et al. |
| 2015/0125901 A1 | 5/2015 | Razavi-Shirazi et al. |
| 2015/0126474 A1 | 5/2015 | Bassler et al. |
| 2015/0132352 A1 | 5/2015 | Sun et al. |
| 2015/0132843 A1 | 5/2015 | Templeton |
| 2015/0136130 A1 | 5/2015 | DeHaan et al. |
| 2015/0147308 A1 | 5/2015 | Fallon et al. |
| 2015/0147311 A1 | 5/2015 | De Silva et al. |
| 2015/0147365 A1 | 5/2015 | Edens et al. |
| 2015/0147775 A1 | 5/2015 | Fiacco et al. |
| 2015/0147786 A1 | 5/2015 | Clarkson et al. |
| 2015/0148286 A1 | 5/2015 | Hakansson et al. |
| 2015/0148612 A1 | 5/2015 | Schaeffer et al. |
| 2015/0150955 A1 | 6/2015 | Fallon et al. |
| 2015/0150959 A1 | 6/2015 | Watnick |
| 2015/0151248 A1 | 6/2015 | Siller et al. |
| 2015/0157542 A1 | 6/2015 | Schaeffer-Korbylo et al. |
| 2015/0159180 A1 | 6/2015 | Prabhune et al. |
| 2015/0165095 A1 | 6/2015 | Mansouri et al. |
| 2015/0166706 A1 | 6/2015 | Hrabie et al. |
| 2015/0166796 A1 | 6/2015 | Sun et al. |
| 2015/0166975 A1 | 6/2015 | Prakash et al. |
| 2015/0167024 A1 | 6/2015 | Dorri et al. |
| 2015/0167046 A1 | 6/2015 | Ramasubramanian et al. |
| 2015/0168403 A1 | 6/2015 | Rao |
| 2015/0173883 A1 | 6/2015 | Ingber et al. |
| 2015/0182667 A1 | 7/2015 | Guelcher et al. |
| 2015/0183746 A1 | 7/2015 | Melander et al. |
| 2015/0190447 A1 | 7/2015 | Luc et al. |
| 2015/0190530 A1 | 7/2015 | Ventosa Rull et al. |
| 2015/0191607 A1 | 7/2015 | McDaniel |
| 2015/0191681 A1 | 7/2015 | Gonzales et al. |
| 2015/0191715 A1 | 7/2015 | Razavi-Shirazi et al. |
| 2015/0197558 A1 | 7/2015 | Kauvar et al. |
| 2015/0197779 A1 | 7/2015 | Saville et al. |
| 2015/0203799 A1 | 7/2015 | Bettiol et al. |

(56) References Cited

U.S. PATENT DOCUMENTS

| | | |
|---|---|---|
| 2015/0209393 A1 | 7/2015 | Chang et al. |
| 2015/0211026 A1 | 7/2015 | Bazzana et al. |
| 2015/0216985 A1 | 8/2015 | Macoviak et al. |
| 2015/0224044 A1 | 8/2015 | Baker et al. |
| 2015/0224220 A1 | 8/2015 | Olson et al. |
| 2015/0225458 A1 | 8/2015 | Rapsch et al. |
| 2015/0225488 A1 | 8/2015 | Schoenfisch et al. |
| 2015/0231045 A1 | 8/2015 | Krohn et al. |
| 2015/0231287 A1 | 8/2015 | Lin et al. |
| 2015/0231589 A1 | 8/2015 | Arumugam et al. |
| 2015/0233001 A1 | 8/2015 | Reguera et al. |
| 2015/0237870 A1 | 8/2015 | Pei |
| 2015/0238543 A1 | 8/2015 | Rickard et al. |
| 2015/0240226 A1 | 8/2015 | Mathur et al. |
| 2015/0246104 A1 | 9/2015 | Fallon et al. |
| 2015/0246105 A1 | 9/2015 | Fallon et al. |
| 2015/0246995 A1 | 9/2015 | Hanson et al. |
| 2015/0250875 A1 | 9/2015 | Lipp et al. |
| 2015/0259389 A9 | 9/2015 | Berka et al. |
| 2015/0259390 A1 | 9/2015 | Zlotkin |
| 2015/0264932 A1 | 9/2015 | Coady et al. |
| 2015/0267225 A1 | 9/2015 | Bazzana et al. |
| 2015/0274639 A1 | 10/2015 | Williams et al. |
| 2015/0283208 A1 | 10/2015 | Ribbeck et al. |
| 2015/0283287 A1 | 10/2015 | Agarwal et al. |
| 2015/0284356 A1 | 10/2015 | McLellan et al. |
| 2015/0293092 A1 | 10/2015 | Webster et al. |
| 2015/0297478 A1 | 10/2015 | Ratcliff et al. |
| 2015/0297642 A1 | 10/2015 | Borody |
| 2015/0299298 A1 | 10/2015 | Kauvar et al. |
| 2015/0299345 A1 | 10/2015 | Xu et al. |
| 2015/0305330 A1 | 10/2015 | Alper |
| 2015/0314119 A1 | 11/2015 | Anderson et al. |
| 2015/0314120 A1 | 11/2015 | Gardner |
| 2015/0315253 A1 | 11/2015 | Zlotkin et al. |
| 2015/0322272 A1 | 11/2015 | Pokroy et al. |
| 2015/0327552 A1 | 11/2015 | Melander et al. |
| 2015/0332151 A1 | 11/2015 | Marculescu et al. |
| 2015/0335013 A1 | 11/2015 | Sabin |
| 2015/0335027 A1 | 11/2015 | Sabin |
| 2015/0335589 A1 | 11/2015 | Fallon et al. |
| 2015/0336855 A1 | 11/2015 | Sabin |
| 2015/0337351 A1 | 11/2015 | Metzger |
| 2015/0351383 A1 | 12/2015 | Kolari et al. |
| 2015/0351392 A1 | 12/2015 | Graber et al. |
| 2015/0366889 A1 | 12/2015 | Brynildsen et al. |
| 2015/0366890 A1 | 12/2015 | Collins et al. |
| 2015/0368480 A1 | 12/2015 | Reches |
| 2015/0374634 A1 | 12/2015 | Koo et al. |
| 2015/0374658 A1 | 12/2015 | Krohn et al. |
| 2015/0374720 A1 | 12/2015 | Genberg et al. |
| 2015/0374786 A1 | 12/2015 | Bochner et al. |
| 2015/0374798 A1 | 12/2015 | Labhasetwar et al. |
| 2015/0376096 A1 | 12/2015 | Anton et al. |
| 2015/0376594 A1 | 12/2015 | Walker et al. |
| 2016/0000064 A1 | 1/2016 | Liu et al. |
| 2016/0002131 A1 | 1/2016 | Glasspool et al. |
| 2016/0002132 A1 | 1/2016 | Zaher |
| 2016/0008275 A1 | 1/2016 | Doxey et al. |
| 2016/0009733 A1 | 1/2016 | Barraud et al. |
| 2016/0009860 A1 | 1/2016 | Fevre et al. |
| 2016/0010137 A1 | 1/2016 | Potnis et al. |
| 2016/0015030 A1 | 1/2016 | Vanlaer et al. |
| 2016/0015047 A1 | 1/2016 | Gawande et al. |
| 2016/0016870 A1 | 1/2016 | Basham et al. |
| 2016/0017303 A1 | 1/2016 | Cascao-Pereira et al. |
| 2016/0017304 A1 | 1/2016 | Cascao-Pereira et al. |
| 2016/0017305 A1 | 1/2016 | Cascao-Pereira et al. |
| 2016/0017382 A1 | 1/2016 | Burk et al. |
| 2016/0021882 A1 | 1/2016 | Wang et al. |
| 2016/0022564 A1 | 1/2016 | Townsend et al. |
| 2016/0022592 A1 | 1/2016 | Kabadi et al. |
| 2016/0022595 A1 | 1/2016 | Shikani et al. |
| 2016/0022598 A1 | 1/2016 | Ortac et al. |
| 2016/0022707 A1 | 1/2016 | Zhong et al. |
| 2016/0022730 A1 | 1/2016 | Baker et al. |
| 2016/0024187 A1 | 1/2016 | Zhu |
| 2016/0024551 A1 | 1/2016 | Hassett et al. |
| 2016/0030327 A1 | 2/2016 | Stein |
| 2016/0030532 A1 | 2/2016 | Godfrin et al. |
| 2016/0031941 A1 | 2/2016 | Eckert et al. |
| 2016/0031948 A1 | 2/2016 | Thompson et al. |
| 2016/0032329 A1 | 2/2016 | Leonetti et al. |
| 2016/0038572 A1 | 2/2016 | Nelson |
| 2016/0038608 A1 | 2/2016 | Mou et al. |
| 2016/0038650 A1 | 2/2016 | Griffith |
| 2016/0045576 A1 | 2/2016 | Fallon et al. |
| 2016/0051484 A1 | 2/2016 | Kataoka et al. |
| 2016/0051697 A1 | 2/2016 | Pope et al. |
| 2016/0058675 A1 | 3/2016 | Xu et al. |
| 2016/0058693 A1 | 3/2016 | Widgerow |
| 2016/0058772 A1 | 3/2016 | Baker |
| 2016/0058816 A1 | 3/2016 | Widgerow |
| 2016/0058834 A1 | 3/2016 | Ghatnekar |
| 2016/0058998 A1 | 3/2016 | Skiba et al. |
| 2016/0059009 A1 | 3/2016 | Skiba et al. |
| 2016/0066578 A1 | 3/2016 | Ala'Aldeen et al. |
| 2016/0067149 A1 | 3/2016 | Kishen |
| 2016/0068560 A1 | 3/2016 | Patel et al. |
| 2016/0073638 A1 | 3/2016 | Li et al. |
| 2016/0074345 A1 | 3/2016 | Holden |
| 2016/0075749 A1 | 3/2016 | Nibbering et al. |
| 2016/0075976 A1 | 3/2016 | Andersen et al. |
| 2016/0081343 A1 | 3/2016 | Coady et al. |
| 2016/0089481 A1 | 3/2016 | Arvidsson et al. |
| 2016/0096865 A1 | 4/2016 | Martinez et al. |
| 2016/0101058 A1 | 4/2016 | Bristol et al. |
| 2016/0106107 A1 | 4/2016 | Marques et al. |
| 2016/0106689 A1 | 4/2016 | O'Neil |
| 2016/0107126 A1 | 4/2016 | Cates |
| 2016/0108096 A1 | 4/2016 | Thompson et al. |
| 2016/0109401 A1 | 4/2016 | Wardell et al. |
| 2016/0120184 A1 | 5/2016 | Gedanken et al. |
| 2016/0120818 A1 | 5/2016 | Grandi et al. |
| 2016/0120956 A1 | 5/2016 | Godfrin et al. |
| 2016/0122697 A1 | 5/2016 | Skiba et al. |
| 2016/0122707 A1 | 5/2016 | Swee et al. |
| 2016/0123925 A1 | 5/2016 | Guzman |
| 2016/0128335 A1 | 5/2016 | Sabin |
| 2016/0129078 A1 | 5/2016 | Ko et al. |
| 2016/0135463 A9 | 5/2016 | Reid et al. |
| 2016/0135469 A1 | 5/2016 | Olson et al. |
| 2016/0137563 A1 | 5/2016 | Sabin |
| 2016/0137564 A1 | 5/2016 | Sabin |
| 2016/0137565 A1 | 5/2016 | Sabin |
| 2016/0143269 A1 | 5/2016 | Liu et al. |
| 2016/0143961 A1 | 5/2016 | Berry et al. |
| 2016/0143962 A1 | 5/2016 | Berry et al. |
| 2016/0144004 A1 | 5/2016 | Pellico |
| 2016/0144012 A1 | 5/2016 | Klumpp et al. |
| 2016/0145573 A1 | 5/2016 | Liu |
| 2016/0151427 A1 | 6/2016 | Whitlock et al. |
| 2016/0153025 A1 | 6/2016 | Wu et al. |
| 2016/0157497 A1 | 6/2016 | Zlotkin |
| 2016/0158169 A1 | 6/2016 | O'Neil et al. |
| 2016/0158353 A1 | 6/2016 | Kielian |
| 2016/0160195 A1 | 6/2016 | Landry et al. |
| 2016/0166712 A1 | 6/2016 | Pavlicek et al. |
| 2016/0167993 A1 | 6/2016 | Razavi-Shirazi et al. |
| 2016/0168559 A1 | 6/2016 | Shahgaldian et al. |
| 2016/0168598 A1 | 6/2016 | Leigh et al. |
| 2016/0174543 A9 | 6/2016 | Liu et al. |
| 2016/0175424 A1 | 6/2016 | Bakaletz et al. |
| 2016/0175634 A1 | 6/2016 | Radian et al. |
| 2016/0176815 A1 | 6/2016 | Li et al. |
| 2016/0177353 A1 | 6/2016 | Yu et al. |
| 2016/0184485 A1 | 6/2016 | Zhang |
| 2016/0185630 A1 | 6/2016 | Gupta et al. |
| 2016/0186147 A1 | 6/2016 | Cady et al. |
| 2016/0193258 A1 | 7/2016 | Berry et al. |
| 2016/0193307 A1 | 7/2016 | Kaleko et al. |
| 2016/0193344 A1 | 7/2016 | Sershen et al. |
| 2016/0194288 A1 | 7/2016 | Melander et al. |
| 2016/0198994 A1 | 7/2016 | Murphy et al. |

(56) References Cited

U.S. PATENT DOCUMENTS

| | | |
|---|---|---|
| 2016/0199295 A1 | 7/2016 | Doxey et al. |
| 2016/0199328 A1 | 7/2016 | Collins et al. |
| 2016/0199424 A1 | 7/2016 | Berry et al. |
| 2016/0199502 A1 | 7/2016 | Devore et al. |
| 2016/0206575 A1 | 7/2016 | O'Neil et al. |
| 2016/0208202 A1 | 7/2016 | Himmrich et al. |
| 2016/0212996 A1 | 7/2016 | Ghigo et al. |
| 2016/0213001 A1 | 7/2016 | Parthasarathy et al. |
| 2016/0215242 A1 | 7/2016 | Himmrich et al. |
| 2016/0215243 A1 | 7/2016 | Himmrich et al. |
| 2016/0220722 A1 | 8/2016 | Wardell et al. |
| 2016/0222068 A1 | 8/2016 | Kerfeld et al. |
| 2016/0222372 A1 | 8/2016 | Walper et al. |
| 2016/0222437 A1 | 8/2016 | Perez Diaz et al. |
| 2016/0223553 A1 | 8/2016 | Sears et al. |
| 2016/0235698 A1 | 8/2016 | Rickard et al. |
| 2016/0235792 A1 | 8/2016 | Berry et al. |
| 2016/0235834 A1 | 8/2016 | Bou Arevalo et al. |
| 2016/0235893 A1 | 8/2016 | Lucchino et al. |
| 2016/0235894 A1 | 8/2016 | Ghigo et al. |
| 2016/0237145 A1 | 8/2016 | Kauvar et al. |
| 2016/0237398 A1 | 8/2016 | Kalyuzhnaya et al. |
| 2016/0242413 A1 | 8/2016 | Wuest et al. |
| 2016/0243262 A1 | 8/2016 | Ortac et al. |
| 2016/0244796 A1 | 8/2016 | Zimmer et al. |
| 2016/0249612 A1 | 9/2016 | Gambogi et al. |
| 2016/0250304 A1 | 9/2016 | Kaleko et al. |
| 2016/0256484 A1 | 9/2016 | Doxey et al. |
| 2016/0262384 A1 | 9/2016 | Wuest et al. |
| 2016/0263225 A1 | 9/2016 | Zakrewsky et al. |
| 2016/0270411 A1 | 9/2016 | Martin Orue et al. |
| 2016/0271188 A1 | 9/2016 | Berry et al. |
| 2016/0278375 A1 | 9/2016 | Wuest et al. |
| 2016/0279191 A1 | 9/2016 | Glasnapp |
| 2016/0279314 A1 | 9/2016 | Eliaz |
| 2016/0280772 A1 | 9/2016 | Salomon et al. |
| 2016/0281179 A1 | 9/2016 | Rey et al. |
| 2016/0281180 A1 | 9/2016 | Rey et al. |
| 2016/0289272 A1 | 10/2016 | Otterlei et al. |
| 2016/0289287 A1 | 10/2016 | Hancock et al. |
| 2016/0291000 A1 | 10/2016 | Filipe et al. |
| 2016/0303062 A1 | 10/2016 | Derby et al. |
| 2016/0303172 A1 | 10/2016 | Zitvogel et al. |
| 2016/0304886 A1 | 10/2016 | Rickard et al. |
| 2016/0309711 A1 | 10/2016 | Jackson et al. |
| 2016/0317556 A1 | 11/2016 | Marsault et al. |
| 2016/0317566 A1 | 11/2016 | Osborne et al. |
| 2016/0317611 A1 | 11/2016 | Nibbering et al. |
| 2016/0317618 A1 | 11/2016 | Fikrig et al. |
| 2016/0324531 A1 | 11/2016 | Gross et al. |
| 2016/0326215 A1 | 11/2016 | Marcu et al. |
| 2016/0326574 A1 | 11/2016 | Gordon et al. |
| 2016/0330962 A1 | 11/2016 | Looper et al. |
| 2016/0330976 A1 | 11/2016 | Mitter et al. |
| 2016/0333307 A1 | 11/2016 | Fong et al. |
| 2016/0333384 A1 | 11/2016 | Silverman et al. |
| 2016/0338360 A1 | 11/2016 | Mitter et al. |
| 2016/0338993 A1 | 11/2016 | Martins-Green et al. |
| 2016/0339071 A1 | 11/2016 | Tufenkji et al. |
| 2016/0339144 A1 | 11/2016 | McEntire et al. |
| 2016/0346115 A1 | 12/2016 | Varga et al. |
| 2016/0346161 A1 | 12/2016 | Varga et al. |
| 2016/0346294 A1 | 12/2016 | Sengupta et al. |
| 2016/0346436 A1 | 12/2016 | Boluk et al. |
| 2016/0353739 A1 | 12/2016 | Melander et al. |
| 2016/0354313 A1 | 12/2016 | De Beer |
| 2016/0355487 A1 | 12/2016 | Huigens et al. |
| 2016/0361342 A1 | 12/2016 | Hansson et al. |
| 2016/0361361 A1 | 12/2016 | Godfrin et al. |
| 2016/0368892 A1 | 12/2016 | Bassler et al. |
| 2016/0369246 A1 | 12/2016 | Saville et al. |
| 2016/0369261 A1 | 12/2016 | Razavi-Shirazi et al. |
| 2016/0375034 A1 | 12/2016 | Baker et al. |
| 2016/0375074 A1 | 12/2016 | Quave et al. |
| 2016/0376449 A1 | 12/2016 | Reches |
| 2016/0376613 A1 | 12/2016 | Bhalla et al. |
| 2017/0002481 A1 | 1/2017 | Zussman et al. |
| 2017/0007733 A1 | 1/2017 | Boyden et al. |
| 2017/0009084 A1 | 1/2017 | Margel et al. |
| 2017/0014208 A1 | 1/2017 | Falcone et al. |
| 2017/0014437 A1 | 1/2017 | Luk et al. |
| 2017/0020139 A1 | 1/2017 | Berkes et al. |
| 2017/0020813 A1 | 1/2017 | Lipp et al. |
| 2017/0022165 A1 | 1/2017 | Lu et al. |
| 2017/0022371 A1 | 1/2017 | Lynn et al. |
| 2017/0028106 A1 | 2/2017 | Brisbois et al. |
| 2017/0029363 A1 | 2/2017 | Caran et al. |
| 2017/0035891 A1 | 2/2017 | Karp et al. |
| 2017/0035955 A1 | 2/2017 | Eliaz |
| 2017/0037363 A1 | 2/2017 | Whitlock et al. |
| 2017/0039314 A1 | 2/2017 | Bremel et al. |
| 2017/0042965 A1 | 2/2017 | Bevilacqua et al. |
| 2017/0043111 A1 | 2/2017 | Hoftman et al. |
| 2017/0044222 A1 | 2/2017 | Alexander et al. |
| 2017/0044472 A1 | 2/2017 | Rasmussen et al. |
| 2017/0049113 A1 | 2/2017 | Duncan et al. |
| 2017/0050893 A1 | 2/2017 | Sabin |
| 2017/0050927 A1 | 2/2017 | Li et al. |
| 2017/0056297 A1 | 3/2017 | Kishen et al. |
| 2017/0056405 A1 | 3/2017 | Sun et al. |
| 2017/0056437 A1 | 3/2017 | Stasko et al. |
| 2017/0056454 A1 | 3/2017 | Berkes et al. |
| 2017/0056455 A1 | 3/2017 | Berkes et al. |
| 2017/0056565 A1 | 3/2017 | Kepler et al. |
| 2017/0064966 A1 | 3/2017 | Opatowsky et al. |
| 2017/0065564 A1 | 3/2017 | Shaw et al. |
| 2017/0065673 A1 | 3/2017 | Birkedal et al. |
| 2017/0071212 A1 | 3/2017 | Sabin |
| 2017/0071986 A1 | 3/2017 | Kovarik et al. |
| 2017/0072024 A1 | 3/2017 | Malepeyre et al. |
| 2017/0072098 A1 | 3/2017 | Drago et al. |
| 2017/0073706 A1 | 3/2017 | Ghigo et al. |
| 2017/0080130 A1 | 3/2017 | Pichler-Wilhelm et al. |
| 2017/0095502 A1 | 4/2017 | Sarangapani |
| 2017/0100328 A1 | 4/2017 | Kovarik et al. |
| 2017/0100348 A1 | 4/2017 | Wright |
| 2017/0100512 A1 | 4/2017 | Matheny |
| 2017/0100513 A1 | 4/2017 | Matheny |
| 2017/0100514 A1 | 4/2017 | Matheny |
| 2017/0100515 A1 | 4/2017 | Matheny |
| 2017/0100516 A1 | 4/2017 | Matheny |
| 2017/0100517 A1 | 4/2017 | Matheny |
| 2017/0100518 A1 | 4/2017 | Matheny |
| 2017/0100522 A1 | 4/2017 | Matheny |
| 2017/0100523 A1 | 4/2017 | Matheny |
| 2017/0106075 A1 | 4/2017 | Bakaletz et al. |
| 2017/0106188 A1 | 4/2017 | King et al. |
| 2017/0107250 A1 | 4/2017 | Stensen et al. |
| 2017/0107461 A1 | 4/2017 | Rasmussen et al. |
| 2017/0107523 A1 | 4/2017 | Kerfeld et al. |
| 2017/0112723 A1 | 4/2017 | Xu et al. |
| 2017/0113038 A1 | 4/2017 | Nagel et al. |
| 2017/0118991 A1 | 5/2017 | Neas et al. |
| 2017/0119805 A1 | 5/2017 | Collins et al. |
| 2017/0119810 A1 | 5/2017 | Baker et al. |
| 2017/0119915 A1 | 5/2017 | Lin et al. |
| 2017/0127683 A1 | 5/2017 | Schuch et al. |
| 2017/0128338 A1 | 5/2017 | Gawande et al. |
| 2017/0128502 A1 | 5/2017 | Berkes et al. |
| 2017/0128720 A1 | 5/2017 | Skiba |
| 2017/0135342 A1 | 5/2017 | Caran et al. |
| 2017/0136056 A1 | 5/2017 | Baker et al. |
| 2017/0136154 A1 | 5/2017 | Ferrari et al. |
| 2017/0137380 A1 | 5/2017 | Rodrigues et al. |
| 2017/0143842 A1 | 5/2017 | Smyth et al. |
| 2017/0145445 A1 | 5/2017 | Bazzana et al. |
| 2017/0150724 A1 | 6/2017 | Baker |
| 2017/0156310 A1 | 6/2017 | Liu et al. |
| 2017/0156321 A1 | 6/2017 | Li et al. |
| 2017/0158727 A1 | 6/2017 | Coenye et al. |
| 2017/0158811 A1 | 6/2017 | Fevre et al. |
| 2017/0161430 A1 | 6/2017 | Bremel et al. |
| 2017/0173186 A9 | 6/2017 | Pavlicek et al. |
| 2017/0176453 A1 | 6/2017 | Bergo |

(56) References Cited

U.S. PATENT DOCUMENTS

| | | |
|---|---|---|
| 2017/0182205 A1 | 6/2017 | Zupancic et al. |
| 2017/0188604 A1 | 7/2017 | Zhang et al. |
| 2017/0189454 A1 | 7/2017 | Heywood et al. |
| 2017/0189501 A1 | 7/2017 | Fallon et al. |
| 2017/0189556 A1 | 7/2017 | Seleem |
| 2017/0190951 A1 | 7/2017 | AlDhufairi et al. |
| 2017/0191005 A1 | 7/2017 | Foverskov et al. |
| 2017/0191109 A1 | 7/2017 | Whitlock et al. |
| 2017/0196967 A1 | 7/2017 | Thess et al. |
| 2017/0197028 A1 | 7/2017 | Goldsmith |
| 2017/0202752 A1 | 7/2017 | Xu et al. |
| 2017/0202888 A1 | 7/2017 | Liles et al. |
| 2017/0202934 A1 | 7/2017 | Fallon et al. |
| 2017/0204316 A1 | 7/2017 | Pop et al. |
| 2017/0204361 A1 | 7/2017 | Eapen et al. |
| 2017/0211023 A1 | 7/2017 | Zhang |
| 2017/0216094 A1 | 8/2017 | Reo et al. |
| 2017/0216197 A1 | 8/2017 | McHale et al. |
| 2017/0216369 A1 | 8/2017 | Sabacinski et al. |
| 2017/0216377 A1 | 8/2017 | Berkes et al. |
| 2017/0216410 A1 | 8/2017 | Howell et al. |
| 2017/0218315 A1 | 8/2017 | Rasmussen et al. |
| 2017/0219601 A1 | 8/2017 | Bergo |
| 2017/0224748 A1 | 8/2017 | Berkes et al. |
| 2017/0232038 A1 | 8/2017 | O'Flaherty et al. |
| 2017/0232048 A1 | 8/2017 | Edwards |
| 2017/0232153 A1 | 8/2017 | Babu et al. |
| 2017/0240618 A1 | 8/2017 | Zurawski |
| 2017/0246205 A1 | 8/2017 | Stasko et al. |
| 2017/0246341 A1 | 8/2017 | Hanson et al. |
| 2017/0247409 A1 | 8/2017 | Moreira et al. |
| 2017/0247414 A1 | 8/2017 | Gruber |
| 2017/0247493 A1 | 8/2017 | Banerjee et al. |
| 2017/0247688 A1 | 8/2017 | Franch et al. |
| 2017/0252320 A1 | 9/2017 | Martins-Green et al. |
| 2017/0252413 A1 | 9/2017 | Esener et al. |
| 2017/0258963 A1 | 9/2017 | Savage et al. |
| 2017/0266215 A1 | 9/2017 | Newman et al. |
| 2017/0266239 A1 | 9/2017 | Borody |
| 2017/0266306 A1 | 9/2017 | Eckert et al. |
| 2017/0271702 A1 | 9/2017 | Reguera et al. |
| 2017/0273301 A1 | 9/2017 | Benson |
| 2017/0274082 A1 | 9/2017 | Sershen et al. |
| 2017/0275597 A1 | 9/2017 | Newman et al. |
| 2017/0280725 A1 | 10/2017 | Jin et al. |
| 2017/0281570 A1 | 10/2017 | Gurtner et al. |
| 2017/0281699 A1 | 10/2017 | Berkes et al. |
| 2017/0281740 A1 | 10/2017 | Rikihisa et al. |
| 2017/0283763 A1 | 10/2017 | Newman et al. |
| 2017/0283765 A1 | 10/2017 | Bhalla et al. |
| 2017/0290339 A1 | 10/2017 | Curtis et al. |
| 2017/0290789 A1 | 10/2017 | Dicosmo |
| 2017/0290854 A1 | 10/2017 | Matlick |
| 2017/0292063 A1 | 10/2017 | Sturtevant et al. |
| 2017/0295784 A1 | 10/2017 | Bolduc et al. |
| 2017/0296599 A1 | 10/2017 | Berkes et al. |
| 2017/0296709 A1 | 10/2017 | Bunge et al. |
| 2017/0297055 A1 | 10/2017 | Detrembleur et al. |
| 2017/0304355 A1 | 10/2017 | Baker et al. |
| 2017/0304489 A1 | 10/2017 | Deschepper et al. |
| 2017/0304501 A1 | 10/2017 | Bunge et al. |
| 2017/0304564 A1 | 10/2017 | DeHaan et al. |
| 2017/0306363 A1 | 10/2017 | Guarnieri et al. |
| 2017/0312307 A1 | 11/2017 | Stasko et al. |
| 2017/0312345 A1 | 11/2017 | Ivanova et al. |
| 2017/0319877 A1 | 11/2017 | Grootveld et al. |
| 2017/0321160 A1 | 11/2017 | Lant et al. |
| 2017/0321161 A1 | 11/2017 | Lant et al. |
| 2017/0321289 A1 | 11/2017 | Rey et al. |
| 2017/0326054 A1 | 11/2017 | Spears et al. |
| 2017/0327910 A1 | 11/2017 | Rey et al. |
| 2017/0333360 A1 | 11/2017 | Zicari et al. |
| 2017/0333363 A1 | 11/2017 | Thayumanavan et al. |
| 2017/0333455 A1 | 11/2017 | Manley et al. |
| 2017/0333601 A1 | 11/2017 | Burgess et al. |
| 2017/0335244 A1 | 11/2017 | Lant et al. |
| 2017/0335255 A1 | 11/2017 | Lant et al. |
| 2017/0339962 A1 | 11/2017 | Sabin |
| 2017/0340779 A1 | 11/2017 | Burgess et al. |
| 2017/0342423 A1 | 11/2017 | Portnoy et al. |
| 2017/0347661 A1 | 12/2017 | Parsons |
| 2017/0347664 A1 | 12/2017 | Thompson et al. |
| 2017/0348337 A1 | 12/2017 | Schmidt et al. |
| 2017/0348402 A1 | 12/2017 | Pfeifer et al. |
| 2017/0349818 A1 | 12/2017 | Mirakyan et al. |
| 2017/0360534 A1 | 12/2017 | Sun et al. |
| 2017/0360982 A1 | 12/2017 | Wardell et al. |
| 2017/0361023 A1 | 12/2017 | Anderson et al. |
| 2017/0362266 A1 | 12/2017 | Ott et al. |
| 2017/0367933 A1 | 12/2017 | Aparicio et al. |
| 2017/0368155 A1 | 12/2017 | Kaleko et al. |
| 2018/0000066 A1 | 1/2018 | Liu et al. |
| 2018/0000993 A1 | 1/2018 | Zhang |
| 2018/0008533 A1 | 1/2018 | McHale et al. |
| 2018/0008549 A1 | 1/2018 | Kataoka et al. |
| 2018/0008550 A1 | 1/2018 | Kataoka et al. |
| 2018/0008742 A1 | 1/2018 | Hoggarth et al. |
| 2018/0014974 A1 | 1/2018 | Hoggarth et al. |
| 2018/0014975 A1 | 1/2018 | Hoggarth et al. |
| 2018/0015061 A1 | 1/2018 | Gawande et al. |
| 2018/0015130 A1 | 1/2018 | Berry et al. |
| 2018/0016311 A1 | 1/2018 | Zlotkin et al. |
| 2018/0016544 A1 | 1/2018 | Whitlock et al. |
| 2018/0016569 A1 | 1/2018 | Fu et al. |
| 2018/0021463 A1 | 1/2018 | Osinski et al. |
| 2018/0023217 A1 | 1/2018 | Patton et al. |
| 2018/0028417 A1 | 2/2018 | Koo et al. |
| 2018/0028701 A1 | 2/2018 | Fu et al. |
| 2018/0028713 A1 | 2/2018 | Agarwal et al. |
| 2018/0030165 A1 | 2/2018 | Finn et al. |
| 2018/0030390 A1 | 2/2018 | Lant et al. |
| 2018/0030403 A1 | 2/2018 | Subhadra |
| 2018/0030404 A1 | 2/2018 | Subhadra |
| 2018/0030405 A1 | 2/2018 | Subhadra |
| 2018/0030406 A1 | 2/2018 | Subhadra |
| 2018/0036286 A1 | 2/2018 | Shaw et al. |
| 2018/0036702 A1 | 2/2018 | Wellings |
| 2018/0037545 A1 | 2/2018 | Silver |
| 2018/0037613 A1 | 2/2018 | Paetzold et al. |
| 2018/0042789 A1 | 2/2018 | Bradford et al. |
| 2018/0042928 A1 | 2/2018 | Sun et al. |
| 2018/0042962 A1 | 2/2018 | Majeti et al. |
| 2018/0043190 A1 | 2/2018 | Myers et al. |
| 2018/0049856 A1 | 2/2018 | Ionescu et al. |
| 2018/0049965 A1 | 2/2018 | Baker et al. |
| 2018/0050115 A1 | 2/2018 | Mou et al. |
| 2018/0051061 A1 | 2/2018 | Wang |
| 2018/0055777 A1 | 3/2018 | McClements et al. |
| 2018/0055913 A1 | 3/2018 | Hudson et al. |
| 2018/0057546 A1 | 3/2018 | Kerfeld et al. |
| 2018/0057822 A1 | 3/2018 | Wang et al. |
| 2018/0065940 A1 | 3/2018 | Pfeifer et al. |
| 2018/0071344 A1 | 3/2018 | Berry et al. |
| 2018/0073046 A1 | 3/2018 | Boeriu et al. |
| 2018/0079757 A1 | 3/2018 | Tse-Dinh et al. |
| 2018/0079912 A1 | 3/2018 | Reches |
| 2018/0085335 A1 | 3/2018 | Sun et al. |
| 2018/0085392 A1 | 3/2018 | Gaspar et al. |
| 2018/0085489 A1 | 3/2018 | Hanson et al. |
| 2018/0085717 A1 | 3/2018 | Ermatov et al. |
| 2018/0092939 A1 | 4/2018 | Onsoyen et al. |
| 2018/0092948 A1 | 4/2018 | Weiss et al. |
| 2018/0093011 A1 | 4/2018 | Kellar et al. |
| 2018/0099999 A1 | 4/2018 | Thompson et al. |
| 2018/0104315 A1 | 4/2018 | Fallon et al. |
| 2018/0105791 A1 | 4/2018 | Stumpe |
| 2018/0105792 A1 | 4/2018 | Subhadra |
| 2018/0110228 A1 | 4/2018 | Myers et al. |
| 2018/0111893 A1 | 4/2018 | Wuest et al. |
| 2018/0112068 A1 | 4/2018 | Segal et al. |
| 2018/0117097 A1 | 5/2018 | Chatila et al. |
| 2018/0117098 A1 | 5/2018 | Chatila et al. |
| 2018/0117099 A1 | 5/2018 | Chatila et al. |
| 2018/0118777 A1 | 5/2018 | Patel et al. |

(56) References Cited

U.S. PATENT DOCUMENTS

| | | |
|---|---|---|
| 2018/0119235 A1 | 5/2018 | Talianski et al. |
| 2018/0125066 A1 | 5/2018 | Bassler et al. |
| 2018/0125070 A1 | 5/2018 | Looper et al. |
| 2018/0127454 A1 | 5/2018 | Patel et al. |
| 2018/0132484 A1 | 5/2018 | Neas et al. |
| 2018/0133326 A1 | 5/2018 | Mcinroy et al. |
| 2018/0139932 A1 | 5/2018 | Ala'Aldeen et al. |
| 2018/0139933 A1 | 5/2018 | Ala'Aldeen et al. |
| 2018/0140581 A1 | 5/2018 | Bergeron, Jr. |
| 2018/0153996 A1 | 6/2018 | Lipp et al. |
| 2018/0161422 A1 | 6/2018 | Thess et al. |
| 2018/0163191 A1 | 6/2018 | Cuevas et al. |
| 2018/0169153 A1 | 6/2018 | Berry et al. |
| 2018/0169218 A1 | 6/2018 | Thess et al. |
| 2018/0193457 A1 | 7/2018 | Sokurenko et al. |
| 2018/0199550 A1 | 7/2018 | Ala'Aldeen et al. |
| 2018/0200286 A1 | 7/2018 | Baker et al. |
| 2018/0201664 A1 | 7/2018 | Hayden-Ledbetter et al. |
| 2018/0201957 A1 | 7/2018 | Hickey |
| 2018/0208630 A1 | 7/2018 | Thompson et al. |
| 2018/0221309 A1 | 8/2018 | Neumann et al. |
| 2018/0235987 A1 | 8/2018 | von Maltzahn et al. |
| 2018/0235998 A1 | 8/2018 | Baker et al. |
| 2018/0237738 A1 | 8/2018 | Whitlock et al. |
| 2018/0256674 A1 | 9/2018 | Jeon et al. |
| 2018/0264053 A1 | 9/2018 | Lynch et al. |
| 2018/0265833 A1 | 9/2018 | Holder et al. |
| 2018/0265905 A1 | 9/2018 | Wencewicz et al. |
| 2018/0272396 A1 | 9/2018 | Farmer et al. |
| 2018/0289609 A1 | 10/2018 | Townsend et al. |
| 2018/0303876 A1 | 10/2018 | Campbell et al. |
| 2018/0303912 A1 | 10/2018 | Bourdillon et al. |
| 2018/0312550 A1 | 11/2018 | Roland et al. |
| 2018/0318313 A1 | 11/2018 | Sengupta et al. |
| 2018/0320215 A1 | 11/2018 | Park et al. |
| 2018/0338475 A1 | 11/2018 | Ala'Aldeen et al. |
| 2018/0354909 A1 | 12/2018 | De Brabander et al. |
| 2018/0361010 A1 | 12/2018 | McDermott et al. |
| 2018/0361030 A1 | 12/2018 | Ferrari et al. |
| 2018/0363012 A1 | 12/2018 | Burk et al. |
| 2018/0369129 A1 | 12/2018 | Weiss et al. |
| 2019/0001025 A1 | 1/2019 | Ferrari et al. |
| 2019/0006694 A1 | 1/2019 | Reguera et al. |
| 2019/0008875 A1 | 1/2019 | Marsault et al. |
| 2019/0010446 A1 | 1/2019 | Whitlock et al. |
| 2019/0015528 A1 | 1/2019 | Moran et al. |
| 2019/0017050 A1 | 1/2019 | Thanos et al. |
| 2019/0021330 A1 | 1/2019 | Neas et al. |
| 2019/0022151 A1 | 1/2019 | Kovarik |
| 2019/0024095 A1 | 1/2019 | Wang et al. |
| 2019/0029998 A1 | 1/2019 | Burns et al. |
| 2019/0037899 A1 | 2/2019 | Juge et al. |
| 2019/0038888 A1 | 2/2019 | Gardner |
| 2019/0040383 A1 | 2/2019 | Klein et al. |
| 2019/0054048 A1 | 2/2019 | Fuchs et al. |
| 2019/0054104 A1 | 2/2019 | Collins et al. |
| 2019/0060446 A1 | 2/2019 | Gao et al. |
| 2019/0070085 A1 | 3/2019 | Shewale et al. |
| 2019/0070132 A1 | 3/2019 | Stanton, Jr. et al. |
| 2019/0070214 A1 | 3/2019 | Baker et al. |
| 2019/0071337 A1 | 3/2019 | Razavi-Shirazi et al. |
| 2019/0083440 A1 | 3/2019 | Day et al. |
| 2019/0083602 A1 | 3/2019 | Roos et al. |
| 2019/0085362 A1 | 3/2019 | Pfleger et al. |
| 2019/0105260 A1 | 4/2019 | Isseroff et al. |
| 2019/0110481 A1 | 4/2019 | Sinclair et al. |
| 2019/0117709 A1 | 4/2019 | Kovarik |
| 2019/0136272 A1 | 5/2019 | Otte et al. |
| 2019/0142864 A1 | 5/2019 | Newman et al. |
| 2019/0142934 A1 | 5/2019 | Kovarik |
| 2019/0144842 A1 | 5/2019 | Cuevas et al. |
| 2019/0192582 A1 | 6/2019 | Chatila et al. |
| 2019/0192691 A1 | 6/2019 | Barrett et al. |
| 2019/0200602 A1 | 7/2019 | Liu et al. |
| 2019/0203175 A1 | 7/2019 | Liu |
| 2019/0218531 A1 | 7/2019 | Ducat et al. |
| 2019/0240287 A1 | 8/2019 | Svanborg et al. |
| 2019/0246629 A1 | 8/2019 | Liu et al. |
| 2019/0247434 A1 | 8/2019 | Wang et al. |
| 2019/0256466 A1 | 8/2019 | Kumar et al. |
| 2019/0256818 A1 | 8/2019 | Swee et al. |
| 2019/0264169 A1 | 8/2019 | Fong et al. |
| 2019/0271019 A1 | 9/2019 | Silverman et al. |
| 2019/0276858 A1 | 9/2019 | Pradella et al. |
| 2019/0282632 A1 | 9/2019 | Zitvogel et al. |
| 2019/0297897 A1 | 10/2019 | Mitter et al. |
| 2019/0300581 A1 | 10/2019 | Zhang |
| 2019/0300831 A1 | 10/2019 | Martinez et al. |
| 2019/0300870 A1 | 10/2019 | Zhang |
| 2019/0308015 A1 | 10/2019 | King et al. |
| 2019/0309310 A1 | 10/2019 | Wang et al. |
| 2019/0315814 A1 | 10/2019 | Handfield et al. |
| 2019/0328687 A1 | 10/2019 | Copp et al. |
| 2019/0336543 A1 | 11/2019 | Berry et al. |
| 2019/0336608 A1 | 11/2019 | Baumhof et al. |
| 2019/0336611 A1 | 11/2019 | Baumhof et al. |
| 2019/0345561 A1 | 11/2019 | Kim et al. |
| 2019/0350977 A1 | 11/2019 | Wang et al. |
| 2019/0358149 A1 | 11/2019 | Sokol et al. |
| 2019/0359933 A1 | 11/2019 | Swee et al. |
| 2019/0365810 A1 | 12/2019 | Wang et al. |
| 2019/0365868 A1 | 12/2019 | Sauer et al. |
| 2019/0367865 A1 | 12/2019 | Johnson et al. |
| 2019/0376052 A1 | 12/2019 | Steer et al. |
| 2019/0381116 A1 | 12/2019 | Reddy |
| 2019/0381180 A1 | 12/2019 | Baumhof et al. |
| 2019/0390158 A1 | 12/2019 | Dyson et al. |
| 2020/0008431 A1 | 1/2020 | Mitter et al. |
| 2020/0009182 A1 | 1/2020 | Baker et al. |
| 2020/0009183 A1 | 1/2020 | Baker et al. |
| 2020/0009200 A1 | 1/2020 | Liles et al. |
| 2020/0017438 A1 | 1/2020 | Voronkov et al. |
| 2020/0031757 A1 | 1/2020 | Looper et al. |
| 2020/0032273 A1 | 1/2020 | Wang et al. |
| 2020/0053986 A1 | 2/2020 | Ala'Aldeen et al. |
| 2020/0061129 A1 | 2/2020 | Berry et al. |
| 2020/0071214 A1 | 3/2020 | Quan et al. |
| 2020/0071603 A1 | 3/2020 | Farmer et al. |
| 2020/0071702 A1 | 3/2020 | Thanos et al. |
| 2020/0087644 A1 | 3/2020 | Cascao-Pereira et al. |
| 2020/0093964 A1 | 3/2020 | Bunge et al. |
| 2020/0102254 A1 | 4/2020 | Sakimoto et al. |
| 2020/0107552 A1 | 4/2020 | Thompson et al. |
| 2020/0121742 A1 | 4/2020 | Lynch et al. |
| 2020/0121743 A1 | 4/2020 | Kovarik |
| 2020/0121858 A1 | 4/2020 | Anderson et al. |
| 2020/0123433 A1 | 4/2020 | Farmer et al. |
| 2020/0123527 A1 | 4/2020 | Shakeel et al. |
| 2020/0131520 A1 | 4/2020 | Wang et al. |
| 2020/0157237 A1 | 5/2020 | Regev et al. |
| 2020/0165733 A1 | 5/2020 | Reed et al. |
| 2020/0172857 A1 | 6/2020 | Falb et al. |
| 2020/0179526 A1 | 6/2020 | Baumhof et al. |
| 2020/0179999 A1 | 6/2020 | Farmer et al. |
| 2020/0190149 A1 | 6/2020 | Thompson et al. |
| 2020/0194126 A1 | 6/2020 | Lim et al. |
| 2020/0197696 A1 | 6/2020 | Nagel et al. |
| 2020/0199586 A1 | 6/2020 | Klein et al. |
| 2020/0206337 A1 | 7/2020 | Bou Arevalo et al. |
| 2020/0208160 A1 | 7/2020 | Zeidler et al. |
| 2020/0215123 A1 | 7/2020 | Thanos et al. |
| 2020/0216797 A1 | 7/2020 | Dyson et al. |
| 2020/0216836 A1 | 7/2020 | Franch et al. |
| 2020/0216864 A1 | 7/2020 | Magalhaes et al. |
| 2020/0222473 A1 | 7/2020 | Chatila et al. |
| 2020/0222687 A1 | 7/2020 | Skiba et al. |
| 2020/0230167 A1 | 7/2020 | Morrison et al. |
| 2020/0239896 A1 | 7/2020 | Daniell |
| 2020/0246398 A1 | 8/2020 | Chatila et al. |
| 2020/0248277 A1 | 8/2020 | Park |
| 2020/0261415 A1 | 8/2020 | Burns et al. |
| 2020/0261667 A1 | 8/2020 | DeHaan et al. |
| 2020/0268692 A1 | 8/2020 | Stanton, Jr. et al. |
| 2020/0268867 A1 | 8/2020 | Watnick et al. |

(56) References Cited

U.S. PATENT DOCUMENTS

| | | |
|---|---|---|
| 2020/0270613 A1 | 8/2020 | Thanos et al. |
| 2020/0276149 A1 | 9/2020 | Neas et al. |
| 2020/0276322 A1 | 9/2020 | Wimley et al. |
| 2020/0277639 A1 | 9/2020 | Alexandrino et al. |
| 2020/0289643 A1 | 9/2020 | Kovarik |
| 2020/0299748 A1 | 9/2020 | Jarvius et al. |
| 2020/0308594 A1 | 10/2020 | Tamsir et al. |
| 2020/0318146 A1 | 10/2020 | Kolling et al. |
| 2020/0323963 A1 | 10/2020 | Bartolo et al. |
| 2020/0324014 A1 | 10/2020 | McDermott et al. |
| 2020/0331820 A1 | 10/2020 | Tamsir et al. |
| 2020/0345707 A1 | 11/2020 | Hultgren et al. |
| 2020/0345831 A1 | 11/2020 | Thess et al. |
| 2020/0354588 A1 | 11/2020 | McDaniel |
| 2020/0354724 A1 | 11/2020 | Wang et al. |
| 2020/0354725 A1 | 11/2020 | Wang et al. |
| 2020/0360449 A1 | 11/2020 | Zitvogel et al. |
| 2020/0362228 A1 | 11/2020 | Farmer et al. |
| 2020/0362299 A1 | 11/2020 | Newman et al. |
| 2020/0368249 A1 | 11/2020 | Rohde et al. |
| 2020/0368276 A1 | 11/2020 | Campbell et al. |
| 2020/0385741 A1 | 12/2020 | Wang et al. |
| 2020/0390809 A1 | 12/2020 | Campbell et al. |
| 2020/0397732 A1 | 12/2020 | Scott et al. |
| 2020/0405691 A1 | 12/2020 | Rajashekara et al. |
| 2021/0017402 A1 | 1/2021 | McDaniel et al. |
| 2021/0023101 A1 | 1/2021 | Conlon et al. |
| 2021/0024655 A1 | 1/2021 | Altae-Tran et al. |
| 2021/0030706 A1 | 2/2021 | Day et al. |
| 2021/0030813 A1 | 2/2021 | Thanos et al. |
| 2021/0032603 A1 | 2/2021 | Newman et al. |
| 2021/0032674 A1 | 2/2021 | Grawe et al. |
| 2021/0038654 A1 | 2/2021 | Culler et al. |
| 2021/0046117 A1 | 2/2021 | Wang et al. |
| 2021/0051956 A1 | 2/2021 | Qian et al. |
| 2021/0052671 A1 | 2/2021 | Mulder et al. |
| 2021/0054423 A1 | 2/2021 | Chou et al. |
| 2021/0060136 A1 | 3/2021 | Zal |
| 2021/0060268 A1 | 3/2021 | DeHaan et al. |

OTHER PUBLICATIONS

Ruppert et al. Efficient Indirect Electrochemical In-Situ Regene. ltation of NADH: Electrochemically Driven Enzymatic Reduction of Pyruvate Catalyzed by D-LDH. Tetrahedron Letters (1987), 28(52), 6583-6586. (Year: 1987).*

Tré-Hardy et al. In vitro activity of antibiotic combinations against Pseudomonas aeruginosa biofilm and planktonic cultures. International Journal of Antimicrobial Agents (2008), 31, 329-336. (Year: 2008).*

Ma et al. (Journal of Molecular Catalysis B: Enzymatic (2009), 56, 102-107. (Year: 2009).*

Jafary et al. Stability Improvement of Immobilized Alkaline Phosphatase Using Chitosan Nanoparticles. Braz. J. Chem. Eng. (2016), 33(2), 243-250. (Year: 2016).*

Alizadeh, Taher, and Somaye Amjadi. "Preparation of nano-sized Pb2+ imprinted polymer and its application as the chemical interface of an electrochemical sensor for toxic lead determination in different real samples." Journal of hazardous materials 190, No. 1-3 (2011): 451-459.

Allegrucci, M., and Sauer, K. (2007) Characterization of colony morphology variants isolated from Streptococcus pneumoniae biofilms. J Bacteriol 189: 2030-2038.

Allegrucci, M., Hu, F.Z., Shen, K., Hayes, J., Ehrlich, G.D., Post, J.C., and Sauer, K. (2006) Phenotypic characterization of Streptococcus pneumoniae biofilm development. J Bacteriol 188: 2325-2335.

Allesen-Holm, M., Barken, K.B., Yang, L., Klausen, M., Webb, J.S., Kjelleberg, S., et al. (2006) A characterization of DNA release in Pseudomonas aeruginosa cultures and biofilms. Mol Microbiol 59: 1114-1128.

Allison DG, Ruiz B, SanJose C, Jaspe A, Gilbert P (1998) Extracellular products as mediators of the formation and detachment of Pseudomonas fluorescens biofilms. FEMS Microbiol Lett 167:179-184.

Allwood A, Walter MR, Burch IW, Kamber BS (2007) 3.43 billion-year-old stromatolite reef from the Pilbara Craton of Western Australia: ecosystem-scale insights to early life on Earth. Precambrian Res 158:198-227.

Alvarez-Ortega, C., and Harwood, C.S. (2007) Responses of Pseudomonas aeruginosa to low oxygen indicate that growth in the cystic fibrosis lung is by aerobic respiration. Mol Microbiol 65:153-165.

An, Shi-qi, and Robert P. Ryan. "Combating chronic bacterial infections by manipulating cyclic nucleotide-regulated biofilm formation." Future medicinal chemistry 8, No. 9 (2016): 949-961.

Anderl, J.N., Franklin, M.J., and Stewart, P.S. (2000) Role of antibiotic penetration limitation in Klebsiella pneumoniae biofilm resistance to ampicillin and ciprofloxacin. Antimicrob Agents Chemother 44: 1818-1824.

Anderl, J.N., Zahller, J., Roe, F., and Stewart, P.S. (2003) Role of nutrient limitation and stationary-phase existence in Klebsiella pneumoniae biofilm resistance to ampicillin and ciprofloxacin. Antimicrob Agents Chemother 47: 1251-1256.

Banin, E., Vasil, M.L., and Greenberg, E.P. (2005) Iron and Pseudomonas aeruginosa biofilm formation. Proc Natl Acad Sci USA 102: 11076-11081.

Barber CE et al (1997) A novel regulatory system required for pathogenicity of Xanthomonas campestris is mediated by a small diffusible signal molecule. Mol Microbiol 24:555-566.

Barbosa, Oveimar, Rodrigo Torres, Claudia Ortiz, Ángel Berenguer-Murcia, Rafael C. Rodrigues, and Roberto Fernandez-Lafuente. "Heterofunctional supports in enzyme immobilization: from traditional immobilization protocols to opportunities in tuning enzyme properties." Biomacromolecules 14, No. 8 (2013): 2433-2462.

Barraud N, Schleheck D, Klebensberger J, Webb JS, Hassett DJ, Rice SA, Kjelleberg S. 2009. Nitric oxide signaling in Pseudomonas aeruginosa biofilms mediates phosphodiesterase activity, decreased cyclic di-GMP levels, and enhanced dispersal. J. Bacteriol. 191:7333-7342.

Barraud, N., Hassett, D.J., Hwang, S.-H., Rice, S.A., Kjelleberg, S., and Webb, J.S. (2006) Involvement of nitric oxide in biofilm dispersal of Pseudomonas aeruginosa. J Bacteriol 188: 7344-7353.

Barraud, Nicolas, Staffan Kjelleberg, and Scott A. Rice. "Dispersal from microbial biofilms." Microbiol Spectr 3, No. 6 (2015).

Basu Roy A, Sauer K. 2014. Diguanylate cyclase NicD-based signalling mechanism of nutrient-induced dispersion by Pseudomonas aeruginosa. Mol. Microbiol. 94:771-793. doi:10.1111/mmi.12802.

Basu Roy, A., Petrova, O.E., Sauer, K. 2012. The phosphodiesterase DipA (PA5017) is essential for Pseudomonas aeruginosa biofilm dispersion. J. Bacteriol. 194:2904-2915.

Battesti, A., N. Majdalani, S. Gottesman, The RpoS-mediated general stress response in Escherichia coli, Annu. Rev. Microbiol., 65 (2011), pp. 189-213.

Baumann, K. W., Baust, J. M., Snyder, K. K., Baust, J. G. & Buskirk, R. G. V. Characterization of Pancreatic Cancer Cell Thermal Response to Heat Ablation or Cryoablation. Technology in Cancer Research & Treatment 16, 393-405, doi:10.1177/1533034616655658 (2017).

Benjamini, Y., and Hochberg, Y. (1995) Controlling the false discovery rate—a practical and powerful approach to multiple testing. J R Stat Soc Ser B Stat Methodol 57: 289-300.

Berk, V., J.C. Fong, G.T. Dempsey, O.N. Develioglu, X. Zhuang, J. Liphardt, F.H. Yildiz, S. Chu, Molecular architecture and assembly principles of Vibrio cholerae biofilms, Science, 337 (2012), pp. 236-239.

Besharova, O., V.M. Suchanek, R. Hartmann, K. Drescher, V. Sourjik, Diversification of gene expression during formation of static submerged biofilms by Escherichia coli, Front. Microbiol., 7 (2016), p. 1568.

Bielecki, P., Puchalka, J., Wos-Oxley, M.L., Loessner, H., Glik, J., Kawecki, M., et al. (2011) In-vivo expression orofiling of Pseudomonas aeruginosa infections reveals nichespecific and strain-independent transcriptional programs. PLoS ONE 6: e24235.

(56) References Cited

OTHER PUBLICATIONS

Biró, Emese, Ágnes Sz Németh, Csaba Sisak, Tivadar Feczkó, and János Gyenis. "Preparation of chitosan particles suitable for enzyme immobilization." Journal of Biochemical and Biophysical Methods 70, No. 6 (2008): 1240-1246.
Bjarnsholt, T. et al. Why chronic wounds will not heal: a novel hypothesis. Wound Repair and Regeneration 16, 2-10 (2008).
Blokesch, M., Chitin colonization, chitin degradation and chitin-induced natural competence of Vibrio cholerae are subject to catabolite repression, Environ. Microbiol., 14 (2012), pp. 1898-1912.
Bobrov, A.G., Kirillina, O., and Perry, P.D. (2005) The phosphodiesterase activity of the HmsP EAL domain is required for negative regulation of biofilm formation in Yersinia pestis. FEMS Microbiol Lett 247: 123-130.
Boes, N., Schreiber, K., and Schobert, M. (2008) SpoT triggered stringent response controls usp gene expression in Pseudomonas aeruginosa. J Bacteriol 190: 7189-7199.
Boes, N., Schreiber, K., Hartig, E., Jaensch, L., and Schobert, M. (2006) The Pseudomonas aeruginosa universal stress protein PA4352 is essential for surviving anaerobic energy stress. J Bacteriol 188: 6529-6538.
Boles BR, Thoendel M, Singh PK (2005) Rhamnolipids mediate detachment of Pseudomonas aeruginosa from biofilms. Mol Microbiol 57:1210-1223.
Boles, B.R., A.R. Horswill, Agr-mediated dispersal of *Staphylococcus aureus* biofilms, PLoS Pathog., 4 (2008), p. e1000052.
Boon C et al (2007) A novel DSF-like signal from Burkholderia cenocepacia interferes with Candida albicans morphological transition. ISME J 2:27-36.
Borriello, G., Werner, E., Roe, F., Kim, A.M., Ehrlich, G.D., and Stewart, P.S. (2004) Oxygen limitation contributes to antibiotic tolerance of Pseudomonas aeruginosa in biofilms. Antimicrob Agents Chemother 48: 2659-2664.
Bowden GH, Li YH (1997) Nutritional influences on biofilm development. Adv Dent Res 11:81-99.
Boyd A, Chakrabarty AM (1994) Role of alginate lyase in cell detachment of Pseudomonas aeruginosa. Appl Environ Microbiol 60:2355-2359.
Brady, Dean, and Justin Jordaan. "Advances in enzyme immobilisation." Biotechnology letters 31, No. 11 (2009): 1639.
Breyers JD (1988) Modeling biofilm accumulation. In: Bazin MJ, Prosser JI (eds) Physiology models in microbiology, vol. 2. Boca Raton, FL, pp. 109-144.
Broughton 2nd, G., Janis, J. E. & Attinger, C. E. The basic science of wound healing. Plastic and reconstructive surgery 117, 12S-34S (2006).
Byrd, Matthew S., Irina Sadovskaya, Evgueny Vinogradov, Haiping Lu, April B. Sprinkle, Stephen H. Richardson, Luyan Ma et al. "Genetic and biochemical analyses of the Pseudomonas aeruginosa Psl exopolysaccharide reveal overlapping roles for polysaccharide synthesis enzymes in Psl and LPS production." Molecular microbiology 73, No. 4 (2009): 622-638.
Caiazza, N.C., and O'Toole, G.A. (2004) SadB is required for the transition from reversible to irreversible attachment during biofilm formation by Pseudomonas aeruginosa PA14. J Bacteriol 186: 4476-4485.
Cancio LC H. P., McManus AT, Kim SH, Goodwin CW, Pruitt, BA Jr. Burn wound infections. In: Holzheimer RG, Mannick JA, editors. Surgical Treatment: Evidence-Based and Problem-Oriented. Munich: Zuckschwerdt (2001).
Cantone, Sara, Valerio Ferrario, Livia Corici, Cynthia Ebert, Diana Fattor, Patrizia Spizzo, and Lucia Gardossi. "Efficient immobilisation of industrial biocatalysts: criteria and constraints for the selection of organic polymeric carriers and immobilisation methods." Chemical Society Reviews 42, No. 15 (2013): 6262-6276.
Cárcamo-Oyarce, G., P. Lumjiaktase, R. Kümmerli, L. Eberl, Quorum sensing triggers the stochastic escape of individual cells from Pseudomonas putida biofilms, Nat. Commun., 6 (2015), p. 5945.

Carlson, C.A., and Ingraham, J.L. (1983) Comparison of denitrification by Pseudomonas stutzeri, Pseudomonas aeruginosa, and Paracoccus denitrificans. Appl Environ Microbiol 45: 1247-1253.
Carlson, C.A., Ferguson, L.P., & Ingraham, J.L. (1982) Properties of dissimilatory nitrate reductase purified from the denitrifier Pseudomonas aeruginosa. J Bacteriol 151: 162-171.
Cazzaniga, A. et al. The effect of an antimicrobial gauze dressing impregnated with 0.2% polyhexamethylene biguanide as a barrier to prevent Pseudomonas aeruginosa wound invasion. Wounds 5, 169-176 (2002).
Chambers, J. R. & Sauer, K. The MerR-like regulator BrlR impairs Pseudomonas aeruginosa biofilm tolerance to colistin by repressing PhoPQ. Journal of Bacteriology 195, 4678-4688, doi:10.1128/jb.00834-13 (2013).
Chambers, J. R., Liao, J., Schurr, M. J. & Sauer, K. BrlR from Pseudomonas aeruginosa is a c-di-GMP-responsive transcription factor. Mol. Microbiol. 92, 471-487, doi:10.1111/mmi.12562 (2014).
Chaterji, Somali, Il Keun Kwon, and Kinam Park. "Smart polymeric gels: redefining the limits of biomedical devices." Progress in polymer science 32, No. 8-9 (2007): 1083-1122.
Chatterjee S, Newman KL, Lindow SE (2008) Cell-to-cell signaling in Xylella fastidiosa suppresses movement and xylem vessel colonization in grape. Mol Plant-Microbe Interact 21:1309-1315.
Chen X, Stewart PS (2000) Biofilm removal caused by chemical treatments. Water Res 34:4229-4233.
Chen, W., Honma, K., Sharma, A., and Kuramitsu, H.K. (2006) A universal stress protein of Porphyromonas gingivalis is involved in stress responses and biofilm formation. FEMS Microbiol Lett 264: 15-21.
Christen M, Christen B, Folcher M, Schauerte A, Jenal U (2005) Identification and characterization of a cyclic di-GMP-specific phosphodiesterase and its allosteric control by GTP. J Biol Chem 280:30829-30837.
Church, D., Elsayed, S., Reid, O., Winston, B. & Lindsay, R. Burn wound infections. Clin. Microbiol. Rev. 19, 403-434, doi:10.1128/cmr.19.2.403-434.2006 (2006).
Comolli, J.C., and Donohue, T.J. (2004) Differences in two Pseudomonas aeruginosa cbb3 cytochrome oxidases. Mol Microbiol 51: 1193-1203.
Conibear, T.C.R., Collins, S.L., and Webb, J.S. (2009) Role of mutation in Pseudomonas aeruginosa biofilm development. PLoS ONE 4: e6289.
Cornforth, D.M., R. Popat, L. McNally, J. Gurney, T.C. Scott-Phillips, A. Ivens, S.P. Diggle, S.P. Brown, Combinatorial quorum sensing allows bacteria to resolve their social and physical environment, Proc. Natl. Acad. Sci. USA, 111 (2014), pp. 4280-4284.
Corr, D. T., Gallant-Behm, C. L., Shrive, N. G. & Hart, D. A. Biomechanical behavior of scar tissue and uninjured skin in a porcine model. Wound Repair and Regeneration 17, 250-259 (2009).
Costerton JW, Lewandowski Z, Caldwell DE, Korber DR, Lappin-Scott HM (1995) Microbial biofilms. Annu Rev Microbiol 49:711-745.
Costerton, J. W., Stewart, P. S. & Greenberg, E. P. Bacterial biofilms: a common cause of persistent infections. Science 284, 1318-1322 (1999).
Danhorn T, Hentzer M, Givskov M, Parsek MR, Fuqua C (2004) Phosphorus limitation enhances biofilm formation of the plant pathogen *Agrobacterium tumefaciens* through the PhoR-PhoB regulatory system. J Bacteriol 186:4492-4501.
Datta, Sumitra, L. Rene Christena, and Yamuna Rani Sriramulu Rajaram. "Enzyme immobilization: an overview on techniques and support materials." 3 Biotech 3, No. 1 (2013):1-9.
Davey, M.E., Caiazza, N.C., and O'Toole, G.A. (2003) Rhamnolipid surfactant production affects biofilm architecture in Pseudomonas aeruginosa PAO1 J Bacteriol 185: 1027-1036.
David GA, Begoña R, Carmen S, Almudena J, Peter G (1998) Extracellular products as mediators of the formation and detachment of Pseudomonas fluorescens biofilms. FEMS Microbiol Lett 167:179-184.
Davies D.G. (2011) Biofilm Dispersion. In: Flemming HC., Wingender J., Szewzyk U. (eds) Biofilm Highlights. Springer Series on Biofilms, vol. 5. Springer, Berlin, Heidelberg.

(56) References Cited

OTHER PUBLICATIONS

Davies DG (1999) Regulation of matrix polymer in biofilm formation and dispersion. In: Wingender J, Neu TR, Flemming H-C (eds) Microbial extrapolymeric substances, characterization, structure and function. Springer, Berlin, pp. 93-112.
Davies DG, Marques CNH (2009) A fatty acid messenger is responsible for inducing dispersion in microbial biofilms. J Bacteriol 191:1393-1403.
Davies, K.J.P., Lloyd, D., and Boddy, L. (1989) The effect of oxygen on denitrification in Paracoccus denitrificans and Pseudomonas aeruginosa. J Gen Microbiol 135: 2445-2451.
Davis, S. C. & Mertz, P. M. Determining the Effect of an Oak Bark Formulation on Methicillin-resistant *Staphylococcus aureus* and Wound Healing in Porcine Wound Models. Ostomy Wound Manage 54, 16-25 (2008).
Davis, S. C et al. Microscopic and physiologic evidence for biofilm-associated wound colonization in vivo. Wound Repair and Regeneration 16, 23-29, doi:10.1111/j.1524-475X.2007.00303.x (2008).
Davis, S. C., Cazzaniga, A. L., Ricotti, C. & et al. Topical oxygen emulsion: A novel wound therapy. Archives of Dermatology 143, 1252-1256, doi:10.1001/archderm.143.10.1252 (2007).
Davis, S. C., Martinez, L. & Kirsner, R. The diabetic foot: the importance of biofilms and wound bed preparation. Current diabetes reports 6, 439-445 (2006).
Davis, S. C., Mertz, P. M. & Eaglstein, W. H. Second-degree burn healing: The effect of occlusive dressings and a cream. Journal of Surgical Research 48, 245-248, doi:10.1016/0022-4804 (90)90220-v.
Davis, S., Cazzaniga, A., Eaglstein, W. & Mertz, P. Over-the-counter topical antimicrobials: effective treatments? Arch Dermatol Res 297, 190-195, doi:10.1007/s00403-005-0612-6 (2005).
De Beer, D., Stoodley, P., and Lewandowski, Z. (1994) Liquid flow in heterogeneous biofilms. Biotechnol Bioeng 44: 636-641.
De Lorenzo, V., K.N. Timmis, Analysis and construction of stable phenotypes in gram-negative bacteria with Tn5and Tn10-derived minitransposons, Methods Enzymol., 235 (1994), pp. 386-405.
Delaquis PJ, Caldwell DE, Lawrence JR, McCurdy AR (1989) Detachment of Pseudomonas fluorescens from biofilms on glass surfaces in response to nutrient stress. Microb Ecol 18:199-210.
Dewanti R, Wong ACL (1995) Influence of culture conditions on biofilm formation by *Escherichia coli* O157:H7. Int J Food Microbiol 26:147-164.
Diaz, J. Felipe, and Kenneth J. Balkus Jr. "Enzyme immobilization in MCM-41 molecular sieve." Journal of Molecular Catalysis B: Enzymatic 2, No. 2-3 (1996): 115-126.
DiCosimo, Robert, Joseph McAuliffe, Ayrookaran J. Poulose, and Gregory Bohlmann. "Industrial use of immobilized enzymes." Chemical Soc. Reviews 42, No. 15 (2013): 6437-6474.
Dietrich, L.E.P., Price-Whelan, A., Petersen, A., Whiteley, M., and Newman, D.K. (2006) The phenazine pyocyanin is a terminal signalling factor in the quorum sensing network of Pseudomonas aeruginosa. Mol Microbiol 61: 1308-1321.
Dietrich, Lars EP, Tracy K. Teal, Alexa Price-Whelan, and Dianne K. Newman. "Redox-active antibiotics control gene expression and community behavior in divergent bacteria." Science 321, No. 5893 (2008): 1203-1206.
Ding, Qinfeng, and Kai Soo Tan. "The danger signal extracellular ATP is an inducer of Fusobacterium nucleatum biofilm dispersal." Frontiers in cellular and infection microbiology 6 (2016): 155.
Doiron, A. L., Chu, K., Ali, A. & Brannon-Peppas, L. Preparation and initial characterization of biodegradable particles containing gadolinium-DTPA contrast agent for enhanced MRI. Proc. Nat. Acad. Sci. 105, 17232-17237, doi:10.1073/pnas.0710205105 (2008).
Donlan, R. M. Biofilms and device-associated infections. Emerg. Infect. Dis. 7, 277-281 (2001).
Dow JM et al (2003) Biofilm dispersal in Xanthomonas campestris is controlled by cell-cell signaling and is required for full virulence to plants. Proc Natl Acad Sci 100:10995-11000.
Dragoš, A., Á.T. Kovács, The peculiar functions of the bacterial extracellular matrix, Trends Microbiol., 25 (2017), pp. 257-266.

Drescher, K., C.D. Nadell, H.A. Stone, N.S. Wingreen, B.L. Bassler, Solutions to the public goods dilemma in bacterial biofilms, Curr. Biol., 24 (2014), pp. 50-55.
Drescher, K., J. Dunkel, C.D. Nadell, S. van Teeffelen, I. Grnja, N.S. Wingreen, H.A. Stone, B.L. Bassler, Architectural transitions in Vibrio cholerae biofilms at single-cell resolution, Proc. Natl. Acad. Sci. USA, 113 (2016), pp. E2066-E2072.
Drumm, J.E., Mi, K., Bilder, P., Sun, M., Lim, J., Bielefeldt-Ohmann, H., et al. (2009) *Mycobacterium tuberculosis* universal stress protein Rv2623 regulates bacillary growth by ATP-binding: requirement for establishing chronic persistent infection. PLoS Pathog 5: e1000460.
Dziubla, T. D., Karim, A. & Muzykantov, V. R. Polymer nanocarriers protecting active enzyme cargo against proteolysis. Journal of Controlled Release 102, 427-439 (2005).
Edwards R, Harding KG. 2004. Bacteria and wound healing. Current opinion in infectious diseases 17:91-96.
Eschbach, M., Schreiber, K., Trunk, K., Buer, J., Jahn, D., and Schobert, M. (2004) Long-term anaerobic survival of the opportunistic pathogen Pseudomonas aeruginosa via pyruvate fermentation. J Bacteriol 186: 4596-4604.
Farid, Mohammad Masoudi, Leila Goudini, Farideh Piri, Abbasali Zamani, and Fariba Saadati. "Molecular imprinting method for fabricating novel glucose sensor: Polyvinyl acetate electrode reinforced by $MnO_2/CuO$ loaded on graphene oxide nanoparticles." Food chemistry 194 (2016): 61-67.
Fernandez-Lafuente, Roberto. "Stabilization of multimeric enzymes: Strategies to prevent subunit dissociation." Enzyme and Microbial Technology 45, No. 6-7 (2009): 405-418.
Ferreira RBR, Antunes LCM, Greenberg EP, McCarter LL (2008) Vibrio parahaemolyticus ScrC modulates cyclic dimeric GMP regulation of gene expression relevant to growth on surfaces. J Bacteriol 190:851-860.
Filiatrault, M.J., Picardo, K.F., Ngai, H., Passador, L., and Iglewski, B.H. (2006) Identification of Pseudomonas aeruginosa genes involved in virulence and anaerobic growth. Infect Immun 74:4237 4245.
Fouhy Y et al (2007) Diffusible signal factor-dependent cell-cell signaling and virulence in the nosocomial pathogen Stenotrophomonas maltophilia. J Bacteriol 189:4964-4968.
Friedman L, Kolter R (2004a) Two genetic loci produce distinct carbohydrate-rich structural components of the Pseudomonas aeruginosa biofilm matrix. J Bacteriol 186:4457-4465.
Friedman L, Kolter R (2004b) Genes involved in matrix formation in Pseudomonas aeruginosa PA14 biofilms. Mol Microbiol 51:675-690.
Gacesa P (1987) Alginate-modifying-enzymes: a proposed unified mechanism of action for the lyases and epimerases. FEBS Lett 212:199-202.
Garcia-Galan, Cristina, Ángel Berenguer-Murcia, Roberto Fernandez-Lafuente, and Rafael C. Rodrigues. "Potential of different enzyme immobilization strategies to improve enzyme performance." Advanced Synthesis & Catalysis 353, No. 16 (2011): 2885-2904.
Garcia-Medina, R., Dunne, W.M., Singh, P.K., and Brody, S.L. (2005) Pseudomonas aeruginosa acquires biofilm-like properties within airway epithelial cells. Infect Immun 73: 8298-8305.
Gjermansen, M., M. Nilsson, L. Yang, T. Tolker-Nielsen, Characterization of starvation-induced dispersion in Pseudomonas putida biofilms: genetic elements and molecular mechanisms, Mol. Microbiol., 75 (2010), pp. 815-826.
Guilhen, C., C. Forestier, D. Balestrino, Biofilm dispersal: multiple elaborate strategies for dissemination of bacteria with unique properties, Mol. Microbiol., 105 (2017), pp. 188-210.
Gupta, A. & Kumar, P. Assessment of the histological state of the healing wound. Plastic and Aesthetic Research 2, 239 (2015).
Gupta, K., Liao, J., Petrova, O. E., Cherny, K. E. & Sauer, K. Elevated levels of the second messenger c-di-GMP contribute to antimicrobial resistance of Pseudomonas aeruginosa. Mol. Microbiol. 92, 488-506, doi:10.1111/mmi.12587 (2014).
Gupta, K., Marques, C. N. H., Petrova, O. E. & Sauer, K. Antimicrobial tolerance of Pseudomonas aeruginosa biofilms is activated during an early developmental stage and requires the two-component hybrid SagS. J. Bacteriol. 195, 4975-4987 doi:10.1128/jb.00732-13 (2013).

(56) References Cited

OTHER PUBLICATIONS

Güvener ZT, Harwood CS (2007) Subcellular location characteristics of the Pseudomonas aeruginosa GGDEF protein, WspR, indicate that it produces cyclic-di-GMP in response to growth on surfaces. Mol Microbiol 66:1459-1473.
Guzik, Urszula, Katarzyna Hupert-Kocurek, and Danuta Wojcieszyńska. "Immobilization as a strategy for improving enzyme properties—application to oxidoreductases." Molecules19, No. 7 (2014): 8995-9018.
Ha, Dae-Gon, and George A. O'Toole. "c-di-GMP and its effects on biofilm formation and dispersion: a Pseudomonas aeruginosa review." Microbiology spectrum 3, No. 2 (2015).
Hammer, B.K., B.L. Bassler, Quorum sensing controls biofilm formation in Vibrio cholera, Mol. Microbiol., 50 (2003), pp. 101-104.
Harrison-Balestra, C., Cazzaniga, A. L., Davis, S. C. & Mertz, P. M. A Wound-Isolated Pseudomonas aeruginosa Grows a Biofilm In Vitro Within 10 Hours and Is Visualized by Light Microscopy. Dermatologic surgery 29, 631-635 (2003).
Hassett, D.J., Cuppoletti, J., Trapnell, B., Lymar, S.V., Rowe, J.J., Yoon, S.S., et al. (2002) Anaerobic metabolism and quorum sensing by Pseudomonas aeruginosa biofilms in chronically infected cystic fibrosis airways: rethinking antibiotic treatment strategies and drug targets. Adv Drug Deliv Rev 54: 1425-1443.
Hassett, D.J., Sutton, M.D., Schurr, M.J., Herr, A.B., Caldwell, C.C., and Matu, J.O. (2009) Pseudomonas aeruginosa hypoxic or anaerobic biofilm infections within cystic fibrosis airways. Trends Microbiol 17: 130-138.
Hay, A.J., J. Zhu, Host intestinal signal-promoted biofilm dispersal induces Vibrio cholerae colonization, Infect. Immun., 83 (2015), pp. 317-323.
Heinrich, W., Lange, P., Stirtz, T., Iancu, C. & Heidemann, E. Isolation and characterization of the large cyanogen bromide peptides from the α1- and α2-chains of pig skin collagen. FEBS letters 16, 63-67 (1971).
Heydorn, A., Nielsen, A.T., Hentzer, M., Sternberg, C., Givskov, M., Ersboll, B.K., and Molin, S. (2000) Quantification of biofilm structures by the novel computer program COMSTAT. Microbiology 146: 2395-2407.
Hickman JW, Tifrea DF, Harwood CS (2005) A chemosensory system that regulates biofilm formation through modulation of cyclic diguanylate levels. Proc Natl Acad Sci USA 102:14422-14427.
Hisatsuka K, Nakahara T, Sano N, Yamada K (1971) Formation of rhamnolipid by Pseudomonas aeruginosa and its function in hydrocarbon fermentation. Agric Biol Chem 35:686-692.
Hofmann HJ, Grey K, Hickman AH, Thorpe RI (1999) Origin of 3.45 Ga coniform stromatolites in Warrawoona group, Western Australia. Geol Soc Am Bull 111:1256-1262.
Høiby, N., Krogh Johansen, H., Moser, C., Song, Z., Ciofu, O., and Kharazmi, A. (2001) Pseudomonas aeruginosa and the in vitro and in vivo biofilm mode of growth. Microbes Infect 3:23-35.
Homaei, Ahmad Abolpour, Reyhaneh Sariri, Fabio Vianello, and Roberto Stevanato. "Enzyme immobilization: an update." Journal of chemical biology 6, No. 4 (2013): 185-205.
Horswill, A.R., P. Stoodley, P. S. Stewart, M.R. Parsek, The effect of the chemical, biological, and physical environment on quorum sensing in structured microbial communities, Anal. Bioanal. Chem., 387 (2007), pp. 371-380.
Hou, Z. et al. Both FA- and mPEG-conjugated chitosan nanoparticles for targeted cellular uptake and enhanced tumor tissue distribution. Nanoscale Research Letters 6, 563, doi:10.1186/1556-276x-6-563 (2011).
Huang T-P, Wong ACL (2007) A cyclic AMP receptor protein-regulated cell-cell communication system mediates expression of a FecA homologue in Stenotrophomonas maltophilia. Appl Environ Microbiol 73:5034 5040.
Hunt SM, Werner EM, Huang B, Hamilton MA, Stewart PS (2004) Hypothesis for the role of nutrient starvation in biofilm detachment. Appl Environ Microbiol 70:7418-7425.

Hwang, Ee Taek, and Man Bock Gu. "Enzyme stabilization by nano/microsized hybrid materials." Engineering in Life Sciences 13, No. 1 (2013): 49-61.
Irie, Y., Starkey, M., Edwards, A.N., Wozniak, D.J., Romeo, T., and Parsek, M.R. (2010) Pseudomonas aeruginosa biofilm matrix polysaccharide Psl is regulated transcriptionally by RpoS and post-transcriptionally by RsmA. Mol Microbiol 78: 158-172.
Itoh Y, Wang X, Hinnebusch BJ, Preston Jf III, Romeo T (2005) Depolymerization of {beta}-1,6-N-acetyl-D-glucosamine disrupts the integrity of diverse bacterial biofilms. J Bacteriol 187:382-387.
Iyer, Padma V., and Laxmi Ananthanarayan. "Enzyme stability and stabilization—aqueous and non-aqueous environment." Process biochemistry 43, No. 10 (2008): 1019-1032.
Jackson DW, Simecka JW, Romeo T (2002) Catabolite repression of *Escherichia coli* biofilm formation. J Bacteriol 184:3406-3410.
Jackson KD, Starkey M, Kremer S, Parsek MR, Wozniak DJ (2004) Identification of psl, a locus encoding a potential exopolysaccharide that is essential for Pseudomonas aeruginosa PAO1 biofilm formation. J Bacteriol 186:4466-4475.
James GA, Korber DR, Caldwell DE, Costerton JW (1995) Digital image analysis of growth and starvation responses of a surface-colonizing *Acinetobacter* sp. J Bacteriol 177:907-915.
Jensen, P. Ø. et al. Rapid necrotic killing of polymorphonuclear leukocytes is caused by quorum-sensing-controlled production of rhamnolipid by Pseudomonas aeruginosa. Microbiology 153, 1329-1338, doi:10.1099/mic.0.2006/003863-0 (2007).
Jesionowski, Teofil, Jakub Zdarta, and Barbara Krajewska. "Enzyme immobilization by adsorption: a review." Adsorption 20, No. 5-6 (2014): 801-821.
Juang, Ruey-Shin, Feng-Chin Wu, and Ru-Ling Tseng. "Use of chemically modified chitosan beads for sorption and enzyme immobilization." Advances in Environmental Research 6, No. 2 (2002): 171-177.
Kaluzhny, Y., Kinuthia, M., Karetsky, V., d'Argembeau-Thornton, L., Hayden, P. and Klausner, K., An in vitro reconstructued normal human corneal tissue model for corneal drug delivery studies of ophthalmic formulations. Internal MatTek Corporation, Publication #803.
Kaneko, Y., Thoendel, M., Olakanmi, O., Britigan, B.E., and Singh, P.K. (2007) The transition metal gallium disrupts Pseudomonas aeruginosa iron metabolism and has antimicrobial and antibiofilm activity. J Clin Invest 117: 877-888.
Kaplan JB, Fine DH (2002) Biofilm dispersal of neisseria subflava and other phylogenetically diverse oral bacteria. Appl Environ Microbiol 68:4943-4950.
Kaplan JB, Ragunath C, Ramasubbu N, Fine DH (2003) Detachment of Actinobacillus actinomycetemcomitans biofilm cells by an endogenous {beta}-hexosaminidase activity. J Bacteriol 185:4693-4698.
Kaplan, J.B., Biofilm dispersal: mechanisms, clinical implications, and potential therapeutic uses, J. Dent. Res., 89 (2010), pp. 205-218.
Karatan E, Watnick P (2009) Signals, regulatory networks, and materials that build and break bacterial biofilms. Microbiol Mol Biol Rev 73:310-347.
Kim Y-K, McCarter LL (2007) ScrG, a GGDEF-EAL protein, participates in regulating swarming and sticking in Vibrio parahaemolyticus. J Bacteriol 189:4094-4107.
Kim, M.K., F. Ingremeau, A. Zhao, B.L. Bassler, H.A. Stone, Local and global consequences of flow on bacterial quorum sensing, Nat. Microbiol., 1 (2016), p. 15005.
Kim, S.M., J.H. Park, H.S. Lee, W.B. Kim, J.M. Ryu, H.J. Han, S.H. Choi, LuxR homologue SmcR is essential for Vibrio vulnificus pathogenesis and biofilm detachment, and its expression is induced by host cells, Infect. Immun., 81 (2013), pp. 3721-3730.
Kirisits, M.J., J.J. Margolis, B.L. Purevdorj-Gage, B. Vaughan, D.L. Chopp, p. Stoodley, M.R. Parsek, Influence of the hydrodynamic environment on quorum sensing in Pseudomonas aeruginosa biofilms, J. Bacteriol., 189 (2007), pp. 8357-8360.
Kuchma, S.L., Brothers, K.M., Merritt, J.H., Liberati, N.T., Ausubel, F.M., and O'Toole, G.A. (2007) BifA, a c-di-GMP phosphodiesterase, inversely regulates biofilm formation and swarming motility by Pseudomonas aeruginosa PA14. J Bacteriol 189: 8165-8178.

(56) References Cited

OTHER PUBLICATIONS

Kudupoje, Manoj B. "Molecularly Imprinted Polymers Synthesized as Adsorbents for Ergot Alkaloids: Characterization and In Vitro and Ex Vivo Assessment of Effects on Ergot Alkaloid Bioavailability." (2017).

Kuramitsu, H.K., Chen, W., and Ikegami, A. (2005) Biofilm formation by the periodontopathic bacteria Treponema denticola and Porphyromonas gingivalis. J Periodontol 76: 2047-2051.

Lam, J., Chan, R., Lam, K., and Costerton, J.W. (1980) Production of mucoid microcolonies by Pseudomonas aeruginosa within infected lungs in cystic fibrosis. Infect Immun 28: 546-556.

Lamed R, Bayer EA (1986) Contact and cellulolysis in Clostridium thermocellum via extensive surface organelles. Experientia 42:72-73.

Lanter, Bernard B., and David G. Davies. "Propionibacterium acnes recovered from atherosclerotic human carotid arteries undergoes biofilm dispersion and releases lipolytic and proteolytic enzymes in response to norepinephrine challenge in vitro." Infection and immunity 83, No. 10 (2015): 3960-3971.

Lee J, Bansal T, Jayaraman A, Bentley WE, Wood TK (2007a) Enterohemorrhagic *Escherichia coli* biofilms are inhibited by 7-hydrozyindole and stimulated by isatin. Appl Environ Microbiol 73:4100-4109.

Lee J, Jayaraman A, Wood TK (2007b) Indole is an inter-species biofilm signal mediated by SdiA. BMC Microbiol 7:1-15.

Lee, Mei-Hwa, Tain-Chin Tsai, James L. Thomas, and Hung-Yin Lin. "Recognition of creatinine by poly (ethylene-co-vinylalcohol) molecular imprinting membrane." Desalination 234, No. 1-3 (2008): 126-133.

Leid, J. G., Shirtliff, M. E., Costerton, J. W., Stoodley & Paul. Human leukocytes adhere to, penetrate, and respond to *Staphylococcus aureus* Biofilms. Infect. Immun. 70, 6339-6345, doi:10.1128/iai.70.11.6339-6345.2002 (2002).

Leistikow, R.L., Morton, R.A., Bartek, I.L., Frimpong, I., Wagner, K., and Voskuil, M.I. (2010) The *Mycobacterium tuberculosis* DosR regulon assists in metabolic homeostasis and enables rapid recovery from nonrespiring dormancy. J Bacteriol 192: 1662-1670.

Lenz, A.P., Williamson, K.S., Pitts, B., Stewart, P.S., and Franklin, M.J. (2008) Localized gene expression in Pseudomonas aeruginosa biofilms. Appl Environ Microbiol 74: 4463-4471.

Lenz, D.H., K.C. Mok, B.N. Lilley, R.V. Kulkarni, N.S. Wingreen, B.L. Bassler, The small RNA chaperone Hfq and multiple small RNAs control quorum sensing in Vibrio harveyi and Vibrio cholera, Cell, 118 (2004), pp. 69-82.

Lewis, K. Multidrug tolerance of biofilms and persister cells. Curr. Top. Microbiol. Immunol. 322, 107-131 (2008).

Li, Ta-Jen, Po-Yen Chen, Po-Chin Nien, Chia-Yu Lin, Ramamurthy Vittal, Tzong-Rong Ling, and Kuo-Chuan Ho. "Preparation of a novel molecularly imprinted polymer by the sol-gel process for sensing creatinine." Analytica chimica acta 711 (2012): 83-90.

Li, Y et al. BdlA, DipA and induced dispersion contribute to acute virulence and chronic persistence of Pseudomonas aeruginosa. PLoS Pathog. 10, e1004168, doi:10.1371/journal.ppat.1004168 (2014).

Li, Y., Cherny, K. E. & Sauer, K. The diguanylate cyclase CrdA contributes to the architecture and the dispersion response of Pseudomonas aeruginosa biofilms. In revision (2016).

Liao, J. & Sauer, K. The MerR-like transcriptional regulator BrlR contributes to Pseudomonas aeruginosa biofilm tolerance. J. Bacteriol. 194, 4823-4836, doi:10.1128/jb.00765-12 (2012).

Liao, J., Schurr, M. J. & Sauer, K. The MerR-like regulator BrlR confers biofilm tolerance by activating multidrug-efflux pumps in Pseudomonas aeruginosa biofilms. J. Bacteriol. 195, 3352-3363 (2013).

Lister JL, Horswill AR. 2014. *Staphylococcus aureus* biofilms: recent developments in biofilm dispersal. Frontiers in Cellular and Infection Microbiology 4:178.

Luckarift, Heather R., Jim C. Spain, Rajesh R. Naik, and Morley O. Stone. "Enzyme immobilization in a biomimetic silica support." Nature biotechnology 22, No. 2 (2004): 211.

Luo, Jing, Sisi Jiang, and Xiaoya Liu. "Efficient one-pot synthesis of mussel-inspired molecularly imprinted polymer coated graphene for protein-specific recognition and fast separation." The Journal of Physical Chemistry C 117, No. 36 (2013): 18448-18456.

Lynch MJ et al (2002) The regulation of biofilm development by quorum sensing in Aeromonas hydrophila. Environ Microbiol 4:18-28.

Ma L, Jackson KD, Landry RM, Parsek MR, Wozniak DJ (2006) Analysis of Pseudomonas aeruginosa conditional Psl variants reveals roles for the Psl polysaccharide in adhesion and maintaining biofilm structure postattachment. J Bacteriol 188:8213-8221.

Ma L, Lu H, Sprinkle A, Parsek MR, Wozniak D (2007) Pseudomonas aeruginosa Psl is a galactose and mannose-rich exopolysaccharide. J Bacteriol. doi: 10.1128/JB.00620-07.

Maisonneuve, E., M. Castro-Camargo, K. Gerdes, (p)ppGpp controls bacterial persistence by stochastic induction of toxin-antitoxin activity, Cell, 154 (2013), pp. 1140-1150 [retracted article].

Mao, Yan, Yu Bao, Shiyu Gan, Fenghua Li, and Li Niu. "Electrochemical sensor for dopamine based on a novel graphene-molecular imprinted polymers composite recognition element." Biosensors and Bioelectronics 28, No. 1 (2011): 291-297.

Marques, Cláudia NH, David G. Davies, and Karin Sauer. "Control of biofilms with the fatty acid signaling molecule cis-2-decenoic acid." Pharmaceuticals 8, No. 4 (2015): 816-835.

Marquette, S. et al. Stability study of full-length antibody (anti-TNF alpha) loaded PLGA microspheres. International journal of pharmaceutics 470, 41-50 (2014).

Marshall JC (1988) Adhesion and growth of bacteria at surfaces in oligotrophic habitats. Can J Microbiol 34:503-506.

Martineau, L. & Davis, S. C. Controlling Methicillin Resistant *Staphyloccocus aureus* and Pseudomonas aeruginosa Wound Infections with a Novel Biomaterial. Journal of Investigative Surgery 20, 217-227, doi:doi:10.1080/10717540701481275 (2007).

Mashburn, L.M., Jett, A.M., Akins, D.R., and Whiteley, M. (2005) *Staphylococcus aureus* serves as an iron source for Pseudomonas aeruginosa during in vivo coculture. J Bacteriol 187: 554-566.

Mateo, Cesar, Jose M. Palomo, Gloria Fernandez-Lorente, Jose M. Guisan, and Roberto Fernandez-Lafuente. "Improvement of enzyme activity, stability and selectivity via immobilization techniques." Enzyme and microbial technology 40, No. 6 (2007): 1451-1463.

Matsukawa M, Greenberg EP (2004) Putative exopolysaccharide synthesis genes influence Pseudomonas aeruginosa biofilm development. J Bacteriol 186:4449-4456.

May TB et al (1991) Alginate synthesis by Pseudomonas aeruginosa: a key pathogenic factor in chronic pulmonary infections of cystic fibrosis patients. Clin Microbiol Rev 4:191-206.

McDougald, D., S.A. Rice, N. Barraud, P.D. Steinberg, S. Kjelleberg, Should we stay or should we go: mechanisms and ecological consequences for biofilm dispersal, Nat. Rev. Microbiol., 10 (2011), pp. 39-50.

Menon, J. U. et al. Polymeric nanoparticles for pulmonary protein and DNA delivery. Acta biomaterialia 10, 2643-2652 (2014).

Merritt JH, Brothers KM, Kuchma SL, O'Toole GA (2007) SadC reciprocally influences biofilm formation and swarming motility via modulation of exopolysaccharide production and flagellar function. J Bacteriol 189(22):8154-8164.

Mertz, P et al. Effects of an arginine-glycine-aspartic acid peptide-containing artificial matrix on epithelial migration in vitro and experimental second-degree burn wound healing in vivo. J Burn Care Rehabil. 17, 199-206 (J 1996).

Mertz, Patricia M., Maria F. Oliveira-Gandia, and Stephen C. Davis. "The evaluation of a cadexomer iodine wound dressing on methicillin resistant *Staphylococcus aureus* (MRSA) in acute wounds." Dermatologic surgery 25, No. 2 (1999): 89-93.

Mertz, Patricia M., Stephen C. Davis, Alejandro L. Cazzaniga, Anna Drosou, and William H. Eaglstein. "Barrier and antibacterial properties of 2-octyl cyanoacrylate-derived wound treatment films." Journal of cutaneous medicine and surgery 7, No. 1 (2003): 1-6.

Meyer W, Schwarz R, Neurand K. The Skin of Domestic Mammals as a Model for the Human Skin, with Special Reference to the Domestic Pig, In Skin-Drug Application and Evaluation of Environmental Hazards, p. 39-52 (Karger Publishers 1978).

(56) References Cited

OTHER PUBLICATIONS

Mikkelsen, H., Bond, N.J., Skindersoe, M.E., Givskov, M., Lilley, K.S., and Welch, M. (2009) Biofilms and type III secretion are not mutually exclusive in Pseudomonas aeruginosa. Microbiology 155: 687-698.
Morgan, R., Kohn, S., Hwang, S.-H., Hassett, D. J. & Sauer, K. BdlA, a chemotaxis regulator essential for biofilm dispersion in Pseudomonas aeruginosa. J. Bacteriol. 188, 7335-7343 (2006).
Morici, L.A., Carterson, A.J., Wagner, V.E., Frisk, A., Schurr, J.R., zu Bentrup, K.H., et al. (2007) Pseudomonas aeruginosa AlgR represses the Rhl quorum-sensing system in a biofilm-specific manner. J Bacteriol 189: 7752-7764.
Müller, J., M.C. Miller, A.T. Nielsen, G.K. Schoolnik, A.M. Spormann, vpsA and luxO-independent biofilms of Vibrio cholera, FEMS Microbiol. Lett., 275 (2007), pp. 199-206.
Nachin, L., Nannmark, U., and Nyström, T. (2005) Differential roles of the universal stress proteins of *Escherichia coli* in oxidative stress resistance, adhesion, and motility. J Bacteriol 187: 6265-6272.
Nadell, C.D., J.B. Xavier, S.A. Levin, K.R. Foster, The evolution of quorum sensing in bacterial biofilms, PLoS Biol., 6 (2008), p. e14.
Nadell, C.D., K. Drescher, K.R. Foster, Spatial structure, cooperation and competition in biofilms, Nat. Rev. Microbiol., 14 (2016), pp. 589-600.
Navarro, Gabriel, Andrew T. Cheng, Kelly C. Peach, Walter M. Bray, Valerie S. Bernan, Fitnat H. Yildiz, and Roger G. Linington. "Image-based 384-well high-throughput screening method for the discovery of skyllamycins A to C as biofilm inhibitors and inducers of biofilm detachment in Pseudomonas aeruginosa." Antimicrobial agents and chemotherapy 58, No. 2 (2014): 1092-1099.
Newman, J.R., and Fuqua, C. (1999) Broad-host-range expression vectors that carry the arabinose-inducible *Escherichia coli* araBAD promoter and the araC regulator. Gene 227: 197-203.
Nielsen, A.T., N.A. Dolganov, G. Otto, M.C. Miller, C.Y. Wu, G.K. Schoolnik, RpoS controls the Vibrio cholerae mucosal escape response, PLoS Pathog., 2 (2006), p. e109.
Niinikoski, J., Jussila, P. & Vihersaari, T. Radical mastectomy wound as a model for studies of human wound metabolism. The American Journal of Surgery 126, 53-58 (1973).
Nunes, Pedro S., Pelle D. Ohlsson, Olga Ordeig, and Jörg P. Kutter. "Cyclic olefin polymers: emerging materials for lab-on-a-chip applications." Microfluidics and nanofluidics 9, No. 2-3 (2010): 145-161.
Nusbaum, A. G et al. Effective Method to Remove Wound Bacteria: Comparison of Various Debridement Modalities in an In Vivo Porcine Model. Journal of Surgical Research 176, 701-707, doi:10. 1016/j.jss.2011.11.1040.
O'Toole G, Kaplan HB, Kolter R (2000) Biofilm formation as microbial development. Annu Rev Microbiol 54:49-79.
O'Toole, G.A., and Kolter, R. (1998) Initiation of biofilm formation in Pseudomonas fluorescens WCS365 proceeds via multiple, convergent signalling pathways: a genetic analysis. Mol Microbiol 28: 449-461.
O'Toole, G.A., G.C. Wong, Sensational biofilms: surface sensing in bacteria, Curr. Opin. Microbiol., 30 (2016), pp. 139-146.
O'Toole, G.A., Gibbs, K.A., Hager, P.W., Phibbs, P.V., Jr, and Kolter, R. (2000) The global carbon metabolism regulator Crc is a component of a signal transduction pathway required for biofilm development by Pseudomonas aeruginosa. J Bacteriol 182: 425-431.
Ochoa, S. Enzymic mechanisms in the citric acid cycle. Adv. Enzymol. Relat. Subj. Biochem. 15 (1954) 183-270.
Ohashi A, Harada H (1994a) Adhesion strength of biofilm developed in an attached-growth reactor. Water Sci Technol 20:10-11.
Ohashi A, Harada H (1994b) Characterization of detachment mode of biofilm developed in an attached-growth reactor. Water Sci Technol 30:35-45.
Ohashi A, Koyama T, Syutsubo K, Harada H (1999) A novel method for evaluation of biofilm tensile strength resisting erosion. Water Sci Technol 39:261-268.
Olga E. Petrova, Jill R. Schurr, Michael J. Schurr, and Karin Sauer, Microcolony formation by the opportunistic pathogen *Pseudomonas aeruginosa* requires pyruvate and pyruvate fermentation, Molecular Microbiology (2012) 86(4), 819-835, doi:10.1111/mmi.12018.
Özkütük, Ebru Birlik, Arzu Ersöz, Adil Denizli, and Rıdvan Say. "Preconcentration of phosphate ion onto ion-imprinted polymer." Journal of hazardous materials 157, No. 1 (2008): 130-136.
Papenfort, K., B.L. Bassler, Quorum sensing signal-response systems in Gram-negative bacteria, Nat. Rev. Microbiol., 14 (2016), pp. 576-588.
Papenfort, K., K.U. Förstner, J.P. Cong, C.M. Sharma, B.L. Bassler, Differential RNA-seq of Vibrio cholerae identifies the VqmR small RNA as a regulator of biofilm formation, Proc. Natl. Acad. Sci. USA, 112 (2015), pp. E766-E775.
Parthasarathy, Ranjani V., and Charles R. Martin. "Synthesis of polymeric microcapsule arrays and their use for enzyme immobilization." Nature 369, No. 6478 (1994): 298.
Pastar, I. et al. Interactions of Methicillin Resistant *Staphylococcus aureus* USA300 and Pseudomonas aeruginosa in Polymicrobial Wound Infection. PLoS ONE 8, e56846, doi:10.1371/journal.pone. 0056846 (2013).
Percival, S. L. & Bowler, P. G. Biofilms and their potential role in wound healing. Wounds—A Compendium of Clinical Research and Practice 16, 234-240 (2004).
Pérez-Osorio, A.C., Williamson, K.S., and Franklin, M.J. (2010) Heterogeneous rpoS and rhlR mRNA levels and 16S rRNA/rDNA (rRNA gene) ratios within Pseudomonas aeruginosa biofilms, sampled by laser capture microdissection. J Bacteriol 192: 2991-3000.
Petrova, O. E. & Sauer, K. Dispersion by Pseudomonas aeruginosa requires an unusual posttranslational modification of BdlA. Proc. National Acad. Sci. 109 16690-16695 (2012).
Petrova, O. E. & Sauer, K. PAS domain residues and prosthetic group involved in BdlA-dependent dispersion response by Pseudomonas aeruginosa biofilms. J. Bacteriol. 194, 5817-5828 (2012).
Petrova, O. E., Cherny, K. E. & Sauer, K. The diguanylate cyclase GcbA facilitates Pseudomonas aeruginosa biofilm dispersion by activating BdlA. Journal of Bacteriology 197.1, 174-187, doi:10.1128/jb.02244-14 (2015).
Petrova, O. E., Cherny, K. E. & Sauer, K. The P. aeruginosa diguanylate cyclase GcbA, a homolog of the P. fluorescens GcbA, promotes initial attachment to surfaces, but not biofilm formation, via regulation of motility. J. Bacteriol. 196, :2827-2841, doi:10.1128/jb.01628-14 (2014).
Petrova, O. E., Gupta, K., Liao, J., Goodwine, J. S. & Sauer, K. Divide and conquer: the Pseudomonas aeruginosa two-component hybrid SagS enables biofilm formation and recalcitrance of biofilm cells to antimicrobial agents via distinct regulatory circuits. Environmental Microbiology 19, 2005-2024, doi:10.1111/1462-2920. 13719 (2017).
Petrova, O. E., Schurr, J. R., Schurr, M. J. & Sauer, K. Microcolony formation by the opportunistic pathogen Pseudomonas aeruginosa requires pyruvate and pyruvate fermentation. Mol. Microbiol. 86, 819-835 (2012).
Petrova, O. E., Schurr, J. R., Schurr, M. J. & Sauer, K. The novel Pseudomonas aeruginosa two-component regulator BfmR controls bacteriophage-mediated lysis and DNA release during biofilm development through PhdA. Mol. Microbiol. 81, 767-783, doi:10.1111/j.1365-2958.2011.07733.x (2011).
Petrova, O.E., and Sauer, K. (2009) A novel signaling network essential for regulating Pseudomonas aeruginosa biofilm development. PLoS Pathog 5: e1000668.
Petrova, O.E., and Sauer, K. (2011) SagS contributes to the motile-sessile switch and acts in concert with BfiSR to enable Pseudomonas aeruginosa biofilm formation. J Bacteriol 193: 6614-6628.
Petrova, O.E., and Sauer, K. (2012) Sticky situations: key components that control bacterial surface attachment. J Bacteriol 194: 2413-2425.
Petrova, O.E., K. Sauer, Escaping the biofilm in more than one way: desorption, detachment or dispersion, Curr. Opin. Microbiol, 30 (2016), pp. 67-78.
Peyton BM, Characklis WG (1993) A statistical analysis of the effect of substrate utilization and shear stress on the kinetics of biofilm detachment. Biotechnol Bioeng 41:728-735.
Pierre, Sébastien J., Jens C. Thies, Alex Dureault, Neil R. Cameron, Jan CM van Hest, Noëlle Carette, Thierry Michon, and Ralf

(56) References Cited

OTHER PUBLICATIONS

Weberskirch. "Covalent enzyme immobilization onto photopolymerized highly porous monoliths." Advanced Materials 18, No. 14 (2006): 1822-1826.
Platt, M.D., Schurr, M.J., Sauer, K., Vazquez, G., KukavicaIbrulj, I., Potvin, E., et al. (2008) Proteomic, microarray, and signature-tagged mutagenesis analyses of anaerobic Pseudomonas aeruginosa at pH 6.5, likely representing chronic, late-stage cystic fibrosis airway conditions. J Bacteriol 190: 2739-2758.
Pollak, Alfred, Hugh Blumenfeld, Michael Wax, Richard L. Baughn, and George M. Whitesides. "Enzyme immobilization by condensation copolymerization into crosslinked polyacrylamide gels." Journal of the American Chemical Society 102, No. 20 (1980): 6324-6336.
Pratt LA, Kolter R (1999) Genetic analyses of bacterial biofilm formation. Curr Opin Microbiol 2:598-603.
Price-Whelan, A., Dietrich, L. E. P. & Newman, D. K. Pyocyanin alters redox homeostasis and carbon flux through central metabolic pathways in Pseudomonas aeruginosa PA14. J. Bacteriol. 189, 6372-6381, doi:10.1128/jb.00505-07 (2007).
Purevdorj-Gage B, Costerton WJ, Stoodley P (2005) Phenotypic differentiation and seeding dispersal in non-mucoid and mucoid Pseudomonas aeruginosa biofilms. Microbiology 151:1569-1576.
Puskas A, Greenberg EP, Kaplan S, Schaefer AL (1997) A quorum-sensing system in the free-living photosynthetic bacterium *Rhodobacter sphaeroides*. J Bacteriol 179:7530-7537.
Qhobosheane, Monde, Swadeshmukul Santra, Peng Zhang, and Weihong Tan. "Biochemically functionalized silica nanoparticles." Analyst 126, No. 8 (2001): 1274-1278.
Rahmani-Badi, Azadeh, Shayesteh Sepehr, Parisa Mohammadi, Mohammad Reza Soudi, Hamta Babaie-Naiej, and Hossein Fallahi. "A combination of cis-2-decenoic acid and antibiotics eradicates pre-established catheter-associated biofilms." Journal of medical microbiology 63, No. 11 (2014): 1509-1516.
Raitman, O. A., V. V. Arslanov, S. P. Pogorelova, and A. B. Kharitonov. "Molecularly imprinted polymer matrices for analysis of the cofactor NADH: a surface plasmon resonance study." In Doklady Physical Chemistry, vol. 392, No. 4-6, pp. 256-258. Kluwer Academic Publishers—Plenum Publishers, 2003.
Rajapaksa, T. E., Stover-Hamer, M., Fernandez, X., Eckelhoefer, H. A. & Lo, D. D. Claudin 4-targeted protein incorporated into PLGA nanoparticles can mediate M cell targeted delivery. Journal of Controlled Release 142, 196-205 (2010).
Ramos, Itzel, Lars EP Dietrich, Alexa Price-Whelan, and Dianne K. Newman. "Phenazines affect biofilm formation by Pseudomonas aeruginosa in similar ways at various scales." Research in microbiology 161, No. 3 (2010): 187-191.
Rani, S.A., Pitts, B., Beyenal, H., Veluchamy, R.A., Lewandowski, Z., Davison, W.M., et al. (2007) Spatial patterns of DNA replication, protein synthesis, and oxygen concentration within bacterial biofilms reveal diverse physiological states. J Bacteriol 189: 4223-4233.
Rasmussen, K., and Lewandowski, Z. (1998) Microelectrode measurements of local mass transport rates in heterogeneous biofilms. Biotechnol Bioeng 59: 302-309.
Rice SA et al (2005) Biofilm formation and sloughing in Serratia marcescens are controlled by quorum sensing and nutrient cues. J Bacteriol 187:3477-3485.
Rittman BR (1982) The effect of shear stress on biofilm loss rate. Biotechnol Bioeng 24:501-506.
Rochex A, Lebeault JM (2007) Effects of nutrients on biofilm formation and detachment of a Pseudomonas putida strain isolated from a paper machine. Water Res 41:2885-2992.
Rodrigues, Rafael C., Ángel Berenguer-Murcia, and Roberto Fernandez-Lafuente. "Coupling chemical modification and immobilization to improve the catalytic performance of enzymes." Advanced Synthesis & Catalysis 353, No. 13 (2011): 2216-2238.
Rodrigues, Rafael C., Claudia Ortiz, Ángel Berenguer-Murcia, Rodrigo Torres, and Roberto Fernández-Lafuente. "Modifying enzyme activity and selectivity by immobilization." Chemical Society Reviews 42, No. 15 (2013): 6290-6307.

Roger S, Michael M, Abdul K, Manfred N, Ute R (2004) GGDEF and EAL domains inversely regulate cyclic di-GMP levels and transition from sessility to motility. Mol Microbiol 53:1123-1134.
Romeo T (1998) Global regulation by the small RNA-binding protein CsrA and the non-coding RNA molecule CsrB. Mol Microbiol 29:1321-1330.
Romeo T, Gong M, Liu MY, Brun-Zinkemagel AM (1993) Identification and molecular characterization of csrA, a pleiotropic gene from *Escherichia coli* that affects glycogen biosynthesis, gluconeogenesis, cell size, and surface properties. J Bacteriol 175:4744-4755.
Rose, S. J. & Bermudez, L. E. *Mycobacterium avium* biofilm attenuates mononuclear phagocyte function by triggering hyperstimulation and apoptosis during early infection. Infect. Immun. 82, 405-412, doi:10.1128/iai.00820-13 (2014).
Ross P et al. (1990) The cyclic diguanylic acid regulatory system of cellulose synthesis in Acetobacter xylinum. Chemical synthesis and biological activity of cyclic nucleotide dimer, trimer, and phosphothioate derivatives. J Biol Chem 265:18933-18943.
Ryan RP et al. (2006) Cell-cell signaling in Xanthomonas campestris involves an HD-GYP domain protein that functions in cyclic di-GMP turnover. Proc Natl Acad Sci USA 103:6712-6717 [retracted article].
Sabnis NA, Yang H, Romeo T (1995) Pleiotropic regulation of central carbohydrate metabolism in *Escherichia coli* via the gene csrA. J Biol Chem 270:29096-29104.
Sah, H., Thoma, L. A., Desu, H. R., Sah, E. & Wood, G. C. Concepts and practices used to develop functional PLGA-based nanoparticulate systems. International Journal of Nanomedicine 8, 747-765, doi:10.2147/ijn.s40579 (2013).
San, K.-Y., Bennett, G.N., Berríos-Rivera, S.J., Vadali, R.V., Yang, Y.-T., Horton, E., et al. (2002) Metabolic engineering through cofactor manipulation and its effects on metabolic flux redistribution in *Escherichia coli*. Metab Eng 4: 182-192.
Sancineto, Luca, Miranda Piccioni, Stefania De Marco, Rita Pagiotti, Vanessa Nascimento, Antonio Luiz Braga, Claudio Santi, and Donatella Pietrella. "Diphenyl diselenide derivatives inhibit microbial biofilm formation involved in wound infection." BMC microbiology 16, No. 1 (2016): 220.
Santander-Ortega, M., Bastos-Gonzalez, D., Ortega-Vinuesa, J. & Alonso, M. Insulin-loaded PLGA nanoparticles for oral administration: an in vitro physico-chemical characterization. Journal of biomedical nanotechnology 5, 45-53 (2009).
Sauer, K., and Camper, A.K. (2001) Characterization of phenotypic changes in Pseudomonas putida in response to surface-associated growth. J Bacteriol 183: 6579-6589.
Sauer, K., Camper, A.K., Ehrlich, G.D., Costerton, J.W., and Davies, D.G. (2002) Pseudomonas aeruginosa displays multiple phenotypes during development as a biofilm. J Bacteriol 184: 1140-1154.
Sauer, K., M.C. Cullen, A.H. Rickard, L.A. Zeef, D.G. Davies, p. Gilbert, Characterization of nutrient-induced dispersion in Pseudomonas aeruginosa PAO1 biofilm, J. Bacteriol., 186 (2004), pp. 7312-7326.
Sauer, K., Steczko, J. & Ash, S. R. Effect of a solution containing citrate/methylene blue/parabens on *Staphylococcus aureus* bacteria and biofilm, and comparison with various heparin solutions. J. Antimicrob. Chemother. 63, 937-945, doi:10.1093/jac/dkp060 (2009).
Sauer, K., Thatcher, E., Northey, R. & Gutierrez, A. A. Neutral super-oxidised solutions are effective in killing P. aeruginosa biofilms. Biofouling 25, 45-54, doi:10.1080/08927010802441412 (2009).
Sawyer LK, Hermanowicz SW (1998) Detachment of biofilm bacteria due to variations in nutrient supply. Water Sci Technol 37:211-214.
Schneider, L. A., Korber, A., Grabbe, S. & Dissemond, J. Influence of pH on wound-healing: a new perspective for wound-therapy? Arch Dermatol Res 298, 413-420 (2007).
Schobert, M., and Jahn, D. (2010) Anaerobic physiology of Pseudomonas aeruginosa in the cystic fibrosis lung. Int J Med Microbiol 300: 549-556.
Schreiber K, Boes N, Eschbach M, Jaensch L, Wehland J, Bjarnsholt T, Givskov M, Hentzer M, Schobert M. Anaerobic survival of Pseudomonas aeruginosa by pyruvate fermentation requires an Usp-type stress protein. J. Bacteriol. 188, 659-668, doi: 10.1128/jb.188.2.659-668.2006 (2006).

(56) References Cited

OTHER PUBLICATIONS

Schweizer, H.P. (1991) The agmR gene, an environmentally responsive gene, complements defective glpR, which encodes the putative activator for glycerol metabolism in Pseudomonas aeruginosa. J Bacteriol 173: 6798-6806.

Scriba, P. and Holzer, H. Gewinnung von αHydroxyäthyl-2-thiaminpyrophosphat mit Pyruvatoxydase aus Schweineherzmuskel. Biochem. Z. 334 (1961) 473-486; Perham, R.N. Swinging arms and swinging domains in multifunctional enzymes: catalytic machines for multistep reactions. Annu. Rev. Biochem., 69, (2000) 961-1004. [PMID: 10966480], www.sbcs.qmul.ac.uk/iubmb/enzyme/EC1/2/4/1.html; en.wikipedia.org/wiki/Pyruvate_dehydrogenase; en.wikipedia.org/wiki/Pyruvate_dehydrogenase_complex.

Seaton, M., Hocking, A. & Gibran, N. S. Porcine models of cutaneous wound healing. ILAR Journal 56, 127-138 (2015).

Sellergren, Börje, ed. Molecularly imprinted polymers: man-made mimics of antibodies and their application in analytical chemistry. vol. 23. Elsevier, 2000.

Sen CK, Gordillo GM, Roy S, Kirsner R, Lambert L, Hunt TK, Gottrup F, Gurtner GC, Longaker MT. 2009. Human skin wounds: a major and snowballing threat to public health and the economy. Wound Repair and Regeneration 17:763-771.

Sepehr, Shayesteh, Azadeh Rahmani-Badi, Hamta Babaie-Naiej, and Mohammad Reza Soudi. "Unsaturated fatty acid, cis-2-decenoic acid, in combination with disinfectants or antibiotics removes pre-established biofilms formed by food-related bacteria." PLoS One 9, No. 7 (2014): e101677.

Seper, A., K. Pressler, A. Kariisa, A.G. Haid, S. Roier, D.R. Leitner, J. Reidl, R. Tamayo, S. Schild, Identification of genes induced in Vibrio cholerae in a dynamic biofilm system, Int. J. Med. Microbiol., 304 (2014), pp. 749-763.

Serralta, Victoria W., Catherine Harrison-Balestra, Alejandro L. Cazzaniga, Stephen C. Davis, and Patricia M. Mertz. "Lifestyles of bacteria in wounds: presence of biofilms?." Wounds 13, No. 1 (2001): 29-34.

Seth AK, Geringer MR, Gurjala AN, Hong SJ, Galiano RD, Leung KP, Mustoe TA. 2012. Treatment of Pseudomonas aeruginosa biofilm-infected wounds with clinical wound care strategies: a quantitative study using an in vivo rabbit ear model. Plastic and reconstructive surgery 129:262e-274e.

Seth AK, Geringer MR, Hong SJ, Leung KP, Galiano RD, Mustoe TA. 2012. Comparative analysis of single-species and polybacterial wound biofilms using a quantitative, in vivo, rabbit ear model. PLoS ONE 7:e42897.

Sharma, G., S. Sharma, P. Sharma, D. Chandola, S. Dang, S. Gupta, and R. Gabrani. "Escherichia coli biofilm: development and therapeutic strategies." Journal of applied microbiology 121, No. 2 (2016): 309-319.

Sheldon, Roger A. "Enzyme immobilization: the quest for optimum performance." Advanced Synthesis & Catalysis 349, No. 8-9 (2007): 1289-1307.

Sheldon, Roger A., and Sander van Pelt. "Enzyme immobilisation in biocatalysis: why, what and how." Chemical Society Reviews 42, No. 15 (2013): 6223-6235.

Shirtliff, M.E., Mader, J.T., and Camper, A.K. (2002) Molecular interactions in biofilms. Chem Biol 9: 859-871.

Shorrock, S. M. The exploration of tissue pH in wounds and its relationship to bacterial contamination. Master Degree Thesis, 20-24 (2000).

Short, M.B., C.A. Solari, S. Ganguly, T.R. Powers, J.O. Kessler, R.E. Goldstein, Flows driven by flagella of multicellular organisms enhance long-range molecular transport, Proc. Natl. Acad. Sci. USA, 103 (2006), pp. 8315-8319.

Siddiqui, A. R. & Bernstein, J. M. Chronic wound infection: facts and controversies. Clinics in dermatology 28, 519-526 (2010).

Silva, A. J., J. A. Benitez, Transcriptional regulation of Vibrio cholerae hemagglutinin/protease by the cyclic AMP receptor protein and RpoS, J. Bacteriol., 186 (2004), pp. 6374-6382.

Simm R, Morr M, Kader A, Nimtz M, Romling U (2004) GGDEF and EAL domains inversely regulate cyclic di-GMP levels and transition from sessility to motility. Mol Microbiol 53:1123-1134.

Singh, Ambareesh Kumar, and Meenakshi Singh. "Designing L-serine targeted molecularly imprinted polymer via theoretical investigation." Journal of Theoretical and Computational Chemistry 15, No. 05 (2016): 1650041.

Singh, Praveen K., Sabina Bartalomej, Raimo Hartmann, Hannah Jeckel, Lucia Vidakovic, Carey D. Nadell, and Knut Drescher. "Vibrio cholerae Combines Individual and Collective Sensing to Trigger Biofilm Dispersal." Current Biology 27, No. 21 (2017): 3359-3366.

Slater H, Alvarez-Morales A, Barber CE, Daniels MJ, Dow JM (2000) A two-component system involving an HD-GYP domain protein links cell-cell signalling to pathogenicity gene expression in Xanthomonas campestris. Mol Microbiol 38:986-1003.

Soheili, Vahid, Neda Khedmatgozar Oghaz, Zahra Sabeti Noughabi, and Bibi Sedigheh Fazly Bazzaz. "The novel effect of cis-2-decenoic acid on biofilm producing Pseudomonas aeruginosa." Microbiology Research 6, No. 1 (2016).

Somerville, G., Mikoryak, C.A., and Reitzer, L. (1999) Physiological characterization of Pseudomonas aeruginosa during exotoxin A synthesis: glutamate, iron limitation, and aconitase activity. J Bacteriol 181: 1072-1078.

Southey-Pillig, C.J., Davies, D.G., and Sauer, K. (2005) Characterization of temporal protein production in Pseudomonas aeruginosa biofilms. J Bacteriol 187: 8114-8126.

Spahn, Cynthia, and Shelley D. Minteer. "Enzyme immobilization in biotechnology." Recent patents on engineering 2, No. 3 (2008): 195-200.

Spoering, A. L. & Lewis, K. Biofilms and planktonic cells of Pseudomonas aeruginosa have similar resistance to killing by antimicrobials. J. Bacteriol. 183, 6746-6751, doi:10.1128/jb.183.23.6746-6751.2001 (2001).

Sriramulu, Dinesh D., Heinrich Liinsdorf, Joseph S. Lam, and Ute Römling. "Microcolony formation: a novel biofilm model of Pseudomonas aeruginosa for the cystic fibrosis lung." Journal of medical microbiology 54, No. 7 (2005): 667-676.

Stacy, A., L. McNally, S.E. Darch, S.P. Brown, M. Whiteley, The biogeography of polymicrobial infection, Nat. Rev. Microbiol., 14 (2016), pp. 93-105.

Stanley NR, Britton RA, Grossman AD, Lazazzera BA (2003) Identification of catabolite repression as a physiological regulator of biofilm formation by Bacillus subtilis by use of DNA microarrays. J Bacteriol 185:1951-1957.

Stewart PS (1993) A model of biofilm detachment. Biotechnol Bioeng 41:111-117.

Stewart, P.S. (1996) Theoretical aspects of antibiotic diffusion into microbial biofilms. Antimicrob Agents Chemother 40: 2517-2522.

Stewart, P.S., M.J. Franklin, Physiological heterogeneity in biofilms, Nat. Rev. Microbiol., 6 (2008), pp. 199-210.

Stewart, P.S., Mini-review: convection around biofilms, Biofouling, 28 (2012), pp. 187-198.

Stoodley P et al. (2001) Growth and detachment of cell clusters from mature mixed-species biofilms. Appl Environ Microbiol 67:5608-5613.

Stoodley, P., deBeer, D., and Lewandowski, Z. (1994) Liquid flow in biofilm systems. Appl Environ Microbiol 60: 2711-2716.

Stoodley, P., Yang, S., Lappin-Scott, H., and Lewandowski, Z. (1997) Relationship between mass transfer coefficient and liquid flow velocity in heterogeneous biofilms using microelectrodes and confocal microscopy. Biotechnol Bioeng 56: 681-688.

Storer, Christopher. "Molecularly Imprinted Polymer Sensors for the Detection of Phosphate in Agriculture." PhD diss., The University of Manchester, 2017.

Sullivan, T. P., Eaglstein, W. H., Davis, S. C. & Mertz, P. The pig as a model for human wound healing. Wound Repair and Regeneration 9, 66-76, doi:10.1046/j.1524-475x.2001.00066.x (2001).

Sumitani, M., Takagi, S., Tanamura, Y., and Inoue, H. (2004) Oxygen indicator composed of an organic/inorganic hybrid compound of methylene blue, reductant, surfactant and saponite. Anal Sci 20: 1153-1157.

(56) References Cited

OTHER PUBLICATIONS

Suriyanarayanan, Subramanian, Piotr J. Cywinski, Artur J. Moro, Gerhard J. Mohr, and Wlodzimierz Kutner. "Chemosensors based on molecularly imprinted polymers." In Molecular Imprinting, pp. 165-265. Springer, Berlin, Heidelberg, 2010.

Tai R et al (1998) Three cdg operons control cellular turnover of cyclic di-GMP in Acetobacter xylinum: genetic organization and occurrence of conserved domains in isoenzymes. J Bacteriol 180:4416 4425.

Taqieddin, Ehab, and Mansoor Amiji. "Enzyme immobilization in novel alginate-chitosan core-shell microcapsules." Biomaterials 25, No. 10 (2004): 1937-1945.

Tegl, G., Schiffer, D., Sigi, E., Heinzle, A. & Guebitz, G. M. Biomarkers for infection: enzymes, microbes, and metabolites. Applied Microbiology and Biotechnology 99, 4595-4614 (2015).

Teschler, J.K., D. Zamorano-Sánchez, A.S. Utada, C.J.A. Warner, G.C.L. Wong, R.G. Linington, F.H. Yildiz, Living in the matrix: assembly and control of Vibrio cholerae biofilms, Nat. Rev. Microbiol., 13 (2015), pp. 255-268.

Thelin, K.H., R.K. Taylor, Toxin-coregulated pilus, but not mannose-sensitive hemagglutinin, is required for colonization by Vibrio cholerae O1 E1 Tor biotype and O139 strains, Infect. Immun., 64 (1996), pp. 2853-2856, Positive selection vectors for allelic exchange, Gene, 169 (1996), pp. 47-52.

Thormann KM et al. (2006) Control of formation and cellular detachment from Shewanella oneidensis MR-1 biofilms by cyclic di-GMP. J Bacteriol 188:2681-2691.

Thormann, K.M., R.M. Saville, S. Shukla, A.M. Spormann, Induction of rapid detachment in Shewanella oneidensis MR-1 biofilms, J. Bacteriol., 187 (2005), pp. 1014-1021.

Tolker-Nielsen et al. T (2000) Development and dynamics of *Pseudomonas* sp. biofilms. J Bacteriol 182:6482-6489.

Toyofuku, M., Nomura, N., Fujii, T., Takaya, N., Maseda, H., Sawada, I., et al. (2007) Quorum sensing regulates denitrification in Pseudomonas aeruginosa PAO1 J Bacteriol 189: 4969-4972.

Trulear MG, Characklis WG (1982) Dynamics of biofilm processes. J Water Pollut Control Fed 9:1288-1301.

Van Alst, N.E., Picardo, K.F., Iglewski, B.H., and Haidaris, C.G. (2007) Nitrate sensing and metabolism modulate motility, biofilm formation, and virulence in Pseudomonas aeruginosa. Infect Immun 75: 3780-3790.

Van Loosdrecht MCM, Picioreanu C, Heijnen JJ (1997) A more unifying hypothesis for the structure of microbial biofilms. FEMS Microbiol Ecol 24:181-183.

Vats N, Lee SF (2000) Active detachment of Streptococcus mutans cells adhered to epon-hydroxylapatite surfaces coated with salivary proteins in vitro. Arch Oral Biol 45:305-314.

Vihersaari, T., Kivisaari, J. & Niinikoski, J. Effect of changes in inspired oxygen tension on wound metabolism. Annals of surgery 179, 889 (1974).

Waite, R., Paccanaro, A., Papakonstantinopoulou, A., Hurst, J., Saqi, M., Littler, E., & Curtis, M. (2006) Clustering of Pseudomonas aeruginosa transcriptomes from planktonic cultures, developing and mature biofilms reveals distinct expression profiles. BMC Genomics 7: 162.

Walters, M.C. III, Roe, F., Bugnicourt, A., Franklin, M.J., and Stewart, P.S. (2003) Contributions of antibiotic penetration, oxygen limitation, and low metabolic activity to tolerance of Pseudomonas aeruginosa biofilms to ciprofloxacin and tobramycin. Antimicrob Agents Chemother 47: 317-323.

Wang LH et al. (2004) A bacterial cell-cell communication signal with cross-kingdom structural analogues. Mol Microbiol 51:903-912.

Wang, J. F., Olson, M. E., Reno, C. R., Wright, J. B. & Hart, D. A. The pig as a model for excisional skin wound healing: characterization of the molecular and cellular biology, and bacteriology of the healing process. Comparative medicine 51, 341-348 (2001).

Wang, Zhen-Gang, Ling-Shu Wan, Zhen-Mei Liu, Xiao-Jun Huang, and Zhi-Kang Xu. "Enzyme immobilization on electrospun polymer nanofibers: an overview." Journal of Molecular Catalysis B: Enzymatic 56, No. 4 (2009): 189-195.

Whitchurch CB, Tolker-Nielsen T, Ragas PC, Mattick JS (2002) Extracellular DNA required for bacterial biofilm formation. Science 295:1487.

Winsor, G.L., Van Rossum, T., Lo, R., Khaira, B., Whiteside, M.D., Hancock, R.E.W., and Brinkman, F.S.L. (2009) Pseudomonas genome database: facilitating user-friendly, comprehensive comparisons of microbial genomes. Nucleic Acids Res 37: D483-D488.

Wolcott R, Rhoads D, Bennett M, Wolcott B, Gogokhia L, Costerton J, Dowd S. Chronic wounds and the medical biofilm paradigm. J. Wound Care 19:45-46,48-50,52-43 (2010).

Wu, M., Guina, T., Brittnacher, M., Nguyen, H., Eng, J., and Miller, S.I. (2005) The Pseudomonas aeruginosa proteome during anaerobic growth. J Bacteriol 187: 8185-8190.

Wu, Z., and Irizarry, R.A. (2004) Preprocessing of oligonucleotide array data. Nat Biotechnol 22: 656-658.

Xing, Rongrong, Shuangshou Wang, Zijun Bie, Hui He, and Zhen Liu. "Preparation of molecularly imprinted polymers specific to glycoproteins, glycans and monosaccharides via boronate affinity controllable-oriented surface imprinting." Nature protocols 12, No. 5 (2017): 964.

Xun L, Mah RA, Boone DR (1990) Isolation and characterization of disaggregatase from Methanosarcina mazei LYC. Appl Environ Microbiol 56:3693-3698.

Yaehne, K. et al. Nanoparticle accumulation in angiogenic tissues: towards predictable pharmacokinetics. Small 9, 3118-3127 (2013).

Yager, D. R. & Nwomeh, B. C. The proteolytic environment of chronic wounds. Wound Repair and Regeneration 7, 433-441 (1999).

Yan, J., C.D. Nadell, B.L. Bassler, Environmental fluctuation governs selection for plasticity in biofilm production, ISME J., 11 (2017), pp. 1569-1577.

Yang, L., Barken, K.B., Skindersoe, M.E., Christensen, A.B., Givskov, M., and Tolker-Nielsen, T. (2007) Effects of iron on DNA release and biofilm development by Pseudomonas aeruginosa. Microbiology 153: 1318-1328.

Yarmush, D. M. et al. Cutaneous burn injury alters relative tricarboxylic acid cycle fluxes in rat liver. Journal of Burn Care & Research 20, 292-302 (1999).

Yarwood, J.M., D.J. Bartels, E.M. Volper, E.P. Greenberg, Quorum sensing in *Staphylococcus aureus* biofilms, J. Bacteriol., 186 (2004), pp. 1838-1850.

Yildiz, F.H., G.K. Schoolnik, Role of rpoS in stress survival and virulence of Vibrio cholera, J. Bacteriol., 180 (1998), pp. 773-784.

Yoon, S.S., Hennigan, R.F., Hilliard, G.M., Ochsner, U.A., Parvatiyar, K., Kamani, M.C., et al. (2002) Pseudomonas aeruginosa anaerobic respiration in biofilms: relationships to cystic fibrosis pathogenesis. Dev Cell 3: 593-603.

Zhu, J., J.J. Mekalanos, Quorum sensing-dependent biofilms enhance colonization in Vibrio cholera, Dev. Cell, 5 (2003), pp. 647-656.

\* cited by examiner

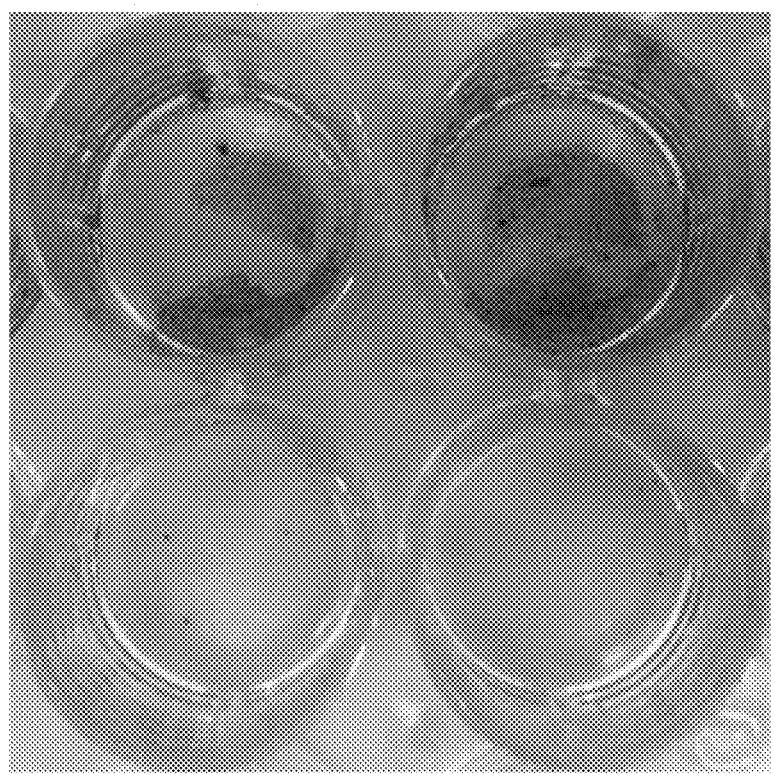
Fig. 2D
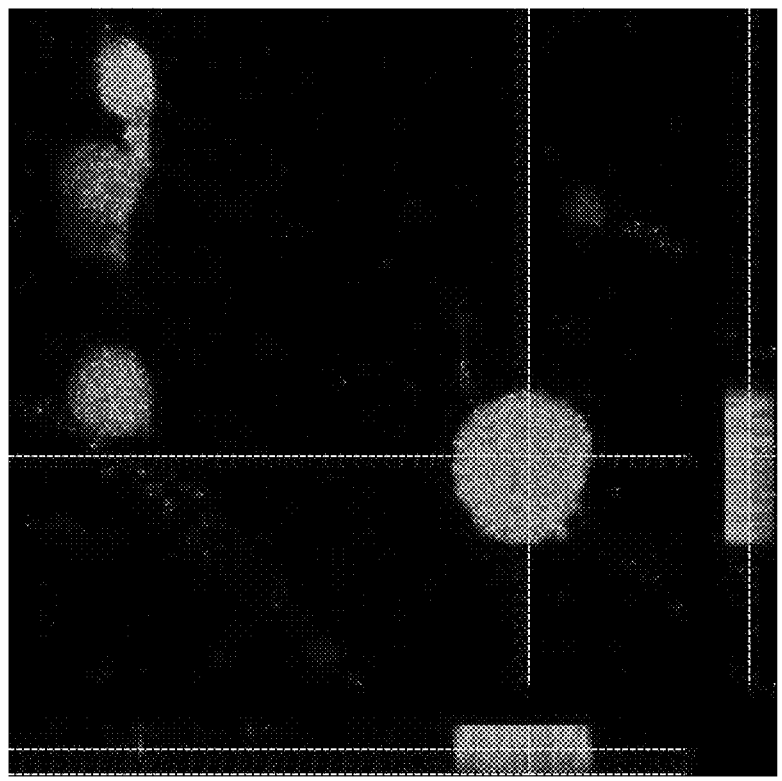
Fig. 2E1
Untreated

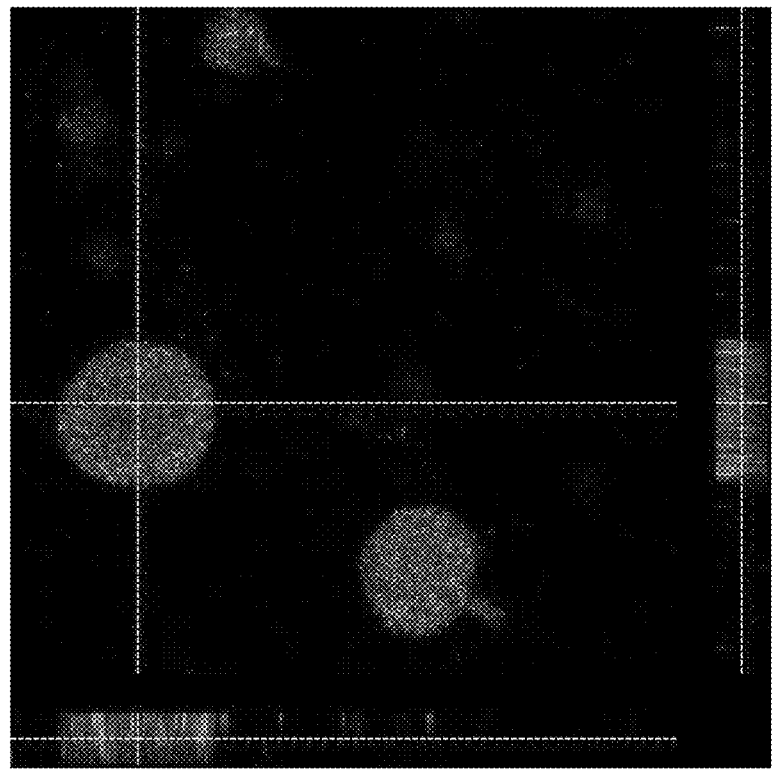
Fig. 2E2
Heat-inactivated PDH
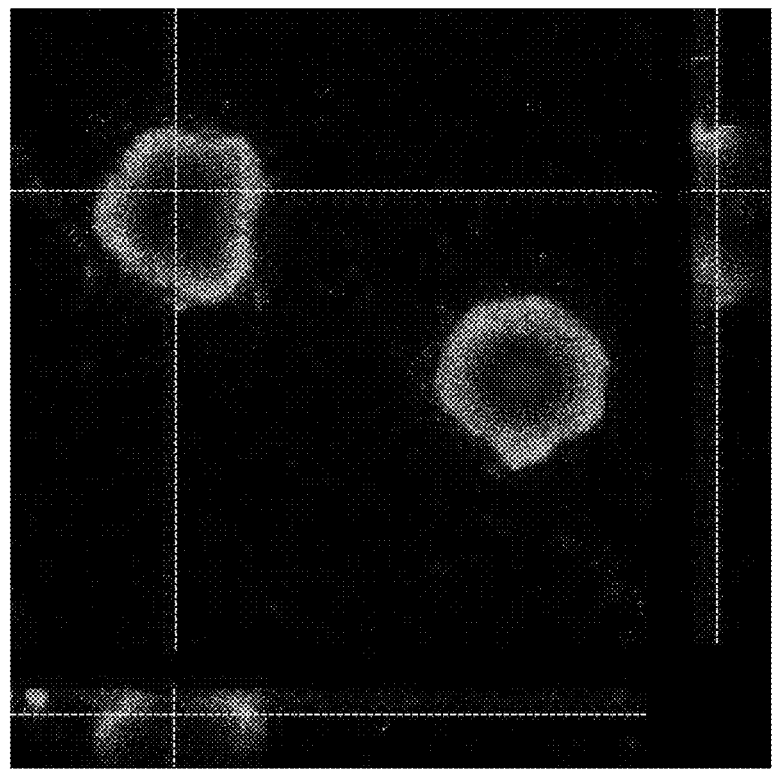
Fig. 2E3
PDH

Fig. 2F1
Not Dispersed

Fig. 2F2
Dispersed

Dispersed

Non-dispersed

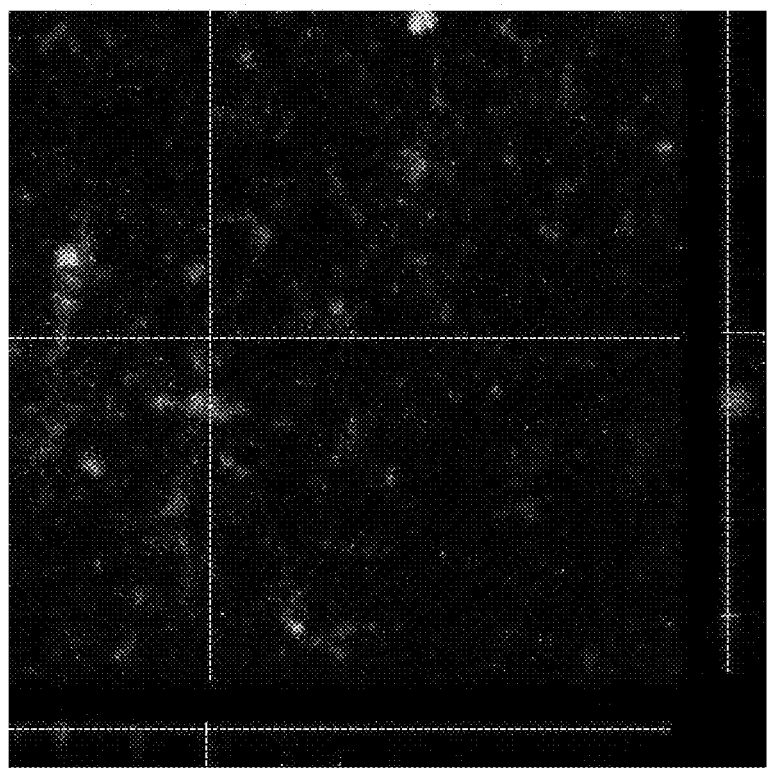
Fig. 4D1
**PAO1 ΔmifR
untreated**
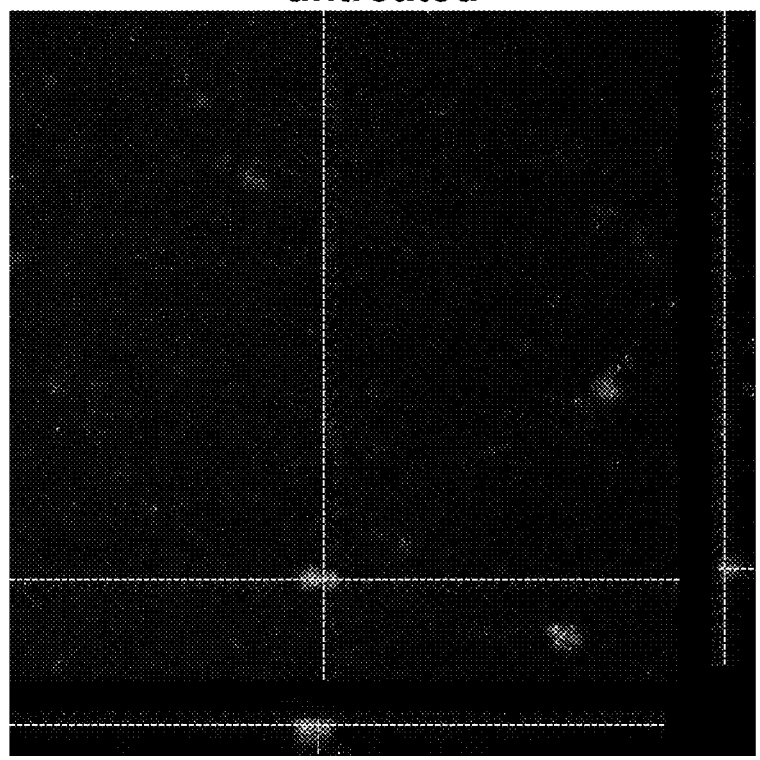
Fig. 4D2
PAO1 ΔmifR + PDH

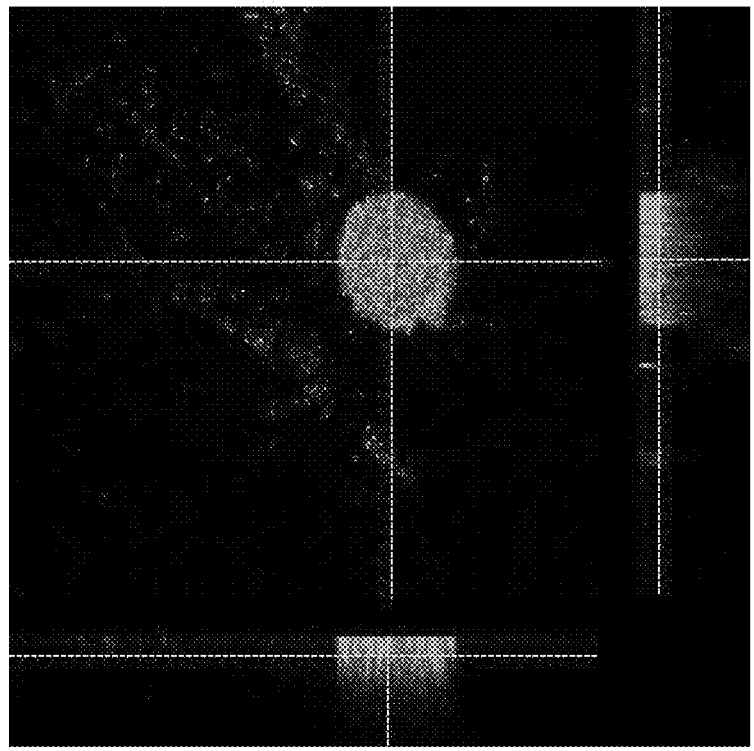
Fig. 4D3
**PAO1 ΔmifR/pJN-*mifR*
untreated**
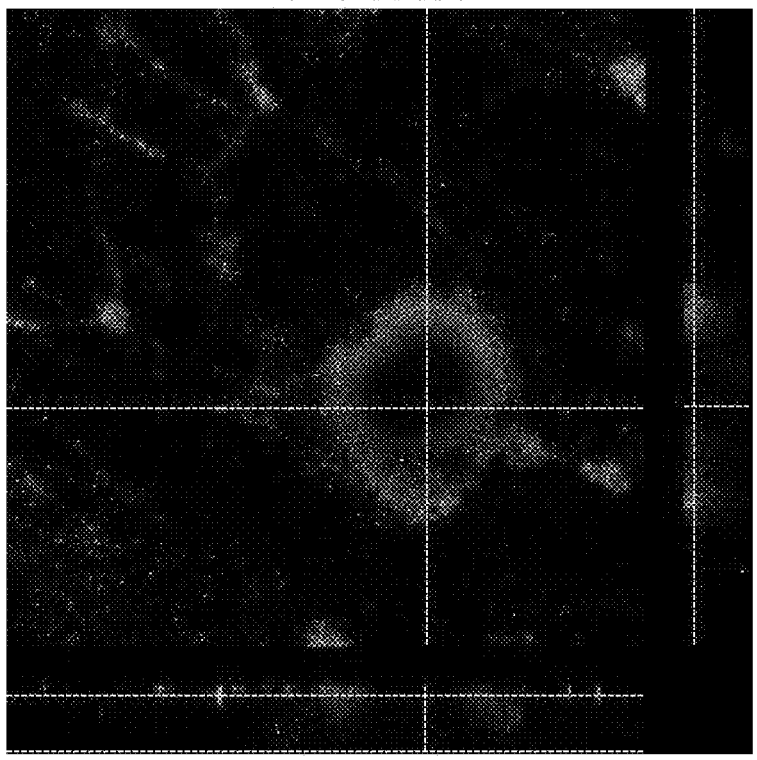
Fig. 4D4
**PAO1 ΔmifR/pJN-*mifR* + PDH**

Pyc: pyruvate carboxylase

Ldh: fermentative lactate dehydrogenase

Pdh: pyruvate dehydrogenase

Pta: phosphotransacetylase;

Ad-DH: aldehyde dehydrogenase

AckA: acetate kinase

Mdh: malate dehydrogenase

Fum: fumarase

Frd: fumarate reductase

PDC Mechanism with pyruvate (R=H)

COMPOSITIONS AND METHODS FOR DISRUPTING BIOFILM FORMATION AND MAINTENANCE

CROSS REFERENCE TO RELATED APPLICATION

The present application is a non-provisional of, and claims benefit of priority under 35 U.S.C. 119(e) from, U.S. Provisional Patent Application No. 62/793,370, filed Jun. 1, 2018, the entirety of which is expressly incorporated herein by reference.

GOVERNMENT LICENSE RIGHTS

This invention was made with government support under 1R56AI127815 awarded by the National Institutes of Health (NIH). The government has certain rights in the invention.

FIELD OF THE INVENTION

The present invention relates to compositions and methods for treating biofilms and infections associated with biofilms, and disrupting biofilm formation and maintenance.

BACKGROUND OF THE INVENTION

Each reference cited herein is expressly incorporated herein in its entirety. Biofilms are surface-associated bacterial communities that are matrix-encased, and may cause persistent and chronic infections in medical settings. Biofilm-related infections include chronic urinary tract infection due to catheters, chronic wounds (e.g., diabetic, burn, surgical), ventilated-associated pneumonia in intubated patients, chronic pulmonary disease in patients with cystic fibrosis or chronic obstructive lung disease. According to the National Institutes of Health, 65 percent of all hospital-acquired infections are due to bacteria growing as biofilms, and 80 percent of chronic infections are linked to biofilms. To put this in perspective, the Center for Disease Control estimates that hospital-acquired infections account for an estimated 1.7 million infections and 99,000 associated deaths each year in American hospitals alone. The high morbidity and mortality rate is due to biofilms being extremely difficult to control in medical settings. In fact, conventional therapies have proven inadequate in the treatment of many (if not most) chronic biofilm infections, due to the extraordinary tolerance of biofilms to available antimicrobial agents relative to their planktonic counterparts, and their ability to inhibit healing.

A hallmark of biofilms is their extreme tolerance to antimicrobial agents, rendering infections by biofilms recalcitrant to conventional treatment therapies. This has brought on the realization that successful treatment of biofilm infections will require the development of novel treatment strategies. It is thus not surprising that biofilm dispersion, a regulatory response to environmental cues, allowing bacterial cells to convert to the planktonic state, has become a major focus of recent research endeavors to combat biofilms. However, while much attention has been paid to agents inducing biofilm dispersion, little is known about the mechanism underlying dispersion. *P. aeruginosa* has been previously shown to require autogenously produced pyruvate and pyruvate fermentative processes as a means of redox balancing to form microcolonies, with depletion of pyruvate or inactivation of components of the pyruvate fermentation pathway impairing biofilm formation (See FIG. 1). Olga E. Petrova, Jill R. Schurr, Michael J. Schurr, and Karin Sauer, Microcolony formation by the opportunistic pathogen *Pseudomonas aeruginosa* requires pyruvate and pyruvate fermentation, Molecular Microbiology (2012) 86(4), 819-835, doi:10.1111/mmi.12018.

Bacterial infections are common complication of burn wounds, with surface-associated communities of bacteria known as biofilms forming within human burn wounds within 10-24 hr. of thermal injury. The presence of biofilms in burns is problematic as biofilms are recalcitrant to killing by antimicrobial agents, thus rendering conventional treatment strategies ineffective, with 75% of extensively burned patients dying as a consequence of severe infection.

Cells associated with biofilms are up to 1000-fold less susceptible to various antibiotics than their planktonic counterparts. For instance, the development of antimicrobial burn creams was considered a major advance in the care of burn wound patients, yet infections of wounds remain the most common cause of morbidity and mortality among the 6.5 million people suffering from wounds in the United States alone, causing over 200,000 deaths annually. The most affected are people suffering from burn wounds, for which almost 61% of deaths are caused by infection. Treatment failure has been primarily attributed to the virulence factors produced by the principal wound pathogens *Staphylococcus aureus* and *Pseudomonas aeruginosa* as well as their ability to form biofilms in wounds, which are recalcitrant to antibiotic treatment and the host immune defense.

*Pseudomonas aeruginosa* is responsible for a wide array of persistent infections including those of non-healing wounds and the lungs of cystic fibrosis sufferers. Within the cystic fibrosis lung, *P. aeruginosa* forms biofilms, defined as complex surface-attached communities encased in an extracellular matrix composed of exopolysaccharides, DNA and proteins. A hallmark of *P. aeruginosa* biofilms is the presence of complex multicellular aggregates or microcolonies, the formation of which has been observed both in vitro and in vivo (Lam et al., 1980; Høiby et al., 2001; Sauer et al., 2002; Davey et al., 2003; Garcia-Medina et al., 2005; Sriramulu et al., 2005) and has been associated with DNA release and elevated mutation rates (Allesen-Holm et al., 2006; Conibear et al., 2009). Iron has been demonstrated to control microcolony formation, as *P. aeruginosa* mutants inactivated in the high-affinity pyoverdine iron acquisition system only form thin unstructured biofilms even when grown in iron-sufficient medium (Banin et al., 2005). While the findings implicated iron as a signal for development of mushroom-like microcolonies, Yang et al. (2007) demonstrated microcolony formation to be favored in media with low iron availability, with increasing iron concentrations resulting in decreased microcolony formation and DNA release. Microcolony formation coincides with the formation of steep oxygen and nutrient gradients, with cells located deep within biofilm structures experiencing stressful, growth-limiting conditions (Anderl et al., 2003; Walters et al., 2003; Borriello et al., 2004). Microelectrode analyses have revealed that, while the concentration of oxygen at the surface of the biofilm is similar to that of the bulk fluid, oxygen levels drop rapidly towards the interior of biofilms with the center of microcolonies being essentially anaerobic (de Beer et al., 1994; Stoodley et al., 1994; 1997; Rasmussen and Lewandowski, 1998; Rani et al., 2007). Additional gradients exist in the biofilm environment with respect to microbial waste products, sulphide and hydrogen ions (pH), which may accumulate within the depths of the biofilm (de Beer et al., 1994; Stoodley et al., 1994; 1997; Rasmussen and Lewandowski, 1998; Raniet al., 2007).

The resident bacterial population has been demonstrated to adjust to these steep gradients through various approaches including the modulation of metabolic rates, dormancy, stress responses and mutation rates (Stewart, 1996; Anderl et al., 2000; Walters et al., 2003; Borriello et al., 2004; Lenz et al., 2008; Perez-Osorio et al., 2010). Selected metabolic pathways have been associated with biofilm formation, serving both as contributing factors and adaptations to the changing biofilm microenvironment. For instance, availability of amino acids appears to contribute to biofilm formation, as inactivation of the stationary phase sigma factor RpoS has been shown to enhance biofilm formation by alleviating potential amino acid limitation (Shirtliff et al., 2002). Inactivation of the catabolite repression control (Crc) protein, involved in carbon metabolism regulation and control of type IV pili gene expression, resulted in the formation of cellular monolayers devoid of microcolonies typically observed during normal biofilm development (O'Toole et al., 2000). Furthermore, under conditions of oxygen absence or limitation, P. aeruginosa is able to respire nitrate or nitrite through the process of denitrification, which sequentially reduces nitrate to nitrogen gas through the action of four reductases (Carlson et al., 1982; Carlson and Ingraham, 1983; Davies et al., 1989). The activation/upregulation of the components of the denitrification pathway has been repeatedly observed within in vitro biofilms and during persistent P. aeruginosa infections, with sensing and processing of nitrate and other intermediate forms playing an essential role in the establishment, maintenance, resistance and dispersal of biofilms in vitro and in vivo (Hassett et al., 2002; 2009; Borriello et al., 2004; Barraud et al., 2006; Filiatrault et al., 2006; Alvarez-Ortega and Harwood, 2007; Toyofuku et al., 2007; Van Alst et al., 2007; Schobert and Jahn, 2010). Many environments, however, do not have sufficient nitrate present to drive nitrate respiration. Under conditions of oxygen limitation in the absence of nitrate, growth is driven by oxygen respiration, done using high-affinity terminal oxidases including cbb3-1 and cbb3-2 (Comolli and Donohue, 2004; Alvarez-Ortega and Harwood, 2007).

UspK has been previously shown to be essential for survival on pyruvate under conditions of oxygen limitation (Schreiber et al., 2006), with P. aeruginosa PA14 being able to release pyruvate, using a pyocyanin-dependent mechanism, and subsequently utilize pyruvate during stationary phase (Price-Whelan et al., 2007). Genes associated with pyruvate fermentation are downregulated in mifR mutant biofilms (Tables 3 and S4), pyruvate utilization contributes to biofilm formation and the establishment of microcolonies. Exogenously added pyruvate supports biofilm development in wild type PA14 biofilms. Addition of pyruvate (0.1-1 mM) to the growth medium (diluted LB medium) resulted in enhanced microcolony formation by wild type biofilms with the average diameter of microcolonies increasing 1.6-fold in the presence of 1 mM pyruvate. Addition of 1 mM pyruvate did not enhance growth of P. aeruginosa grown planktonically under fully aerated conditions. However, the presence of 25 mM pyruvate as the sole carbon source supported some growth by P. aeruginosa.

As increased availability of pyruvate coincided with enhanced microcolony formation, when grown in LB or VBMM medium, lack of pyruvate abrogates microcolony formation by enzymatically depleting pyruvate from the growth medium using pyruvate dehydrogenase (PDH). Under the conditions tested, the presence of pyruvate dehydrogenase and the appropriate cofactors (CoA, NADH) did not affect growth in broth when grown in microtiter plates, as determined by absorbance (not shown). However, presence of PDH during the early stages of biofilm development impaired microcolony formation, with PDH-treated biofilms containing infrequent thin and unstructured clusters not exceeding 20 μm in diameter. In contrast, biofilms treated with heat-inactivated PDH or cofactors alone were similar to untreated biofilms and characterized by widespread microcolonies exceeding 150 μm in diameter.

The findings strongly supported a requirement for pyruvate in the process of biofilm microcolony formation regardless of medium used.

NADH-dependent lactate dehydrogenase LdhA has been previously shown to be required for anaerobic pyruvate utilization and long-time survival on pyruvate (Eschbach et al., 2004). In addition, aconitate hydratase AcnA, plays a role in tricarboxylic acid cycle, glyoxylate bypass and acetyl-CoA assimilation (and only indirectly in pyruvate utilization) (Somerville et al., 1999; Winsor et al., 2009). Inactivation of acnA resulted in impaired biofilm formation as indicated by biofilms being characterized by up to 10-fold reduced biofilm biomass and thickness as compared to wild type biofilms. Complementation restored biofilm formation to wild type levels. Similarly, expression of mifR in the acnA mutant did result in significantly enhanced biofilm and microcolony formation, with parameters including biomass and thickness increasing more than fourfold when compared to the acnA mutant alone. These suggest that, while AcnA contributes to biofilm formation, AcnA acts downstream of MifR and is probably not the direct cause of the MifR or pyruvate-dependent microcolony formation phenotypes. This is in part based on the finding of AcnA being required not only for pyruvate utilization but also for the tricarboxylic acid cycle, glyoxylate bypass and acetyl-CoA assimilation.

Inactivation of ldhA resulted in fourfold reduced biofilm biomass accumulation and reduced thickness while complementation restored biofilm formation to wild type levels. Overall, the architecture of ldhA mutant biofilms was similar to that observed for mifR mutant biofilms and was only composed of small clusters less than 20 μm in diameter. Furthermore, in contrast to the results observed for acnA::Mar, expression of mifR in ldhA mutant biofilms failed to restore biofilm and microcolony formation to wild type levels, with ldhA::Mar/pMJT-mifR demonstrating the same biofilm architecture as the ldhA mutant. This supports a role for LdhA and pyruvate fermentation in microcolony formation.

Exogenous pyruvate and lactate dehydrogenase, associated with pyruvate utilization under limited-oxygen conditions, are required for microcolony formation. The ldhA mutant did not respond to the addition of pyruvate (grown in diluted LB), with the strain demonstrating similar defects in biofilm formation in the absence and presence of exogenous pyruvate. Similar results were obtained when VBMM medium was used. Expression of ldhA in PA14, while not increasing the overall biofilm biomass, correlated with a significant increase in microcolony formation. The increase in microcolony formation was comparable to the increase observed upon pyruvate addition. Expression of ldhA in mifR mutant biofilms fully restored the biofilm architecture to wild type levels, resulting in a significant increase in biofilm biomass accumulation and more importantly, the formation of microcolonies exceeding >150 μm in diameter. To determine whether ldhA mutant biofilms demonstrated a significantly increased NADH/NAD+ratio compared to wild type, while overexpression of ldhA significantly decreased the available NADH as indicated by a decreased NADH/NAD+ratio compared to wild type biofilms. There is thus an inverse correlation between NADH/NAD+ratio and microcolony formation. The presence of pyocyanin has been demonstrated to alter NADH/NAD+ratios (Price-Whelan et al., 2007).

Differential expression of ldhA resulted in an overall similar trend with respect to NADH/NAD+ratios as those obtained under biofilm growth conditions, with ldhA mutant demonstrating increased NADH/NAD+ratios and overexpression of ldhA correlating with decreased NADH/NAD+ ratios compared to wild type. Inactivation of mifR resulted in significantly increased NADH/NAD+ratio compared to wild type, while expression of mifR or ldhA in mifR mutants restored the NADH/NAD+ratio to wild type levels. There is thus a requirement for pyruvate in biofilm microcolony formation, with the observed effects likely being mediated via the pyruvate fermentation pathway, probably as a means of redox balancing.

*P. aeruginosa* is capable of fermentatively utilizing pyruvate for survival under conditions of oxygen limitation in the absence of nitrite and nitrate (Eschbach et al., 2004; Schreiber et al., 2006). The process involves the conversion of pyruvate to lactate, acetate and/or succinate, with the lactate and acetate-producing branches of the pathway apparently predominating. Inactivation of lactate dehydrogenase (LdhA), which converts pyruvate to lactate and regenerates NAD+, severely impairs pyruvate fermentation and compromises survival on pyruvate under conditions of energy (electron) richness (Eschbach et al., 2004). Pyruvate does not support growth under strictly anaerobic growth conditions. Moreover, while addition of 0.1-1 mM of pyruvate to 24-well grown *P. aeruginosa* is not sufficient to increase growth, higher concentrations of pyruvate are capable of sustaining growth under aerobic and oxygen limiting (but not anaerobic) conditions. Pyruvate therefore appears to be used as a means of redox balancing. Consistent with a role of LdhA in regenerating reducing equivalents under oxygen-limiting conditions, expression of LdhA in *P. aeruginosa* wild type correlated with a significant increase in biofilm biomass accumulation and microcolony formation as well as restoration of the mifR mutant biofilm phenotype to wild type levels and decreased NADH/NAD+ratios. Redox balancing appears required to enable microcolony formation in biofilms.

Pyruvate appears to be produced by the resident biofilm bacteria. A model recently proposed by Schobert and Jahn (2010) places *P. aeruginosa* biofilm cells within different niches, with metabolically active cells exposed to oxygen secreting pyruvate, which then diffuses into the anoxic zones to be utilized by cells residing within these layers. Consistent with this model is the pyruvate-dependent formation of microcolonies, with depletion of extracellular pyruvate impairing biofilm development and abrogating microcolony formation, while addition of exogenous pyruvate enhances biofilm development by specifically promoting microcolony formation. Pyruvate is released into the extracellular environment by *P. aeruginosa* PA14 during stationary phase in a manner dependent on the redox-active phenazine pyocyanin (Price-Whelan et al., 2007). Although phenazine production does not impact the ability of *P. aeruginosa* PA14 to attach to surfaces, mutants unable to synthesize phenazines including pyocyanin were impaired in microcolony formation (Dietrich et al., 2008; Ramos et al., 2010). Moreover, *P. aeruginosa* PA14 differs from PAO1 with respect to pyocyanin levels with PA14 producing more pyocyanin than PAO1 (Dietrich et al., 2006) as well as secreting more pyruvate (Price-Whelan et al., 2007). Increased pyocyanin and pyruvate release correlates with observation of *P. aeruginosa* PA14 biofilms forming significantly larger microcolonies following 6 days of growth under continuous flowing conditions and earlier initiation of microcolony formation compared to PAO1.

Usp proteins, which are conserved across all domains of life, have been implicated in the response to hypoxic conditions and establishment of chronic, persistent infections by *Mycobacterium tuberculosis* (Drumm et al., 2009), stress-mediated adhesion and motility in *Escherichia coli* (Nachin et al., 2005) and the process of biofilm formation by *Porhyromonas gingivalis* (Kuramitsu et al., 2005; Chen et al., 2006). In *P. aeruginosa*, increased expression of all five Usp proteins has been consistently observed under conditions of oxygen limitation, in laboratory-grown biofilms (Yoon et al., 2002; Waite et al., 2006; Alvarez-Ortega and Harwood, 2007), and in the context of in vivo infections (Mashburn et al., 2005; Bielecki et al., 2011). Usp proteins enable anaerobic growth and/or survival of *P. aeruginosa*, with inactivation of uspN and uspK having been linked to premature cell death during long-term anaerobic existence (Eschbach et al., 2004; Boes et al., 2006; Schreiber et al., 2006). However, UspN and UspK do so via distinct rather than converging mechanisms. UspN is required for survival when cells experience anaerobic energy stress and starvation, with a mutant strain demonstrating significantly reduced cell recovery after prolonged exposure to such conditions (Boes et al., 2006; 2008), while UspK is essential for *P. aeruginosa* anaerobic survival via pyruvate fermentation (Eschbach et al., 2004; Schreiber et al., 2006). This difference in mechanisms was apparent with respect to microcolony formation. The small biomass accumulation defect observed following UspN inactivation suggests that subpopulations of biofilm cells experiencing anaerobic energy starvation likely utilize systems such as UspN to promote survival. In contrast, inactivation of UspK resulted in severely reduced microcolonies and biomass, strongly supporting a requirement for UspK in microcolony formation. Given that UspK plays a substantial role during fermentative growth on pyruvate, but is not required for denitrification (Schreiber et al., 2006), these findings strongly underscore the requirement for pyruvate fermentation as a means of addressing oxygen limitation of the biofilm microcolony microenvironment and the need for redox balancing.

Bacteria present within microcolonies experience an environment that is distinct from environmental conditions elsewhere in the biofilm. Within microcolonies, *P. aeruginosa* cells experience low oxygen but energy (electron)-rich conditions and use fermentative processes for survival and growth. In particular, pyruvate is required for microcolony formation by *P. aeruginosa* with changes in extracellular pyruvate levels positively correlating with average biofilm cellular aggregate sizes. Pyruvate contributes to growth of biofilm microcolonies via pyruvate fermentation as a means of redox balancing with inactivation of lactate dehydrogenase preventing biofilm development and microcolony formation.

Pyruvate dehydrogenase is the enzyme that catalyzes conversion of pyruvate to acetyl-CoA and NADH, with an intermediate decarboxylation, in the presence of CoA and NAD+. Thiamine phosphate (TPP) is required for pyruvate dehydrogenase activity, but TPP is not involved in the biochemical reaction. See FIG. 18, which represents various standard biochemical pathways involving pyruvate.

*P. aeruginosa* produces and secretes up to 10 mM pyruvate, with pyruvate having been shown to be required for long-term bacterial survival (without serving as a carbon source).

Pyruvate plays an essential role in the formation of biofilms, as continuous depletion of pyruvate (via pyruvate dehydrogenase [PDH, 0.57 U/mg specific activity] plus cofactors) from the growth medium prevented biofilm formation. Pyruvate is required to cope with stressful, oxygen-limiting but electron-rich conditions, referred to as 'reductive stress' (too much NADH/electrons, not enough $O_2$) present in biofilms. This is apparent by the activation of pyruvate fermentation pathways in biofilms, and mutant strains inactivated in genes involved in pyruvate fermentation, including acnA and ldhA encoding aconitase and lactate dehydrogenase, respectively, being unable to form biofilms.

Dispersion is a regulated process by which biofilm bacteria liberate themselves from the matrix-encased biofilms and transition to the planktonic, free-living state that is less protected from the immune system, and more susceptible to antimicrobial agents.

To maintain their three-dimensional, aggregated structure, biofilms require pyruvate to cope with the stressful, oxygen-limiting but electron-rich conditions.

Pyruvate dehydrogenase (acyl transferring) (e.g., E.C. 1.2.4.1) is the first component enzyme of pyruvate dehydrogenase complex (PDC)(E.C. 2.3.1.12 and E.C. 1.8.1.4). The pyruvate dehydrogenase complex contributes to transforming pyruvate into acetyl-CoA by a process called pyruvate decarboxylation. Acetyl-CoA may then be used in the citric acid cycle to carry out cellular respiration, so pyruvate dehydrogenase contributes to linking the glycolysis metabolic pathway to the citric acid cycle and releasing energy via NADH. The pyruvate decarboxylase (PDC) mechanism with pyruvate (R=H) is shown in FIG. 19.

Formally, the reaction catalyzed is pyruvate+[dihydrolipoyllysine-residue acetyltransferase] lipoyllysine→[dihydrolipoyllysine-residue acetyltransferase] S-acetyldihydrolipoyllysine+$CO_2$ Other names for this enzyme are: MtPDC (mitochondrial pyruvate dehydrogenase complex); pyruvate decarboxylase; pyruvate dehydrogenase; pyruvate dehydrogenase (lipoamide); pyruvate dehydrogenase complex; pyruvate:lipoamide 2-oxidoreductase (decarboxylating and acceptor-acetylating); pyruvic acid dehydrogenase; pyruvic dehydrogenase.

See, Ochoa, S. Enzymic mechanisms in the citric acid cycle. Adv. Enzymol. Relat. Subj. Biochem. 15 (1954) 183-270; Scriba, P. and Holzer, H. Gewinnung von αHydroxyäthyl-2-thiaminpyrophosphat mit Pyruvatoxydase aus Schweineherzmuskel. Biochem. Z. 334 (1961) 473-486; Perham, R. N. Swinging arms and swinging domains in multifunctional enzymes: catalytic machines for multistep reactions. Annu. Rev. Biochem., 69, (2000) 961-1004. [PMID: 10966480], www.sbcs.qmul.ac.uk/iubmb/enzyme/EC1/2/4/1.html; en.wikipedia.org/wiki/Pyruvate_dehydrogenase; en.wikipedia.org/wiki/Pyruvate_dehydrogenase_complex.

In Gram-negative bacteria, e.g., *Escherichia coli*, PDC consists of a central cubic core made up from 24 molecules of dihydrolipoyl transacetylase (E2). Up to 24 copies of pyruvate dehydrogenase (E1) and 12 molecules of dihydrolipoyl dehydrogenase (E3) bind to the outside of the E2 core. In contrast, in Gram-positive bacteria (e.g. *Bacillus stearothermophilus*) and eukaryotes the central PDC core contains 60 E2 molecules arranged into an icosahedron. Eukaryotes also contain 12 copies of an additional core protein, E3 binding protein (E3BP). Up to 60 E1 or E3 molecules can associate with the E2 core from Gram-positive bacteria binding is mutually exclusive. In eukaryotes E1 is specifically bound by E2, while E3 associates with E3BP. It is thought that up to 30 E1 and 6 E3 enzymes are present, although the exact number of molecules can vary in vivo and often reflects the metabolic requirements of the tissue in question.

Pyruvate dehydrogenase (E1) performs the first two reactions within the pyruvate dehydrogenase complex (PDC): a decarboxylation of substrate 1 (pyruvate) and a reductive acetylation of substrate 2 (lipoic acid). Lipoic acid is covalently bound to dihydrolipoamide acetyltransferase (E2), which is the second catalytic component enzyme of PDC. The reaction catalyzed by pyruvate dehydrogenase (E1) is considered to be the rate-limiting step for the pyruvate dehydrogenase complex (PDHc). See FIG. 19.

Phosphorylation of E1 by pyruvate dehydrogenase kinase (PDK) inactivates E1 and subsequently the entire complex. PDK is inhibited by dichloroacetic acid and pyruvate, resulting in a higher quantity of active, unphosphorylated PDH. Phosphorylation is reversed by pyruvate dehydrogenase phosphatase, which is stimulated by insulin, PEP, and AMP, but competitively inhibited by ATP, NADH, and Acetyl-CoA.

The ylide resonance form of thiamine pyrophosphate (TPP) begins by attacking the electrophilic ketone of pyruvate. See FIG. 20. The intermediate β-alkoxide then decarboxylates and the resulting enol is deprotonated on the carbon atom to form a stabilized 1,3-dipole involving a positively charged nitrogen atom of the thiamine heterocycle. This 1,3-dipole undergoes a reductive acetylation with lipoamide-E2.

Biochemical and structural data for E1 revealed a mechanism of activation of TPP coenzyme by forming the conserved hydrogen bond with glutamate residue (Glu59 in human E1) and by imposing a V-conformation that brings the N4' atom of the aminopyrimidine to intramolecular hydrogen bonding with the thiazolium C2 atom. This unique combination of contacts and conformations of TPP leads to formation of the reactive C2-carbanion, eventually. After the cofactor TPP decarboxylates pyruvate, the acetyl portion becomes a hydroxyethyl derivative covalently attached to TPP.

E1 is a multimeric protein. Mammalian E1s, including human E1, are tetrameric, composed of two αand two βsubunits. Some bacterial E1s, including E1 from *Escherichia coli*, are composed of two similar subunits, each being as large as the sum of molecular masses of αand βsubunits.

E1 has two catalytic sites, each providing thiamine pyrophosphate (TPP) and magnesium ion as cofactors. The βsubunit binds magnesium ion and pyrophosphate fragment while the β-subunit binds pyrimidine fragment of TPP, forming together a catalytic site at the interface of subunits.

Initially, pyruvate and thiamine pyrophosphate (TPP or vitamin B1) are bound by pyruvate dehydrogenase subunits. The thiazolium ring of TPP is in a zwitterionic form, and the anionic C2 carbon performs a nucleophilic attack on the C2 (ketone) carbonyl of pyruvate. The resulting hemithioacetal undergoes decarboxylation to produce an acyl anion equivalent (see cyanohydrin or aldehyde-dithiane umpolung chemistry, as well as benzoin condensation). This anion attacks S1 of an oxidized lipoate species that is attached to a lysine residue. In a ring-opening SN2-like mechanism, S2 is displaced as a sulfide or sulfhydryl moiety. Subsequent collapse of the tetrahedral hemithioacetal ejects thiazole, releasing the TPP cofactor and generating a thioacetate on S1 of lipoate. The E1-catalyzed process is the rate-limiting step of the whole pyruvate dehydrogenase complex.

At this point, the lipoate-thioester functionality is translocated into the dihydrolipoyl transacetylase (E2) active site, where a transacylation reaction transfers the acetyl from the "swinging arm" of lipoyl to the thiol of coenzyme A. This produces acetyl-CoA, which is released from the enzyme complex and subsequently enters the citric acid cycle. E2 can also be known as lipoamide reductase-transacetylase.

The dihydrolipoate, still bound to a lysine residue of the complex, then migrates to the dihydrolipoyl dehydrogenase (E3) active site where it undergoes a flavin-mediated oxidation, identical in chemistry to disulfide isomerase. First, FAD oxidizes dihydrolipoate back to its lipoate resting state, producing FADH2. Then, a NAD+cofactor oxidizes FADH2 back to its FAD resting state, producing NADH.

The reaction tends to be irreversible, for example because of the decarboxylation. The enzyme has a high substrate affinity, and therefore can reduce pyruvate to very low levels.

Pyruvate can also be specifically depleted using other enzymes such as lactate dehydrogenase (LDH) that catalyzes the conversion of pyruvate (plus NADH) to lactate and NAD+. Pyruvate carboxylase catalyzes the conversion of pyruvate and $CO_2$ to oxaloacetate, but is ATP dependent. Alanine transaminase produces alanine from pyruvate, and glutamate to α-ketoglutarate, in a reversible reaction. Pyruvate decarboxylase is TPP dependent, and produces acetaldehyde and $CO_2$. $E.\ coli$ has a pyruvic formate lyase enzyme that catalyzes the reaction acetyl-CoA+formate=CoA+pyruvate.

Other enzymes are available that degrade pyruvate, such as pyruvate oxidase (en.wikipedia.org/wiki/Pyruvate_oxidase)(EC 1.2.3.3) is an enzyme that catalyzes the reaction:

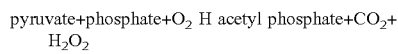

pyruvate+phosphate+$O_2$ H acetyl phosphate+$CO_2$+$H_2O_2$

The 3 substrates of this enzyme are pyruvate, phosphate, and $O_2$, whereas its 3 products are acetyl phosphate, $CO_2$, and $H_2O_2$. This enzyme belongs to the family of oxidoreductases, specifically those acting on the aldehyde or oxo group of donor with oxygen as acceptor. It has 2 cofactors: FAD, and Thiamin diphosphate.

See, Caiazza N C, O'Toole G A. 2004. SadB is required for the transition from reversible to irreversible attachment during biofilm formation by *Pseudomonas aeruginosa* PA14. J. Bacteriol. 186:4476-4485.

Models of biofilm formation by *Pseudomonas aeruginosa* propose that (i) planktonic cells become surface associated in a monolayer, (ii) surface-associated cells form microcolonies by clonal growth and/or aggregation, (iii) microcolonies transition to a mature biofilm comprised of exopolysaccharide-encased macrocolonies, and (iv) cells exit the mature biofilm and reenter the planktonic state.

*Pseudomonas aeruginosa* is a model organism for studying biofilm formation in gram-negative bacteria. Planktonic (free-swimming) *P. aeruginosa* initiates surface colonization in a flagellum-dependent manner, then forms transient ("reversible") surface interactions, and subsequently becomes firmly ("irreversibly") attached. It has been recently demonstrated for *P. fluorescens* that an ABC transporter and a large secreted protein are necessary for irreversible attachment by this organism. The earliest events in the pathway whereby planktonic bacteria form surface-associated microbial communities are unclear; however, it is clear that bacteria sample surface niches via reversible attachment before taking up permanent residence. This commitment to irreversible attachment is a crucial step in biofilm formation because initial surface colonizers are likely the foundation upon which the mature biofilm will be built. After irreversibly attaching, *P. aeruginosa* proceeds to form microcolonies in a type IV pilus and a GacA-dependent manner. As microcolonies become matrix-enclosed macrocolonies, cell-to-cell signaling is thought to become increasingly important. It has been proposed that this transition from a planktonic to a biofilm lifestyle is a developmental process.

See:

Allegrucci, M., and Sauer, K. (2007) Characterization of colony morphology variants isolated from *Streptococcus pneumoniae* biofilms. J Bacteriol 189: 2030-2038.

Allegrucci, M., Hu, F. Z., Shen, K., Hayes, J., Ehrlich, G. D., Post, J. C., and Sauer, K. (2006) Phenotypic characterization of Streptococcus pneumoniae biofilm development. J Bacteriol 188: 2325-2335.

Allesen-Holm, M., Barken, K. B., Yang, L., Klausen, M., Webb, J. S., Kjelleberg, S., et al. (2006) A characterization of DNA release in *Pseudomonas aeruginosa* cultures and biofilms. Mol Microbiol 59: 1114-1128.

Allison D G, Ruiz B, SanJose C, Jaspe A, Gilbert P (1998) Extracellular products as mediators of the formation and detachment of Pseudomonas fluorescens biofilms. FEMS Microbiol Lett 167:179-184

Allwood A, Walter M R, Burch I W, Kamber B S (2007) 3.43 billion-year-old stromatolite reef from the Pilbara Craton of Western Australia: ecosystem-scale insights to early life on Earth. Precambrian Res 158:198-227

Alvarez-Ortega, C., and Harwood, C. S. (2007) Responses of *Pseudomonas aeruginosa* to low oxygen indicate that growth in the cystic fibrosis lung is by aerobic respiration. Mol Microbiol 65: 153-165.

An, Shi-qi, and Robert P. Ryan. "Combating chronic bacterial infections by manipulating cyclic nucleotide-regulated biofilm formation." Future medicinal chemistry 8, no. 9 (2016): 949-961.

Anderl, J. N., Franklin, M. J., and Stewart, P. S. (2000) Role of antibiotic penetration limitation in Klebsiella pneumoniae biofilm resistance to ampicillin and ciprofloxacin. Antimicrob Agents Chemother 44: 1818-1824.

Anderl, J. N., Zahller, J., Roe, F., and Stewart, P. S. (2003) Role of nutrient limitation and stationary-phase existence in Klebsiella pneumoniae biofilm resistance to ampicillin and ciprofloxacin. Antimicrob Agents Chemother 47: 1251-1256.

Banin, E., Vasil, M. L., and Greenberg, E. P. (2005) Iron and *Pseudomonas aeruginosa* biofilm formation. Proc Natl Acad Sci USA 102: 11076-11081.

Barber C E et al (1997) A novel regulatory system required for pathogenicity of Xanthomonas campestris is mediated by a small diffusible signal molecule. Mol Microbiol 24:555-566

Barraud N, Schleheck D, Klebensberger J, Webb J S, Hassett D J, Rice S A, Kjelleberg S. 2009. Nitric oxide signaling in *Pseudomonas aeruginosa* biofilms mediates phosphodiesterase activity, decreased cyclic di-GMP levels, and enhanced dispersal. J. Bacteriol. 191:7333-7342.

Barraud, N., Hassett, D. J., Hwang, S.-H., Rice, S. A., Kjelleberg, S., and Webb, J. S. (2006) Involvement of nitric oxide in biofilm dispersal of *Pseudomonas aeruginosa.* J Bacteriol 188: 7344-7353.

Barraud, Nicolas, Staffan Kjelleberg, and SCOTT A. Rice. "Dispersal from microbial biofilms." Microbiol Spectr 3, no. 6 (2015).

Basu Roy, A., Petrova, O. E., Sauer, K. 2012. The phosphodiesterase DipA (PA5017) is essential for *Pseudomonas aeruginosa* biofilm dispersion. J. Bacteriol. 194:2904-2915.

Basu Roy A, Sauer K. 2014. Diguanylate cyclase NicD-based signalling mechanism of nutrient-induced dispersion by *Pseudomonas aeruginosa*. Mol. Microbiol. 94:771-793. doi:10.1111/mmi.12802

Battesti, A., N. Majdalani, S. Gottesman, The RpoS-mediated general stress response in *Escherichia coli*, Annu. Rev. Microbiol., 65 (2011), pp. 189-213

Baumann, K. W., Baust, J. M., Snyder, K. K., Baust, J. G. & Buskirk, R. G. V. Characterization of Pancreatic Cancer Cell Thermal Response to Heat Ablation or Cryoablation. *Technology in Cancer Research & Treatment* 16, 393-405, doi:10.1177/1533034616655658 (2017).

Benjamini, Y., and Hochberg, Y. (1995) Controlling the false discovery rate—a practical and powerful approach to multiple testing. J R Stat Soc Ser B Stat Methodol 57: 289-300.

Berk, V., J. C. Fong, G. T. Dempsey, O. N. Develioglu, X. Zhuang, J. Liphardt, F. H. Yildiz, S. Chu, Molecular architecture and assembly principles of Vibrio cholerae biofilms, Science, 337 (2012), pp. 236-239

Besharova, O., V. M. Suchanek, R. Hartmann, K. Drescher, V. Sourjik, Diversification of gene expression during formation of static submerged biofilms by *Escherichia coli*, Front. Microbiol., 7 (2016), p. 1568

Bielecki, P., Puchalka, J., Wos-Oxley, M. L., Loessner, H., Glik, J., Kawecki, M., et al. (2011) In-vivo expression orofiling of *Pseudomonas aeruginosa* infections reveals nichespecific and strain-independent transcriptional programs. PLoS ONE 6: e24235.

Bjarnsholt, T. et al. Why chronic wounds will not heal: a novel hypothesis. *Wound Repair and Regeneration* 16, 2-10 (2008).

Blokesch, M., Chitin colonization, chitin degradation and chitin-induced natural competence of Vibrio cholerae are subject to catabolite repression, Environ. Microbiol., 14 (2012), pp. 1898-1912

Bobrov, A. G., Kirillina, O., and Perry, P. D. (2005) The phosphodiesterase activity of the HmsP EAL domain is required for negative regulation of biofilm formation in Yersinia pestis. FEMS Microbiol Lett 247: 123-130.

Boes, N., Schreiber, K., and Schobert, M. (2008) SpoTriggered stringent response controls usp gene expression in *Pseudomonas aeruginosa*. J Bacteriol 190: 7189-7199.

Boes, N., Schreiber, K., Hartig, E., Jaensch, L., and Schobert, M. (2006) The *Pseudomonas aeruginosa* universal stress protein PA4352 is essential for surviving anaerobic energy stress. J Bacteriol 188: 6529-6538.

Boles B R, Thoendel M, Singh P K (2005) Rhamnolipids mediate detachment of *Pseudomonas aeruginosa* from biofilms. Mol Microbiol 57:1210-1223

Boles, B. R., A. R. Horswill, Agr-mediated dispersal of *Staphylococcus aureus* biofilms, PLoS Pathog., 4 (2008), p. e1000052

Boon C et al (2007) A novel DSF-like signal from Burkholderia cenocepacia interferes with *Candida albicans* morphological transition. ISME J 2:27-36

Borriello, G., Werner, E., Roe, F., Kim, A. M., Ehrlich, G. D., and Stewart, P. S. (2004) Oxygen limitation contributes to antibiotic tolerance of *Pseudomonas aeruginosa* in biofilms. Antimicrob Agents Chemother 48: 2659-2664.

Bowden G H, Li YH (1997) Nutritional influences on biofilm development. Adv Dent Res 11:81-99

Boyd A, Chakrabarty A M (1994) Role of alginate lyase in cell detachment of *Pseudomonas aeruginosa*. Appl Environ Microbiol 60:2355-2359

Breyers JD (1988) Modeling biofilm accumulation. In: Bazin M J, Prosser J I (eds) Physiology models in microbiology, vol 2. Boca Raton, Fla., pp 109-144

Broughton 2nd, G., Janis, J. E. & Attinger, C. E. The basic science of wound healing. *Plastic and reconstructive surgery* 117, 12S-34S (2006).

Byrd, Matthew S., Inna Sadovskaya, Evgueny Vinogradov, Haiping Lu, April B. Sprinkle, Stephen H. Richardson, Luyan Ma et al. "Genetic and biochemical analyses of the *Pseudomonas aeruginosa* Psl exopolysaccharide reveal overlapping roles for polysaccharide synthesis enzymes in Psl and LPS production." *Molecular microbiology* 73, no. 4 (2009): 622-638.

Caiazza, N. C., and O'Toole, G. A. (2004) SadB is required for the transition from reversible to irreversible attachment during biofilm formation by *Pseudomonas aeruginosa* PA14. J Bacteriol 186: 4476-4485.

Cancio L C, H. P., McManus A T, Kim S H, Goodwin C W, Pruitt, B A Jr. Burn wound infections. In: Holzheimer R G, Mannick J A, editors. *Surgical Treatment: Evidence-Based and Problem-Oriented*. Munich: Zuckschwerdt (2001).

Cárcamo-Oyarce, G., P. Lumjiaktase, R. Kümmerli, L. Eberl, Quorum sensing triggers the stochastic escape of individual cells from Pseudomonas putida biofilms, Nat. Commun., 6 (2015), p. 5945

Carlson, C. A., and Ingraham, J. L. (1983) Comparison of denitrification by Pseudomonas stutzeri, *Pseudomonas aeruginosa*, and Paracoccus denitrificans. Appl Environ Microbiol 45: 1247-1253.

Carlson, C. A., Ferguson, L. P., & Ingraham, J. L. (1982) Properties of dissimilatory nitrate reductase purified from the denitrifier *Pseudomonas aeruginosa*. J Bacteriol 151: 162-171.

Cazzaniga, A. et al. The effect of an antimicrobial gauze dressing impregnated with 0.2% polyhexamethylene biguanide as a barrier to prevent *Pseudomonas aeruginosa* wound invasion. *Wounds* 5, 169-176 (2002).

Chambers, J. R. & Sauer, K. The MerR-like regulator BrlR impairs *Pseudomonas aeruginosa* biofilm tolerance to colistin by repressing PhoPQ. *Journal of Bacteriology* 195, 4678-4688, doi:10.1128/jb.00834-13 (2013).

Chambers, J. R., Liao, J., Schurr, M. J. & Sauer, K. BrlR from *Pseudomonas aeruginosa* is a c-di-GMP-responsive transcription factor. *Mol. Microbiol.* 92, 471-487, doi: 10.1111/mmi.12562 (2014).

Chatterjee S, Newman K L, Lindow SE (2008) Cell-to-cell signaling in Xylella fastidiosa suppresses movement and xylem vessel colonization in grape. Mol Plant-Microbe Interact 21:1309-1315

Chen X, Stewart PS (2000) Biofilm removal caused by chemical treatments. Water Res 34:4229-4233

Chen, W., Honma, K., Sharma, A., and Kuramitsu, H. K. (2006) A universal stress protein of Porphyromonas gingivalis is involved in stress responses and biofilm formation. FEMS Microbiol Lett 264: 15-21.

Christen M, Christen B, Folcher M, Schauerte A, Jenal U (2005) Identification and characterization of a cyclic di-GMP-specific phosphodiesterase and its allosteric control by GTP. J Biol Chem 280:30829-30837

Church, D., Elsayed, S., Reid, O., Winston, B. & Lindsay, R. Burn wound infections. *Clin. Microbiol. Rev.* 19, 403-434, doi:10.1128/cmr.19.2.403-434.2006 (2006).

Comolli, J. C., and Donohue, T. J. (2004) Differences in two *Pseudomonas aeruginosa* cbb3 cytochrome oxidases. Mol Microbiol 51: 1193-1203.

Conibear, T. C. R., Collins, S. L., and Webb, J. S. (2009) Role of mutation in *Pseudomonas aeruginosa* biofilm development. PLoS ONE 4: e6289.

Cornforth, D. M., R. Popat, L. McNally, J. Gurney, T. C. Scott-Phillips, A. Ivens, S. P. Diggle, S. P. Brown, Combinatorial quorum sensing allows bacteria to resolve their social and physical environment, Proc. Natl. Acad. Sci. USA, 111 (2014), pp. 4280-4284

Corr, D. T., Gallant-Behm, C. L., Shrive, N. G. & Hart, D. A. Biomechanical behavior of scar tissue and uninjured skin in a porcine model. *Wound Repair and Regeneration* 17, 250-259 (2009).

Costerton J. W., Lewandowski Z, Caldwell D E, Korber D R, Lappin-Scott H M (1995) Microbial biofilms. Annu Rev Microbiol 49:711-745

Costerton, J. W., Stewart, P. S. & Greenberg, E. P. Bacterial biofilms: a common cause of persistent infections. *Science* 284, 1318-1322 (1999).

Danhorn T, Hentzer M, Givskov M, Parsek M R, Fuqua C (2004) Phosphorus limitation enhances biofilm formation of the plant pathogen *Agrobacterium tumefaciens* through the PhoR-PhoB regulatory system. J Bacteriol 186:4492-4501

Davey, M. E., Caiazza, N. C., and O'Toole, G. A. (2003) Rhamnolipid surfactant production affects biofilm architecture in *Pseudomonas aeruginosa* PAO1. J Bacteriol 185: 1027-1036.

David G A, Begoña R, Carmen S, Almudena J, Peter G (1998) Extracellular products as mediators of the formation and detachment of Pseudomonas fluorescens biofilms. FEMS Microbiol Lett 167:179-184

Davies D. G. (2011) Biofilm Dispersion. In: Flemming HC., Wingender J., Szewzyk U. (eds) Biofilm Highlights. Springer Series on Biofilms, vol 5. Springer, Berlin, Heidelberg Davies D G (1999) Regulation of matrix polymer in biofilm formation and dispersion. In: Wingender J, Neu T R, Flemming H-C (eds) Microbial extrapolymeric substances, characterization, structure and function. Springer, Berlin, pp 93-112

Davies D G, Marques C N H (2009) A fatty acid messenger is responsible for inducing dispersion in microbial biofilms. J Bacteriol 191:1393-1403

Davies, K. J. P., Lloyd, D., and Boddy, L. (1989) The effect of oxygen on denitrification in Paracoccus denitrificans and *Pseudomonas aeruginosa*. J Gen Microbiol 135: 2445-2451.

Davis, S. C. & Mertz, P. M. Determining the Effect of an Oak Bark Formulation on Methicillin-resistant *Staphylococcus aureus* and Wound Healing in Porcine Wound Models. Ostomy Wound Manage 54, 16-25 (2008).

Davis, S. C. et al. Microscopic and physiologic evidence for biofilm-associated wound colonization in vivo. *Wound Repair and Regeneration* 16, 23-29, doi:10.1111/j.1524-475X.2007.00303.x (2008).

Davis, S. C., Cazzaniga, A. L., Ricotti, C. & et al. Topical oxygen emulsion: A novel wound therapy. *Archives of Dermatology* 143, 1252-1256, doi:10.1001/archderm.143.10.1252 (2007).

Davis, S. C., Martinez, L. & Kirsner, R. The diabetic foot: the importance of biofilms and wound bed preparation. *Current diabetes reports* 6, 439-445 (2006).

Davis, S. C., Mertz, P. M. & Eaglstein, W. H. Second-degree burn healing: The effect of occlusive dressings and a cream. *Journal of Surgical Research* 48, 245-248, doi: 10.1016/0022-4804(90)90220-v.

Davis, S., Cazzaniga, A., Eaglstein, W. & Mertz, P. Over-the-counter topical antimicrobials: effective treatments? *Arch Dermatol Res* 297, 190-195, doi:10.1007/s00403-005-0612-6 (2005).

de Beer, D., Stoodley, P., and Lewandowski, Z. (1994) Liquid flow in heterogeneous biofilms. Biotechnol Bioeng 44: 636-641.

de Lorenzo, V., K. N. Timmis, Analysis and construction of stable phenotypes in gram-negative bacteria with Tn5 and Tn10-derived minitransposons, Methods Enzymol., 235 (1994), pp. 386-405

Delaquis P J, Caldwell D E, Lawrence J R, McCurdy A R (1989) Detachment of Pseudomonas fluorescens from biofilms on glass surfaces in response to nutrient stress. Microb Ecol 18:199-210

Dewanti R, Wong A C L (1995) Influence of culture conditions on biofilm formation by *Escherichia coli* O157: H7. Int J Food Microbiol 26:147-164

Dietrich, L. E. P., Price-Whelan, A., Petersen, A., Whiteley, M., and Newman, D. K. (2006) The phenazine pyocyanin is a terminal signalling factor in the quorum sensing network of *Pseudomonas aeruginosa*. Mol Microbiol 61: 1308-1321. Dietrich, L. E. P., Teal, T. K., Price-Whelan, A., and Newman, Dietrich, Lars E P, Tracy K. Teal, Alexa Price-Whelan, and Dianne K. Newman. "Redox-active antibiotics control gene expression and community behavior in divergent bacteria." *Science* 321, no. 5893 (2008): 1203-4206.

Ding, Qinfeng, and Kai Soo Tan. "The danger signal extracellular ATP is an inducer of Fusobacterium nucleatum biofilm dispersal." *Frontiers in cellular and infection microbiology* 6 (2016): 155.

Doiron, A. L., Chu, K., Ali, A. & Brannon-Peppas, L. Preparation and initial characterization of biodegradable particles containing gadolinium-DTPA contrast agent for enhanced MRI. *Proc. Nat. Acad. Sci.* 105, 17232-17237, doi:10.1073/pnas.0710205105 (2008).

Donlan, R. M. Biofilms and device-associated infections. *Emerg. Infect. Dis.* 7, 277-281 (2001).

Dow J M et al (2003) Biofilm dispersal in Xanthomonas campestris is controlled by cell-cell signaling and is required for full virulence to plants. Proc Natl Acad Sci 100:10995-11000

Dragoŝ, A., A. T. Kovacs, The peculiar functions of the bacterial extracellular matrix, Trends Microbiol., 25 (2017), pp. 257-266

Drescher, K., C. D. Nadell, H. A. Stone, N. S. Wingreen, B. L. Bassler, Solutions to the public goods dilemma in bacterial biofilms, Curr. Biol., 24 (2014), pp. 50-55

Drescher, K., J. Dunkel, C. D. Nadell, S. van Teeffelen, I. Grnja, N. S. Wingreen, H. A. Stone, B. L. Bassler, Architectural transitions in Vibrio cholerae biofilms at single-cell resolution, Proc. Natl. Acad. Sci. USA, 113 (2016), pp. E2066-E2072

Drumm, J. E., Mi, K., Bilder, P., Sun, M., Lim, J., Bielefeldt-Ohmann, H., et al. (2009) Mycobacterium tuberculosis universal stress protein Rv2623 regulates bacillary growth by ATP-binding: requirement for establishing chronic persistent infection. PLoS Pathog 5: e1000460.

Dziubla, T. D., Karim, A. & Muzykantov, V. R. Polymer nanocarriers protecting active enzyme cargo against proteolysis. *Journal of Controlled Release* 102, 427-439 (2005).

Edwards R, Harding K G. 2004. Bacteria and wound healing. Current opinion in infectious diseases 17:91-96.

Eschbach, M., Schreiber, K., Trunk, K., Buer, J., Jahn, D., and Schobert, M. (2004) Long-term anaerobic survival of the opportunistic pathogen *Pseudomonas aeruginosa* via pyruvate fermentation. J Bacteriol 186: 4596-4604.

Ferreira R B R, Antunes L C M, Greenberg E P, McCarter L L (2008) Vibrio parahaemolyticus ScrC modulates cyclic dimeric GMP regulation of gene expression relevant to growth on surfaces. J Bacteriol 190:851-860

Filiatrault, M. J., Picardo, K. F., Ngai, H., Passador, L., and Iglewski, B. H. (2006) Identification of *Pseudomonas aeruginosa* genes involved in virulence and anaerobic growth. Infect Immun 74: 4237-4245.

Fouhy Y et al (2007) Diffusible signal factor-dependent cell-cell signaling and virulence in the nosocomial pathogen *Stenotrophomonas maltophilia*. J Bacteriol 189:4964-4968

Friedman L, Kolter R (2004a) Two genetic loci produce distinct carbohydrate-rich structural components of the *Pseudomonas aeruginosa* biofilm matrix. J Bacteriol 186: 4457-4465

Friedman L, Kolter R (2004b) Genes involved in matrix formation in *Pseudomonas aeruginosa* PA14 biofilms. Mol Microbiol 51:675-690

Gacesa P (1987) Alginate-modifying-enzymes: a proposed unified mechanism of action for the lyases and epimerases. FEBS Lett 212:199-202

Garcia-Medina, R., Dunne, W. M., Singh, P. K., and Brody, S. L. (2005) *Pseudomonas aeruginosa* acquires biofilm-like properties within airway epithelial cells. Infect Immun 73: 8298-8305.

Gjermansen, M., M. Nilsson, L. Yang, T. Tolker-Nielsen, Characterization of starvation-induced dispersion in Pseudomonas putida biofilms: genetic elements and molecular mechanisms, Mol. Microbiol., 75 (2010), pp. 815-826

Guilhen, C., C. Forestier, D. Balestrino, Biofilm dispersal: multiple elaborate strategies for dissemination of bacteria with unique properties, Mol. Microbiol., 105 (2017), pp. 188-210

Gupta, A. & Kumar, P. Assessment of the histological state of the healing wound. *Plastic and Aesthetic Research* 2, 239 (2015).

Gupta, K., Liao, J., Petrova, O. E., Cherny, K. E. & Sauer, K. Elevated levels of the second messenger c-di-GMP contribute to antimicrobial resistance of *Pseudomonas aeruginosa. Mol. Microbiol.* 92, 488-506, doi:10.1111/mmi.12587 (2014).

Gupta, K., Marques, C. N. H., Petrova, O. E. & Sauer, K. Antimicrobial tolerance of *Pseudomonas aeruginosa* biofilms is activated during an early developmental stage and requires the two-component hybrid SagS. *J. Bacteriol.* 195, 4975-4987 doi:10.1128/jb.00732-13 (2013).

Güvener Z T, Harwood C S (2007) Subcellular location characteristics of the *Pseudomonas aeruginosa* GGDEF protein, WspR, indicate that it produces cyclic-di-GMP in response to growth on surfaces. Mol Microbiol 66:1459-1473

Ha, Dae-Gon, and George A. O'Toole. "c-di-GMP and its effects on biofilm formation and dispersion: a *Pseudomonas aeruginosa* review." Microbiology spectrum 3, no. 2 (2015).

Hammer, B. K., B. L. Bassler, Quorum sensing controls biofilm formation in Vibrio cholera, Mol. Microbiol., 50 (2003), pp. 101-104

Harrison-Balestra, C., Cazzaniga, A. L., Davis, S. C. & Mertz, P. M. A Wound-Isolated *Pseudomonas aeruginosa* Grows a Biofilm In Vitro Within 10 Hours and Is Visualized by Light Microscopy. *Dermatologic surgery* 29, 631-635 (2003).

Hassett, D. J., Cuppoletti, J., Trapnell, B., Lymar, S. V., Rowe, J. J., Yoon, S. S., et al. (2002) Anaerobic metabolism and quorum sensing by *Pseudomonas aeruginosa* biofilms in chronically infected cystic fibrosis airways: rethinking antibiotic treatment strategies and drug targets. Adv Drug Deliv Rev 54: 1425-1443.

Hassett, D. J., Sutton, M. D., Schurr, M. J., Herr, A. B., Caldwell, C. C., and Matu, J. O. (2009) *Pseudomonas aeruginosa* hypoxic or anaerobic biofilm infections within cystic fibrosis airways. Trends Microbiol 17: 130-138.

Hay, A. J., J. Zhu, Host intestinal signal-promoted biofilm dispersal induces Vibrio cholerae colonization, Infect. Immun., 83 (2015), pp. 317-323

Heinrich, W., Lange, P., Stirtz, T., Iancu, C. & Heidemann, E. Isolation and characterization of the large cyanogen bromide peptides from the $\alpha$1-and $\alpha$2-chains of pig skin collagen. *FEBS letters* 16, 63-67 (1971).

Heydorn, A., Nielsen, A. T., Hentzer, M., Sternberg, C., Givskov, M., Ersboll, B. K., and Molin, S. (2000) Quantification of biofilm structures by the novel computer program COMSTAT. Microbiology 146: 2395-2407.

Hickman J W, Tifrea D F, Harwood CS (2005) A chemosensory system that regulates biofilm formation through modulation of cyclic diguanylate levels. Proc Natl Acad Sci USA 102:14422-14427

Hisatsuka K, Nakahara T, Sano N, Yamada K (1971) Formation of rhamnolipid by *Pseudomonas aeruginosa* and its function in hydrocarbon fermentation. Agric Biol Chem 35:686-692

Hofmann H J, Grey K, Hickman A H, Thorpe R I (1999) Origin of 3.45 Ga coniform stromatolites in Warrawoona group, Western Australia. Geol Soc nm Bull 111:1256-1262

Høiby, N., Krogh Johansen, H., Moser, C., Song, Z., Ciofu, O., and Kharazmi, A. (2001) *Pseudomonas aeruginosa* and the in vitro and in vivo biofilm mode of growth. Microbes Infect 3: 23-35.

Horswill, A. R., P. Stoodley, P. S. Stewart, M. R. Parsek, The effect of the chemical, biological, and physical environment on quorum sensing in structured microbial communities, Anal. Bioanal. Chem., 387 (2007), pp. 371-380

Hou, Z. et al. Both F A- and mPEG-conjugated chitosan nanoparticles for targeted cellular uptake and enhanced tumor tissue distribution. *Nanoscale Research Letters* 6, 563, doi:10.1186/1556-276x-6-563 (2011).

Huang T-P, Wong ACL (2007) A cyclic AMP receptor protein-regulated cell-cell communication system mediates expression of a FecA homologue in Stenotrophomonas maltophilia. Appl Environ Microbiol 73:5034-5040

Hunt S M, Werner E M, Huang B, Hamilton M A, Stewart P S (2004) Hypothesis for the role of nutrient starvation in biofilm detachment. Appl Environ Microbiol 70:7418-7425

Irie, Y., Starkey, M., Edwards, A. N., Wozniak, D. J., Romeo, T., and Parsek, M. R. (2010) *Pseudomonas aeruginosa* biofilm matrix polysaccharide Psl is regulated transcriptionally by RpoS and post-transcriptionally by RsmA. Mol Microbiol 78: 158-172.

Itoh Y, Wang X, Hinnebusch B J, Preston J F III, Romeo T (2005) Depolymerization of {beta}-1,6-N-acetyl-D-glucosamine disrupts the integrity of diverse bacterial biofilms. J Bacteriol 187:382-387

Jackson D W, Simecka J W, Romeo T (2002) Catabolite repression of *Escherichia coli* biofilm formation. J Bacteriol 184:3406-3410

Jackson K D, Starkey M, Kremer S, Parsek M R, Wozniak D J (2004) Identification of psl, a locus encoding a potential exopolysaccharide that is essential for *Pseudomonas aeruginosa* PAO1 biofilm formation. J Bacteriol 186:4466-4475

James G A, Korber D R, Caldwell D E, Costerton J W (1995) Digital image analysis of growth and starvation responses of a surface-colonizing *Acinetobacter* sp. J Bacteriol 177:907-915

Jensen, P. Ø. et al. Rapid necrotic killing of polymorphonuclear leukocytes is caused by quorum-sensing-controlled production of rhamnolipid by *Pseudomonas aeruginosa*. Microbiology 153, 1329-1338, doi:10.1099/mic.0.2006/003863-0 (2007).

Kaluzhny, Y., Kinuthia, M., Karetsky, V., d'Argembeau-Thornton, L., Hayden, P. and Klausner, K., An in vitro reconstructued normal human corneal tissue model for corneal drug delivery studies of ophthalmic formulations. *Internal MatTek Corporation*, Publication #803.

Kaneko, Y., Thoendel, M., Olakanmi, O., Britigan, B. E., and Singh, P. K. (2007) The transition metal gallium disrupts *Pseudomonas aeruginosa* iron metabolism and has antimicrobial and antibiofilm activity. J Clin Invest 117: 877-888.

Kaplan J B, Fine D H (2002) Biofilm dispersal of neisseria subflava and other phylogenetically diverse oral bacteria. Appl Environ Microbiol 68:4943-4950

Kaplan J B, Ragunath C, Ramasubbu N, Fine D H (2003) Detachment of Actinobacillus actinomycetemcomitans biofilm cells by an endogenous {beta}-hexosaminidase activity. J Bacteriol 185:4693-4698

Kaplan, J. B., Biofilm dispersal: mechanisms, clinical implications, and potential therapeutic uses, J. Dent. Res., 89 (2010), pp. 205-218

Karatan E, Watnick P (2009) Signals, regulatory networks, and materials that build and break bacterial biofilms. Microbiol Mol Biol Rev 73:310-347

Kim Y-K, McCarter L L (2007) ScrG, a GGDEF-EAL protein, participates in regulating swarming and sticking in Vibrio parahaemolyticus. J Bacteriol 189:4094-4107

Kim, M. K., F. Ingremeau, A. Zhao, B. L. Bassler, H. A. Stone, Local and global consequences of flow on bacterial quorum sensing, Nat. Microbiol., 1 (2016), p. 15005

Kim, S. M., J. H. Park, H. S. Lee, W. B. Kim, J. M. Ryu, H. J. Han, S. H. Choi, LuxR homologue SmcR is essential for Vibrio vulnificus pathogenesis and biofilm detachment, and its expression is induced by host cells, Infect. Immun., 81 (2013), pp. 3721-3730

Kirisits, M. J., J. J. Margolis, B. L. Purevdorj-Gage, B. Vaughan, D. L. Chopp, P. Stoodley, M. R. Parsek, Influence of the hydrodynamic environment on quorum sensing in *Pseudomonas aeruginosa* biofilms, J. Bacteriol., 189 (2007), pp. 8357-8360

Kuchma, S. L., Brothers, K. M., Merritt, J. H., Liberati, N. T., Ausubel, F. M., and O'Toole, G. A. (2007) BifA, a c-di-GMP phosphodiesterase, inversely regulates biofilm formation and swarming motility by *Pseudomonas aeruginosa* PA14. J Bacteriol 189: 8165-8178.

Kuramitsu, H. K., Chen, W., and Ikegami, A. (2005) Biofilm formation by the periodontopathic bacteria Treponema denticola and Porphyromonas gingivalis. J Periodontol 76: 2047-2051.

Lam, J., Chan, R., Lam, K., and Costerton, J. W. (1980) Production of mucoid microcolonies by *Pseudomonas aeruginosa* within infected lungs in cystic fibrosis. Infect Immun 28: 546-556.

Lamed R, Bayer E A (1986) Contact and cellulolysis in Clostridium thermocellum via extensive surface organelles. Experientia 42:72-73

Lanter, Bernard B., and David G. Davies. "Propionibacterium acnes recovered from atherosclerotic human carotid arteries undergoes biofilm dispersion and releases lipolytic and proteolytic enzymes in response to norepinephrine challenge in vitro." Infection and immunity 83, no. 10 (2015): 3960-3971.

Lee J, Bansal T, Jayaraman A, Bentley W E, Wood T K (2007a) Enterohemorrhagic *Escherichia coli* biofilms are inhibited by 7-hydrozyindole and stimulated by isatin. Appl Environ Microbiol 73:4100-4109

Lee J, Jayaraman A, Wood T K (2007b) Indole is an inter-species biofilm signal mediated by SdiA. BMC Microbiol 7:1-15

Leid, J. G., Shirtliff, M. E., Costerton, J. W., Stoodley & Paul. Human leukocytes adhere to, penetrate, and respond to *Staphylococcus aureus* Biofilms. *Infect. Immun.* 70, 6339-6345, doi:10.1128/iai.70.11.6339-6345.2002 (2002).

Leistikow, R. L., Morton, R. A., Bartek, I. L., Frimpong, I., Wagner, K., and Voskuil, M. I. (2010) The Mycobacterium tuberculosis DosR regulon assists in metabolic homeostasis and enables rapid recovery from nonrespiring dormancy. J Bacteriol 192: 1662-1670.

Lenz, A. P., Williamson, K. S., Pitts, B., Stewart, P. S., and Franklin, M. J. (2008) Localized gene expression in *Pseudomonas aeruginosa* biofilms. Appl Environ Microbiol 74: 4463-4471.

Lenz, D. H., K. C. Mok, B. N. Lilley, R. V. Kulkarni, N. S. Wingreen, B. L. Bassler, The small RNA chaperone Hfq and multiple small RNAs control quorum sensing in Vibrio harveyi and Vibrio cholera, Cell, 118 (2004), pp. 69-82

Lewis, K. Multidrug tolerance of biofilms and persister cells. *Curr. Top. Microbiol. Immunol.* 322, 107-131 (2008).

Li, Y. et al. Bd1A, DipA and induced dispersion contribute to acute virulence and chronic persistence of *Pseudomonas aeruginosa*. PLoS Pathog. 10, e1004168, doi:10.1371/journal.ppat.1004168 (2014).

Li, Y., Cherny, K. E. & Sauer, K. The diguanylate cyclase CrdA contributes to the architecture and the dispersion response of *Pseudomonas aeruginosa* biofilms. In revision (2016).

Liao, J. & Sauer, K. The MerR-like transcriptional regulator BrlR contributes to *Pseudomonas aeruginosa* biofilm tolerance. *J. Bacteriol.* 194, 4823-4836, doi:10.1128/jb.00765-12 (2012).

Liao, J., Schurr, M. J. & Sauer, K. The MerR-like regulator BrlR confers biofilm tolerance by activating multidrug-efflux pumps in *Pseudomonas aeruginosa* biofilms. *J. Bacteriol.* 195, 3352-3363 (2013).

Lister J L, Horswill A R. 2014. *Staphylococcus aureus* biofilms: recent developments in biofilm dispersal. Frontiers in Cellular and Infection Microbiology 4:178.

Lynch M J et al (2002) The regulation of biofilm development by quorum sensing in Aeromonas hydrophila. Environ Microbiol 4:18-28

Ma L, Jackson K D, Landry R M, Parsek M R, Wozniak D J (2006) Analysis of *Pseudomonas aeruginosa* conditional Psl variants reveals roles for the Psl polysaccharide in adhesion and maintaining biofilm structure postattachment. J Bacteriol 188:8213-8221

Ma L, Lu H, Sprinkle A, Parsek M R, Wozniak D (2007) *Pseudomonas aeruginosa* Psl is a galactoseand mannose-rich exopolysaccharide. J Bacteriol. doi: 10.1128/JB.00620-07

Maisonneuve, E., M. Castro-Camargo, K. Gerdes, (p)ppGpp controls bacterial persistence by stochastic induction of toxin-antitoxin activity, Cell, 154 (2013), pp. 1140-1150

Marques, Claudia N H, David G. Davies, and Karin Sauer. "Control of biofilms with the fatty acid signaling molecule cis-2-decenoic acid." Pharmaceuticals 8, no. 4 (2015): 816-835.

Marquette, S. et al. Stability study of full-length antibody (anti-TNF alpha) loaded PLGA microspheres. *International journal of pharmaceutics* 470, 41-50 (2014).

Marshall J C (1988) Adhesion and growth of bacteria at surfaces in oligotrophic habitats. Can J Microbiol 34:503-506

Martineau, L. & Davis, S. C. Controlling Methicillin Resistant *Staphyloccocus aureus* and *Pseudomonas aeruginosa* Wound Infections with a Novel Biomaterial. *Journal of Investigative Surgery* 20, 217-227, doi:doi:10.1080/10717540701481275 (2007).

Mashburn, L. M., Jett, A. M., Akins, D. R., and Whiteley, M. (2005) *Staphylococcus aureus* serves as an iron source for *Pseudomonas aeruginosa* during in vivo coculture. J Bacteriol 187: 554-566.

Matsukawa M, Greenberg E P (2004) Putative exopolysaccharide synthesis genes influence *Pseudomonas aeruginosa* biofilm development. J Bacteriol 186:4449-4456

May T B et al (1991) Alginate synthesis by *Pseudomonas aeruginosa*: a key pathogenic factor in chronic pulmonary infections of cystic fibrosis patients. Clin Microbiol Rev 4:191-206

McDougald, D., S. A. Rice, N. Barraud, P. D. Steinberg, S. Kjelleberg, Should we stay or should we go: mechanisms and ecological consequences for biofilm dispersal, Nat. Rev. Microbiol., 10 (2011), pp. 39-50

Menon, J. U. et al. Polymeric nanoparticles for pulmonary protein and DNA delivery. *Acta biomaterialia* 10, 2643-2652 (2014).

Merritt J H, Brothers K M, Kuchma S L, O'Toole GA (2007) SadC reciprocally influences biofilm formation and swarming motility via modulation of exopolysaccharide production and flagellar function. J Bacteriol 189(22):8154-8164

Mertz, P. et al. Effects of an arginine-glycine-aspartic acid peptide-containing artificial matrix on epithelial migration in vitro and experimental second-degree burn wound healing in vivo. *J Burn Care Rehabil.* 17, 199-206 (J 1996).

Mertz, Patricia M., Stephen C. Davis, Alejandro L. Cazzangga, Anna Drosou, and William H. Eagistein. "Barrier and antibacterial properties of 2-octyl cyanoacrylate-derived wound treatment films." *Journal of cutaneous medicine and surgery* 7, no. 1 (2003): 1-6.

Mertz, Patricia M., Maria F. Oliveira-Gandia, and Stephen C. Davis. "The evaluation of a cadexomer iodine wound dressing on methicillin resistant *Staphylococcus aureus* (MRSA) in acute wounds." Dermatologic surgery 25, no. 2 (1999): 89-93.

Meyer W, Schwarz R, Neurand K. The Skin of Domestic Mammals as a Model for the Human Skin, with Special Reference to the Domestic Pig, In Skin-Drug Application and Evaluation of Environmental Hazards. p. 39-52 (Karger Publishers 1978).

Mikkelsen, H., Bond, N. J., Skindersoe, M. E., Givskov, M., Lilley, K. S., and Welch, M. (2009) Biofilms and type III secretion are not mutually exclusive in *Pseudomonas aeruginosa*. Microbiology 155: 687-698.

Morgan, R., Kohn, S., Hwang, S.-H., Hassett, D. J. & Sauer, K. BdlA, a chemotaxis regulator essential for biofilm dispersion in *Pseudomonas aeruginosa*. *J. Bacteriol.* 188, 7335-7343 (2006).

Morici, L. A., Carterson, A. J., Wagner, V. E., Frisk, A., Schurr, J. R., zu Bentrup, K. H., et al. (2007) *Pseudomonas aeruginosa* AlgR represses the Rhl quorum-sensing system in a biofilm-specific manner. J Bacteriol 189: 7752-7764.

Müller, J., M. C. Miller, A. T. Nielsen, G. K. Schoolnik, A. M. Spormann, vpsA and luxO-independent biofilms of Vibrio cholera, FEMS Microbiol. Lett., 275 (2007), pp. 199-206

Nachin, L., Nannmark, U., and Nystrom, T. (2005) Differential roles of the universal stress proteins of *Escherichia coli* in oxidative stress resistance, adhesion, and motility. J Bacteriol 187: 6265-6272.

Nadell, C. D., J. B. Xavier, S. A. Levin, K. R. Foster, The evolution of quorum sensing in bacterial biofilms, PLoS Biol., 6 (2008), p. e14

Nadell, C. D., K. Drescher, K. R. Foster, Spatial structure, cooperation and competition in biofilms, Nat. Rev. Microbiol., 14 (2016), pp. 589-600

Navarro, Gabriel, Andrew T. Cheng, Kelly C. Peach, Walter M. Bray, Valerie S. Bernan, Fitnat H. Yildiz, and Roger G. Linington. "Image-based 384-well high-throughput screening method for the discovery of skyllamycins A to C as biofilm inhibitors and inducers of biofilm detachment in *Pseudomonas aeruginosa*." Antimicrobial agents and chemotherapy 58, no. 2 (2014): 1092-1099.

Newman, J. R., and Fuqua, C. (1999) Broad-host-range expression vectors that carry the arabinose-inducible *Escherichia coli* araBAD promoter and the araC regulator. Gene 227: 197-203.

Nielsen, A. T., N. A. Dolganov, G. Otto, M. C. Miller, C. Y. Wu, G. K. Schoolnik, RpoS controls the Vibrio cholerae mucosal escape response, PLoS Pathog., 2 (2006), p. e109

Niinikoski, J., Jussila, P. & Vihersaari, T. Radical mastectomy wound as a model for studies of human wound metabolism. *The American Journal of Surgery* 126, 53-58 (1973).

Nusbaum, A. G. et al. Effective Method to Remove Wound Bacteria: Comparison of Various Debridement Modalities in an In Vivo Porcine Model. *Journal of Surgical Research* 176, 701-707, doi:10.1016/j.jss.2011.11.1040.

O'Toole G, Kaplan H B, Kolter R (2000) Biofilm formation as microbial development. Annu Rev Microbiol 54:49-79

O'Toole, G. A., and Kolter, R. (1998) Initiation of biofilm formation in Pseudomonas fluorescens WCS365 proceeds via multiple, convergent signalling pathways: a genetic analysis. Mol Microbiol 28: 449-461.

O'Toole, G. A., G. C. Wong, Sensational biofilms: surface sensing in bacteria, Curr. Opin. Microbiol., 30 (2016), pp. 139-146

O'Toole, G. A., Gibbs, K. A., Hager, P. W., Phibbs, P. V., Jr, and Kolter, R. (2000) The global carbon metabolism regulator Crc is a component of a signal transduction pathway required for biofilm development by *Pseudomonas aeruginosa*. J Bacteriol 182: 425-431.

Ohashi A, Harada H (1994a) Adhesion strength of biofilm developed in an attached-growth reactor. Water Sci Technol 20:10-11

Ohashi A, Harada H (1994b) Characterization of detachment mode of biofilm developed in an attached-growth reactor. Water Sci Technol 30:35-45

Ohashi A, Koyama T, Syutsubo K, Harada H (1999) A novel method for evaluation of biofilm tensile strength resisting erosion. Water Sci Technol 39:261-268

Papenfort, K., B. L. Bassler, Quorum sensing signal-response systems in Gram-negative bacteria, Nat. Rev. Microbiol., 14 (2016), pp. 576-588

Papenfort, K., K. U. Förstner, J. P. Cong, C. M. Sharma, B. L. Bassler, Differential RNA-seq of Vibrio cholerae identifies the VqmR small RNA as a regulator of biofilm formation, Proc. Natl. Acad. Sci. USA, 112 (2015), pp. E766-E775

Pastar, I. et al. Interactions of Methicillin Resistant *Staphylococcus aureus* USA300 and *Pseudomonas aeruginosa* in Polymicrobial Wound Infection. PLoS ONE 8, e56846, doi:10.1371/journal.pone.0056846 (2013).

Percival, S. L. & Bowler, P. G. Biofilms and. their potential role in wound healing. *Wounds—A Compendium of Clinical Research and Practice* 16, 234-240 (2004).

Perez-Osorio, A. C., Williamson, K. S., and Franklin, M. J. (2010) Heterogeneous rpoS and rhlR mRNA levels and 16S rRNA/rDNA (rRNA gene) ratios within *Pseudomonas aeruginosa* biofilms, sampled by laser capture microdissection. J Bacteriol 192: 2991-3000.

Petrova, O. E. & Sauer, K. Dispersion by *Pseudomonas aeruginosa* requires an unusual posttranslational modification of BdlA. *Proc. National Acad. Sci* 109 16690-16695 (2012).

Petrova, O. E. & Sauer, K. PAS domain residues and prosthetic group involved in BdlA-dependent dispersion response by *Pseudomonas aeruginosa* biofilms. *J. Bacteriol.* 194, 5817-5828 (2012).

Petrova, O. E., Cherny, K. E. & Sauer, K. The diguanylate cyclase GcbA facilitates *Pseudomonas aeruginosa* biofilm dispersion by activating BdlA. *Journal of Bacteriology* 197.1, 174-187, doi:10.1128/jb.02244-14 (2015).

Petrova, O. E., Cherny, K. E. & Sauer, K. The *P. aeruginosa* diguanylate cyclase GcbA, a homolog of the *P. fluorescens* GcbA, promotes initial attachment to surfaces, but not biofilm formation, via regulation of motility. *J. Bacteriol.* 196, :2827-2841, doi:10.1128/jb.01628-14 (2014).

Petrova, O. E., Gupta, K., Liao, J., Goodwine, J. S. & Sauer, K. Divide and conquer: the *Pseudomonas aeruginosa* two-component hybrid SagS enables biofilm formation and recalcitrance of biofilm cells to antimicrobial agents via distinct regulatory circuits. *Environmental Microbiology* 19, 2005-2024, doi:10.1111/1462-2920.13719 (2017).

Petrova, O. E., Schurr, J. R., Schurr, M. J. & Sauer, K. Microcolony formation by the opportunistic pathogen *Pseudomonas aeruginosa* requires pyruvate and pyruvate fermentation. *Mol. Microbiol.* 86, 819-835 (2012).

Petrova, O. E., Schurr, J. R., Schurr, M. J. & Sauer, K. The novel *Pseudomonas aeruginosa* two-component regulator BfmR controls bacteriophage-mediated lysis and DNA release during biofilm development through PhdA. *Mol. Microbiol.* 81, 767-783, doi:10.1111/j.1365-2958.2011.07733.x (2011).

Petrova, O. E., and Sauer, K. (2009) A novel signaling network essential for regulating *Pseudomonas aeruginosa* biofilm development. PLoS Pathog 5: e1000668.

Petrova, O. E., and Sauer, K. (2011) SagS contributes to the motile-sessile switch and acts in concert with BfiSR to enable *Pseudomonas aeruginosa* biofilm formation. J Bacteriol 193: 6614-6628.

Petrova, O. E., and Sauer, K. (2012) Sticky situations: key components that control bacterial surface attachment. J Bacteriol 194: 2413-2425.

Petrova, O. E., K. Sauer, Escaping the biofilm in more than one way: desorption, detachment or dispersion, Curr. Opin. Microbiol., 30 (2016), pp. 67-78

Peyton B M, Characklis W G (1993) A statistical analysis of the effect of substrate utilization and shear stress on the kinetics of biofilm detachment. Biotechnol Bioeng 41:728-735

Platt, M. D., Schurr, M. J., Sauer, K., Vazquez, G., Kukavicalbrulj, I., Potvin, E., et al. (2008) Proteomic, microarray, and signature-tagged mutagenesis analyses of anaerobic *Pseudomonas aeruginosa* at pH 6.5, likely representing chronic, late-stage cystic fibrosis airway conditions. J Bacteriol 190: 2739-2758.

Pratt L A, Kolter R (1999) Genetic analyses of bacterial biofilm formation. Curr Opin Microbiol 2:598-603

Price-Whelan, A., Dietrich, L. E. P. & Newman, D. K. Pyocyanin alters redox homeostasis and carbon flux through central metabolic pathways in *Pseudomonas aeruginosa* PA14. J. Bacteriol. 189, 6372-6381, doi:10.1128/jb.00505-07 (2007).

Purevdorj-Gage B, Costerton W J, Stoodley P (2005) Phenotypic differentiation and seeding dispersal in non-mucoid and mucoid *Pseudomonas aeruginosa* biofilms. Microbiology 151:1569-1576

Puskas A, Greenberg E P, Kaplan S, Schaefer A L (1997) A quorum-sensing system in the free-living photosynthetic bacterium Rhodobacter sphaeroides. J Bacteriol 179:7530-7537

Rahmani-Badi, Azadeh, Shayesteh Sepehr, Parisa Mohammadi, Mohammad Reza Soudi, Hamta Babaie-Naiej, and Hossein Fallahi. "A combination of cis-2-decenoic acid and antibiotics eradicates pre-established catheter-associated biofilms." Journal of medical microbiology 63, no. 11 (2014): 1509-1516.

Rajapaksa, T. E., Stover-Hamer, M., Fernandez, X., Eckelhoefer, H. A. & Lo, D. D. Claudin 4-targeted protein incorporated into PLGA nanoparticles can mediate M cell targeted delivery. *Journal of Controlled Release* 142, 196-205 (2010).

Ramos, Itzel, Lars EP Dietrich, Alexa Price-Whelan, and Dianne K. Newman. "Phenazines affect biofilm formation by *Pseudomonas aeruginosa* in similar ways at various scales." Research in microbiology 161, no. 3 (2010): 187-191.

Rani, S. A., Pitts, B., Beyenal, H., Veluchamy, R. A., Lewandowski, Z., Davison, W. M., et al. (2007) Spatial patterns of DNA replication, protein synthesis, and oxygen concentration within bacterial biofilms reveal diverse physiological states. J Bacteriol 189: 4223-4233.

Rasmussen, K., and Lewandowski, Z. (1998) Microelectrode measurements of local mass transport rates in heterogeneous biofilms. Biotechnol Bioeng 59: 302-309.

Rice S A et al (2005) Biofilm formation and sloughing in Serratia marcescens are controlled by quorum sensing and nutrient cues. J Bacteriol 187:3477-3485

Rittman B R (1982) The effect of shear stress on biofilm loss rate. Biotechnol Bioeng 24:501-506

Rochex A, Lebeault J M (2007) Effects of nutrients on biofilm formation and detachment of a Pseudomonas putida strain isolated from a paper machine. Water Res 41:2885-2992

Roger S, Michael M, Abdul K, Manfred N, Ute R (2004) GGDEF and EAL domains inversely regulate cyclic di-GMP levels and transition from sessility to motility. Mol Microbiol 53:1123-1134

Romeo T (1998) Global regulation by the small RNA-binding protein CsrA and the non-coding RNA molecule CsrB. Mol Microbiol 29:1321-1330

Romeo T, Gong M, Liu M Y, Brun-Zinkernagel A M (1993) Identification and molecular characterization of csrA, a pleiotropic gene from *Escherichia coli* that affects glycogen biosynthesis, gluconeogenesis, cell size, and surface properties. J Bacteriol 175:4744-4755

Rose, S. J. & Bermudez, L. E. *Mycobacterium avium* biofilm attenuates mononuclear phagocyte function by triggering hyperstimulation and apoptosis during early infection. *Infect. Immun.* 82, 405-412, doi:10.1128/iai.00820-13 (2014).

Ross P et al (1990) The cyclic diguanylic acid regulatory system of cellulose synthesis in Acetobacter xylinum. Chemical synthesis and biological activity of cyclic nucleotide dimer, trimer, and phosphothioate derivatives. J Biol Chem 265:18933-18943

Ryan R P et al (2006) Cell-cell signaling in Xanthomonas campestris involves an HD-GYP domain protein that functions in cyclic di-GMP turnover. Proc Natl Acad Sci USA 103:6712-6717

Sabnis N A, Yang H, Romeo T (1995) Pleiotropic regulation of central carbohydrate metabolism in *Escherichia coli* via the gene csrA. J Biol Chem 270:29096-29104

Sah, H., Thoma, L. A., Desu, H. R., Sah, E. & Wood, G. C. Concepts and practices used to develop functional PLGA-based nanoparticulate systems. *International Journal of Nanomedicine* 8, 747-765, doi:10.2147/ijn.s40579 (2013).

San, K.-Y., Bennett, G. N., Berrios-Rivera, S. J., Vadali, R. V., Yang, Y.-T., Horton, E., et al. (2002) Metabolic engineering through cofactor manipulation and its effects on metabolic flux redistribution in *Escherichia coli*. Metab Eng 4: 182-192.

Sancineto, Luca, Miranda Piccioni, Stefania De Marco, Rita Pagiotti, Vanessa Nascimento, Antonio Luiz Braga, Claudio Santi, and Donatella Pietrella. "Diphenyl diselenide derivatives inhibit microbial biofilm formation involved in wound infection." BMC microbiology 16, no. 1 (2016): 220.

Santander-Ortega, M., Bastos-Gonzalez, D., Ortega-Vinuesa, J. & Alonso, M. Insulin-loaded PLGA nanoparticles for oral administration: an in vitro physico-chemical characterization. *Journal of biomedical nanotechnology* 5, 45-53 (2009).

Sauer, K., and Camper, A. K. (2001) Characterization of phenotypic changes in Pseudomonas putida in response to surface-associated growth. J Bacteriol 183: 6579-6589.

Sauer, K., Camper, A. K., Ehrlich, G. D., Costerton, J. W., and Davies, D. G. (2002) *Pseudomonas aeruginosa* displays multiple phenotypes during development as a biofilm. J Bacteriol 184: 1140-1154.

Sauer, K., M. C. Cullen, A. H. Rickard, L. A. Zeef, D. G. Davies, P. Gilbert, Characterization of nutrient-induced dispersion in *Pseudomonas aeruginosa* PAO1 biofilm, J. Bacteriol., 186 (2004), pp. 7312-7326

Sauer, K., Steczko, J. & Ash, S. R. Effect of a solution containing citrate/methylene blue/parabens on *Staphylococcus aureus* bacteria and biofilm, and comparison with various heparin solutions. *J. Antimicrob. Chemother.* 63, 937-945, doi:10.1093/jac/dkp060 (2009).

Sauer, K., Thatcher, E., Northey, R. & Gutierrez, A. A. Neutral super-oxidised solutions are effective in killing *P. aeruginosa* biofilms. Bifilms. *Biofouling* 25, 45-54, doi: 10.1080/08927010802441412 (2009).

Sawyer L K, Hermanowicz SW (1998) Detachment of biofilm bacteria due to variations in nutrient supply. Water Sci Technol 37:211-214

Schneider, L. A., Korber, A., Grabbe, S. & Dissemond, J. Influence of pH on wound-healing: a new perspective for wound-therapy? *Arch Dermatol Res* 298, 413-420 (2007).

Schobert, M., and Jahn, D. (2010) Anaerobic physiology of *Pseudomonas aeruginosa* in the cystic fibrosis lung. Int J Med Microbiol 300: 549-556.

Schreiber K, Boes N, Eschbach M, Jaensch L, Wehland J, Bjarnsholt T, Givskov M, Hentzer M, Schobert M. Anaerobic survival of *Pseudomonas aeruginosa* by pyruvate fermentation requires an Usp-type stress protein. *J. Bacteriol.* 188, 659-668, doi:10.1128/jb.188.2.659-668.2006 (2006).

Schweizer, H. P. (1991) The agmR gene, an environmentally responsive gene, complements defective glpR, which encodes the putative activator for glycerol metabolism in *Pseudomonas aeruginosa*. J Bacteriol 173: 6798-6806.

Seaton, M., Hocking, A. & Gibran, N. S. Porcine models of cutaneous wound healing. *ILAR Journal* 56, 127-138 (2015).

Sen C K, Gordillo G M, Roy S, Kirsner R, Lambert L, Hunt TK, Gottrup F, Gurtner G C, Longaker M T. 2009. Human skin wounds: a major and snowballing threat to public health and the economy. Wound Repair and Regeneration 17:763-771.

Sepehr, Shayesteh, Azadeh Rahmani-Badi, Hamta Babaie-Naiej, and Mohammad Reza Soudi. "Unsaturated fatty acid, cis-2-decenoic acid, in combination with disinfectants or antibiotics removes pre-established biofilms formed by food-related bacteria." PLoS One 9, no. 7 (2014): e101677.

Seper, A., K. Pressler, A. Kariisa, A. G. Haid, S. Roier, D. R. Leitner, J. Reidl, R. Tamayo, S. Schild, Identification of genes induced in Vibrio cholerae in a dynamic biofilm system, Int. J. Med. Microbiol., 304 (2014), pp. 749-763

Serralta, Victoria W., Catherine Harrison-Balestra, Alejandro L. Cazzaniga, Stephen C. Davis, and Patricia M. Mertz. "Lifestyles of bacteria in wounds: presence of biofilms?." Wounds 13, no. 1 (2001): 29-34.

Seth A K, Geringer M R, Gurjala A N, Hong S J, Galiano R D, Leung K P, Mustoe T A. 2012. Treatment of *Pseudomonas aeruginosa* biofilm-infected wounds with clinical wound care strategies: a quantitative study using an in vivo rabbit ear model. Plastic and reconstructive surgery 129: 262e-274e.

Seth A K, Geringer M R, Hong S J, Leung K P, Galiano R D, Mustoe T A. 2012. Comparative analysis of single-species and polybacterial wound biofilms using a quantitative, in vivo, rabbit ear model. PLoS ONE 7:e42897.

Sharma, G., S. Sharma, P. Sharma, D. Chandoia, S. Dang, S. Gupta, and R. Gabrani. "*Escherichia coli* biolfilm: development and therapeutic strategies." *Journal of applied microbiology* 121, no. 2 (2016): 309-319.

Shirtliff, M. E., Mader, J. T., and Camper, A. K. (2002) Molecular interactions in biofilms. Chem Biol 9: 859-871.

Shorrock, S. M., Kun, S. & Peura, R. The exploration of tissue pH in wounds and its relationship to bacterial contamination. *Master Degree Thesis,* 20-24 (2000).

Short, M. B., C. A. Solari, S. Ganguly, T. R. Powers, J. O. Kessler, R. E. Goldstein, Flows driven by flagella of multicellular organisms enhance long-range molecular transport, Proc. Natl. Acad. Sci. USA, 103 (2006), pp. 8315-8319

Siddiqui, A. R. & Bernstein, J. M. Chronic wound infection: facts and controversies. *Clinics in dermatology* 28, 519-526 (2010).

Silva, A. J., J. A. Benitez, Transcriptional regulation of Vibrio cholerae hemagglutinin/protease by the cyclic AMP receptor protein and RpoS, J. Bacteriol., 186 (2004), pp. 6374-6382

Simm R, Mon M, Kader A, Nimtz M, Romling U (2004) GGDEF and EAL domains inversely regulate cyclic di-GMP levels and transition from sessility to motility. Mol Microbiol 53:1123-1134

Singh, Praveen K., Sabina Bartalomej, Raimo Hartmann, Hannah Jeckel, Lucia Vidakovic, Carey D. Nadell, and Knut Drescher. "Vibrio cholerae Combines Individual and Collective Sensing to Trigger Biofilm Dispersal." Current Biology 27, no. 21 (2017): 3359-3366.

Slater H, Alvarez-Morales A, Barber C E, Daniels M J, Dow J M (2000) A two-component system involving an HD-GYP domain protein links cell-cell signalling to pathogenicity gene expression in Xanthomonas campestris. Mol Microbiol 38:986-1003

Soheili, Vahid, Neda Khedmatgozar Oghaz, Zahra Sabeti Noughabi, and Bibi Sedigheh Fazly Bazzaz. "The novel effect of cis-2-decenoic acid on biofilm producing *Pseudomonas aeruginosa*." Microbiology Research 6, no. 1 (2016).

Somerville, G., Mikoryak, C. A., and Reitzer, L. (1999) Physiological characterization of *Pseudomonas aeruginosa* during exotoxin A synthesis: glutamate, iron limitation, and aconitase activity. J Bacteriol 181: 1072-1078.

Southey-Pillig, C. J., Davies, D. G., and Sauer, K. (2005) Characterization of temporal protein production in *Pseudomonas aeruginosa* biofilms. J Bacteriol 187: 8114-8126. Sriramulu, D. D., Lünsdorf, H., Lam, J. S., and Römling, U. (2005) Microcolony formation: a novel biofilm model of *Pseudomonas aeruginosa* for the cystic fibrosis lung. J Spoering, A. L. & Lewis, K. Biofilms and planktonic cells of *Pseudomonas aeruginosa* have similar resistance to killing by antimicrobials. *J. Bacteriol.* 183, 6746-6751, doi: 10.1128/jb.183.23.6746-6751.2001 (2001).

Sriramulu, Dinesh D., Heinrich Lünsdorf, Joseph S. Lam, and Ute Romling. "Microcolony formation: a novel biofilm model of *Pseudomonas aeruginosa* for the cystic fibrosis lung." *Journal of medical microbiology* 54, no. 7 (2005): 667-676.

Stacy, A., L. McNally, S. E. Darch, S. P. Brown, M. Whiteley, The biogeography of polymicrobial infection, Nat. Rev. Microbiol., 14 (2016), pp. 93-105

Stanley N R, Britton R A, Grossman A D, Lazazzera B A (2003) Identification of catabolite repression as a physiological regulator of biofilm formation by Bacillus subtilis by use of DNA microarrays. J Bacteriol 185:1951-1957

Stewart P S (1993) A model of biofilm detachment. Biotechnol Bioeng 41:111-117

Stewart, P. S. (1996) Theoretical aspects of antibiotic diffusion into microbial biofilms. Antimicrob Agents Chemother 40: 2517-2522.

Stewart, P. S., M. J. Franklin, Physiological heterogeneity in biofilms, Nat. Rev. Microbiol., 6 (2008), pp. 199-210

Stewart, P. S., Mini-review: convection around biofilms, Biofouling, 28 (2012), pp. 187-198

Stoodley P et al (2001) Growth and detachment of cell clusters from mature mixed-species biofilms. Appl Environ Microbiol 67:5608-5613

Stoodley, P., deBeer, D., and Lewandowski, Z. (1994) Liquid flow in biofilm systems. Appl Environ Microbiol 60: 2711-2716.

Stoodley, P., Yang, S., Lappin-Scott, H., and Lewandowski, Z. (1997) Relationship between mass transfer coefficient and liquid flow velocity in heterogeneous biofilms using microelectrodes and confocal microscopy. Biotechnol Bioeng 56: 681-688.

Sullivan, T. P., Eaglstein, W. H., Davis, S. C. & Mertz, P. The pig as a model for human wound healing. *Wound Repair and Regeneration* 9, 66-76, doi:10.1046/j.1524-475x.2001.00066.x (2001).

Sumitani, M., Takagi, S., Tanamura, Y., and Inoue, H. (2004) Oxygen indicator composed of an organic/inorganic hybrid compound of methylene blue, reductant, surfactant and saponite. Anal Sci 20: 1153-1157.

Tal R et al (1998) Three cdg operons control cellular turnover of cyclic di-GMP in Acetobacter xylinum: genetic organization and occurrence of conserved domains in isoenzymes. J Bacteriol 180:4416-4425

Tegl, G., Schiffer, D., Sigl, E., Heinzle, A. & Guebitz, G. M. Biomarkers for infection: enzymes, microbes, and metabolites. *Applied Microbiology and Biotechnology* 99, 4595-4614 (2015).

Teschler, J. K., D. Zamorano-Sanchez, A. S. Utada, C. J. A. Warner, G. C. L. Wong, R. G. Linington, F. H. Yildiz, Living in the matrix: assembly and control of Vibrio cholerae biofilms, Nat. Rev. Microbiol., 13 (2015), pp. 255-268

Thelin, K. H., R. K. Taylor, Toxin-coregulated pilus, but not mannose-sensitive hemagglutinin, is required for colonization by Vibrio cholerae O1 E1 Tor biotype and O139 strains, Infect. Immun., 64 (1996), pp. 2853-2856, Positive selection vectors for allelic exchange, Gene, 169 (1996), pp. 47-52

Thormann KM et al (2006) Control of formation and cellular detachment from Shewanella oneidensis MR-1 biofilms by cyclic di-GMP. J Bacteriol 188:2681-2691

Thormann, K. M., R. M. Saville, S. Shukla, A. M. Spormann, Induction of rapid detachment in Shewanella oneidensis MR-1 biofilms, J. Bacteriol., 187 (2005), pp. 1014-1021

Tolker-Nielsen et al T (2000) Development and dynamics of *Pseudomonas* sp. biofilms. J Bacteriol 182:6482-6489

Toyofuku, M., Nomura, N., Fujii, T., Takaya, N., Maseda, H., Sawada, I., et al. (2007) Quorum sensing regulates denitrification in *Pseudomonas aeruginosa* PAO1. J Bacteriol 189: 4969-4972.

Trulear M G, Characklis W G (1982) Dynamics of biofilm processes. J Water Pollut Control Fed 9:1288-1301

Van Alst, N. E., Picardo, K. F., Iglewski, B. H., and Haidaris, C. G. (2007) Nitrate sensing and metabolism modulate motility, biofilm formation, and virulence in *Pseudomonas aeruginosa*. Infect Immun 75: 3780-3790.

van Loosdrecht M C M, Picioreanu C, Heijnen J J (1997) A more unifying hypothesis for the structure of microbial biofilms. FEMS Microbiol Ecol 24:181-183

Vats N, Lee SF (2000) Active detachment of Streptococcus mutans cells adhered to epon-hydroxylapatite surfaces coated with salivary proteins in vitro. Arch Oral Biol 45:305-314

Vihersaari, T., Kivisaari, J. & Niinikoski, J. Effect of changes in inspired oxygen tension on wound metabolism. *Annals of surgery* 179, 889 (1974).

Waite, R., Paccanaro, A., Papakonstantinopoulou, A., Hurst, J., Saqi, M., Littler, E., & Curtis, M. (2006) Clustering of *Pseudomonas aeruginosa* transcriptomes from planktonic cultures, developing and mature biofilms reveals distinct expression profiles. BMC Genomics 7: 162.

Walters, M. C. III, Roe, F., Bugnicourt, A., Franklin, M. J., and Stewart, P. S. (2003) Contributions of antibiotic penetration, oxygen limitation, and low metabolic activity to tolerance of *Pseudomonas aeruginosa* biofilms to ciprofloxacin and tobramycin. Antimicrob Agents Chemother 47: 317-323.

Wang L H et al (2004) A bacterial cell-cell communication signal with cross-kingdom structural analogues. Mol Microbiol 51:903-912

Wang, J. F., Olson, M. E., Reno, C. R., Wright, J. B. & Hart, D. A. The pig as a model for excisional skin wound healing: characterization of the molecular and cellular biology, and bacteriology of the healing process. *Comparative medicine* 51, 341-348 (2001).

Whitchurch C B, Tolker-Nielsen T, Ragas P C, Mattick J S (2002) Extracellular DNA required for bacterial biofilm formation. Science 295:1487

Winsor, G. L., Van Rossum, T., Lo, R., Khaira, B., Whiteside, M. D., Hancock, R. E. W., and Brinkman, F. S. L. (2009) Pseudomonas genome database: facilitating user-friendly, comprehensive comparisons of microbial genomes. Nucleic Acids Res 37: D483-D488.

Wolcott R, Rhoads D, Bennett M, Wolcott B, Gogokhia L, Costerton J, Dowd S. Chronic wounds and the medical biofilm paradigm. J. Wound Care 19:45-46,48-50,52-43 (2010).

Wu, M., Guina, T., Brittnacher, M., Nguyen, H., Eng, J., and Miller, S. I. (2005) The *Pseudomonas aeruginosa* proteome during anaerobic growth. J Bacteriol 187: 8185-8190.

Wu, Z., and Irizarry, R. A. (2004) Preprocessing of oligonucleotide array data. Nat Biotechnol 22: 656-658.

Xun L, Mah R A, Boone D R (1990) Isolation and characterization of disaggregatase from Methanosarcina mazei LYC. Appl Environ Microbiol 56:3693-3698.

Yaehne, K. et al. Nanoparticle accumulation in angiogenic tissues: towards predictable pharmacokinetics. *Small* 9, 3118-3127 (2013).

Yager, D. R. & Nwomeh, B. C. The proteolytic environment of chronic wounds. *Wound Repair and Regeneration* 7, 433-441 (1999).

Yan, J., C. D. Nadell, B. L. Bassler, Environmental fluctuation governs selection for plasticity in biofilm production, ISME J., 11 (2017), pp. 1569-1577

Yang, L., Barken, K. B., Skindersoe, M. E., Christensen, A. B., Givskov, M., and Tolker-Nielsen, T. (2007) Effects of iron on DNA release and biofilm development by *Pseudomonas aeruginosa*. Microbiology 153: 1318-1328.

Yarmush, D. M. et al. Cutaneous burn injury alters relative tricarboxylic acid cycle fluxes in rat liver. *Journal of Burn Care & Research* 20, 292-302 (1999).

Yarwood, J. M., D. J. Bartels, E. M. Volper, E. P. Greenberg, Quorum sensing in *Staphylococcus aureus* biofilms, J. Bacteriol., 186 (2004), pp. 1838-1850

Yildiz, F. H., G. K. Schoolnik, Role of rpoS in stress survival and virulence of Vibrio cholera, J. Bacteriol., 180 (1998), pp. 773-784

Yoon, S. S., Hennigan, R. F., Hilliard, G. M., Ochsner, U. A., Parvatiyar, K., Kamani, M. C., et al. (2002) *Pseudomonas aeruginosa* anaerobic respiration in biofilms: relationships to cystic fibrosis pathogenesis. Dev Cell 3: 593-603.

Zhu, J., J. J. Mekalanos, Quorum sensing-dependent biofilms enhance colonization in Vibrio cholera, Dev. Cell, 5 (2003), pp. 647-656.

U.S. Patent App. 20130302390; 20130216637; 20080317815; 20070207095.

Dispersion inducers and quorum sensing factors may include various factors, such as ATP, c-di-GMP, other cyclic nucleotides, cis-2-decenoic acid, Skyllamycins A to C, nitric oxide, diphenyl selenide, etc.

Known antimicrobial agent include (poly)peptides, amikacin, aminoglycosides, amoxicillin, amoxicillin/clavulanate, amphotericin B, ampicillin, ampicillin-sulbactam, anidulafungin, ansamycins, arsphenamine, azithromycin, azlocillin, aztreonam, bacitracin, bacteriocins, bismuth thiols, carbacephems, carbapenems, carbenicillin, caspofungin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftaroline, ceftazidime, ceftibuten, ceftizoxime, ceftobiprole, ceftriaxone, cefuroxime, cephalexin, cephalosporins, chloramphenicol, ciprofloxacin, clarithromycin, clindamycin, clofazimine, cloxacillin, colicins, colistin, dalbavancin, daptomycin, demeclocycline, dicloxacillin, dirithromycin, doripenem, doxycycline, enoxacin, ertapenem, erythromycin, ethambutol, fecluroxime, flucloxacillin, fluconazole, flucytosine, fosfomycin, furazolidone, gatifloxacin, gemifloxacin, gentamicin, glycopeptides, grepafloxacin, imipenem, imipenem/cilastatin, isoniazid, itraconazole, kanamycin, ketoconazole, levofloxacin, lincomycin, lincosamides, linezolid, lomefloxacin, loracarbef, macrolides, mafenide, meropenem, metronidazole, mezlocillin, micafungin, microcins, minocycline, moxifloxacin, mupirocin, nafcillin, naldixic acid, neomycin, netilmicin, nitrofurans, nitrofurantoin, norfloxacin, ofloxacin, oritavancin, oxazolidinones, oxycycline, oxytetracycline, paromomycin, penicillins, piperacillin, piperacillin-tazobactam, polymyxin B, polypeptides, posaconazole, posizolid, prontosil, pyrazinamide, quinolones, quinupristin/dalfopristin, radezolid, rifampicin, rifampin, rifaximin, roxithromycin, sparfloxacin, spectinomycin, spiramycin, streptomycin, suflonamides, sulfacetamide, sulfadiazine, sulfadimethoxine, sulfamethizole, sulfamethoxazole, sulfasalazine, sulfisoxazole, sulfonamides, teicoplanin, telavancin, telithromycin, temafloxacin, tetracyclines, ticarcillin, ticarcillin/clavulanate, tigecycline, tobramycin, torezolid, trimethoprim, trimethoprim-sulfamethoxazole, trovafloxacin, vancomycin, and voriconazole.

Known antibiofilm agents include: 6086921; 6106854; 6248371; 6641739; 6692757; 6793900; 6887270; 6908912; 7025986; 7052614; 7087661; 7144992; 7147888; 7151139; 7189329; 7189351; 7201925; 7217425; 7255881; 7314857; 7399742; 7402722; 7419607; 7427416; 7446089; 7450228; 7452345; 7556807; 7601731; 7628929; 7691418; 7744555; 7760353; 7781166; 7790947; 7794698; 7829305; 7863029; 7897631; 7906544; 7927496; 7993390; 7998919; 8071540; 8076117; 8105520; 8133501; 8142764; 8153119; 8153410; 8153412; 8162924; 8168072; 8173673; 8211361; 8216173; 8227017; 8231686; 8236545; 8246691; 8257827; 8267883; 8273104; 8278340; 8282593; 8282967; 8309590; 8318180; 8329758; 8343086; 8343911; 8349368; 8366652; 8367713; 8367716; 8367823; 8377455; 8383101; 8383582; 8389021; 8389679; 8398705; 8399235; 8399649; 8414517; 8415159; 8425880; 8431151; 8444858; 8460229; 8460916; 8461106; 8476425; 8481138; 8486428; 8501969; 8507244; 8545951; 8546121; 8552147; 8552208; 8569449; 8574660; 8585627; 8591876; 8591961; 8592473; 8609110; 8617523; 8617542; 8618149; 8623340; 8632838; 8637090; 8641686; 8647292; 8652829; 8653124; 8658225; 8680072; 8680148; 8684732; 8685427; 8685957; 8691264; 8697102; 8697375; 8702640; 8706211; 8709342; 8710082; 8715733; 8728467; 8734718; 8741855; 8753304; 8753692; 8754039; 8758781; 8778370; 8778387; 8778889; 8779023; 8785399; 8795727; 8796252; 8802059; 8802414; 8808718; 8809031; 8809314; 8821862; 8821910; 8828910; 8829053; 8835644; 8840912; 8846008; 8846009; 8846605; 8852912; 8853278; 8865909; 8884022; 8888731; 8889196; 8906349; 8906364; 8906393; 8906898; 8906915; 8920826; 8926951; 8927029; 8940911; 8945142; 8952192; 8956658; 8956663; 8962029; 8962283; 8968753; 8968765; 8981139; 8992223; 8999265; 9005263; 9005643; 9028878; 9029318; 9034346; 9034927; 9044485; 9045550; 9056899; 9073884; 9078441; 9084423; 9085608; 9096703; 9125408; 9125853; 9139622; 9145395; 9149648; 9150453; 9156855; 9161923; 9161984; 9167820; 9169319; 9180157; 9180158; 9181290; 9187501; 9198957; 9220267; 9221765; 9221875; 9227980; 9242951; 9247734; 9253987; 9265820; 9271493; 9271502; 9273096; 9283283; 9284351; 9289442; 9289449; 9295257; 9308298; 9320740; 9321030; 9326511; 9326924; 9326925; 9334466; 9339525; 9351491; 9351492; 9358274; 9364491; 9370187; 9376430; 9387189; 9402394; 9403851; 9403852; 9408393; 9415144; 9423532; 9427605; 9433527; 9439433; 9439436; 9439803; 9446090; 9452107; 9469616; 9474831; 9480260; 9480541; 9487453; 9492596;

9499594; 9504688; 9504739; 9518013; 9526738; 9526766; 9539233; 9539367; 9539373; 9540471; 9550005; 9554971; 9556109; 9556223; 9561168; 9562085; 9562254; 9565857; 9566247; 9566341; 9566372; 9574185; 9586871; 9592299; 9592324; 9597407; 9603859; 9603877; 9603977; 9603979; 9612246; 9617176; 9622481; 9631100; 9642829; 9644194; 9648876; 9657132; 9669001; 9669041; 9675077; 9675736; 9682023; 9683197; 9687670; 9694114; 9700058; 9700650; 9706778; 9713631; 9713652; 9717251; 9717765; 9718739; 9723833; 9723837; 9723843; 9724353; 9732124; 9737561; 9737571; 9737591; 9744270; 9757397; 9764069; 9770418; 9777050; 9782388; 9782423; 9789005; 9795762; 9801982; 9808496; 9814719; 9815794; 9833528; 9834744; 9839219; 9849182; 9850322; 9854807; 9855211; 9856225; 9861701; 9861723; 9862837; 9867906; 9872491; 9872893; 9872906; 9872917; 9877983; 9889077; 9895469; 9907584; 9914750; 9918473; 9919012; 9919072; 9919079; 9926526; 9931300; 9931381; 9932484; 9937104; 9956319; 9956322; 9975857; 20020066702; 20020123077; 20030065292; 20030079758; 20030091641; 20030099602; 20030103912; 20030111420; 20030121868; 20030134783; 20030178044; 20040110738; 20040116371; 20040116845; 20040129112; 20040131698; 20040156883; 20040156884; 20040176312; 20040191329; 20040254545; 20050003725; 20050013836; 20050032093; 20050049181; 20050064019; 20050143286; 20050147719; 20050158263; 20050202424; 20050233950; 20050249695; 20060001865; 20060018945; 20060034782; 20060067951; 20060110456; 20060120916; 20060138058; 20060162014; 20060177384; 20060180552; 20060224103; 20060243297; 20070009566; 20070010856; 20070020309; 20070062884; 20070083156; 20070098651; 20070098674; 20070098745; 20070106232; 20070109535; 20070116750; 20070116798; 20070134649; 20070190090; 20070202770; 20070224161; 20070231406; 20070232167; 20070244059; 20070258913; 20080014247; 20080014278; 20080014286; 20080044491; 20080050452; 20080075730; 20080085282; 20080085866; 20080107707; 20080109017; 20080113001; 20080138634; 20080181923; 20080206183; 20080206305; 20080248087; 20080268189; 20080286847; 20080293607; 20080318268; 20080318269; 20090033930; 20090048324; 20090050575; 20090069406; 20090074825; 20090099533; 20090112186; 20090133810; 20090143230; 20090155215; 20090163964; 20090163965; 20090163977; 20090171263; 20090177139; 20090177254; 20090181106; 20090202516; 20090214603; 20090221704; 20090238923; 20090260632; 20090263438; 20090270475; 20090318382; 20090324574; 20100015245; 20100016767; 20100021587; 20100028396; 20100048446; 20100055086; 20100056415; 20100059433; 20100096340; 20100129297; 20100129466; 20100130450; 20100133114; 20100136072; 20100136143; 20100145412; 20100152101; 20100158966; 20100158967; 20100173366; 20100174346; 20100178268; 20100183738; 20100189706; 20100221198; 20100234792; 20100234793; 20100240017; 20100241048; 20100241049; 20100241050; 20100241051; 20100241052; 20100241053; 20100241054; 20100241055; 20100247374; 20100249692; 20100254967; 20100255178; 20100266716; 20100272768; 20100286198; 20100292629; 20100298208; 20100305062; 20100316643; 20100322903; 20110003001; 20110008402; 20110008786; 20110027252; 20110027384; 20110029076; 20110033520; 20110033882; 20110039761; 20110039762; 20110039763; 20110046041; 20110052664; 20110077192; 20110086101; 20110098323; 20110104179; 20110105376; 20110117158; 20110117160; 20110119774; 20110124716; 20110129454; 20110135621; 20110144566; 20110150819; 20110152176; 20110152750; 20110152751; 20110152752; 20110152789; 20110152790; 20110152978; 20110160643; 20110160644; 20110160681; 20110171123; 20110171189; 20110172704; 20110177048; 20110177049; 20110177050; 20110177111; 20110182873; 20110182874; 20110201692; 20110207816; 20110208021; 20110208023; 20110208026; 20110217544; 20110229586; 20110236453; 20110250290; 20110256187; 20110262511; 20110266724; 20110274730; 20110275518; 20110275912; 20110280920; 20110281921; 20110294668; 20110295088; 20110295089; 20110295090; 20110301076; 20110305872; 20110305881; 20110305895; 20110305898; 20110305909; 20110306699; 20110311647; 20110319808; 20120010187; 20120010481; 20120015870; 20120020896; 20120039945; 20120040030; 20120041285; 20120041286; 20120041287; 20120045817; 20120052052; 20120058076; 20120058167; 20120058169; 20120058933; 20120077736; 20120087887; 20120088671; 20120094007; 20120107258; 20120122729; 20120128599; 20120129794; 20120134951; 20120135925; 20120136323; 20120142583; 20120149631; 20120150119; 20120152149; 20120156645; 20120157548; 20120160779; 20120171129; 20120178971; 20120189682; 20120201869; 20120209090; 20120213697; 20120219638; 20120225098; 20120238644; 20120244126; 20120252101; 20120258089; 20120258141; 20120283174; 20120288566; 20120288571; 20120294900; 20120301433; 20120308632; 20120315260; 20120321566; 20120328577; 20120328671; 20120328683; 20120328684; 20120328708; 20120328713; 20120329675; 20120329746; 20130005029; 20130022578; 20130029981; 20130039978; 20130045182; 20130052250; 20130058983; 20130059096; 20130059113; 20130059929; 20130071439; 20130095184; 20130101678; 20130101963; 20130102679; 20130108708; 20130110162; 20130123225; 20130123319; 20130129768; 20130129795; 20130129800; 20130131575; 20130136730; 20130136782; 20130149542; 20130150451; 20130158127; 20130158488; 20130158517; 20130158518; 20130164228; 20130164363; 20130165595; 20130171210; 20130171224; 20130171228; 20130172187; 20130183435; 20130190699; 20130196365; 20130197455; 20130210708; 20130220331; 20130224258; 20130224260; 20130225675; 20130231302; 20130252818; 20130252945; 20130266522; 20130266629; 20130267471; 20130281503; 20130287860; 20130287861; 20130309219; 20130310346; 20130315874; 20130315967; 20130330386; 20130330388; 20130337088; 20130344542; 20130345261; 20140005605; 20140020138; 20140023691; 20140037688; 20140037967; 20140039195; 20140039357; 20140056951; 20140056952; 20140056993; 20140057324; 20140065200; 20140072525; 20140073560; 20140073690; 20140079741; 20140079808; 20140105986; 20140107071; 20140120052; 20140127273; 20140128313; 20140142028; 20140147481; 20140155318; 20140155478; 20140161728; 20140161772; 20140161845; 20140170238; 20140171438; 20140172117; 20140186318; 20140187666; 20140193489; 20140194594; 20140205586; 20140205643; 20140212828; 20140221331; 20140221610; 20140223602; 20140228327; 20140234380; 20140241997; 20140242023; 20140243725; 20140255318; 20140257482; 20140271763; 20140271777; 20140276253; 20140276254; 20140277301; 20140288007; 20140288171; 20140294907; 20140302113; 20140308217; 20140308317; 20140308361; 20140322351; 20140322362; 20140328887; 20140328890; 20140328895; 20140328999; 20140335144; 20140342954; 20140348780; 20140349917; 20140350017; 20140357592; 20140370078; 20140371171; 20150005228; 20150011504; 20150018284; 20150018330; 20150024000; 20150024017; 20150024052; 20150031738; 20150038512; 20150038705; 20150044147; 20150044260; 20150045515; 20150050717; 20150056411; 20150080289; 20150080290; 20150086561; 20150086631; 20150087573; 20150087582; 20150099020; 20150110898; 20150111813; 20150118219; 20150132352; 20150147775; 20150148286;

20150148612; 20150157542; 20150159180; 20150165095; 20150166706; 20150166796; 20150167046; 20150173883; 20150182667; 20150183746; 20150190447; 20150197558; 20150209393; 20150224220; 20150225458; 20150225488; 20150231045; 20150231287; 20150237870; 20150238543; 20150246995; 20150259390; 20150274639; 20150283208; 20150283287; 20150297478; 20150297642; 20150299298; 20150299345; 20150315253; 20150322272; 20150327552; 20150332151; 20150335013; 20150335027; 20150336855; 20150351383; 20150351392; 20150368480; 20150374634; 20150374658; 20150374720; 20160008275; 20160009733; 20160010137; 20160015047; 20160021882; 20160022564; 20160022595; 20160022707; 20160024551; 20160030327; 20160031941; 20160038572; 20160038650; 20160058675; 20160058693; 20160058772; 20160058816; 20160058834; 20160058998; 20160067149; 20160073638; 20160074345; 20160075749; 20160089481; 20160096865; 20160106107; 20160106689; 20160107126; 20160109401; 20160120184; 20160122697; 20160128335; 20160129078; 20160135463; 20160135469; 20160137563; 20160137564; 20160137565; 20160157497; 20160158169; 20160158353; 20160166712; 20160176815; 20160184485; 20160185630; 20160186147; 20160193344; 20160194288; 20160198994; 20160199295; 20160206575; 20160212996; 20160213001; 20160220722; 20160223553; 20160235698; 20160235893; 20160235894; 20160237145; 20160242413; 20160249612; 20160256484; 20160262384; 20160263225; 20160270411; 20160278375; 20160279191; 20160279314; 20160280772; 20160289272; 20160289287; 20160304886; 20160309711; 20160317611; 20160317618; 20160324531; 20160330962; 20160338993; 20160339071; 20160346115; 20160346161; 20160346436; 20160353739; 20160355487; 20160375034; 20160375074; 20160376449; 20170007733; 20170009084; 20170014208; 20170014437; 20170020139; 20170022165; 20170022371; 20170028106; 20170029363; 20170035955; 20170042965; 20170043111; 20170044222; 20170049113; 20170050893; 20170050927; 20170056297; 20170056405; 20170056437; 20170056454; 20170056455; 20170056565; 20170064966; 20170065564; 20170065673; 20170071212; 20170071986; 20170072024; 20170072098; 20170073706; 20170080130; 20170095502; 20170100328; 20170100348; 20170100512; 20170100513; 20170100514; 20170100515; 20170100516; 20170100517; 20170100518; 20170100522; 20170100523; 20170106188; 20170107250; 20170112723; 20170113038; 20170119915; 20170127683; 20170128338; 20170128502; 20170128720; 20170135342; 20170137380; 20170143842; 20170150724; 20170156321; 20170158727; 20170173186; 20170182205; 20170189556; 20170197028; 20170202752; 20170216094; 20170216197; 20170216369; 20170216377; 20170216410; 20170224748; 20170232038; 20170232048; 20170232153; 20170240618; 20170246205; 20170246341; 20170247409; 20170247414; 20170252320; 20170258963; 20170266239; 20170266306; 20170273301; 20170274082; 20170280725; 20170281570; 20170281699; 20170283763; 20170290789; 20170290854; 20170295784; 20170296599; 20170297055; 20170312307; 20170312345; 20170326054; 20170333455; 20170333601; 20170339962; 20170340779; 20170347661; 20170347664; 20170360534; 20170360982; 20170367933; 20180000993; 20180008533; 20180008742; 20180014974; 20180014975; 20180015061; 20180016311; 20180021463; 20180028417; 20180028701; 20180028713; 20180030403; 20180030404; 20180030405; 20180030607; 20180036286; 20180036702; 20180037545; 20180037613; 20180042789; 20180042928; 20180043190; 20180049856; 20180051061; 20180079757; 20180079912; 20180085335; 20180085392; 20180085489; 20180085717; 20180092939; 20180093011; 20180105792; 20180110228; 20180111893; 20180112068; 20180119235; 20180125066; 20180125070; and 20180133326.

Enzyme encapsulation technologies include: 4006056; 4183960; 4257884; 4310554; 4342826; 4401122; 4418148; 4431428; 4458686; 4463090; 4483921; 4622294; 4666830; 4693970; 4756844; 4783400; 4861597; 4863626; 4876039; 4898781; 4900556; 4933185; 4963368; 4965012; 5015483; 5064669; 5068198; 5089278; 5093021; 5139803; 5147641; 5167854; 5190762; 5200236; 5200334; 5225102; 5230822; 5254287; 5258132; 5262313; 5272079; 5275154; 5281355; 5281356; 5281357; 5296231; 5324436; 5352458; 5385959; 5413804; 5434069; 5437331; 5441660; 5492646; 5505713; 5506271; 5523232; 5538511; 5545519; 5589370; 5604186; 5665380; 5693513; 5698083; 5752981; 5753152; 5777078; 5788678; 5830663; 5846927; 5858117; 5858430; 5861366; 5868720; 5895757; 5929214; 6017528; 6022500; 6051541; 6127499; 6197739; 6209646; 6225372; 6242405; 6258771; 6280980; 6303290; 6313197; 6359031; 6362156; 6368619; 6369018; 6395299; 6495352; 6500463; 6541606; 6608187; 6630436; 6730212; 6730651; 6818594; 6833192; 6927201; 6943200; 6972278; 6974706; 6979669; 7008524; 7033980; 7034677; 7052913; 7060299; 7153407; 7171312; 7172682; 7195780; 7198785; 7201923; 7250095; 7267837; 7267958; 7285523; 7329388; 7351798; 7375168; 7427497; 7491699; 7553653; 7723056; 7736480; 7740821; 7750050; 7750135; 7763097; 7786086; 7811436; 7846747; 7858561; 7927629; 7939061; 7942201; 7998714; 8007724; 8007725; 8030092; 8043411; 8053554; 8066818; 8101562; 8178332; 8182746; 8226996; 8268247; 8297959; 8313757; 8318156; 8323379; 8329225; 8350004; 8354366; 8361239; 8393395; 8399230; 8404469; 8460907; 8546316; 8558048; 8568786; 8575083; 8617623; 8685171; 8709487; 8759270; 8796023; 8810417; 8834865; 8852880; 8877506; 8898069; 8927689; 8932578; 8951749; 8961544; 8974802; 8980252; 8992986; 9012378; 9024766; 9056050; 9068109; 9074195; 9084784; 9089498; 9102860; 9107419; 9109189; 9121017; 9125876; 9146234; 9187766; 9200265; 9222060; 9273305; 9321030; 9333244; 9339529; 9376479; 9393217; 9415014; 9441157; 9458448; 9464368; 9492515; 9511125; 9562251; 9580739; 9618520; 9631215; 9637729; 9687452; 9700519; 9708640; 9717688; 9738689; 9744141; 9744221; 9744247; 9765324; 9782358; 9789439; 9790254; 9895427; 9907755; 9909143; 9931302; 9931433; 9957540; 9968663; 9970000; 20010044193; 20020045582; 20020058027; 20020094367; 20020106511; 20030045441; 20030059449; 20030060378; 20030062263; 20030082238; 20030158344; 20030162284; 20030162293; 20030175239; 20030219491; 20040061841; 20040076681; 20040121926; 20040135684; 20040147427; 20040149577; 20040175429; 20040198629; 20040204915; 20040241205; 20040249082; 20040265835; 20050037374; 20050053954; 20050123529; 20050130845; 20050150762; 20050150763; 20050153934; 20050155861; 20050163714; 20050176610; 20050245418; 20050245419; 20050255543; 20060045904; 20060079454; 20060110494; 20060159671; 20060160134; 20060280799; 20070001156; 20070003607; 20070048855; 20070059779; 20070098807; 20070111329; 20070116671; 20070128714; 20070134812; 20070141096; 20070141217; 20070154466; 20070166285; 20070224273; 20070258894; 20070296099; 20080009434; 20080014622; 20080090276; 20080115945; 20080145477; 20080187487; 20080220487; 20080223722; 20080226623; 20080274092; 20080283242; 20080302669; 20080311177; 20090035381; 20090075845; 20090088329; 20090110741; 20090123553; 20090162337; 20090169677; 20090181874; 20090186077; 20090202836; 20090246318; 20090288826; 20090297592; 20090301885; 20090324476; 20100015635; 20100034799; 20100074933;

20100081849; 20100086983; 20100125046; 20100159508; 20100192986; 20100196986; 20100197548; 20100197549; 20100197550; 20100197551; 20100197552; 20100197553; 20100197554; 20100210745; 20100213062; 20100239559; 20100240116; 20100255100; 20100258116; 20100260857; 20100267594; 20100291162; 20100291828; 20100307744; 20100310612; 20100316571; 20100316620; 20110015088; 20110039164; 20110039314; 20110039751; 20110045517; 20110050431; 20110053173; 20110053283; 20110054938; 20110081394; 20110111425; 20110117623; 20110177982; 20110217363; 20110217368; 20110217553; 20110229565; 20110229580; 20110269029; 20110280853; 20110280854; 20110300201; 20110300623; 20120016217; 20120021964; 20120027848; 20120028872; 20120028873; 20120040429; 20120063276; 20120066851; 20120071379; 20120071383; 20120121570; 20120143027; 20120189703; 20120220025; 20120240961; 20120258149; 20120261256; 20120318515; 20120322713; 20130017148; 20130017610; 20130029894; 20130029895; 20130067669; 20130084312; 20130108737; 20130113129; 20130131701; 20130133102; 20130136728; 20130149357; 20130195948; 20130195985; 20130197100; 20130207042; 20130219643; 20130224172; 20130224828; 20130244301; 20130251786; 20130284637; 20130323223; 20130345099; 20140027655; 20140045241; 20140046181; 20140086988; 20140127184; 20140127305; 20140127778; 20140151042; 20140219980; 20140295520; 20140323330; 20140328801; 20140335148; 20140348815; 20150010453; 20150026840; 20150030641; 20150071894; 20150086521; 20150086599; 20150099289; 20150147308; 20150147311; 20150147365; 20150147786; 20150150955; 20150151248; 20150166975; 20150190530; 20150191607; 20150191681; 20150203799; 20150231589; 20150246104; 20150246105; 20150335589; 20150374798; 20150376594; 20160022592; 20160022598; 20160030532; 20160038608; 20160045576; 20160051484; 20160051697; 20160075976; 20160101058; 20160120956; 20160123925; 20160153025; 20160160195; 20160168559; 20160175634; 20160193307; 20160208202; 20160215242; 20160215243; 20160222068; 20160222372; 20160222437; 20160243262; 20160250304; 20160291000; 20160326215; 20160354313; 20160361361; 20170002481; 20170035891; 20170044472; 20170107461; 20170107523; 20170176453; 20170188604; 20170189501; 20170190951; 20170191005; 20170202934; 20170204316; 20170211023; 20170218315; 20170219601; 20170247493; 20170252413; 20170292063; 20170304489; 20170321160; 20170321161; 20170333360; 20170333363; 20170335244; 20170335255; 20170349818; 20170368155; 20180008549; 20180008550; 20180016569; 20180030390; 20180050115; 20180055777; 20180073046; and 20180104315.

Enzyme immobilization technologies are known. See:

Barbosa, Oveimar, Rodrigo Tones, Claudia Ortiz:, Angel Berenguer-Murcia, Rafael C. Rodrigues, and Roberto Fernandez-Lafuente. "Heterofunctional supports in enzyme immobilization: from traditional immobilization protocols to opportunities in tuning enzyme properties." *Biomacromolecules* 14, no. 8 (2013): 2433-2462.

Biró, Emese, Agnes Sz Németh, Csaba Sisak, Tivadar Feczkó, and János Gyenis. "Preparation of chitosan particles suitable for enzyme immobilization." *Journal of Biochemical and Biophysical Methods* 70, no. 6 (2008): 1240-1246.

Brady, Dean, and Justin Jordaan. "Advances in enzyme immobilisation." *Biotechnology letters* 31, no. 11 (2009): 1639.

Cantone, Sara, Valerio Ferrario, Livia Coric Cynthia Ebert, Diana Fattor, Patrizia Spizzo, and Lucia Gardossi. "Efficient immobilisation of industrial biocatalysts: criteria and constraints for the selection of organic polymeric carriers and immobilisation methods." *Chemical Society Reviews* 42, no. 15 (2013): 6262-6276.

Datta, Sumitra, L. Rene Christena, and Yamuna Rani Sriramulu Rajaram. "Enzyme immobilization: an overview on techniques and support materials." 3 *Biotech* 3, no. 1 (2013):1-9.

Diaz, J. Felipe, and Kenneth J. Balkus Jr. "Enzyme immobilzation in MCM-41 molecular sieve." *Journal of Molecular Catalysis B. Enzymatic* 2, no. 2-3 (1996): 115-126.

DiCosimo, Robert, Joseph McAuliffe, Ayrookaran J. Poulose, and Gregory Bohlmann. "Industrial use of immobilized enzymes." *Chemical Soc. Reviews* 42, no. 15 (2013): 6437-6474.

Fernandez-Lafuente, Roberto. "Stabilization of multimeric enzymes: Strategies to prevent subunit dissociation." *Enzyme and Microbial Technology* 45, no. 6-7 (2009): 405-418.

Garcia-Galan, Cristina, Ángel Berenguer-Murcia, Roberto Fernandez-Lafuente, and Rafael C. Rodrigues. "Potential of different enzyme immobilization strategies to improve enzvtrle performance." *Advanced Synthesis & Catalysis* 353, no. 16 (2011): 2885-2904.

Guzik, Urszula, Katarzyna Hupert-Kocurek, and Danuta Wojcieszynska. "Immobilization as a strategy for improving enzyme properties-application to oxidoreductases," *Molecules* 19, no. 7 (2014): 8995-9018.

Homaei, Ahmad Abolpour, Reyhaneh Sariri, Fabio Vianello, and Roberto Stevanato. "Enzyme immobilization: an update." *Journal of chemical biology* 6, no. 4 (2013); 185-205.

Hwang, Fe lack, and Man Bock Gu. "Enzyme stabilization by nano/microsized hybrid materials." *Engineering in Life Sciences* 13, no. 1 (2013): 49-61.

Iyer, Padma V., and Laxmi Ananthanarayan. "Enzyme stability and stabilization aqueous and non-aqueous environment." *Process biochemicstry* 43, no. 10 (2008): 1019-1032.

Jesionowski, Teofil, Jakub Zdarta, and Barbara Krajewska. "Enzyme immobilization by adsorption: a review." *Adsorption* 20, no. 5-6 (2014): 801-821.

Juang, Ruey-Shin, Feng-Chin Wu, and Ru-Ling Tseng. "Use of chemically modified cliitosan beads for sorption and enzyme immobilization." *Advances in Environmental Research* 6, no. 2 (2002): 171-177.

Luckarift, Heather R., Jim C. Spain, Rajesh R. Naik, and Morley O. Stone. "Enzyme immobilization in a biomimetic silica support." *Nature biotechnology* 22, no. 2 (2004): 211.

Mateo, Cesar, Jose M. Palomo, Gloria Fernandez-Lorente, Jose M. Guisan, and Roberto Fernandez-Lafuente. "Improvement of enzyme activity, stability and selectivity via inamobilization techniques." *Enzyme and microbial technology* 40, no. 6 (2007): 1451-1463.

Paribasarothy, Ranjani V., and Charles R. Martin. "Synthesis of polymeric microcapsule arrays and their use for enzyme immobilization," *Nature* 369, no. 6478 (1994): 298.

Pierre, Sbbashen J. Jens C. Thies, Alex Dureault, Neil R. Cameron, pari C M van Hest, Noëlle Carette, Thierry Michon, and Ralf Weberskircli. "Covalent enzyme immobilization onto photopolyrnerized highly porous monoliths." *Advanced Materials* 18, no. 14 (2006): 1822-1826.

Pollak, Alfred, Hugh Blumenfeld, Michael Wax, Richard L. Baugh z, and George M. Whitesides. "Enzyme immobilization by condensation copolymerization into crosslinked polyacrylamide gels." *Journal of the American Chemical Society* 102 no. 20 (1980): 6324-6336.

Qhobosheane, Monde, Swadeshmukul Santra, :hang, and Weihong Tan, "Biochemically functionalized silica nanoparticles." *Analyst* 126, no. 8 (2001): 1274-1278.

Rodrigues, Rafael C., Ángel Berenguer-Murcia, and Roberto Fernandez-Lafuente. "Coupling chemical modification and immobilization to improve the catalytic performance of enzymes." *Advances Synthesis * Catalysis* 353, no. 13 (2011): 2216-2238.

Rodrigues, Rafael C., Claudia Ortiz, Ángel Berenguer-Murcia, Rodrigo Tones, and Roberto Fernandez-Lafuente. "Modifying enzyme activity and selectivity by immobilization." *Chemical Society Reviews* 42, no. 15 (2013): 6290-6307.

Sheldon, Roger A. "Enzyme immobilization: the quest For optimum performance." *Advances Synthesis & Catalysis* 349, no. 8-9 (2007): 1289-1307.

Sheldon, Roger A., and Sander an Pelt, "Enzyme immobilisation in biocatalysis: why, what and how." *Chemical Soceity Reviews* 42, no, 15 (2013): 6223-6235.

Spahn, Cynthia, and Shelley D. Minteer. "Enzyme immobilization in biotechnology." *Recent patents on engineering* 2, no. 3 (2008): 195-200.

Taqieddin, Ehab, and Mansoor Amiji. "Enzyme immobilization in novel alginate-chitosan core-shell microcapsules." *Biomaterials* 25, no. 10 (2004): 1937-1945.

Wang, Zhen-Gang, Ling-Shu Wan, Zhen-Mei Liu, Xiao-Jun Huang, and Zhi-Kang Xu. "Enzyme mmobilization electrospun polymer nanofibers: an overview." *Journal of Molecular Catalysis B. Enzymatic* 56, no. 4 (2009): 189-195.

The following enzymes are known to adversely impact biofilms:

Proteases:
    Aureolysin (Aur)
    LapG Protease
    Pronase
    Proteinase K
    Savinase
    Spl Proteases
    Staphopain A (ScpA)1 Staphopain B (SspB)
    Streptococcal Cysteine Protease (SpeB)
    Surface-protein-releasing enzyme (SPRE)
    Trypsin
    V8 Serine Protease (SspA)

DNases
    DNase I
    DNase 1L2
    Dornase alpha
    λ Exonuclease
    NucB
    Streptodornase Glycoside Hydrolases
    Alginate lyase
    α-amylase
    α-mannosidase
    β-mannosidase
    Cellulase
    Dispersin B
    Hyaluronidase
    PelAh
    PslGH Qurom-Sensing Signal-Degrading Enzymes
    Acylase
    Lactonase Combinations
    Glucose oxidase+lactoperoxidase
    Acylase I+proteinase K
    Cellulase+pronase

SUMMARY OF THE INVENTION

The use of exogenously provided pyruvate dehydrogenase as an adjuvant in treating biofilm-related wound infections is based an experimental finding that depleting pyruvate from the extracellular environment using this enzyme severely impairs the formation of structured *Pseudomonas aeruginosa* biofilms. The resulting unstructured biofilms are more susceptible to antimicrobial treatment than structured, fully mature biofilms.

See, Goodwine, James, Joel Gil, Amber Doiron, Jose Valdes, Michael Solis, Alex Higa, Stephen Davis, and Karin Sauer. "Pyruvate-depleting conditions induce biofilm dispersion and enhance the efficacy of antibiotics in killing biofilms in vitro and in vivo." Scientific reports 9, no. 1 (2019): 3763; Goodwine, James Stephen. Enzymatic Depletion of Pyruvate using Pyruvate Dehydrogenase Induces Dispersion of *Pseudomonas aeruginosa* and *Staphylococcus aureus* Biofilms and Poses a Potentially Powerful Anti-Biofilm Treatment Strategy for Chronic Burn Wound Infections. State University of New York at Binghamton, ProQuest Dissertations Publishing, 2018. 10928981; Han, Chendong, Enzyme-Encapsulating Polymeric Nanoparticles as a Novel Approach in Biofilm Treatments, State University of New York at Binghamton, ProQuest Dissertations Publishing, 2018. 1342216, expressly incorporated herein by reference in their entirety.

However, pyruvate dehydrogenase has limited environmental stability, and is thermally sensitive and pH sensitive. The enzyme is also costly. The use of free pyruvate dehydrogenase to deplete pyruvate in the growth medium requires treatment of the entire fluid volume, and in the case of biofilms, chronic therapy is appropriate, rather than intermittent depletion of pyruvate. Therefore, for practical applications, such as a medical therapy or industrial biofouling remediation, the use of free enzyme is a poor match. However, it has been found that pyruvate dehydrogenase may be encapsulated, for example in a permeable polymer particle, with over 10% retention of activity, resulting in an enzyme use form that can be applied locally, and has increased stability and half-life.

Nanoparticles were found to tightly adhere to biofilms, thus, enabling direct delivery of pyruvate dehydrogenase where it is needed most.

Pyruvate-depleting conditions, such as this achieved through use of immobilized or encapsulated pyruvate dehydrogenase, are used to enhance the ability of antimicrobial agents and/or the immune system to control the growth and persistence of microorganisms as surface-attached communities or biofilms. Applications arise in medical settings, aqueous systems, and where disinfection of surfaces is required. Pyruvate-depleting conditions may be used as an adjuvant to antimicrobial agents to treat microbial biofilms, such as those related to human infections and diseases, Pyruvate depletion with an antimicrobial agent may also be used to combat microbial biofilms and biofouling in aquatic systems including but not limited to cooling towers, swimming pools and spas, water distribution systems, water handling systems, industrial water systems and environmental water systems. Pyruvate-depleting conditions, with or without antimicrobial agents, can be used to prevent biofilm growth on surfaces such as indwelling medical devices, dental water units and other medical devices prone to contamination with bacteria.

Pyruvate appears to be a key regulator for biofilm formation and biofilm dispersion, with pyruvate acting as a switch to control biofilm formation, biofilm dispersion, and biofilm drug tolerance. This is supported by the findings that while biofilm formation is enhanced by the presence of pyruvate, depletion of pyruvate from the growth environment coincides with impaired biofilm formation, disaggregation of existing biofilms, and dispersed biofilms being rendered susceptible to antibiotics relative to biofilms. Pyruvate utilization appears to be a biofilm-specific adaptation of the P. aeruginosa biofilm environment to cope with reductive stress.

Pyruvate is required for both biofilm formation and maintenance of the biofilm structure, with enzymatic depletion of pyruvate coinciding with impaired biofilm formation and dispersion of established biofilms; depletion of pyruvate can achieve both prevention of biofilm formation and induction of biofilm dispersion. Pyruvate can be depleted enzymatically using pyruvate dehydrogenase (PDH).

Pyruvate dehydrogenase-treated in vitro P. aeruginosa are significantly more susceptible (>2.5 log) to tobramycin. Pyruvate dehydrogenase-treated in vivo wound biofilms are significantly more susceptible (>2.5 log) to tobramycin, as indicated using porcine burn wounds infected with a clinical P. aeruginosa isolate. Additionally, pyruvate dehydrogenase enhancing the efficacy of antibiotics is not limited to P. aeruginosa, as pyruvate dehydrogenase-treated in vitro biofilms by Staph. aureus or E. coli are significantly more susceptible to antimicrobials.

According to one embodiment, a drug delivery strategy for pyruvate dehydrogenase is provided for pyruvate management using a simple, well established drug delivery vehicle to encapsulate PDH, with encapsulation intended to enhance PDH stability while protecting the enzyme from the wound environment and the immune system.

While several molecules or dispersion cues have been reported to induce the dispersion of biofilms, with dispersed cells being more susceptible to antimicrobial agents, pyruvate-depletion inducing conditions are capable of inducing dispersion of biofilms that are insensitive to other dispersion cues or signals. This is supported by the finding that biofilms by the mutant strains bdlA, rbdA, and dipA, that are impaired in the dispersion response upon exposure to nitric oxide or nutrient cues, disperse upon induction of pyruvate-depleting conditions.

Pyruvate depletion resulting in dispersion is not being limited to the laboratory PAO1 strain OF P. aeruginosa, as pyruvate dehydrogenase (PDH) likewise induced dispersion of biofilms by clinical P. aeruginosa isolates. Moreover, consistent with dispersed cells being more susceptible to antibiotics, pyruvate-depleting conditions also render P. aeruginosa biofilms present in porcine burn wounds significantly more susceptible (5.9 log reduction) to the antibiotic tobramycin relative to treatment with tobramycin alone (2.5 log reduction). Moreover, pyruvate-depleting conditions also impair biofilm formation by Staphylococcus aureus and Escherichia coli, with depletion of pyruvate from established S. aureus and E. coli biofilms resulting in biofilm dispersion.

Thus, pyruvate-depletion may be effective when other strategies fail, and has the capacity to have an additive effect with other dispersion cues or signals.

Pyruvate-depleting conditions provide an anti-biofilm treatment strategy capable of controlling the growth and persistence of microbial biofilms. It can be combined with antimicrobial agents and the immune system, to control the growth and persistence of biofilms.

Because the utilization of pyruvate for the formation of structured biofilms appears universal, it is not limited to P. aeruginosa, and for example will apply to other pathogens and industrially important biofilm forming organisms, such as Staphylococcus aureus. Pyruvate utilization is an essential adaptation for survival during oxygen limiting conditions (such as those found in biofilms) and for the formation of high-biomass structured biofilms. Max Schobert and colleagues demonstrated that P. aeruginosa is capable of fermentatively utilizing pyruvate for survival under conditions of oxygen limitation in the absence of nitrite and nitrate (Eschbach et al., 2004, Schreiber et al., 2006). The process involves the conversion of pyruvate to lactate, acetate, and/or succinate, with the lactate and acetate-producing branches of the pathway predominating. Schobert and Jahn (Schobert & Jahn, 2010) extrapolated these findings to a model that places P. aeruginosa biofilm cells within different niches, with metabolically active cells exposed to oxygen secreting pyruvate, which then diffuses into the anoxic zones to be utilized by cells residing within these layers. Moreover, the pyruvate fermentation pathway branch converting pyruvate to lactate is required for biofilm maturation, and utilization of pyruvate for structured biofilms formation to occur both in the absence or presence of nitrate.

Research findings by the group of Dianne Newman provide further support for the importance of pyruvate utilization by P. aeruginosa. Newman's group showed that pyruvate is released into the extracellular environment by P. aeruginosa in a manner dependent on the redox-active phenazine pyocyanin (Price-Whelan et al., 2007) and that phenazines are required for microcolony formation (Dietrich et al., 2008, Ramos et al., 2010).

Birkenstock et al (2013) recently described a Pyruvate dehydrogenase inhibitor (TPBC) that has potent antimicrobial activity against many bacterial pathogens. The use of TPBC is distinct from using exogenously provided pyruvate dehydrogenase. TPBC acts intracellularly by inhibiting pyruvate dehydrogenase, and thus a major catabolic pathway used by bacteria. This toxicity may induce distinct responses in the bacteria, development of immunity or tolerance, or other escape mechanism. Further, TPBC may be toxic or non-environmentally benign.

The pyruvate fermentation pathway branch converting pyruvate to lactate is required for biofilm maturation, and this utilization of pyruvate for the formation of structured biofilms occurs both in the absence or presence of nitrate. The required pyruvate is produced by the resident bacteria and subsequently released into the extracellular environment. The use of exogenously provided pyruvate dehydrogenase removes this pyruvate and thus, prevents biofilm maturation.

Using exogenously provided pyruvate dehydrogenase does not interfere with growth of the bacterium. Moreover, pyruvate dehydrogenase has no bactericidal activity, furthermore reducing the risk of bacteria developing resistance. However, exogenously provided pyruvate dehydrogenase depletes exogenously available pyruvate. This pyruvate is used to build structured biofilms. Depleting pyruvate impairs the formation of structured biofilms and renders biofilms more susceptible to antibiotics.

In addition to medical applications, and in particular surfaces with chronic contact with body fluids, there are also oral and dental applications.

The present technology therefore provides compositions which contain one or more enzymes that convert pyruvate to another form, preferably irreversibly under the conditions of administration or use, and necessary cofactors.

The enzyme may be administered as a therapy in a liquid, lyophilized powder, freeze dried powder, granulated powder, liposomal suspension, cream, ointment, gel, patch or film, spray coating, pill, or other pharmaceutically or dentally acceptable form. The enzyme in this case is preferably a low antigenicity form, such as mammalian or human form.

For industrial uses, the enzyme may be provided in liquid, lyophilized powder, granulated powder, liposomal suspension form, immobilized on a substrate, or other form. The enzyme in this case may be a plant, bacterial or yeast produced form.

Pyruvate dehydrogenase loses its activity at physiological temperature and high/low pH. The enzyme is active at pH 7.0-7.5. In order to prolong the activity of the enzyme, a nanoparticle can be used to encapsulate and protect it. Up to 10% of the enzyme can be encapsulated in a final formulation according to a prototype process, with encapsulated enzyme retaining bioactivity, and enzyme-loaded nanoparticles inducing biofilm dispersion in vitro.

The enzyme may be used in conjunction with a biofilm dispersion inducer, such as cis-2-decenoic acid (see, U.S. Pat. No. 8,513,305, expressly incorporated by reference in its entirety), and/or an antibiotic that targets the planktonic forms of the biofilm cells. (The sessile forms may also be targeted, but typically the agents have low efficacy).

Dispersion inducers and quorum sensing factors, as discussed above, may include various factors, such as ATP, c-di-GMP, other cyclic nucleotides, cis-2-decenoic acid, Skyllamycins A to C, nitric oxide, diphenyl selenide, etc.

Various known antimicrobial treatments, as discussed above, may be employed in conjunction with the pyruvate-diminishing enzyme(s) and/or biofilm dispersing and/or disrupting treatment.

Known antibiofilm agents, which may be used in conjunction with the present technology, are discussed above.

The encapsulation process may be accompanied by various modifications of the enzyme to increase thermal and pH stability, as discussed above.

A pyruvate depleting or degrading enzyme may be provided in various forms, e.g.:

Antimicrobial cream
Antimicrobial adhesive bandages or wound dressing,
Cleaning solution for contact lenses
Cleaning solutions in general to prevent biofouling
Chewing gum, mouth rinse
Aerosol/inhaler/nebulizer, for the treatment of CF lung infections
Vesicles including outer membrane and lipid vesicles enabling targeted delivery to site of infection
Surface coating of indwelling devices Typically, the enzymes for depletion of pyruvate are incompatible with certain other agents or conditions, particularly those which denature the enzymes, inhibit the enzyme, or serve to increase available pyruvate. For example, silver-based or oxidizing antimicrobial agents or agents that are protein denaturing are typically to be avoided. In some cases, the active enzyme may be protected against certain denaturing treatments, such as by encapsulation.

The enzyme may also be immobilized on an insoluble support, as discussed in detail above. The depletion of pyruvate, such as by pyruvate dehydrogenase may be concurrently or sequentially provided with a treatment using cis-2-decenoic acid (cis-DA), or nitric oxide and compounds delivering nitric oxide. Some of these compounds are co-delivered with an antibiotic (the antibiotic serves as targeted delivery mechanisms with the design being such that when antibiotic is deactivated, nitric oxide is being released).

The enzyme is biodegradable, and generally considered non-toxic. For medical application, antigenicity is a concern.

Pyruvate management is biofilm specific. Pyruvate is an energy source (not carbon source). Pyruvate utilization by *P. aeruginosa* has only been linked to biofilm growth and long-term bacterial survival under oxygen limiting conditions. Moreover, pyruvate depletion by pyruvate dehydrogenase does not affect bacterial growth in liquid or susceptibility of planktonic cells. Thus, pyruvate is effective to transition the cells from sessile to planktonic state, but another therapy would normally be used to kill the cells if desired.

Long-term survival and biofilm studies have not given rise to pyruvate-insensitive mutants. Therefore, the technology may be used in chronic-type applications.

While pyruvate insensitivity has been noted upon inactivation of genes contributing to pyruvate fermentation (e.g. acnA, ldhA, mifR), these mutants were incapable of coping with the reductive stress and therefore, were unable to form biofilms.

Pyruvate dehydrogenase-induced dispersion is independent of other factors previously described to contribute to dispersion by *P. aeruginosa* biofilms. For instance, while biofilms by mutant strains bdlA, dipA and rbdA are impaired in their dispersion response upon sensing the dispersion cue nitric oxide, biofilms by the respective strains dispersed upon treatment with pyruvate dehydrogenase. This means that pyruvate dehydrogenase treatment should be capable of enhancing dispersion induced by other compounds such as cis-2-decenoic acid or nitric oxide releasing compounds.

Pyruvate depletion via pyruvate dehydrogenase requires pyruvate dehydrogenase to remain active. Activity is affected by environmental conditions such as pH and proteases. Therefore, the technology may be provided with pH buffers, stabilizers, antioxidants, an excess of cofactors, and in some cases, binding factors for expected inhibitors.

The pyruvate dehydrogenase enzyme shows potential for preventing bacterial infection, thus making the composition suitable for coatings to medical devices that are at risk for infection, such as heart valves, orthopedic implants, catheters, and dental implants.

Testing shows that pyruvate dehydrogenase can prevent formation of biofilms, and therefore the technology may be used preemptively, before the biofilm forms. This technology would therefore make infections much easier to treat and may be able to prevent infections if used preemptively because pyruvate depletion prevents the formation of biofilms. Furthermore, in contrast to conventional antibiotics, it is very unlikely that bacteria could become resistant to the removal of pyruvate as an energy source.

For medical use, human pyruvate dehydrogenase is preferred. Pyruvate dehydrogenase can be cloned into a vector (starting out from cDNA) and then mass produced in a bacterial or eukaryotic expression system.

Encapsulation of the enzyme, especially in a shell-core particle, can isolate the enzyme from the immune system, and thereby reduce antigenicity. Further, incorporating poly(ethylene glycol) into the polymer particle can help to combat the immune response.

The composition may be provided in gels, polymers, pastes, edible products, and chewable products.

The stabilized pyruvate diminishing enzyme may be coadministered with an additive component selected from one or more of the group consisting of biocides, surfactants, antibiotics, antiseptics, detergents, chelating agents, and/or virulence factor inhibitors.

Another aspect of the present technology relates to a method of treating or preventing a condition mediated by a biofilm in a subject. This method involves providing a subject having, or susceptible to, a condition mediated by a biofilm produced by a microorganism, whereby the biofilm comprises a matrix and the micro-organism on a surface. A stabilized pyruvate diminishing enzyme or treatment, such as encapsulated pyruvate dehydrogenase, is administered to the subject under conditions effective for to selectively act on the microorganism and have a suitable biological response without a required direct effect on the matrix, whereby the condition mediated by a biofilm in the subject is treated or prevented. Of course, direct matrix-active treatments may be provided in conjunction.

According to one embodiment, the enzyme is immobilized to biofilm matrix components or to sterile particles of formed biofilm matrix.

A further embodiment is directed to a method of treating or inhibiting formation of a biofilm on a surface. This involves providing a surface having or being susceptible to formation of a biofilm produced by a microorganism, whereby the biofilm comprises a matrix and the micro-organism on the surface. A stabilized pyruvate diminishing agent is deployed at the surface under conditions effective reduce pyruvate concentration in the medium surrounding the microorganism and have a suitable biological response, whereby formation of the biofilm on the surface is prevented, or treated.

One way to reduce the concentration of pyruvate in a medium, especially when produced in small quantities by the biofilm itself, is by absorption of pyruvate to an affinity material, such as a molecularly imprinted polymer sheet. While such materials typically do not chemically alter the pyruvate, the same material may include enzymes, catalysts, reagents, reactants, etc., that act on the relatively higher concentrations of pyruvate absorbed in the material to alter or degrade it. The imprinting may be guided by the active site of enzymes or pyruvate transporters, which have a high affinity for pyruvate; for example. All or portions of the enzymes or transports themselves may be included in the imprinting. Since retention of catalytic or transport activity, or other biologic function is not necessarily required for the affinity to be maintained, the preparation, storage, or use may include or be subject to relatively harsher conditions than would be required for retention of specific biological activity. See:

Alizadeh, Taher, and Somaye Amjadi. "Preparation of nano-sized Pb2+imprinted polymer and its application as the chemical interface of an electrochemical sensor for toxic lead determination in different real samples." Journal of hazardous materials 190, no. 1-3 (2011): 451-459.

Chaterji, Somali, Il Keun Kwon, and Kinam Park. "Smart polymeric gels: redefining the limits of biomedical devices." Progress in polymer science 32, no. 8-9 (2007): 1083-1122;

Farid, Mohammad Masoudi, Leila Goudini, Farideh Piri, Abbasali Zamani, and Fariba Saadati. "Molecular imprinting method for fabricating novel glucose sensor: Polyvinyl acetate electrode reinforced by MnO2/CuO loaded on graphene oxide nanoparticles." Food chemistry 194 (2016): 61-67.

Kudupoje, Manoj B. "Molecularly Imprinted Polymers Synthesized As Adsorbents For Ergot Alkaloids: Characterization And In Vitro And Ex Vivo Assessment Of Effects On Ergot Alkaloid Bioavailability." (2017).

Lee, Mei-Hwa, Tain-Chin Tsai, James L. Thomas, and Hung-Yin Lin. "Recognition of creatinine by poly (ethylene-co-vinylalcohol) molecular imprinting membrane." Desalination 234, no. 1-3 (2008): 126-133.

Li, Ta-Jen, Po-Yen Chen, Po-Chin Nien, Chia-Yu Lin, Ramamurthy Vittal, Tzong-Rong Ling, and Kuo-Chuan Ho. "Preparation of a novel molecularly imprinted polymer by the sol-gel process for sensing creatinine." Analytica chimica acta 711 (2012): 83-90.

Luo, Jing, Sisi Jiang, and Xiaoya Liu. "Efficient one-pot synthesis of mussel-inspired molecularly imprinted polymer coated graphene for protein-specific recognition and fast separation." The Journal of Physical Chemistry C 117, no. 36 (2013): 18448-18456.

Mao, Yan, Yu Bao, Shiyu Gan, Fenghua Li, and Li Niu. "Electrochemical sensor for dopamine based on a novel graphene-molecular imprinted polymers composite recognition element." Biosensors and Bioelectronics 28, no. 1 (2011): 291-297;

Nunes, Pedro S., Pelle D. Ohlsson, Olga Ordeig, and Jorg P. Kutter. "Cyclic olefin polymers: emerging materials for lab-on-a-chip applications." Microfluidics and nanofluidics 9, no. 2-3 (2010): 145-161;

Özkütük, ebru Birlik, Arzu Ersoz, Adil Denizli, and Ridvan Say. "Preconcentration of phosphate ion onto ion-imprinted polymer." Journal of hazardous materials 157, no. 1 (2008): 130-136.

Raitman, O. A., V. V. Arslanov, S. P. Pogorelova, and A. B. Kharitonov. "Molecularly imprinted polymer matrices for analysis of the cofactor NADH: a surface plasmon resonance study." In Doklady Physical Chemistry, vol. 392, no. 4-6, pp. 256-258. Kluwer Academic Publishers-Plenum Publishers, 2003.

Sellergren, Börje, ed. Molecularly imprinted polymers: man-made mimics of antibodies and their application in analytical chemistry. Vol. 23. Elsevier, 2000;

Singh, Ambareesh Kumar, and Meenakshi Singh. "Designing L-serine targeted molecularly imprinted polymer via theoretical investigation." Journal of Theoretical and Computational Chemistry 15, no. 05 (2016): 1650041.

Storer, Christopher. "Molecularly Imprinted Polymer Sensors for the Detection of Phosphate in Agriculture." PhD diss., The University of Manchester, 2017.

Suriyanarayanan, Subramanian, Piotr J. Cywinski, Artur J. Moro, Gerhard J. Mohr, and Wlodzimierz Kutner. "Chemosensors based on molecularly imprinted polymers." In Molecular Imprinting, pp. 165-265. Springer, Berlin, Heidelberg, 2010.

Xing, Rongrong, Shuangshou Wang, Zijun Bie, Hui He, and Zhen Liu. "Preparation of molecularly imprinted polymers specific to glycoproteins, glycans and monosaccharides via boronate affinity controllable-oriented surface imprinting." Nature protocols 12, no. 5 (2017): 964.

The examples of situations in which disruption of biofilm formation or maintenance would be of benefit include improved cleaning of contact lenses and teeth, improved antiseptic activity in the home, in industry, and in the medical community and enhanced cidal activity for existing antibiotic treatments such as with burn patients infected with *Pseudomonas aeruginosa.*

The method may further include administering to the biofilm, an antimicrobial treatment. The treatment can be the administration of biocides, surfactants, antibiotics, antiseptics, detergents, chelating agents, virulence factor inhibitors, gels, polymers, pastes, edible products, chewable products, ultrasonic treatment, radiation treatment, thermal treatment, and/or mechanical treatment.

In one embodiment, the surface to be treated includes indwelling medical devices, such as catheters, respirators, and ventilators. In addition, the surface can be in implanted medical devices, including stents, artificial valves, joints, pins, bone implants, sutures, staples, pacemakers, and other temporary or permanent devices. The pyruvate diminishing treatment, e.g., enzyme, can also be included in surgical glue, or in a coating on the medical device.

In another embodiment, the surface to be treated includes drains, tubs, kitchen appliances, countertops, shower curtains, grout, toilets, industrial food and beverage production facilities, flooring, and food processing equipment.

In a further embodiment, the surface to be treated is a heat exchanger surface or a filter surface. Thus, treatment provides a means for reducing the degree of biofouling of the heat exchanger or filter.

In another embodiment, the surface to be treated is a marine structure which includes boats, piers, oil platforms, water intake ports, sieves, and viewing ports.

The surface can alternatively be associated with a system for water treatment and/or distribution (e.g., a system for drinking water treatment and/or distributing, a system for pool and spa water treatment, a system for treatment and/or distribution of water in manufacturing operations, and a system for dental water treatment and/or distribution).

The surface can also be associated with a system for petroleum drilling, storage, separation, refining and/or distribution (e.g., a petroleum separation train, a petroleum container, petroleum distributing pipes, and petroleum drilling equipment).

The treatment can also be included in formulations directed at reducing or eliminating biofilm deposits or biofouling in porous medium, such as with oil and gas bearing geological formations. The treatment may be accomplished by applying a coating, such as paint, to the surface.

The treatment may include, in addition to a pyruvate diminishing component, e.g., pyruvate dehydrogenase, a dispersion inducer and/or a biocide. Enzymatic components may be encapsulated and/or immobilized, to improve thermal and chemical stability, maintain localization, and reduce antigenicity, for example. The antibiotic or biocide, and dispersion inducer, mat be provided in a controlled or extended release formulation. In some cases, the same particles that encapsulate or immobilize the enzyme, may also serve as extended release reservoirs for a biocide and/or a dispersion inducer.

The method of inhibiting formation of a biofilm on a surface may further involve administering to the surface, an antimicrobial treatment. The treatment can be administration of biocides, surfactants, antibiotics, antiseptics, disinfectants, medicines, detergents, chelating agents, virulence factor inhibitors, ultrasonic treatment, radiation treatment, thermal treatment, and mechanical treatment.

The pyruvate diminishing component can be coated on, or impregnated in, a surface in order to inhibit formation of a biofilm on the surface. The pyruvate diminishing component can also be in a copolymer or a gel coating over the surface.

The present technology also relates to a method of treating subjects with burns. The method involves administering the pyruvate diminishing component under conditions effective to treat burns in the subject. A specific application provides a topical dressing for burn patients comprising an encapsulated or immobilized mammalian or human pyruvate dehydrogenase, in micron or nanoparticle form, as a powder, cream, ointment, dressing, or flowing medium over the wound. In some cases, the fluid is transported to an immobilized enzyme filter, which reduces the pyruvate concentration to a very low level, e.g., <0.1 mM, and the fluid may be recirculated back to the wound. The fluid may be unfused with an antibiotic and/or dispersion inducer. The fluid drawn from the would may be filtered, such as through a 0.2 μm filter, to remove bacteria, or treated with an antibacterial process, such as ultraviolet light. However, the recycling of at least a portion of the same fluid back to the would be advantageous because it contains various growth factors, which assist in would healing, which would otherwise be lost in the case of mere flushing of the wound.

The present technology further relates to a method of treating and/or preventing dental plaque, dental carries, gingival disease, periodontal disease, and oral infection in a subject by providing a pyruvate diminishing component which acts to reduce pyruvate in the oral cavity. The method involves treating the oral cavity of the subject with the pyruvate diminishing component, such as pyruvate dehydrogenase in a composition that deposits stabilized (e.g., immobilized or encapsulated) enzyme on tooth surfaces, and other oral tissues. Treating can be carried out with a dentifrice, mouthwash, dental floss, gum, strip, toothpaste, a toothbrush, and other preparations, containing the stabilized pyruvate dehydrogenase. The composition may also contain other compounds known in the dental arts that are typically added to dental compositions. For example, the composition may also include fluoride, desensitizing agents, anti-tartar agents, anti-bacterial agents, remineralization agents, whitening agents, and anti-caries agents.

The amount of pyruvate diminishing component (and any necessary cofactors) is preferably sufficient to reduce the medium concentration by at least 90%, and preferably at least 95%, for example to less than 1 mM, and preferably less than 0.1 mM, and more preferably less than 0.05 mM, over the course of less than 30 minutes at 37° C.

The present technology may also be used for cleaning and/or disinfecting contact lenses. The method involves treating contact lenses with a cleaning and/or disinfecting solution containing a pyruvate diminishing component. The contact lens may be treated in this manner while being stored in solution or while being used in vivo. Alternatively, the pyruvate diminishing component can be used in eye drops. According to one embodiment, the contact lenses are disposable, and the pyruvate dehydrogenase or other enzyme is immobilized on or in the lens itself.

The present technology further relates to a method of treating and/or preventing acne or other biofilm-associated skin infections on the skin of a subject. The method involves treating the skin of the subject with the pyruvate diminishing component according to the present technology under conditions effective to treat and/or prevent the acne or biofilm-associated skin infections. The pyruvate diminishing component may be present in an ointment, cream, liniment, salves, shaving lotion, or aftershave. It may also be present in a powder, cosmetic, ointment, cream, liquid, soap, gel, cosmetic applicator, and/or solid, woven or non-woven material intended to contact or be proximate with the skin.

The present technology also relates to a method of treating and/or preventing a chronic biofilm-associated disease in a living subject. The method involves administering to the subject a pyruvate diminishing component under conditions effective to treat and/or prevent the chronic biofilm-associated disease. The chronic biofilm-associated diseases to be treated and/or prevented include, but are not limited to, middle ear infections, osteomyelitis, prostatitis, colitis, vaginitis, urethritis, sinovial infections, infections along tissue fascia, respiratory tract infections (e.g., infections associated with lung infections of cystic fibrosis patients, pneumonia, pleurisy, pericardial infections), genito-urinary infections, and gastric or duodenal ulcer infections. For gastric or duodenal ulcers caused by Helicobacter pylori, the pyruvate diminishing component will need to function at a pH of below 5.5. The pyruvate diminishing component, e.g., immobilized enzyme, may be administered in combination with an antimicrobial agent, such as biocides, surfactants, antibiotics, antiseptics, detergents, chelating agents, or virulence factor inhibitors. In the case of gastric therapies, acid reducing therapies, such as antacids, proton pump inhibitors, antihistamines, and the like may also be employed.

Note that systemic administration of pyruvate dehydrogenase to reduce pyruvate levels of plasma is likely infeasible, and possibly toxic. Therefore, the therapy is preferably applied extracorporeally, in or on medical devices, or in body compartments other than the vasculature.

The present technology may provide compositions and methods in which the encapsulated, immobilized, or otherwise stabilized enzyme is provided in a personal care product, such as eye drops, eyewash solution, contact lens care solution, contact lens cleaning solution, contact lens storing solution, contact lens disinfectant, contact lens cleaning-storing solution, and contact lens cleaning disinfecting-storing solution, contact lens containers, contact lenses, as well as podiatric, manicure and pedicure solutions, gels, creams, jellies, powders, pastes, lotions, soaps and cleaners.

A further aspect of the present technology is directed to a composition comprising: a component selected from one or more of the group consisting of biocides, surfactants, antibiotics, antiseptics, detergents, chelating agents, virulence factor inhibitors, gels, polymers, pastes, edible products, and chewable products. For example, pyruvate dehydrogenase may be provided in a chewing gum or gel, which is active when chewed to reduce oral pyruvate levels over the course of a duration of at least 30 minutes.

The composition, in the case of a contact lens cleaning product, may comprise one or more ingredients selected from the group consisting of: water, citrate buffer, citric acid, stabilizing agent, a flavoring agent, vitamins, minerals, herbals, a surfactant, an antimicrobial peptide, an antimicrobial and a pH adjuster. The antimicrobial preservatives can be selected from potassium sorbate, potassium benzoate, sodium benzoate and benzoic acid, and can, in particular be used in contact lens cleaning and disinfecting solutions. The antimicrobial preservative can be in a concentration ranging from 0.25 g/L to 3 g/L.

The technology may further provide methods of preparing suitable formulations for treating or impregnating personal care products, including contact lenses, contact lens containers, and manicure, pedicure and podiatry tools and containers.

The technology may also provide methods of preparing a suitable formulation for use with the personal care products in a variety of ways, for example in a disinfecting solution, a lotion, cream, a gel, a spray, a thermoreversible gel spray, and a paste.

The formulations can also include natural or synthetic flavorings and coloring agents. Thickening agents can also be added to compositions of the invention such as guar gum, carbopol, polyethylene glycol, pluronic F-127, sodium alginate, carboxymethyl cellulose, xanthan gum and other personal care acceptable thickening agents.

Other formulations will be readily apparent to one skilled in the art. A composition of the invention can include antibiofilm enzymes (cellulase, beta-N-acetylgluconase, DispersinB, papain, DNase 1, etc.), antimicrobial peptides, antibiotics (gentamicin, ciprofloxacin, ampicillin, cefamendole nafate, rifambicin, etc.), antimicrobials (triclosan, chlorhexidine, quaternary ammonium compounds, silver, silver salts, etc.) and other antibiofilm compounds.

The technology may also provide liposomal or nanoparticle delivery systems that enhance the stability and efficacy of compounds in the compositions.

The technology also provides personal care products treated, coated, or impregnated with a composition of the invention, such as a contact lens, a contact lens container, a hand washing container, a hand or foot scrubber, and a foot washing container.

In an embodiment, a composition comprises an antibiotic, optionally with chelating agents and a metal ion salt. Groups of antibiotics useful in conjunction with the technology include, but are not limited to, β-lactam inhibitors (e.g., penicillin, ampicillin, amoxicillin, methicillin, etc.), cephalosporins (e.g., cephalothin, cephamycin, etc.), aminoglycosides (e.g., streptomycin, tobramycin, etc.), polyenes (e.g., amphotericin, nystatin, etc.), macrolides (e.g., erythromycin, etc.), tetracyclines (e.g., tetracycline, doxycycline, etc.), nitroimidazole (e.g., metronidazole), quinolones (e.g., nalidixic acid), rifamycins (e.g., rifampin), and sulfonamides (e.g., sulfanilamide), nitroaromatics (e.g., chloramphenicol) and pyridines (e.g., isoniazid).

In an embodiment, a composition comprises an antiseptic, a pyruvate depleting enzyme and associated cofactors. Antiseptics are agents that kill or inhibit the growth of microorganisms on the external surfaces of the body. Antiseptics include, but are not limited to, triclosan, chlorhexidine salt, and cetylpyridinium chloride.

Antibiofilm compounds include, but not limited to, DispersinB, DNase I, Proteinase K, apyrase, cis-2-decenoic acid, nitric oxide, alginate lyase, lactoferrin, gallium, cellulase, and 5-fluorouracil.

In general, methods of manufacturing anti-infective compositions may comprise combining a personal care or pharmaceutically acceptable carrier and an effective amount of a pyruvate depleting composition, and optionally other agents, such as a biofilm dispersion inducer, chelating agents and a metal ion salt with an antiseptic, an antibiotic, a bacteriocin, an antimicrobial peptide or chitosan.

It is therefore an object to provide a composition, comprising purified pyruvate dehydrogenase, encapsulated in a polymeric nanoparticle, and being stable when hydrated at up to 37° C. for at least 48 hrs.

It is also an object to provide a method of modifying a biofilm, comprising administering a stabilized form of pyruvate dehydrogenase, which retains at least 50% of its initial activity after 48 hrs at 37° C., and required cofactors, in a sufficient quantity to reduce a pyruvate level in an aqueous medium surrounding the biofilm, to cause a biological response of hypoxic cells within the biofilm to the reduction in pyruvate.

It is a further object to provide a method of treating or preventing a biofilm, comprising: providing a subject having, or susceptible to, a condition mediated by a biofilm produced by a microorganism, whereby the biofilm comprises a matrix and the microorganism on a surface; and administering to the subject a nanoparticle formulation having pyruvate dehydrogenase activity, under conditions effective for the condition caused by a biofilm in the subject to be treated or prevented.

It is also an object to provide a method of treating or inhibiting formation of a biofilm on a surface, comprising: providing a surface having or being susceptible to formation of a biofilm produced by a microorganism, whereby the biofilm comprises a matrix and the microorganism on the surface; and administering to the surface a pyruvate degrading enzyme under conditions effective reducing formation or maintenance of the biofilm on the surface to be treated or inhibited.

A composition, comprising purified enzyme, within a particle, effective for reducing pyruvate concentration in an aqueous suspension of the composition.

The composition may be provided in combination with CoA and NADH or an enzyme cofactor redox agent. The enzyme in hydrated form, is preferably stable for at least 48 hrs at 37° C., and e.g., maintain at least 50% of its initial activity after 48 hrs at 37° C.

The particle may comprise a liposome, or a nanoparticle. The particle may have a mean diameter of less than 1 micron. The particle may comprise a polymeric matrix, polymeric nanoparticle, a carbohydrate matrix, poly(lactic-co-glycolic acid), or chitosan. The enzyme may comprise pyruvate dehydrogenase, lactate dehydrogenase, formate dehydrogenase, or a transaminase. The particle may selectively bind to biofilms. The enzyme may be immobilized to a particle matrix, or encapsulated within a particle matrix, or within a liposome or vesicle. The particle may comprise an ionic exchange resin or matrix or other material, with an affinity for pyruvic acid. The composition may be provided in combination with a bacterial biofilm dispersion inducer, e.g., cis-2-decenoic acid, nitric oxide, and/or an antibiotic. The particle may further comprise cis-2-decenoic acid. The antibiotic may be an aminoglycoside, tobramycin, gentamicin, amikacin, a quinolone, ciprofloxacin, levofloxacin, a cephalosporin, ceftazidime, cefepime, cefoperazone, cefpirome, ceftobiprole, an antipseudomonal penicillin selected from the group consisting of a: carboxypenicillin, carbenicillin, ticarcillin, a ureidopenicillin, mezlocillin, azlocillin, and piperacillin, a carbapenem, meropenem, imipenem, doripenem, polymyxin B, colistin, colicin, a bacteriocin, a microcin, a monobactam, or aztreonam.

It is a further object to provide a method of inducing a dispersion of sessile organisms of a biofilm in an aqueous medium, comprising depleting pyruvate in the aqueous medium to a sufficient amount to induce a dispersion response of the sessile organisms. The depletion of pyruvate in the aqueous medium is preferably sufficient to alter response of cells in the biofilm to hypoxic stress. The depletion may comprise enzymatically altering the pyruvate to another chemical species. The enzymatic alteration may be reversible or irreversible, e.g., a decarboxylation, or a phosphorylation. The depletion may comprise absorbing pyruvate to an insoluble resin or other matrix or material, chemically transforming the pyruvate to another chemical species, decarboxylation reaction, an electrochemical reaction, an imine-forming reaction, absorption of pyruvate in a molecular sieve, absorption of pyruvate in a weakly basic anion exchange resin, operation of a transaminase in presence of pyridoxal phosphate, operation of pyruvate decarboxylase, use of a bioreactor comprising pyruvate fermentative organisms, transport of pyruvate across a lipid bilayer membrane with a pyruvate carrier. The dispersion response may be secondary to a hypoxic response of cells in the biofilm. The pyruvate may be produced, at least in part, by cells at the periphery of the biofilm.

It is another object to provide a method of modifying a biofilm, reducing a pyruvate level in an aqueous medium surrounding the biofilm, to cause a biological response of hypoxic cells within the biofilm to the reduction in pyruvate. The reduction may comprise administering an enzyme preparation. The enzyme preferably retains at least 50% of its initial activity after 48 hrs at 37° C. The enzyme may comprise purified pyruvate dehydrogenase, purified pyruvate oxidase, purified lactate dehydrogenase, a purified transaminase, e.g., alanine transaminase. The reduction may comprise absorbing the pyruvate, decarboxylating the pyruvate, aminating the pyruvate, amidating the pyruvate, phosphorylating the pyruvate, adsorbing the pyruvate, reacting the pyruvate with an immobilized enzyme, reacting the pyruvate with an encapsulated enzyme. The method may further comprise administering a bacterial biofilm dispersion inducer, or administering an antibiotic.

It is a further object to provide a method of treating a biofilm, comprising administering to a subject having a biofilm-associated infection, a nanoparticle formulation comprising an enzyme having a pyruvate substrate specificity, under conditions effective for the condition caused by a biofilm in the subject to be treated by a response of the biofilm to a reduction in environmental pyruvate. The method may further comprise administering a bacterial biofilm dispersion inducer to the subject, or administering to the subject an antimicrobial treatment selected from the group consisting of one or more of biocides, surfactants, antibiotics, antiseptics, detergents, chelating agents, and virulence factor inhibitors. The biofilm-associated infection is caused by a burn, caused by at least one of dental plaque, dental caries, gingival disease, and an oral infection, caused by at least one of dental plaque, dental caries, gingival disease, and an oral infection, associated with acne, or associated with a chronic biofilm infection. The administering may be carried out with a dentifrice, mouthwash, dental floss, gum, strip, brush, bandage, irrigator, bioerodable polymer, hypodermic needle, a lotion, cream, ointment, or gel.

Another object provides a method of treating a biofilm on a surface, comprising: providing a surface having a biofilm; and administering to the surface a treatment that reduces a concentration of pyruvate of the biofilm, comprising pyruvate produced by at least a portion the biofilm, under conditions effective reducing maintenance of the biofilm on the surface.

The treatment may comprise a pyruvate degrading enzyme, e.g., pyruvate dehydrogenase, pyruvate decarboxylase, or lactate dehydrogenase. The enzyme may be encapsulated. The surface may be part of a contact lens, an indwelling medical device selected from the group consisting of a catheter, a respirator, and a ventilator, an implanted medical device selected from the group consisting of a stent, an artificial valve, a joint, a suture, a staple, a pacemaker, a bone implant, and a pin, a drain, a tubs, a kitchen appliance, a countertop, a shower curtain, grout, a toilet, an industrial food and beverage production facility, a floor, and a piece of food processing equipment, a heat exchanger surface or a filter surface, a marine structure selected from the group consisting of a boat, a pier, an oil platform, a water intake port, a sieve, and a viewing port, or a water treatment system or a water distribution system. The water treatment system or a water distribution system is selected from the group consisting of a system for drinking water treatment and/or distribution, a system for pool and spa water treatment, a system for treatment and/or distribution of water in manufacturing operations, and a system for dental water treatment and/or distribution. The method may comprise coadministering to the surface, in conjunction with said administering the treatment, at least one antimicrobial treatment selected from the group consisting of biocides, surfactants, antibiotics, antiseptics, detergents, chelating agents, virulence factor inhibitors, ultrasonic treatment, radiation treatment, thermal treatment, and a mechanical treatment. The treatment and the antimicrobial treatment may be administered simultaneously. The method may further comprise coadministering to the surface, in conjunction with said administering the treatment, at least one physiological dispersion inducer. The treatment and the physiological dispersion inducer may be administered simultaneously. The treatment may comprise an enzyme administered in a copolymer or a gel coating over the surface.

BRIEF DESCRIPTION OF THE DRAWINGS

FIGS. 2A-2H show that pyruvate depletion induces biofilm dispersion within 24 h of exposure to PDH or heat-inactivated (HK) PDH, as indicated by (2A) crystal violet (CV) staining of the attached biofilm biomass, (2B) increased turbidity and (2C) number of viable cells in the supernatant. (2D) CV stained biofilms obtained in the absence (top wells) and presence (bottom wells) of PDH. (2E) Confocal images of biofilms in the absence (2E1)/presence of active (2E3) or heat-inactivated (2E2) PDH. (2F1, 2F2) intact and dispersed biofilm microcolony. (2G, 2H) Dispersion proportion and microcolony diameter in absence, and presence of active or heat-inactivated PDH. Error bars represent standard deviation.

DETAILED DESCRIPTION

A hallmark of biofilms is their extreme tolerance to antimicrobial agents, rendering infections by biofilms to conventional treatment therapies. This has brought on the realization that successful treatment of biofilm infections will require the development of novel treatment strategies. It is thus not surprising that biofilm dispersion, a regulatory response to environmental cues, allowing bacterial cells to convert to the planktonic state, has become a major focus of recent research endeavors to combat biofilms. However, while much attention has been paid to agents inducing biofilm dispersion, little is known about the mechanism underlying dispersion.

Depletion of Pyruvate Coincides With Reduced Biofilm Biomass

*P. aeruginosa* has been demonstrated to require autogenously produced pyruvate and pyruvate fermentative processes as a means of redox balancing to form microcolonies, with depletion of pyruvate or inactivation of components of the pyruvate fermentation pathway impairing biofilm formation. Considering that transition to the free-living state is initiated within microcolonies as indicated by microcolonies having central voids, pyruvate availability was hypothesized to play a role in dispersion. Enzymatic depletion of pyruvate from the growth medium of established *P. aeruginosa* biofilms coincided with a significant decrease in biofilm biomass, and central hollowing of microcolonies indicative of dispersion.

No dispersion was noted by strains inactivated in components of the pyruvate fermentation pathway, in the presence of excess pyruvate or heat-inactivated enzyme. Moreover, pyruvate depletion-induced dispersion coincided with enhanced killing of biofilm cells by the aminoglycoside tobramycin.

Pyruvate plays an essential role in the formation of biofilms, as continuous depletion of pyruvate (via pyruvate dehydrogenase plus cofactors) from the growth medium prevented biofilm formation. Given the role of pyruvate in establishing biofilms characterized by a three-dimensional architecture, the requirement for pyruvate by biofilms to remain surface-attached and maintain their three-dimensional architecture was investigated.

Figure 1:
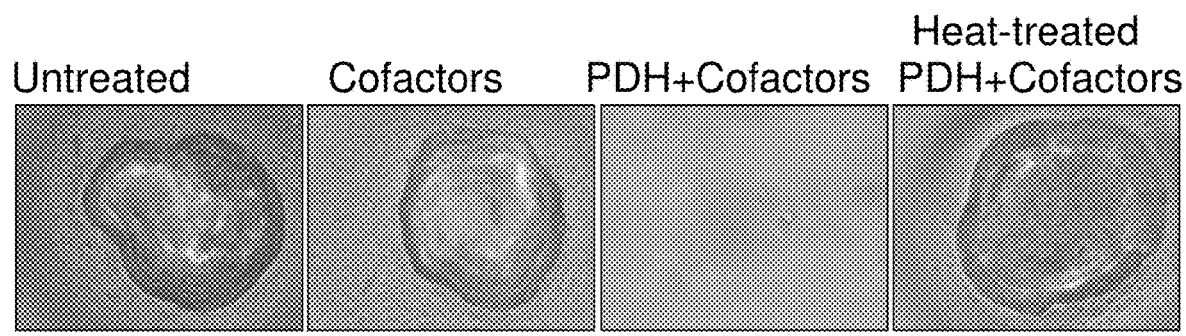
FIG. 1 shows that depletion of pyruvate from the growth medium via pyruvate dehydrogenase (PDH) impairs biofilm formation.

FIG. 1 shows that depletion of pyruvate from the growth medium via pyruvate dehydrogenase (PDH) impairs biofilm formation.

FIGS. 2A-2H show that pyruvate depletion induces biofilm dispersion within 24 h of exposure to PDH or heat-inactivated (HK) PDH, as indicated by (2A) crystal violet (CV) staining of the attached biofilm biomass, (2B) increased turbidity and (2C) number of viable cells in the supernatant. (2D) CV stained biofilms obtained in the absence (top wells) and presence (bottom wells) of PDH. (2E) Confocal images of biofilms in the absence (2E1)/ presence of active (2E3) or heat-inactivated (2E2) PDH. (2F1, 2F2) intact and dispersed biofilm microcolony. (2G, 2H) Dispersion proportion and microcolony diameter in absence, and presence of active or heat-inactivated PDH. Error bars represent standard deviation.

Figure 3A:
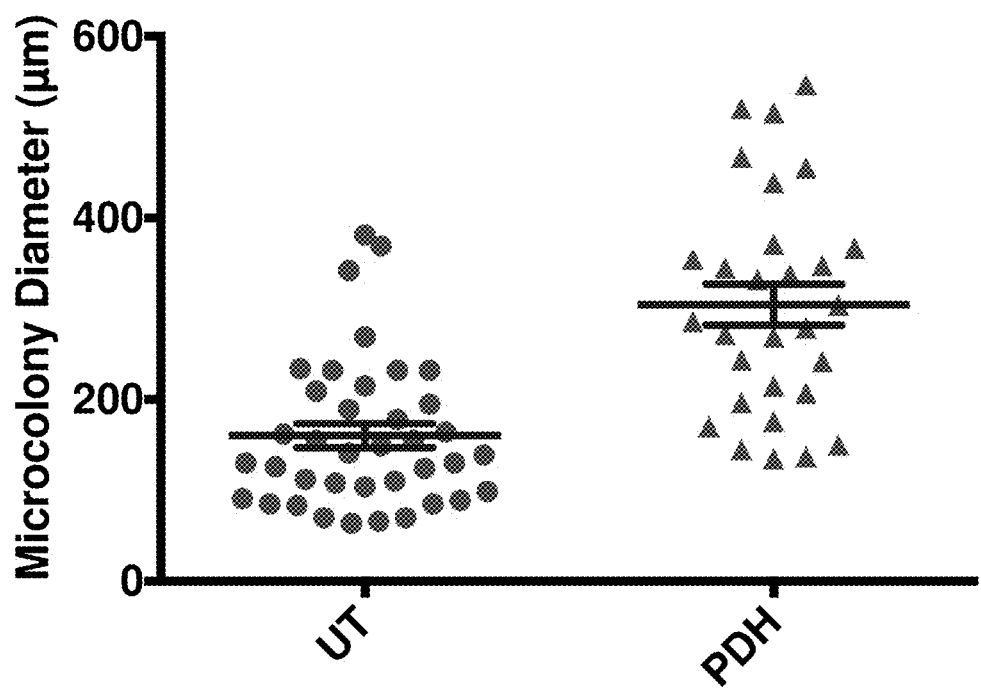
FIGS. 3A and 3B show that pyruvate depletion-induced dispersion is dependent on the diameter of microcolonies. Microcolony diameter of (3A) dispersed and (3B) non-dispersed biofilm microcolonies following exposure to PDH. Untreated biofilms were used as control. On average, 100 microcolonies per biofilm were evaluated.
Figure 3B:
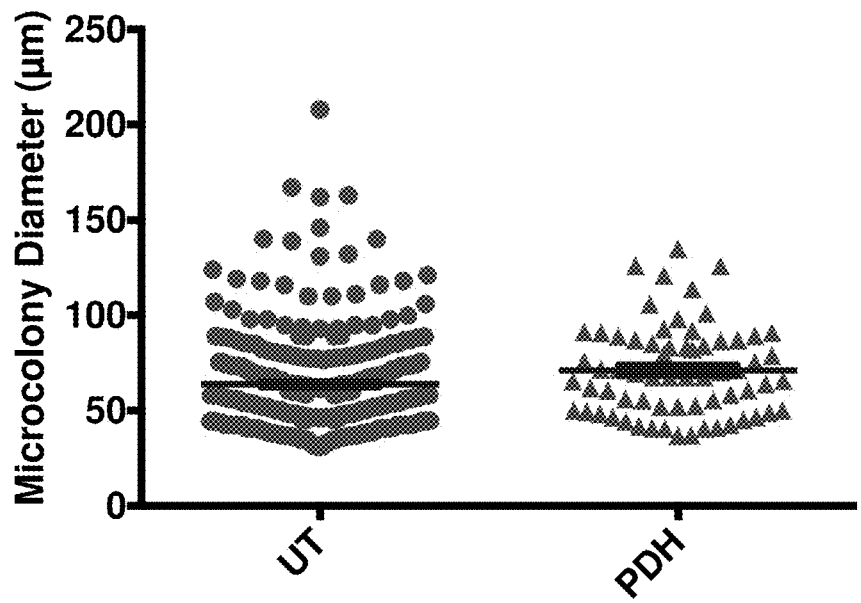

FIGS. 3A and 3B show that pyruvate depletion-induced dispersion is dependent on the diameter of microcolonies. Microcolony diameter of (3A) dispersed and (3B) non-dispersed biofilm microcolonies following exposure to PDH. Untreated biofilms were used as control. On average, 100 microcolonies per biofilm were evaluated.

Figure 4A:
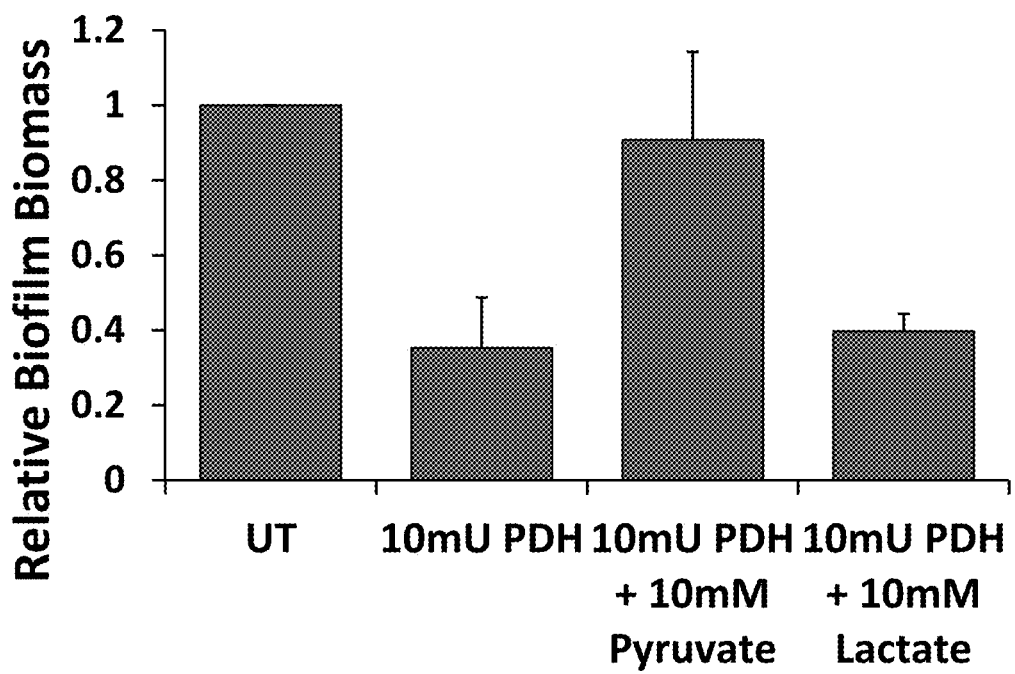
FIGS. 4A-4D4 show that excess pyruvate or inactivation of genes involved in pyruvate fermentation processes abrogate the dispersion response. (4A) Remaining PAO1 biofilm biomass post PDH treatment in the absence/presence of excess lactate and pyruvate. Inactivation of (4B) ldhA or (4C) mifR encoding lactate dehydrogenase and microcolony formation regulator MifR, respectively, renders mutant biofilms insensitive to pyruvate depletion. Error bars represent standard deviation. (4D) Confocal images of untreated (4D1, 4D3) or PDH-treated biofilms by AmifR (4D2) and AmifR/pJN-mifR (4D4).
Figure 4B:
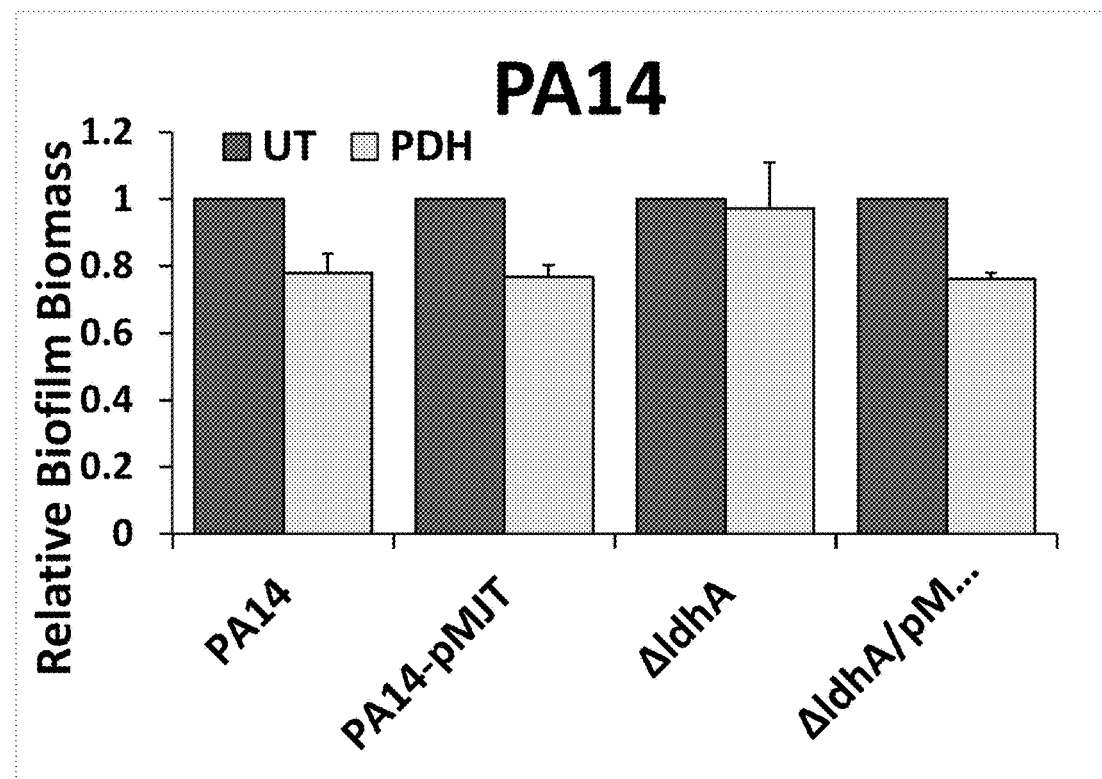
Figure 4C:
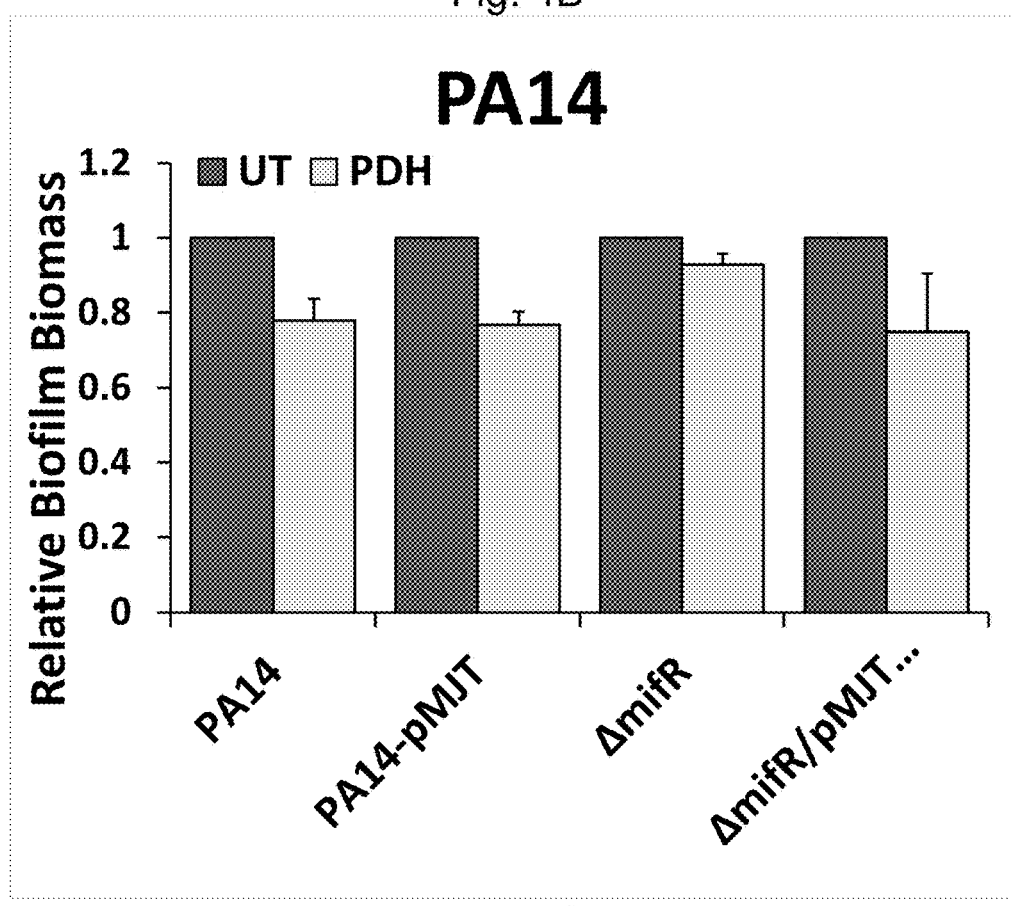

FIGS. 4A-4D4 show that excess pyruvate or inactivation of genes involved in pyruvate fermentation processes abrogate the dispersion response. (4A) Remaining PAO1 biofilm biomass post PDH treatment in the absence/presence of excess lactate and pyruvate. Inactivation of (4B) ldhA or (4C) mifR encoding lactate dehydrogenase and microcolony formation regulator MifR, respectively, renders mutant biofilms insensitive to pyruvate depletion. Error bars represent standard deviation. (4D) Confocal images of untreated (4D1, 4D3) or PDH-treated biofilms by AmifR (4D2) and AmifR/ pJN-mifR (4D4).

Figure 5A:
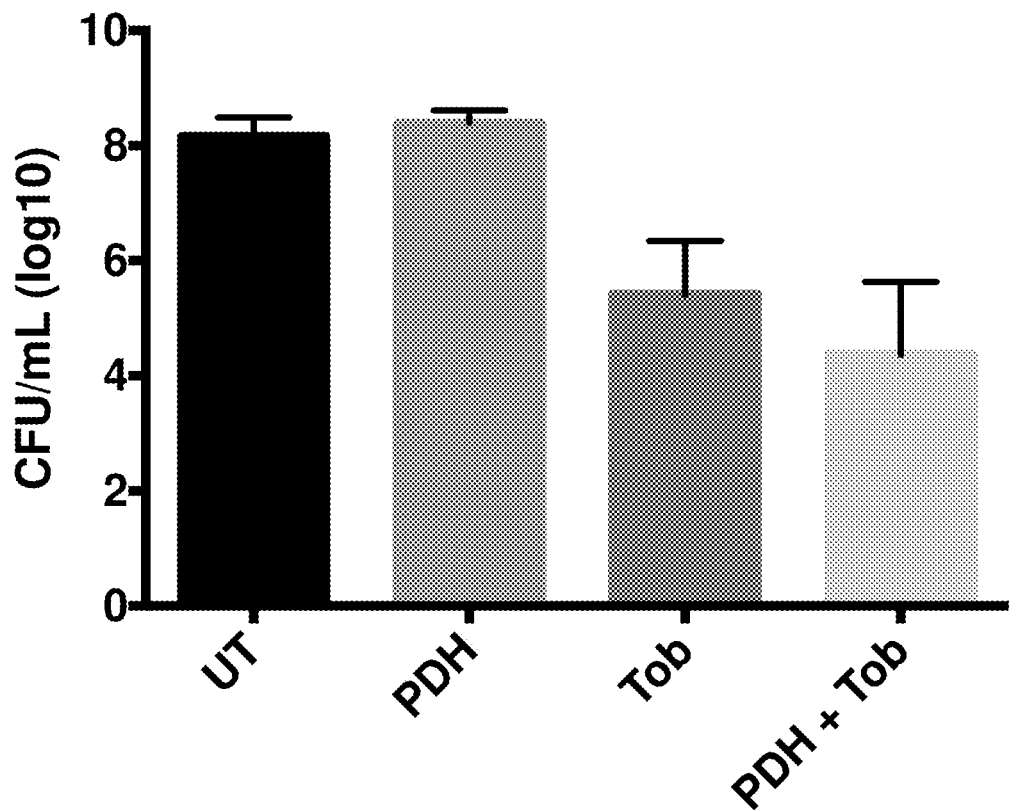
FIGS. 5A and 5B show that PDH treatment increases the efficacy of tobramycin in killing PAO1 biofilms. (5A) Number of viable biofilm cells remaining post treatment. (5B) Log reduction. Biofilms were treated with tobramycin (Tob, 150 µg/mL). Error bars represent standard deviation.
Figure 5B:
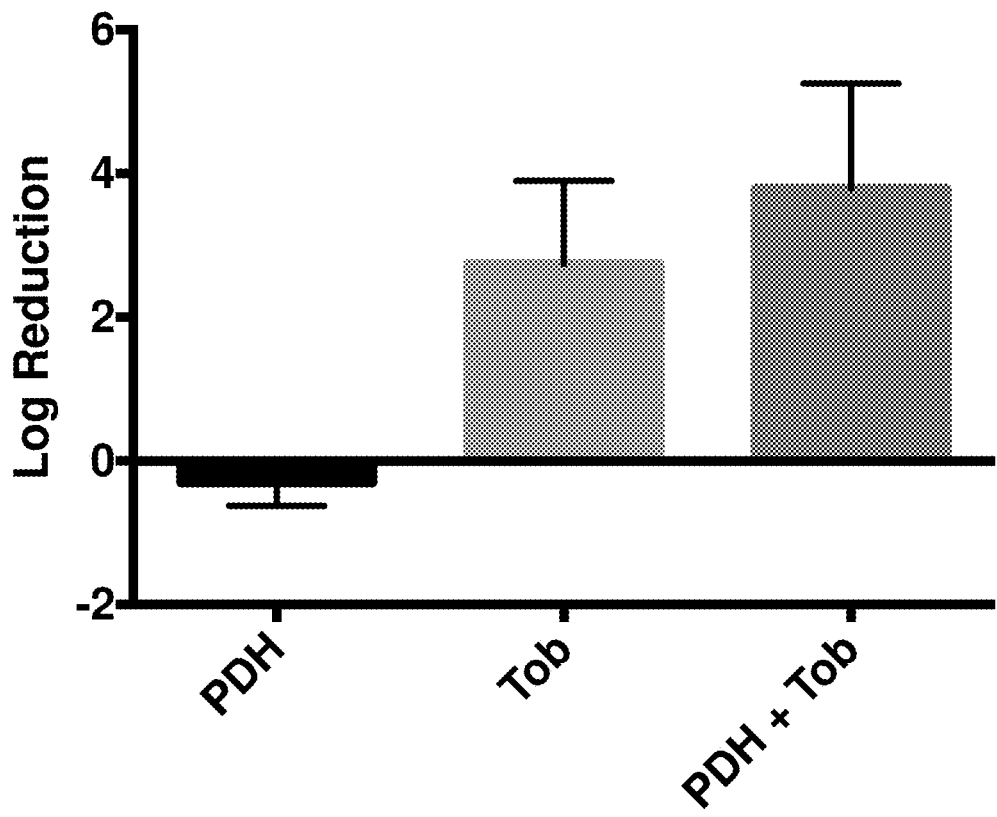

FIGS. 5A and 5B show that PDH treatment increases the efficacy of tobramycin in killing PAO1 biofilms. (5A) Number of viable biofilm cells remaining post treatment. (5B) Log reduction. Biofilms were treated with tobramycin (Tob, 150 µg/mL). Error bars represent standard deviation.

Figure 6:
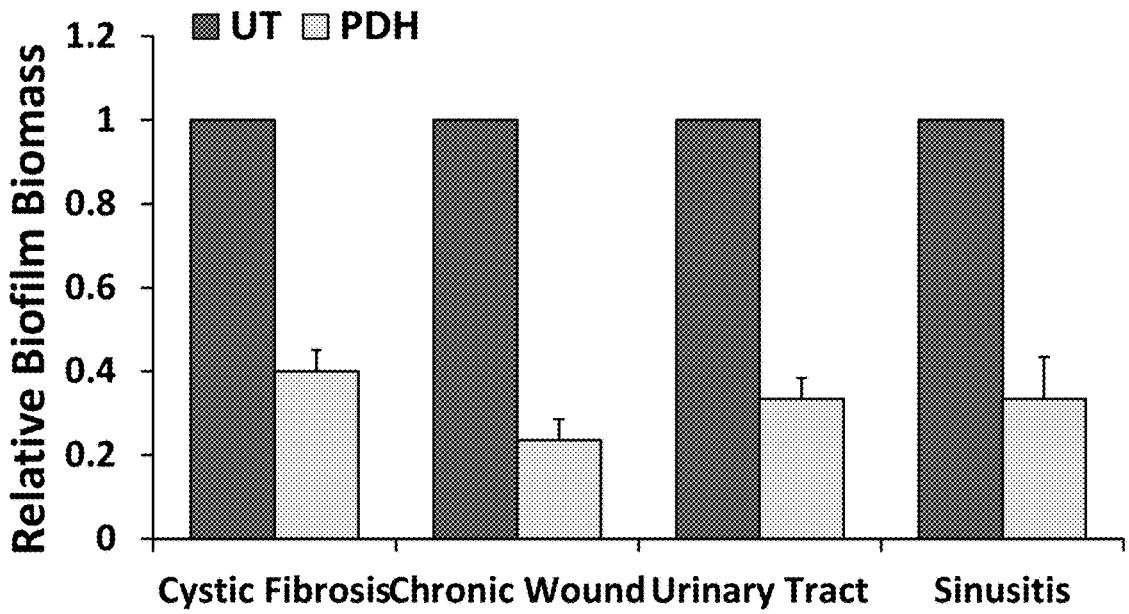
FIG. 6 shows that PDH treatment induces dispersion of biofilms by clinical isolate. *P. aeruginosa* clinical isolates were isolated from indicated sites. Error bars represent standard deviation.

FIG. 6 shows that PDH treatment induces dispersion of biofilms by clinical isolate. *P aeruginosa* clinical isolates were isolated from indicated sites. Error bars represent standard deviation.

Figure 7A:
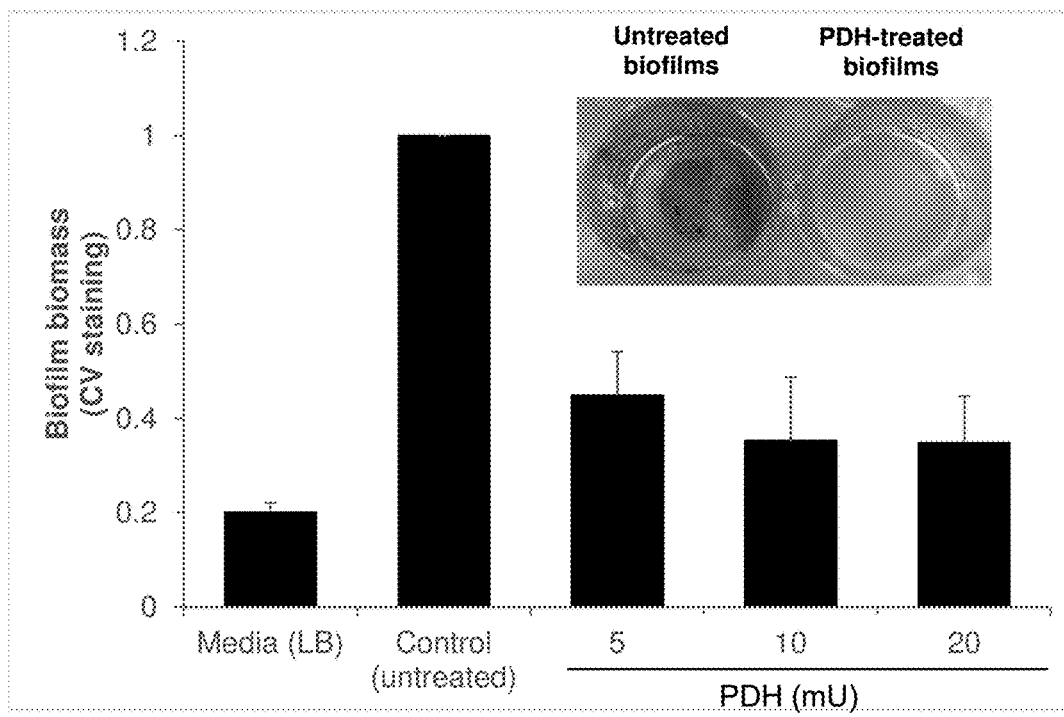
FIGS. 7A-7C show CV staining (see 7A inset) of microcolonies, showing (7A) biofilm biomass after treatment with LB media, control, 5, 10 and 20 mU/ml PDH. (7B) brightfield microscopy. (7C) biofim biomass for control, 5 and 10 mU/ml.

*P. aeruginosa* biofilms grown for 4 days in 24-well plates were exposed to pyruvate-depleting conditions. This was accomplished by exposing biofilms to increasing concentration of the enzyme pyruvate dehydrogenase (PDH) having a specific activity of 0.57 U/mg. PDH catalyzes the conversion of pyruvate to acetyl-CoA in the presence of CoA and $NAD^+$. Specifically, biofilms were exposed to 5, 10, and 20 mU (8.7, 17.4, and 32.8 mg enzyme) of PDH in the presence of $NAD^+$ and CoA. Biofilms grown in LB but left untreated were used as controls. Following overnight incubation, the remaining biofilm was stained using crystal violet. Relative to untreated biofilms, PDH treatment coincided with a significant loss in the CV-stainable biofilm biomass, with exposure to 5 mU resulting in a 2.2-fold reduction in the biofilm biomass while exposure to 10 and 20 mU resulted on average in a 2.9-fold reduction (FIG. 7A).

Figure 7B:
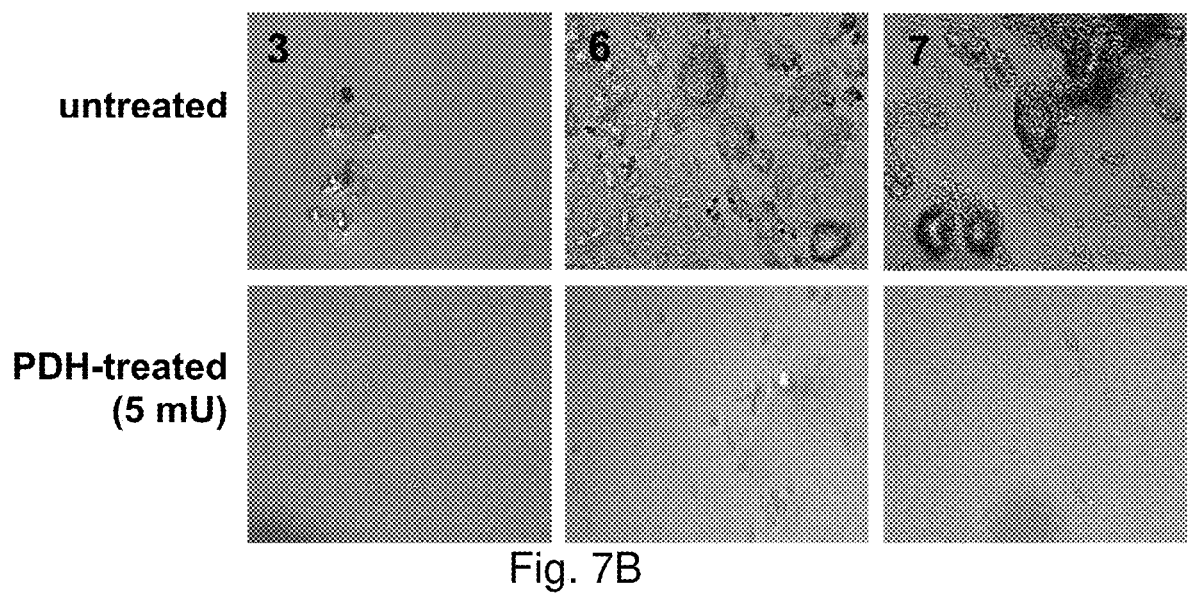

To determine whether biofilms of different age are susceptible to pyruvate depleting conditions, biofilms grown for 2, 5, and 6 days were exposed to pyruvate depleting conditions, by treating biofilms with 10 mU PDH in the presence of cofactors. Following incubation for 16 hr, microscopic evaluation of the remaining biofilms indicated exposure of biofilms to PDH and thus, pyruvate depleting conditions, to coincide with a significant reduction in the biofilm biomass relative to the biofilms that were left untreated (FIG. 7B).

Figure 7C:
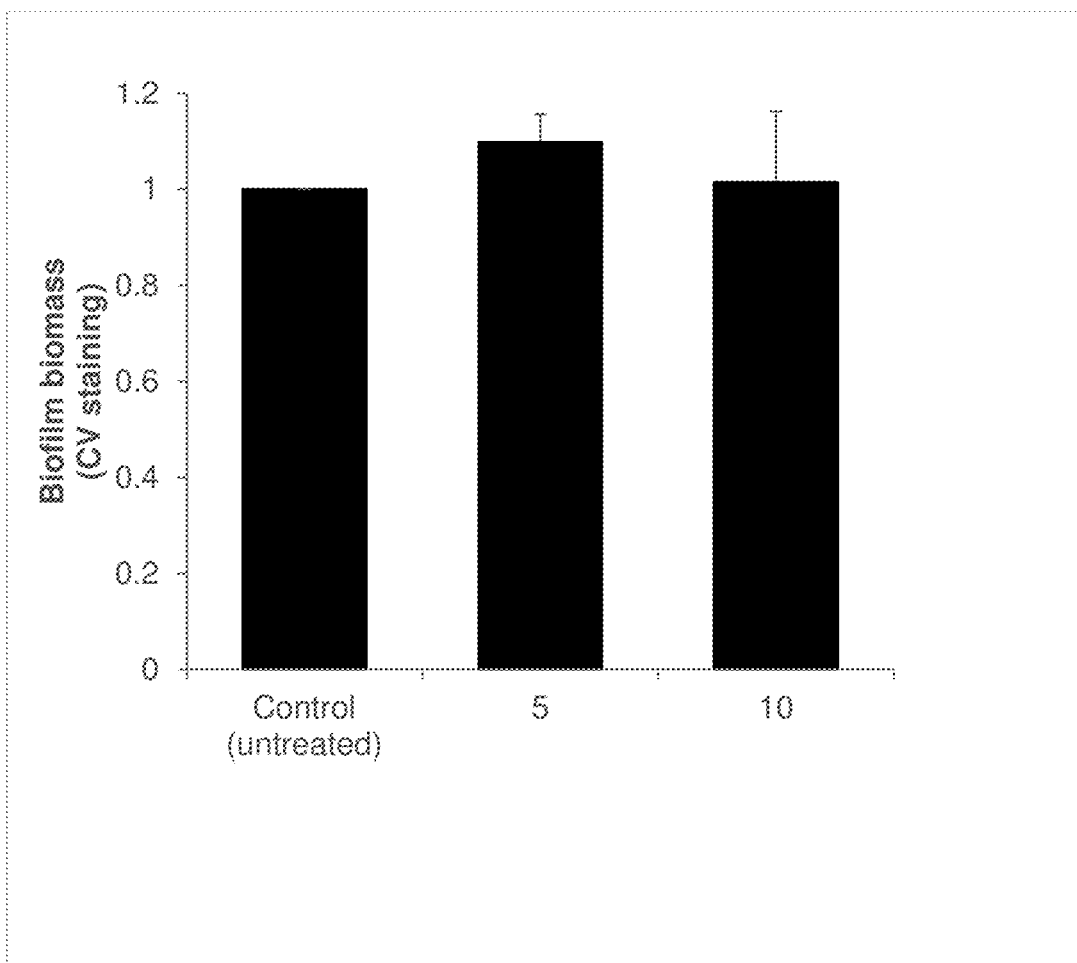

These findings suggested exposure to PDH contributes to the loss of biofilm biomass regardless of the biofilm age, likely by inducing pyruvate-depleting conditions. This was further supported by the finding that exposure of biofilms to increasing concentrations of heat-inactivated PDH had no effect on the biofilm biomass relative to untreated biofilms (FIG. 7C).

Pyruvate-depletion induced dispersion is inhibited by pyruvate but not by acetyl-CoA or lactate.

Figure 8A:
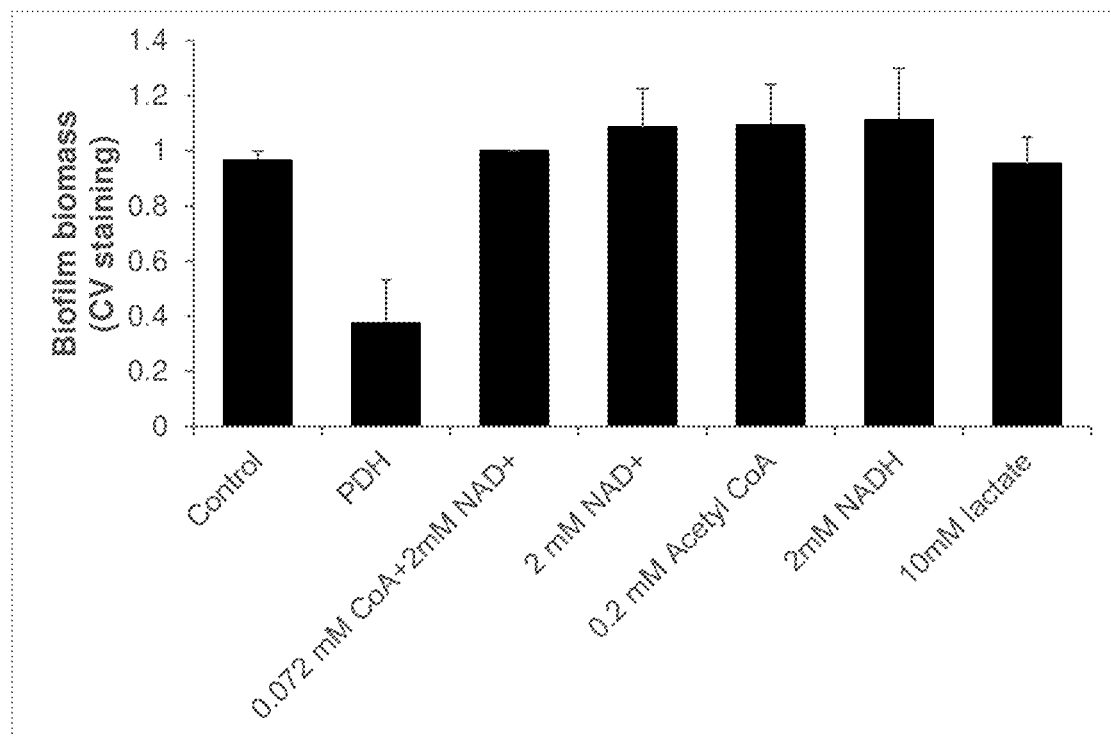
FIGS. 8A-8B show CV staining biomass for (8A) PDH and cofactors, and (8B) exogenous pyruvate.

The effect of cofactors on the biofilm biomass was determined to ensure that PDH affects the biofilm biomass by inducing pyruvate-depleting conditions. PDH requires $NAD^+$ and CoA as cofactors to enzymatically convert pyruvate to acetyl-CoA and NADH. Exposure of biofilms to $NAD^+$ and CoA or NAD+ alone had no effect on the biofilm biomass accumulation (FIG. 8A). In addition, to determine whether exposure to PDH is due to pyruvate depletion or the accumulation of the end products of the PDH catalyzed reaction, acetyl-CoA and NADH, biofilms were exposed to 0.2 mM acetyl-CoA or 2 mM NADH. Analysis of the biofilm biomass relative to untreated biofilms indicated that exposure of biofilms to acetyl-CoA or NADH did not result in increased biofilm biomass accumulation (FIG. 8A). As in *P. aeruginosa*, pyruvate dehydrogenase contributes to the formation of lactate, the effect of lactate on the biofilm biomass was evaluated. However, relative no untreated biofilms, no difference in the biofilms following exposure to 10 mM lactate was noted (FIG. 8A).

Figure 8B:
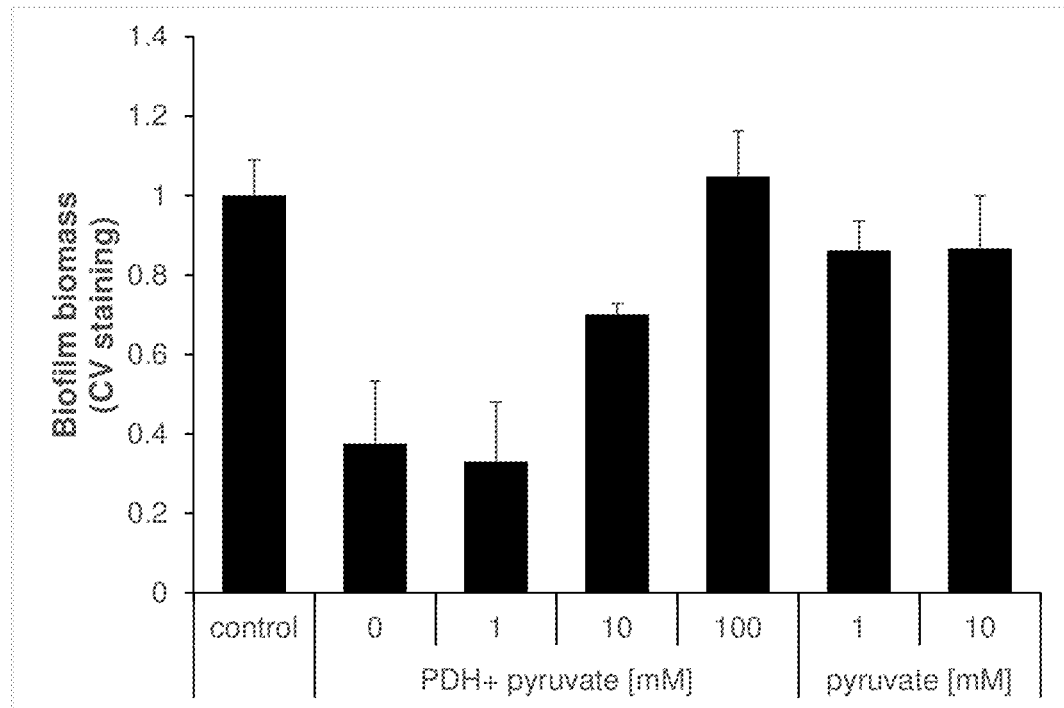

Biofilms were exposed to increasing concentrations of pyruvate in the absence or presence of pyruvate to ensure PDH-induced loss of the biofilm biomass is due to pyruvate depletion. If PDH induces dispersion by depleting pyruvate, the presence of additional pyruvate would overwhelm PDH and thus reduce the efficacy of PDH in inducing loss of biofilm biomass. Biofilms were exposed to increasing concentrations of exogenously added pyruvate (1-100 mM), in the presence of 10 mM PDH and cofactors. Relative to untreated biofilms, treatment with PDH in the presence of 1 and 10 mM pyruvate significantly reduced the crystal violet-stainable biofilm biomass (FIG. 8B). However, while no difference in the fold reduction of the biofilm biomass was noted in the presence of 1 mM pyruvate, the fold reduction in the biofilm biomass decreased to less than 2-fold in the presence of 10 mM pyruvate. In contrast, no difference in the biofilm biomass was noted in the presence of 100 mM pyruvate relative to untreated biofilms (FIG. 8B). These findings strongly suggest PDH to reduce the biofilm biomass in a manner dependent on pyruvate.

Depletion of Pyruvate Coincides With Dispersion Events.

Figure 2A:
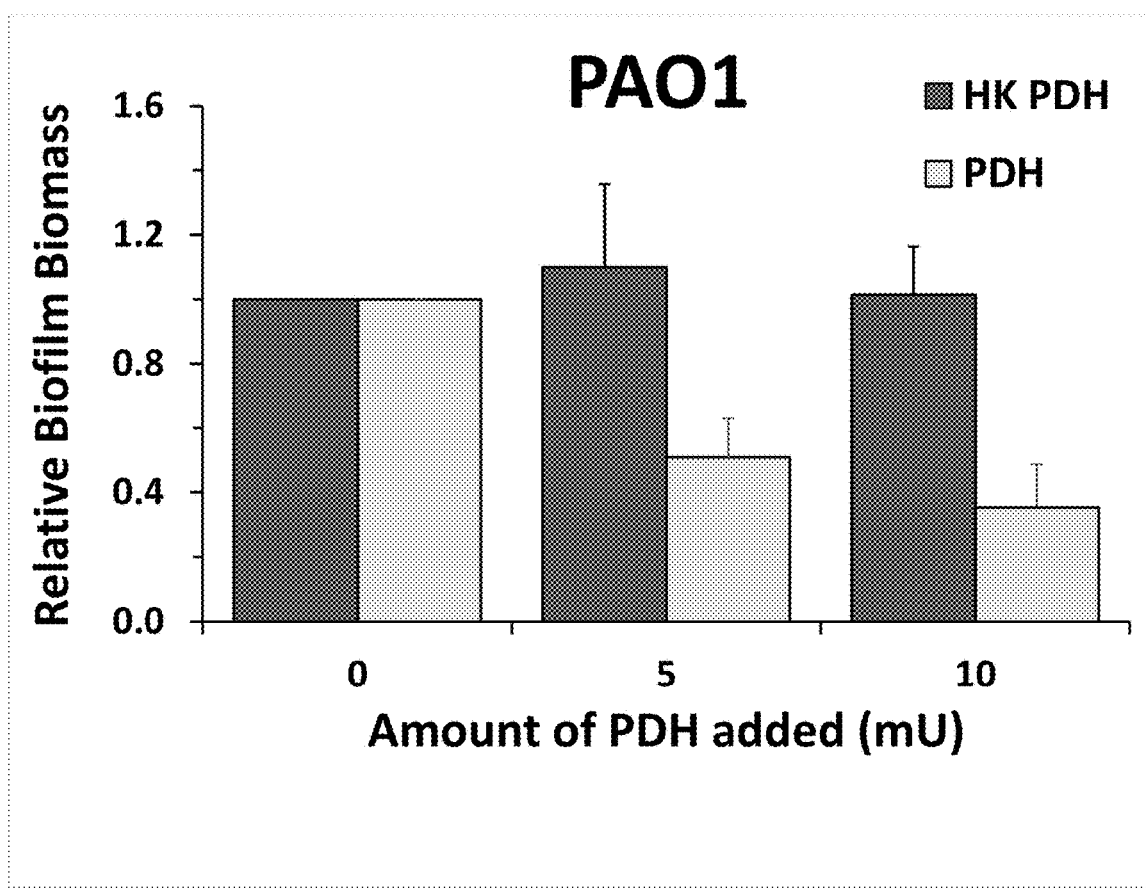
Figure 2B:
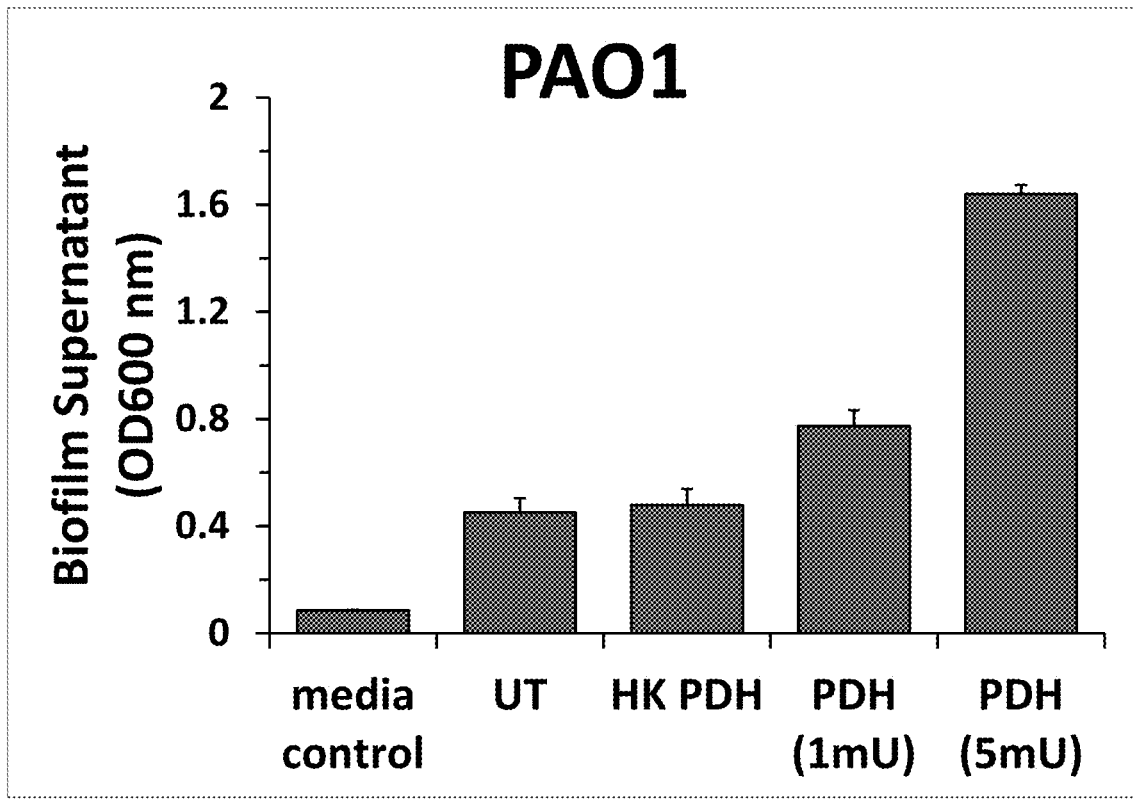
Figure 2C:
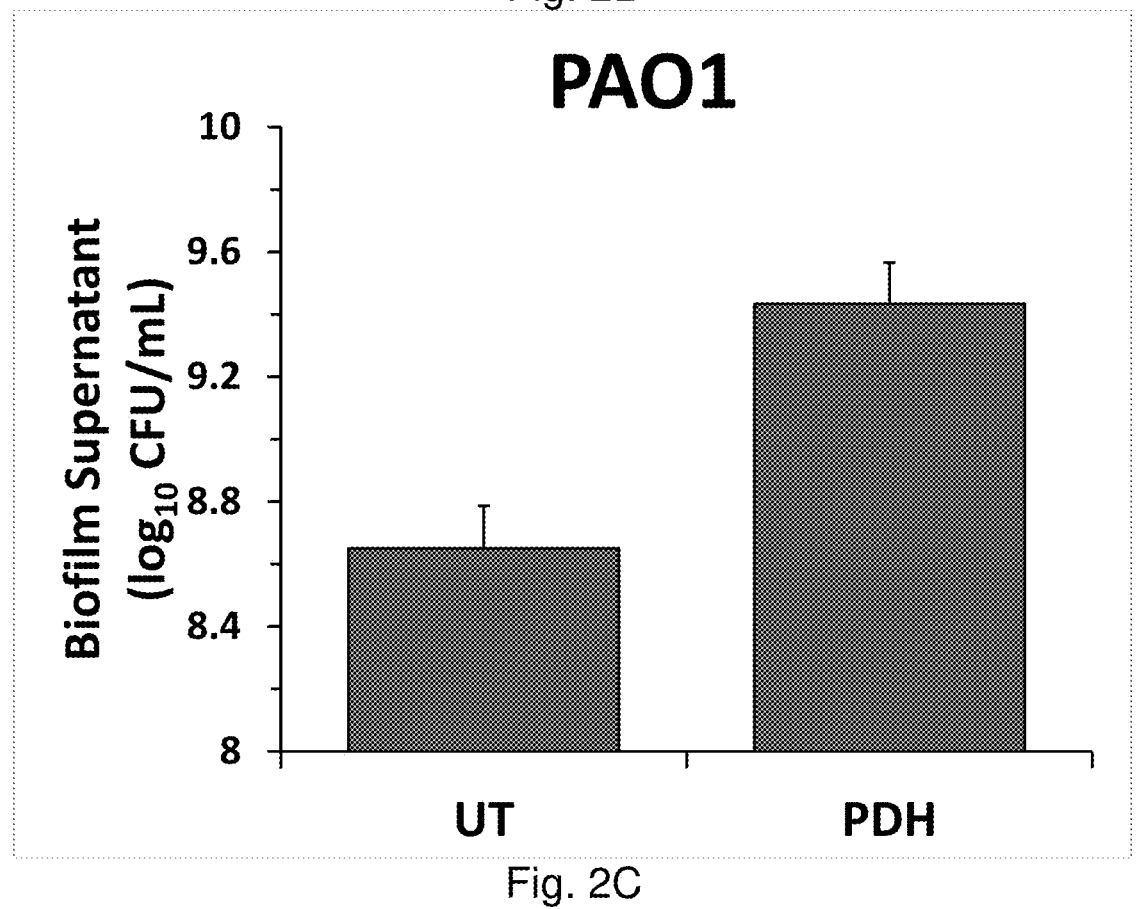
Figure 2G:
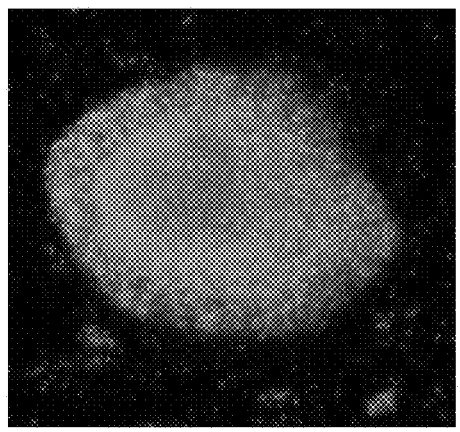
Figure 2G:
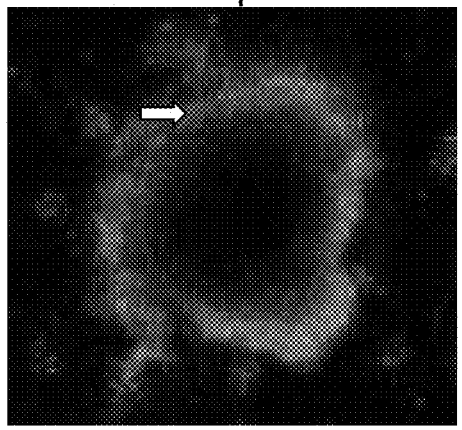
Figure 2G:
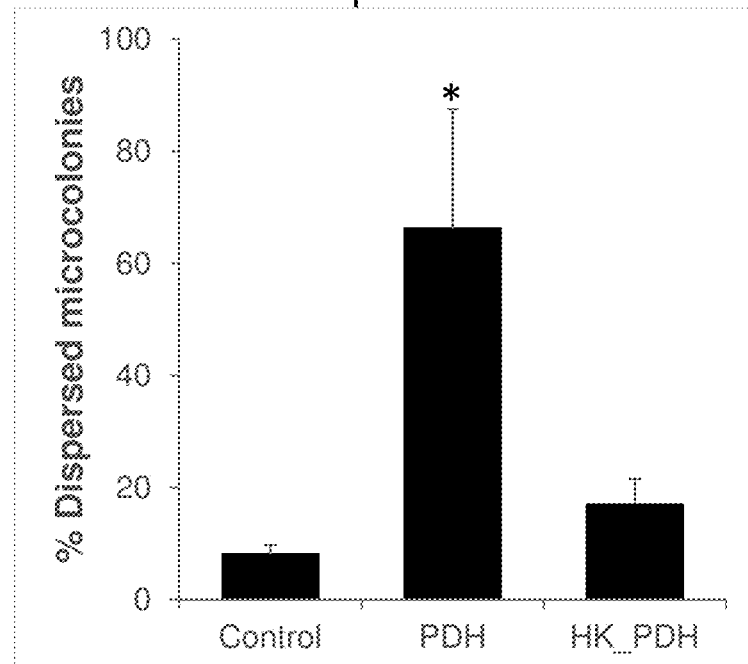

Crystal Violet staining of biofilms in the presence and absence of pyruvate-depleting conditions suggested to significantly reduce the biofilm biomass (FIGS. 7A-B). To determine how exposure to PDH accomplished a reduction in the biofilm biomass, the remaining biofilm architecture was visually analyzed by confocal microscopy. Relative to untreated biofilms, biofilms exposed to PDH were not only characterized by an overall reduced biofilm biomass but by microcolonies having central voids (FIGS. 2E3 and 2F2). Void formation has previously linked with biofilm dispersion, a process in which sessile, surface-attached organisms liberate themselves from the biofilm to return to the planktonic state. Overall, more than 60% of the detectable microcolonies present in PDH treated biofilms showed signs of dispersion apparent by central voids (FIG. 2E3). In contrast, the vast majority of microcolonies by untreated biofilms were intact (FIG. 2E1), with only less than 8% of the microcolonies featuring central void formation (FIG. 2G). Similar results were obtained when biofilms were treated with heat-inactivated PDH (FIG. 2E2).

Figure 2H:
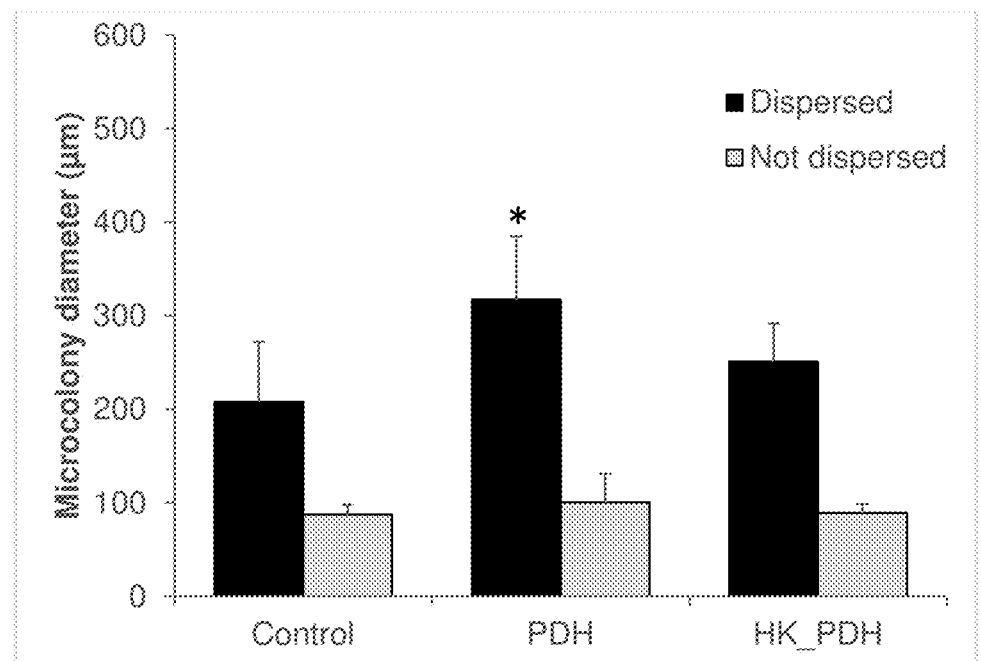

Previous findings suggested microcolonies of *P. aeruginosa* form hollow voids at their center when they attain a minimum diameter of 40 microns and thickness of 10 microns, with the microcolony size within which these voids form being dependent on the fluid flow rate. Given that exposure to PDH was found to coincide with a larger percentage of microcolonies showing void formation, the effect of pyruvate-depleting conditions on the minimum diameter of microcolonies that disperse was investigated. Analysis of the microcolony size in untreated biofilms suggested that microcolonies having an average diameter of 90 microns were non-dispersed while larger microcolonies having an average size of 210 microns showed signs of dispersion (FIG. 2H). Exposure of biofilms to heat-inactivated PDH (HK_PDH) had little to no effect on the microcolony size of dispersed and non-dispersed microcolonies (FIG. 2H). Moreover, no significant difference in the size of non-dispersed microcolonies following exposure to PDH was noted. In contrast, however, an overall significant increase in the size of dispersed microcolonies of PDH treated biofilms was observed (FIG. 2H). Based on visual observations, the increase in the size of dispersed microcolonies is likely due to "sagging", with the remaining microcolony structure bulging downward under weight or pressure or through lack of strength.

Overall, these findings suggest exposure of biofilms to PDH and thus, pyruvate depleting conditions to coincide with dispersion events. Considering that PDH treatment does not affect the overall size of microcolonies that remain intact, these findings furthermore suggest that pyruvate depletion enhances dispersion.

Pyruvate-Depletion Induced Dispersion is Independent of Previously Described Factors Contributing to Dispersion Considering that PDH exposure of biofilms coincided with dispersion events, factors previously demonstrated to be important in the dispersion response following exposure to nitric oxide or nutrients was required for pyruvate-depletion induced dispersion. Specifically, the role of chemotaxis transducer protein BdlA, and two phosphodiesterases, RbdA and DipA, in the pyruvate-depletion induced dispersion response was investigated. The factors were chosen as they appear to play a central role in the dispersion response by *P. aeruginosa* biofilms, with inactivation of bdlA, rbdA, and dipA impairing the dispersion by *P. aeruginosa* biofilms in response to various dispersion cues including nutrients, NO, ammonium chloride, and heavy metals (16-18).

Figure 9A:
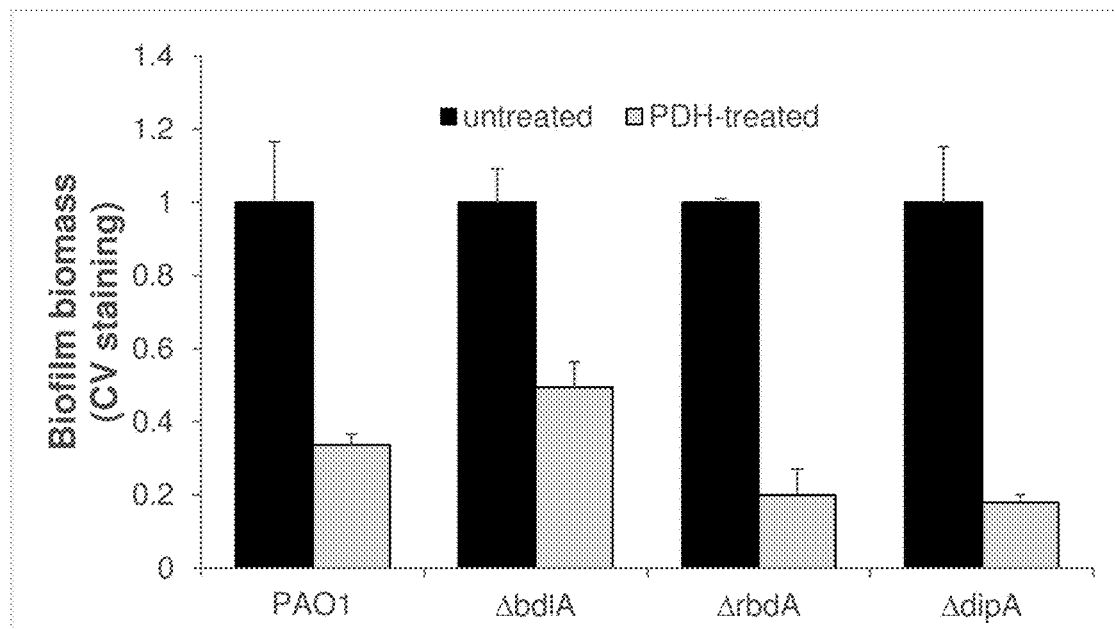
FIGS. 9A and 9B show CV staining, (9A) biomass and (9B) brightfield microscopy, of PAO1 and mutants for control and PDH.
Figure 9B:
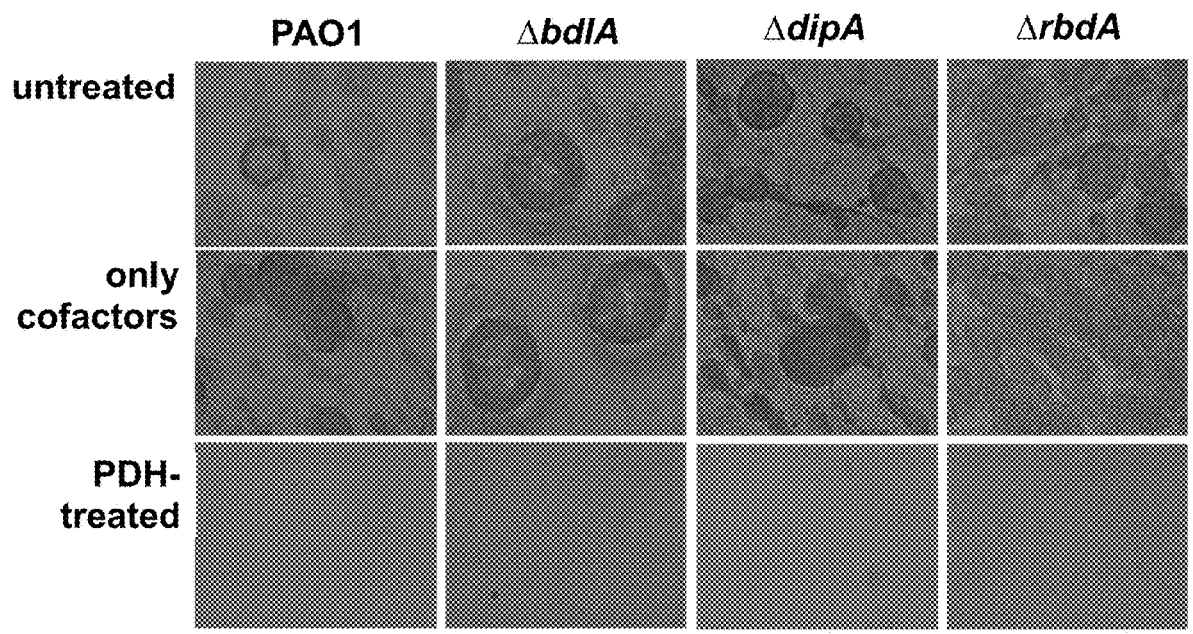

Biofilms by strains ΔbdlA, ΔdipA, and ΔrbdA were grown for 4 days in 24-well plates, and subsequently exposed to 10 mU PDH to induce pyruvate-depleting conditions. Biofilms grown in LB but left untreated were used as controls. Following overnight incubation, the remaining biofilm was stained using crystal violet. Relative to untreated biofilms, PDH treatment coincided with a significant loss in the crystal violet-stainable biofilm biomass, with exposure of ΔdipA, and ΔrbdA biofilms to PDH resulting in a >60% loss of the biofilm biomass (FIG. 9A). Under the conditions analyzed, the reduction of the biofilm biomass was comparable or exceeded to the loss noted for wild-type biofilms (FIG. 9A). In contrast, the crystal violet-stainable biomass by ΔbdlA biofilms was only reduced by 2-fold (FIG. 9A). However, the reduction in the biofilm biomass was significant. The reduction in biomass resulting from PDH treatment on strains ΔbdlA, ΔdipA, and ΔrbdA were confirmed visually using brightfield microscopy (FIG. 9B).

Pyruvate-Depletion Induced Dispersion is Dependent on Lactate Dehydrogenase LdhA and the Microcolony Formation Regulator MifR These findings suggested that dispersion induced by pyruvate depletion is independent of previously identified factors playing a role in the dispersion of *P. aeruginosa* biofilms in response to previously described dispersion cues. However, this raised the question of how pyruvate-depleting conditions contribute to biofilm dispersion. The formation of biofilms by *P. aeruginosa* was previously demonstrated to require pyruvate and pyruvate fermentation, with the biofilm-dependent utilization of pyruvate requiring lactate dehydrogenase LdhA and the microcolony formation regulator MifR. These findings furthermore demonstrated that biofilm formation is associated with stressful, oxygen-limiting but electron-rich conditions, suggesting pyruvate to be required to cope with stressful, oxygen-limiting but electron-rich conditions, referred to as 'reductive stress' (too much NADH/electrons, not enough $O_2$) present in biofilms.

Figure 10A:
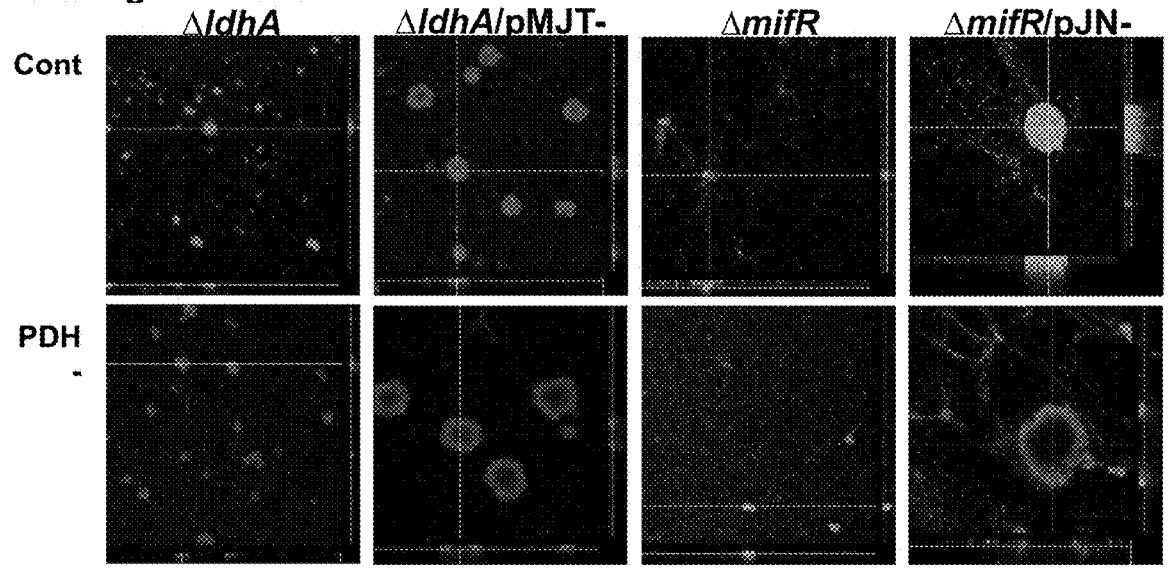
FIGS. 10A and 10B show control and PDH of (10A) confocal fluorescence microscopy and (10B) biofilm biomass for PA14 and mutants.

Biofilms by mutant strains ΔldhA and ΔmifR were exposed to PDH, and the biofilm structure of the respective mutant strains exposed to PDH analyzed relative to untreated biofilms, to determine whether the factors contributing to the formation of biofilms by *P. aeruginosa* also play a role in dispersion. Based on visual comparison, no difference in the biofilm architecture by ΔldhA and ΔmifR in the presence of absence of PDH was noted (FIG. 10A). However, dispersion in response to pyruvate-depleting conditions was restored upon complementation, apparent by biofilms by the complemented strains ΔldhA/pMJT-ldhA and ΔmifR/pJN-mifR demonstrating voids upon exposure to PDH (FIG. 10A).

Figure 10B:
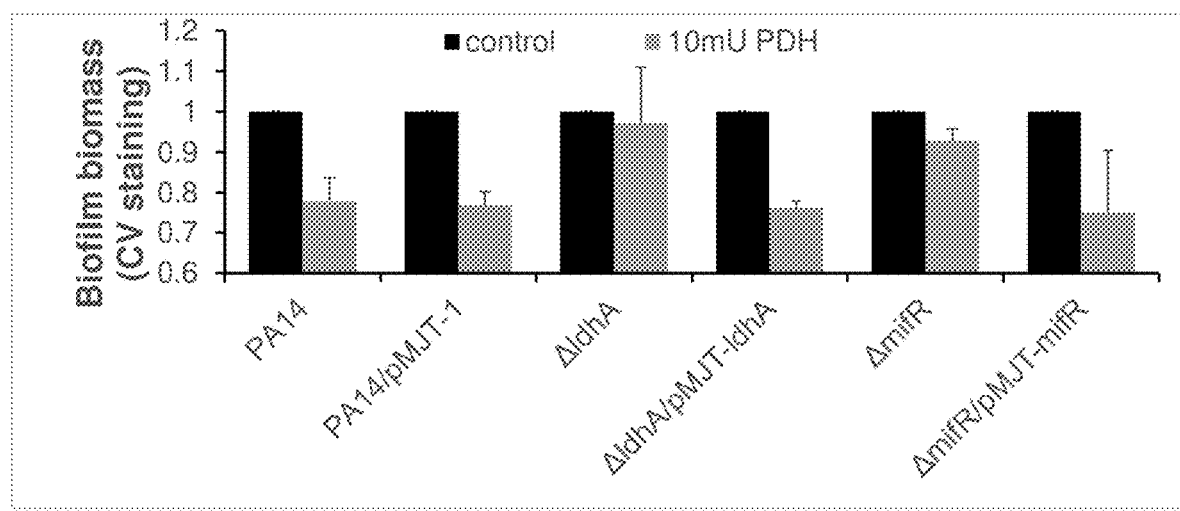
Figure 13:
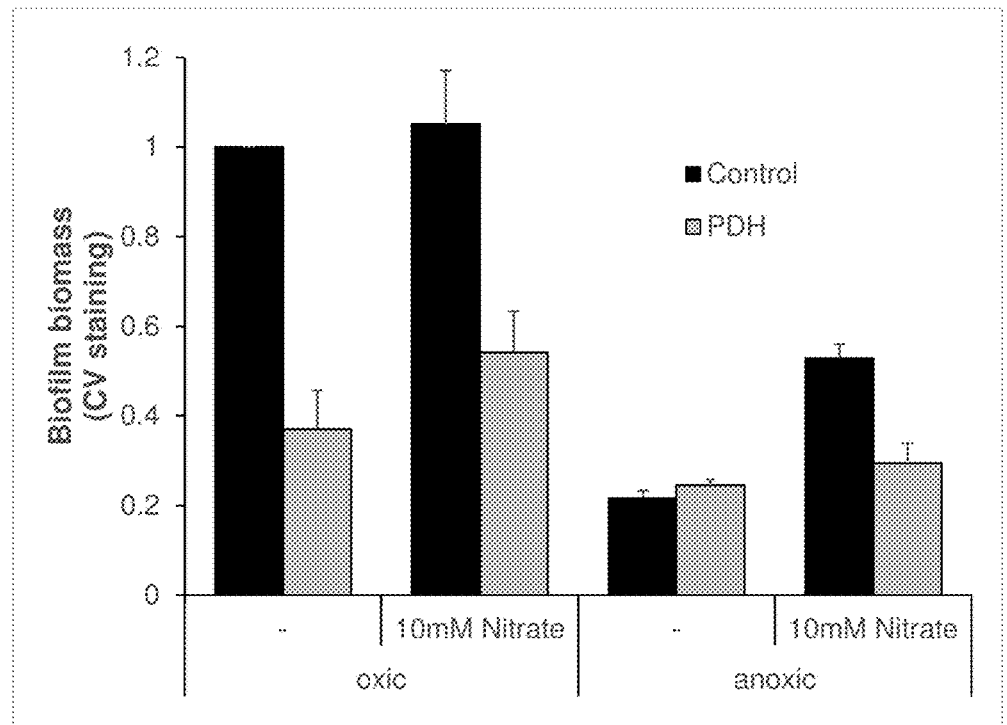
FIG. 13 shows the effect of nitrate on CV staining biofilm mass, for control and PDH treated microcolonies.

Visual observations of inactivation of ldhA and mifR showed impaired pyruvate-depletion induced dispersion response, were confirmed using crystal violet staining. Using biofilms by *P. aeruginosa* wild-type PA14 and corresponding isogenic mutant strains ΔldhA and ΔmifR, no reduction in the biofilm biomass was noted upon exposure of biofilms by the mutant strains ΔldhA and ΔmifR to PDH (FIG. 10B). In contrast, complementation of the ΔldhA and ΔmifR mutant strains coincided with a reduction in the CV-stainable biofilm biomass in a manner similar to the loss of biofilm biomass noted for *P. aeruginosa* wild-type PA14 (FIG. 10B). These findings strongly suggest exposure to PDH and thus, the pyruvate-depletion induced dispersion response, to require LdhA and MifR. These findings furthermore suggest that dispersion induced by pyruvate depletion may be in response to biofilms no longer being capable of coping with stressful, oxygen-limiting but electron-rich conditions, referred to as 'reductive stress' (too much NADH/electrons, not enough $O_2$) present in biofilms. FIG. 13 shows the effect of 10 mM nitrate under oxic and anoxic conditions, on biofilm crystal violet staining.

Pyruvate-Depletion Induced Dispersion is Not Limited to the *P. aeruginosa* Laboratory Strain PAO1

Figure 11:
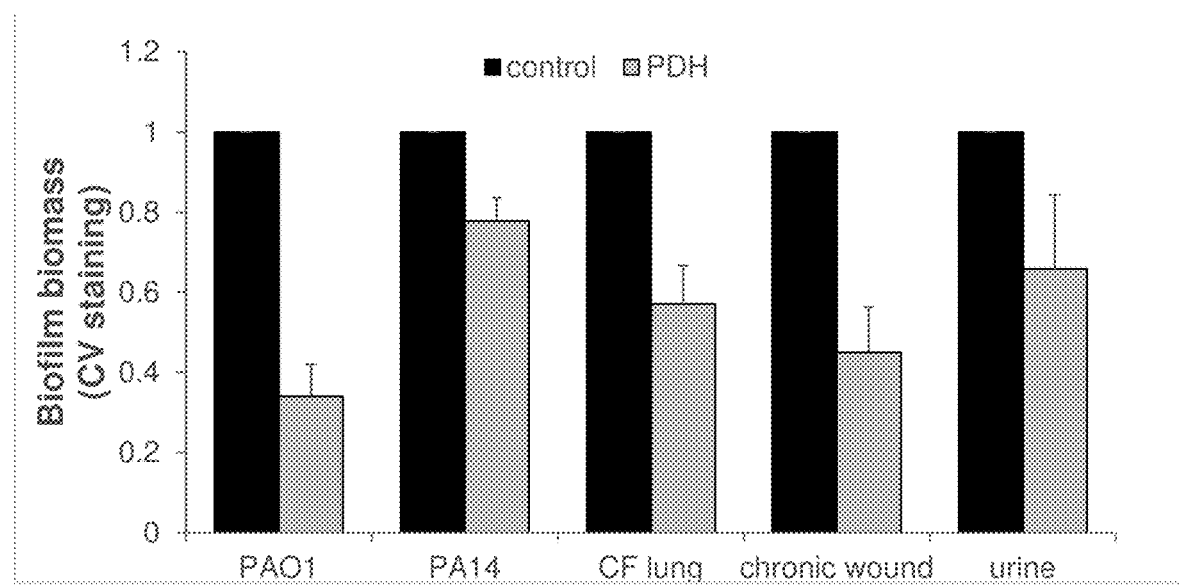
FIG. 11 shows CV staining biofilm biomass for PAO1, PA14, CF lung, chronic wound, and using *P aeruginosa* clinical isolates with and without PDH.

The findings suggest that *P. aeruginosa* biofilms disperse in response to PDH. Given that both *P. aeruginosa* strain PAO1 and strain PA14 dispersed under the conditions tested (FIGS. 10A & 10B), dispersion in response to PDH was predicted not to be limited to laboratory strains. Instead, three *P. aeruginosa* clinical strains, isolated from various infection sites, including the urinary tract, burn wounds, and the lungs of cystic fibrosis patients, exhibited dispersion upon exposure to PDH (FIG. 11). It is of interest to note, however, that the efficiency by PDH in reducing the biofilm biomass varied between 40-60%. The variability in the extent of the loss of crystal violet-stainable biomass noted for clinical isolates, however, was within the range of the biofilm biomass loss noted for biofilms by the laboratory strains PAO1 and PA14 (FIG. 11).

To determine whether dispersion upon depletion of pyruvate is limited to biofilms by *P. aeruginosa*, two facultative anaerobic bacteria, the Gram-negative bacterium *Escherichia coli* BW25113 and the Gram-positive *Staphylococcus aureus*, that represent significant burden on the healthcare system, were used. *S. aureus* is a major cause of nosocomial and community-acquired infections. *E. coli* is considered the major causative agent for recurrent urinary tract infections, with *E. coli* biofilm also being responsible for indwelling medical device-related infectivity. Biofilms by *E. coli* were grown in 24-well plates, and subsequently exposed to 10 mU PDH. Likewise, biofilms by *S. aureus* were grown in 24-well plates, and exposed to PDH. Following overnight incubation, the remaining biofilm was stained using crystal violet. Relative to untreated biofilms, PDH treatment coincided with a significant loss in the crystal violet-stainable biofilm biomass, with exposure to 10 mU resulting in a reduction in the biomass of *E. coli* biofilm while exposure of *S. aureus* biofilms to 10 mU also resulted on average in a reduction. Dispersion in response to PDH was confirmed by microscopic evaluation of the remaining biofilms. Exposure of *S. aureus* and *E. coli* biofilms to PDH and thus, pyruvate depleting conditions, coincided with a reduction in the biofilm biomass relative to the biofilms that were left untreated.

Pyruvate-depletion induced dispersion coincides with biofilms being rendered susceptible to tobramycin.

Figure 12A:
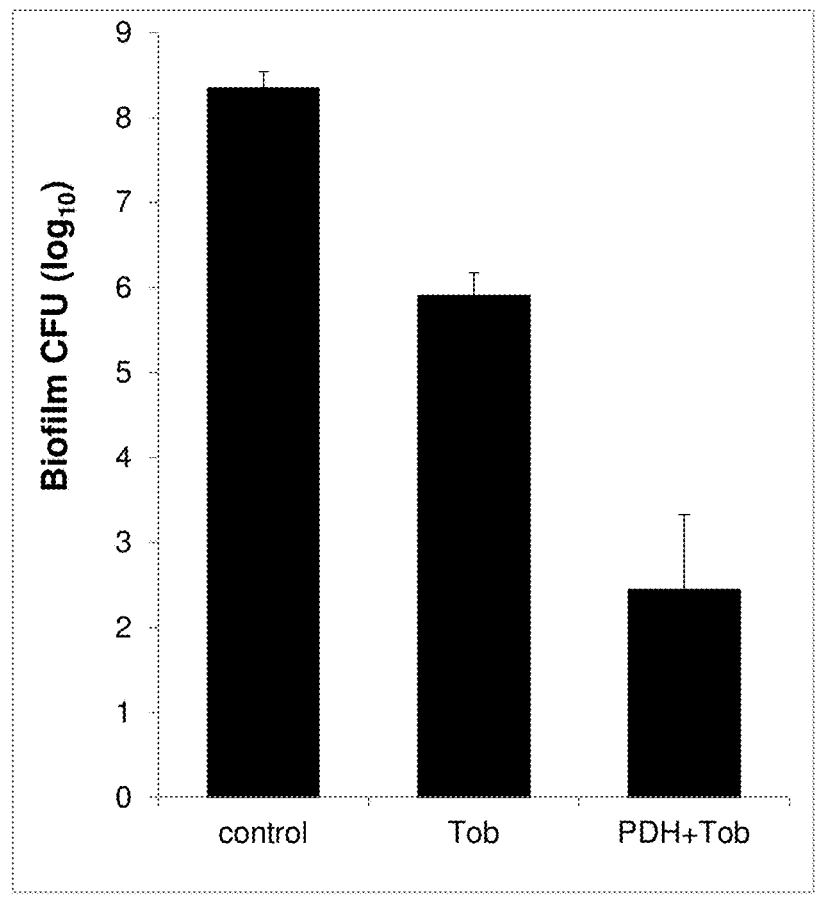
FIGS. 12A-12C show the effect of (12A) tobramycin alone, or with PDH, (12B, 12C) tobramycin, tobramycin with PDH or PDH on log reduction of biofilm CFU.

It is well established that planktonic cells are more susceptible to antimicrobial agents than their counterparts growing as a biofilm, and that dispersion coincides with bacteria transitioning to the planktonic mode of growth. Considering that PDH treatment resulted in biofilm dispersion, treatment with dispersion-inducing PDH was investigated to see if it coincides with biofilms being more susceptible to antimicrobial agents. *P. aeruginosa* biofilms grown for 4 days in 24-well plates were exposed to 100 μg/ml tobramycin in the absence of presence of PDH. Following overnight incubation, the number of viable biofilm cells were determined using viability count. Treatment of biofilms with tobramycin alone resulted in a 2.5-log reduction of the overall biofilm biomass, effectively reducing the number of viable cells from $2.4 \times 10^8$ to $1.2 \times 10^5$ cells per biofilm (FIG. 12A). Tobramycin in the presence of 10 mU PDH coincided with a reduction in the biofilm biomass to $3.5 \times 10^3$ cells/biofilm (FIG. 12A), with the reduction in the viable cells being equivalent to an overall 5.9-log reduction in the biofilm biomass relative to untreated biofilms. These findings clearly indicate that co-treatment with tobramycin in the presence of pyruvate-depleting conditions resulting in biofilm dispersion, renders the antibiotic tobramycin more effective in killing biofilm cells. Overall, co-treatment enhanced the efficacy of tobramycin by 2.4-logs.

Pyruvate-Depletion Reduces the Biofilm Burden in Porcine Burn Wounds and Enhances the Efficacy of Tobramycin in Killing Biofilm Cells.

The data indicate that PDH treatment to induce pyruvate depletion is capable of inducing dispersion of established biofilms and render biofilms more susceptible to the antibiotic tobramycin relative to tobramycin alone. Pyruvate depletion was then investigated in vivo as an anti-biofilm strategy to reduce the bacterial burden of established biofilms, and enhance killing of biofilm cells and thus, reduce or eliminate biofilm-related infections. As *P. aeruginosa* is considered the $2^{nd}$ leading cause of biofilm infections, and is one of the principal pathogens associated with wound infections, a wound model of infection was employed. A porcine rather than a rodent model was employed, as pig skin is more similar to human skin, including similar epidermal/dermal-epidermal thickness ratios, dermal collagen, dermal elastic content similar patterns of hair follicles, blood vessels, and physical and molecular responses to various growth factors. Moreover, while rodent models heal primarily by contraction, pig skin heals in a manner similar to human skin by epithelialization. The well-known clinical burn wound isolate *P. aeruginosa* ATCC 27312 was employed.

Figure 12B:
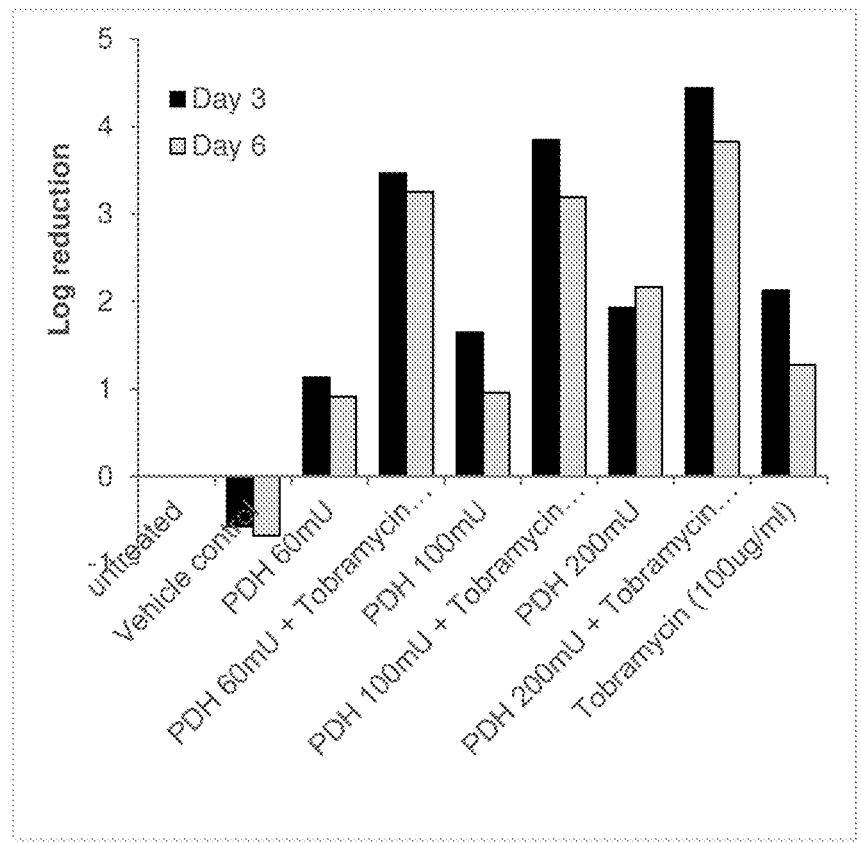
Figure 12C:
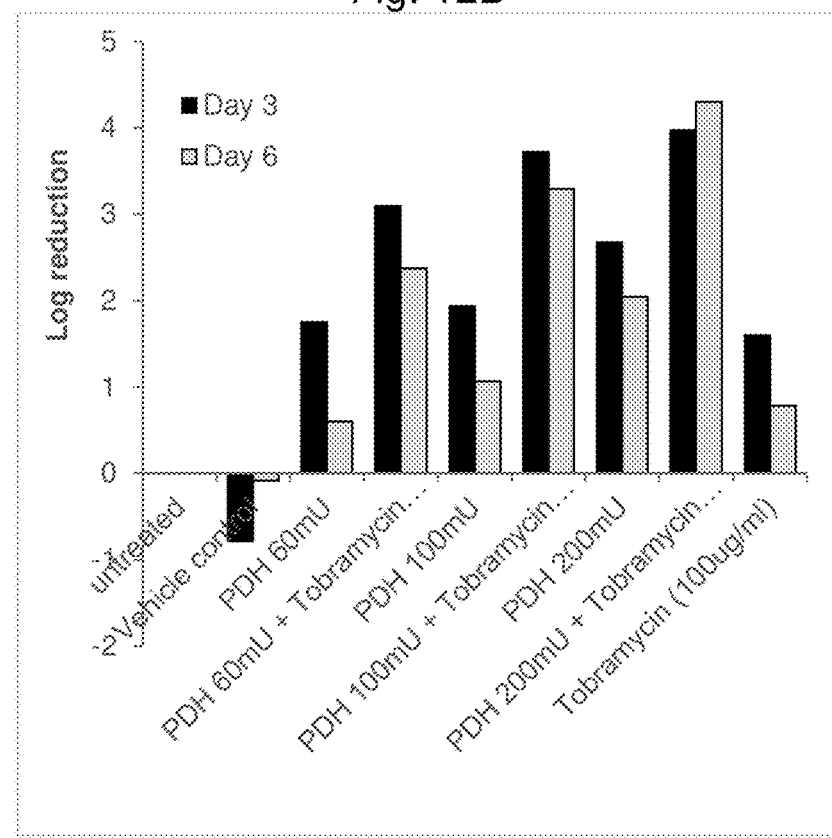

Burn wounds were inoculated with 25 μl of a standardized *P. aeruginosa* suspension harboring $10^6$ CFU/ml and allowed to establish biofilms for 24 h. Infected wounds were subsequently treated daily with 100 and 200 mU PDH in the absence of presence of 100 μg/ml tobramycin. Untreated wounds and wounds only exposed to carrier solution were used as controls. Following 3 and 6 days of treatment, bacterial cells present in wounds were harvested using a flush and scrub technique that separates biofilm bacteria from planktonic bacteria, by flushing the non-adherent (planktonic) bacteria off the wound, followed by scrubbing of the wound to remove adherent biofilm-associated bacteria from the wound bed. Relative to untreated wound biofilms, exposure to 100 mU PDH coincided with up to 2-log reduction in scrub fraction. Similar results for 200 mU PDH (FIG. 12B). Treatment with tobramycin likewise coincided with a 2-log reduction in viable biofilm cells (scrub) relative to untreated biofilms (FIG. 12B). Co-treatment significantly increased the efficacy of tobramycin, apparent by an average reduction in the biofilm CFU/wound of 3.5 and 4-log reduction in the presence of 100 mU and 200 mU PDH, respectively (FIG. 12B). Increased killing of bacteria present in flush in wounds treated with PDH alone and wounds treated with PDH and tobramycin (FIG. 12C) was noted.

The data indicate pyruvate to act as a switch to control biofilm formation, biofilm dispersion, and tolerance, with depletion of pyruvate coinciding with prevention of biofilm formation, disaggregation of existing biofilms, and dispersed biofilms being rendered susceptible to lower doses of antibiotics relative to biofilms.

Pyruvate Depletion is an Effective Anti-Biofilm Therapy, Capable of Controlling and Eradicating Biofilms in Wounds, by Enhancing the Efficacy of Antibiotics and the Immune System.

A treatment strategy based on pyruvate depletion has several added benefits. In *P. aeruginosa*, pyruvate (i) is an energy source, does not promote growth (not a carbon source), and (ii) has only been linked to biofilm growth and long-term bacterial survival under oxygen limiting conditions. (iii) Long-term survival and biofilm studies have not given rise to pyruvate-insensitive mutants. (iv) While pyruvate insensitivity has been noted upon inactivation of genes contributing to pyruvate fermentation (e.g. acnA, ldhA, mifR), these mutants were incapable of coping with the reductive stress and therefore, were unable to form biofilms. (v) Pyruvate depletion by PDH does not affect bacterial growth in liquid or susceptibility of planktonic cells, All of the above lessen the possible selection of pyruvate-insensitive bacteria.

Experimental Procedure

Biofilms were grown in a 24-well plate system modified from the procedure described by Caiazza and O'Toole (2004) to elucidate the role of pyruvate in biofilm formation and biofilm dispersion.

Overnight cultures grown in LB medium were adjusted to an OD600 of 0.05 in fresh 5-fold diluted LB VBMM and grown at 37° C. and rotated at 220 r.p.m. in 24-well microtiter plates at a 45° angle, ensuring that the bottom of the wells is at the air-liquid interface, with the medium exchanged every 12 h.

For biofilm prevention, the growth medium contained 10 mU porcine pyruvate dehydrogenase, cofactors (1 mM b-NAD, 1 mM sodium Co-A, 20 µM thiamine phosphate (TPP)) at the time of inoculation.

For biofilm dispersion, biofilms were first grown for 4 days after which time the growth medium was supplemented with 10 mU porcine pyruvate dehydrogenase, cofactors (1 mM b-NAD, 1 mM sodium Co-A, 20 µM TPP) and allowed to incubate for an additional 16 h.

For susceptibility assays, biofilms were grown as for dispersion assays, but following 4 days of growth, the growth medium was supplemented the aminoglycoside antibiotic tobramycin (100 µg/ml), 10 mU porcine pyruvate dehydrogenase, and cofactors (1 mM b-NAD, 1 mM sodium Co-A, 20 µM TPP). Untreated biofilms or biofilms only exposed to cofactors alone were used as controls.

Differences in the biofilm architecture were visualized by crystal violet staining or microscopy (brightfield, confocal laser scanning). Differences in drug susceptibility were evaluated by viability count.

In vivo biofilms such as those present in porcine burn wounds were found to require increased pyruvate dehydrogenase activity. A pyruvate dehydrogenase activity of 100-200 mU appeared to have maximal activity in dispersing biofilms as well as having maximal adjunctive activity when used in combination with 100 µg/ml tobramycin in eradicating biofilms present in wounds.

Encapsulation of Pyruvate Dehydrogenase

Pyruvate dehydrogenase can be encapsulated in a poly (lactic-co-glycolic acid) (PLGA) particle formulation while maintaining enzymatic activity. PLGA is FDA-approved, degradable, and can protect encapsulated proteins from proteolysis and immune attack.

Pyruvate dehydrogenase-loaded PLGA nanoparticles were made by water-in-oil-in-water double emulsion and had an average size of 360±10 nm and a zeta-potential of −11±3 mV. Based on Western blots, the encapsulation efficiency was approximately 10%. PLGA-immobilization had several benefits:

Free/Unencapsulated pyruvate dehydrogenase was inactive when stored for 2 days at 37° C., yet PLGA-immobilized pyruvate dehydrogenase was still active after 4 days at 4-37° C. PLGA-immobilized pyruvate dehydrogenase was as effective in inducing biofilm dispersion as free pyruvate dehydrogenase (stored at −20° C. until use). PLGA-immobilized pyruvate dehydrogenase particles adhere to biofilm cells.

Figure 15A:
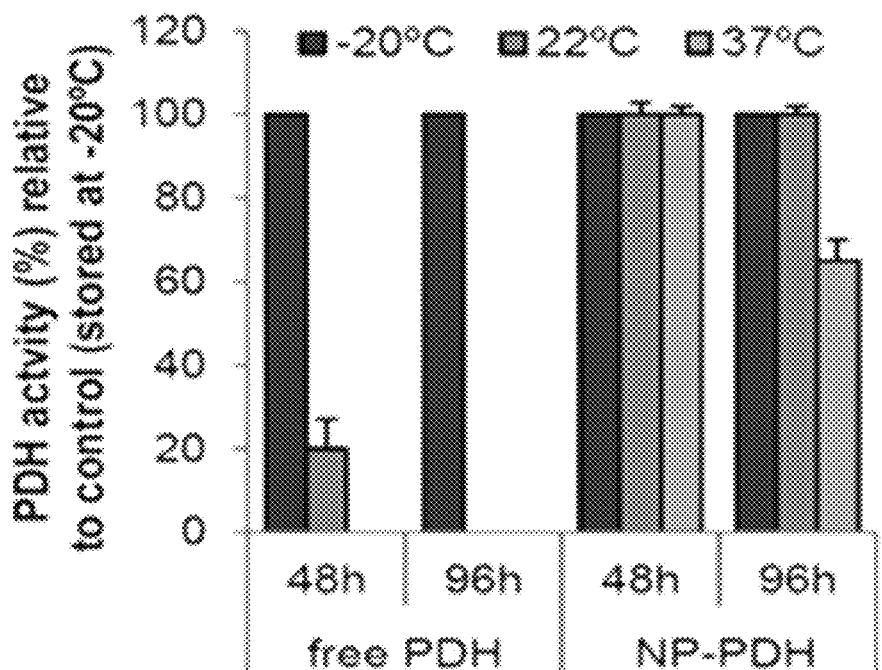
FIGS. 15A-15F show the effect of PDH nanoparticles (NP) on biofilms.

PLGA-immobilized PDH maintained 100% of its activity when stored for 4 days at −20° C., 4° C., or 20° C. and approximately 75% of its activity when stored at 37° C. (FIG. 15A).

Figure 15B:
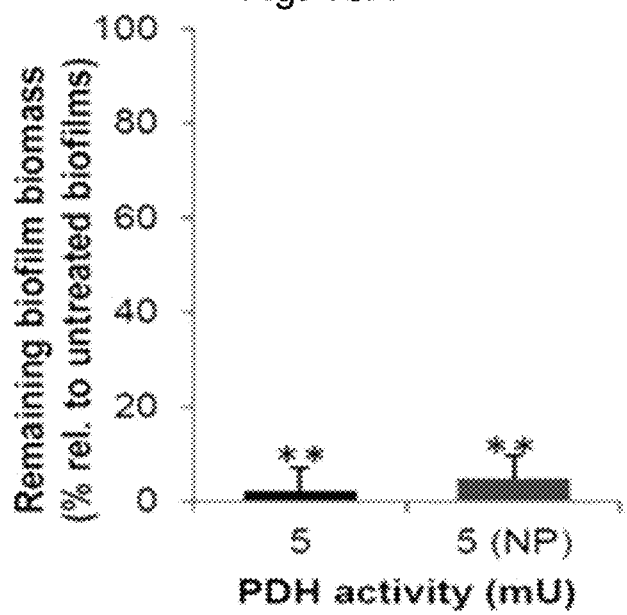
Figure 15C:
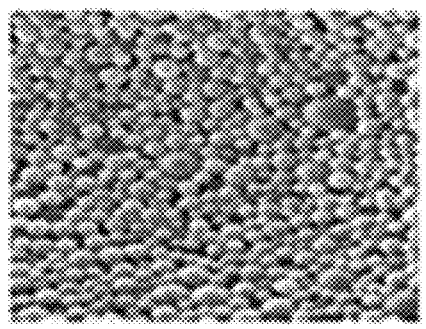
Figure 15D:
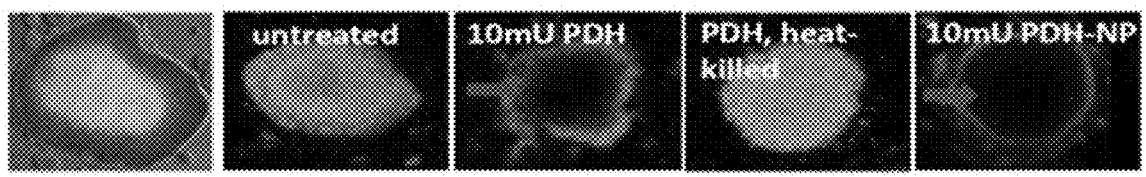
Figure 15E:
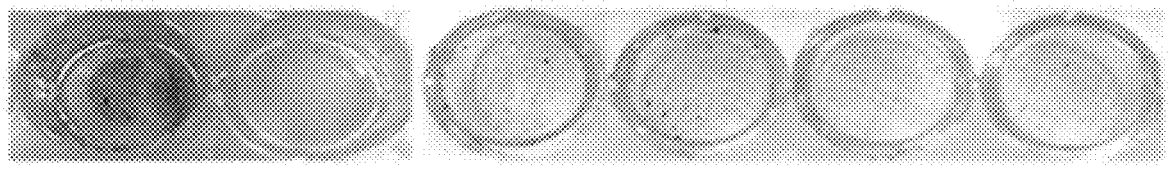

PLGA-immobilized PDH was as effective in inducing biofilm dispersion as free PDH (stored at −20° C. until use, FIGS. 15B, 15E). PLGA-immobilized PDH adhered to peripheral biofilm cells (FIG. 15D), which produce and secrete pyruvate.

An alternative particle substrate is chitosan, a natural, biodegradable polysaccharide with high biocompatibility and mucoadhesive properties. Chitosan nanoparticles were produced encapsulating pyruvate dehydrogenase, formed through ionic gelation. N-trimethyl chitosan chloride (TMC) particles were prepared by ionic crosslinking with tripolyphosphate. Chitosan particles encapsulating pyruvate dehydrogenase had similar activity (ability to convert pyruvate) as PLGA particles.

Therefore, pyruvate dehydrogenase can be encapsulated in a variety of forms, while retaining activity and gaining stability.

Pyruvate dehydrogenase-containing nanoparticles or microparticles may be provided in conjunction with numerous medical applications, including, for example, deposition on medical devices, in wounds or on wound dressings, or as a therapy for cystic fibrosis patients, such as an inhaled micronized or nanoparticle powder inhalant. A nebulizer may also be used for administration.

Figure 14A:
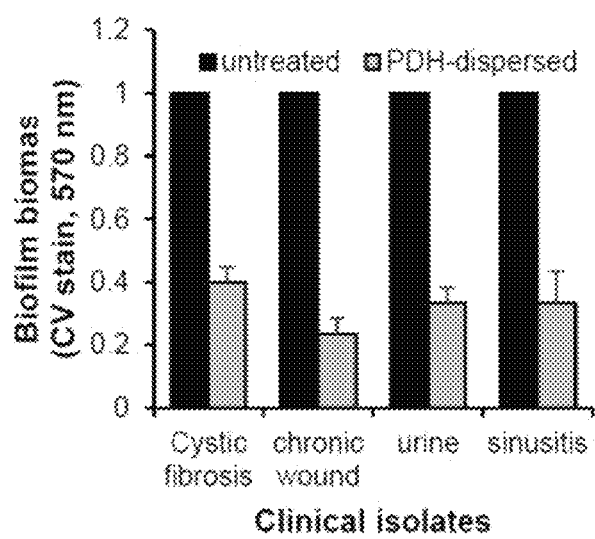
FIGS. 14A and 14B show the in vivo relevance of the technology.
Figure 14B:
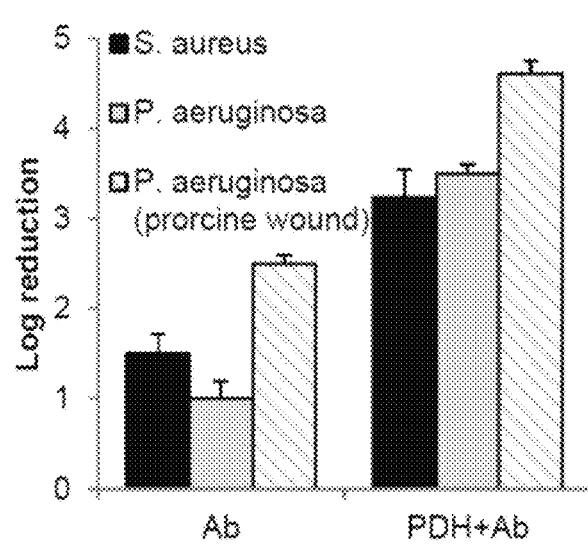

FIGS. 14A and 14B show the in vivo relevance of the technology. FIG. 14A shows PDH treatment (5 mU) disperses biofilms by clinical isolates, as indicated by CV staining. FIG. 14B shows PDH treatment (5 mU) renders in vitro biofilms by P. aeruginosa and S. aureus and biofilms by P. aeruginosa burn wound isolate ATCC27312 in porcine wounds significantly more susceptible to antimicrobial agents (Ab) In vitro biofilms were treated with tobramycin (150 µg/ml, P. aeruginosa) or vancomycin (100 µg/ml, S. aureus) for 1 h; in vivo wound biofilms were treated with silver sulfadiazine for 1 d. Log reduction refers to reduction in viable cells post treatment. All experiments were done in triplicate.

Figure 15F:
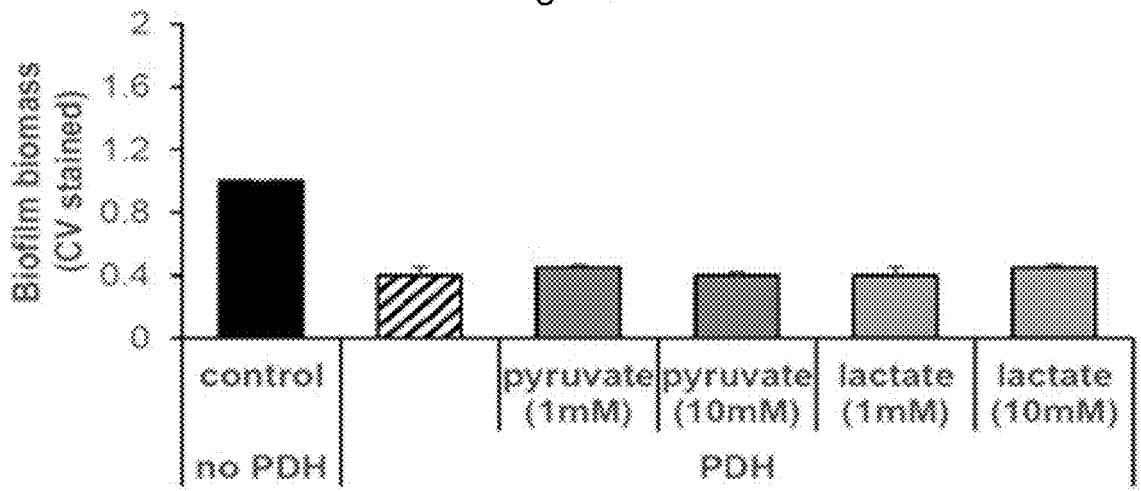

FIGS. 15A-15F show the effect of PDH nanoparticles (NP) on biofilms. FIG. 15A shows PDH activity, determined spectrophotometrically via NADH conversion, is affected by storage temperature, storage time, and NP encapsulation (NP-PDH). FIG. 15B shows PLGA-immobilized PDH (NP) is as effective in reducing biofilm biomass as free PDH. Biofilm biomass was quantitatively determined by confocal microscopy and COMSTAT analysis prior/post 24 h PDH treatment. FIG. 15C shows an SEM image of NPs, scale bar=500 nm. (15D) Confocal images of NPs (red) surrounding biofilm cells (green) FIG. 15E shows biofilm microcolonies (bacteria in green) prior/post dispersion (arrows mark voids indicative of dispersion). FIG. 15F shows PDH-induced dispersion is not affected by excess lactate and pyruvate (10 mM), as determined using CV staining of remaining biofilm biomass. PDH, 5 mU. Inset, corresponding CV-stained biofilms post indicated treatment. Experiments done in triplicate.

Figure 16:
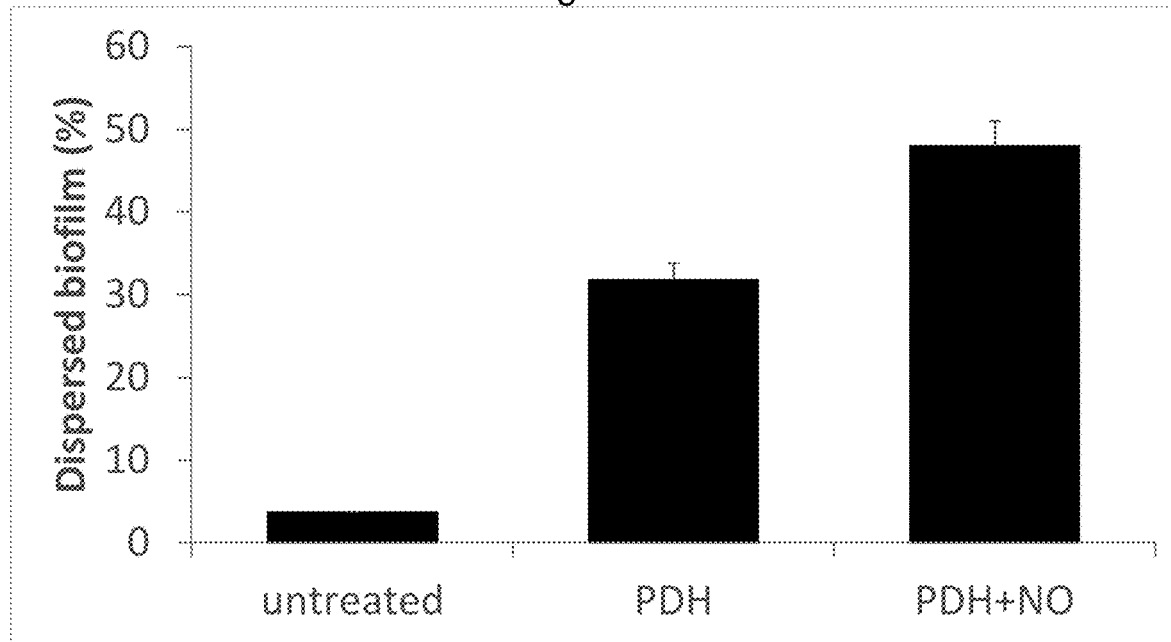
FIG. 16 shows that nitric oxide can enhance pyruvate dehydrogenase-induced dispersion in biofilms.

FIG. 16 shows that nitric oxide (NO) can enhance PDH-induced dispersion of biofilms. Biofilms were grown for 4 days in 24-well polystyrene plates in five-fold diluted LB. Post 4 days, biofilms were either left untreated or exposed to pyruvate dehydrogenase (PDH, 10 mU) or PDH plus 500 uM SNP. SNP was used as a source of nitric oxide (NO). PDH treatment was done in the presence of CoA, B-NAD+, TPP, and MgSO4. Following 16 h of treatment, biofilms were viewed by confocal microscopy to determine the number of microcolonies showing void formation indicative of dispersion. Number of microcolonies as percent of the total colonies counted per treatment group is shown. All experiments were carried out in triplicate. Error bars denote standard deviation.

Figure 17A:
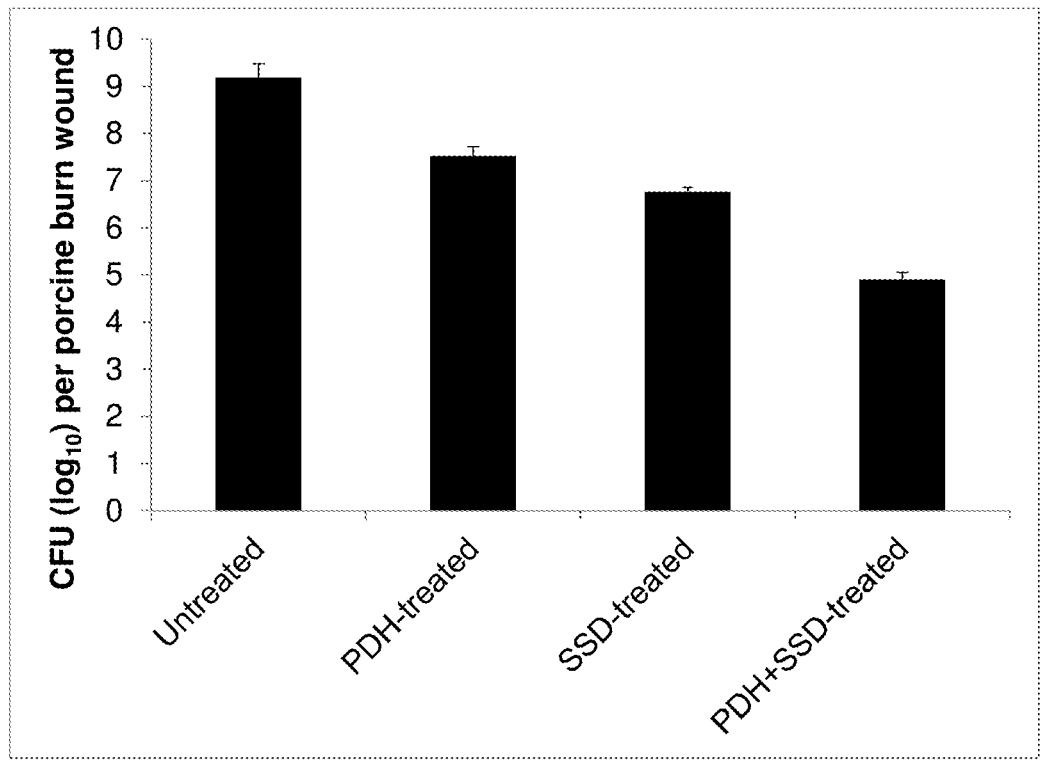
FIGS. 17A and 17B shows reduction in biofilm burden in wounds by reduction in colony forming units (CFU) (17A) and $\log_{10}$ reduction (17B) by use of pyruvate dehydrogenase (PDH) alone, silver sulfadiazine (SSD) cream alone, and PDH and SSD together.
Figure 17B:
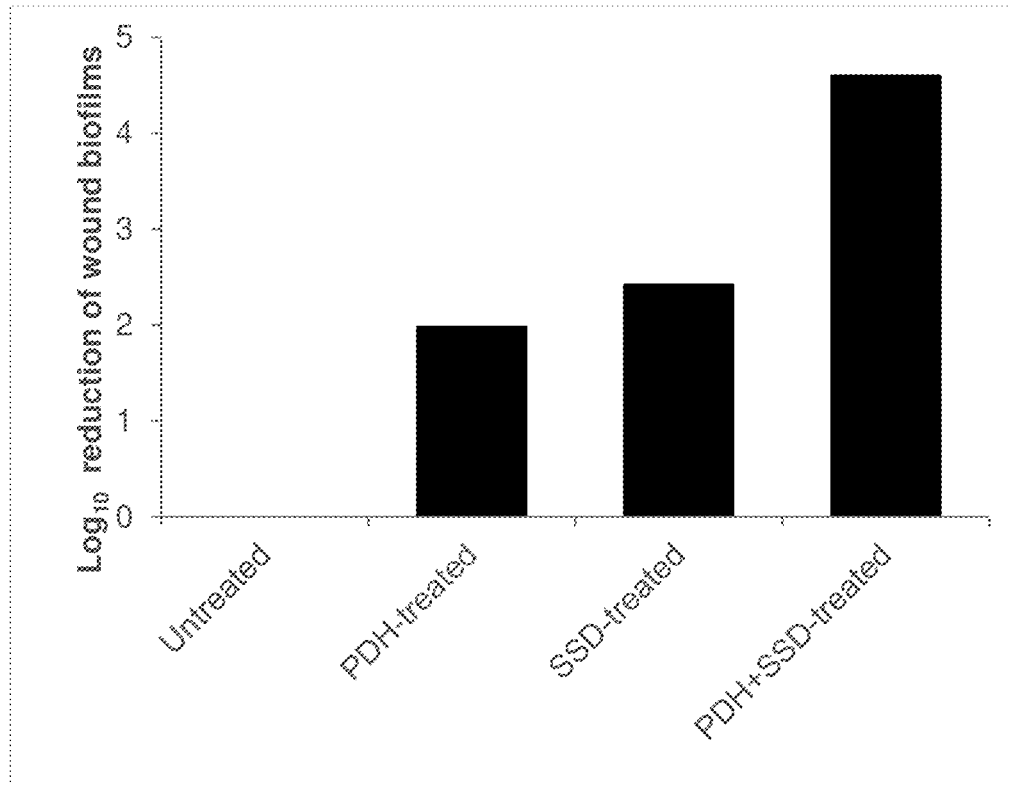
Figure 18:
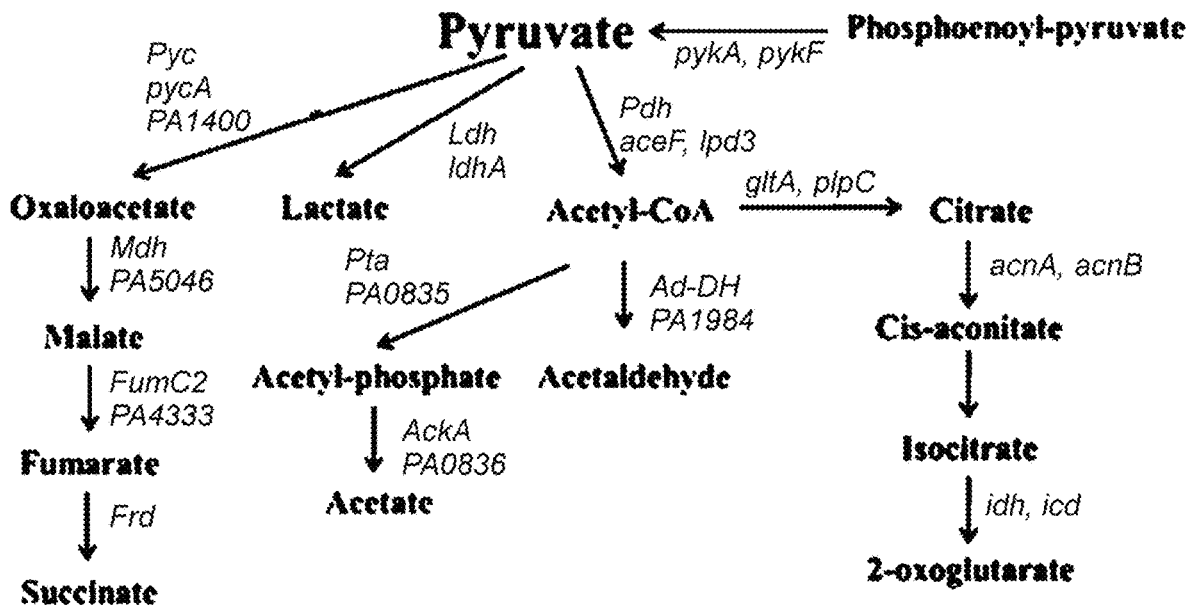
FIG. 18 shows biochemical pathways of pyruvate.
Figure 19:
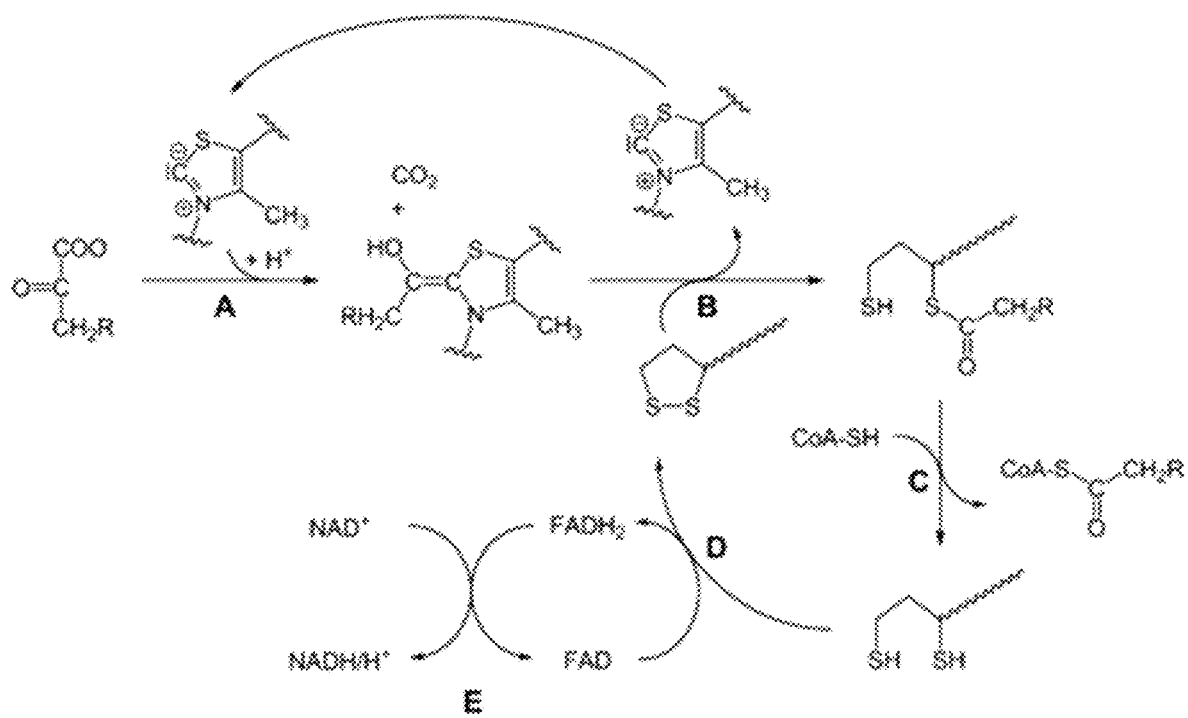
FIG. 19 shows the pyruvate decarboxylase mechanism.
Figure 20:
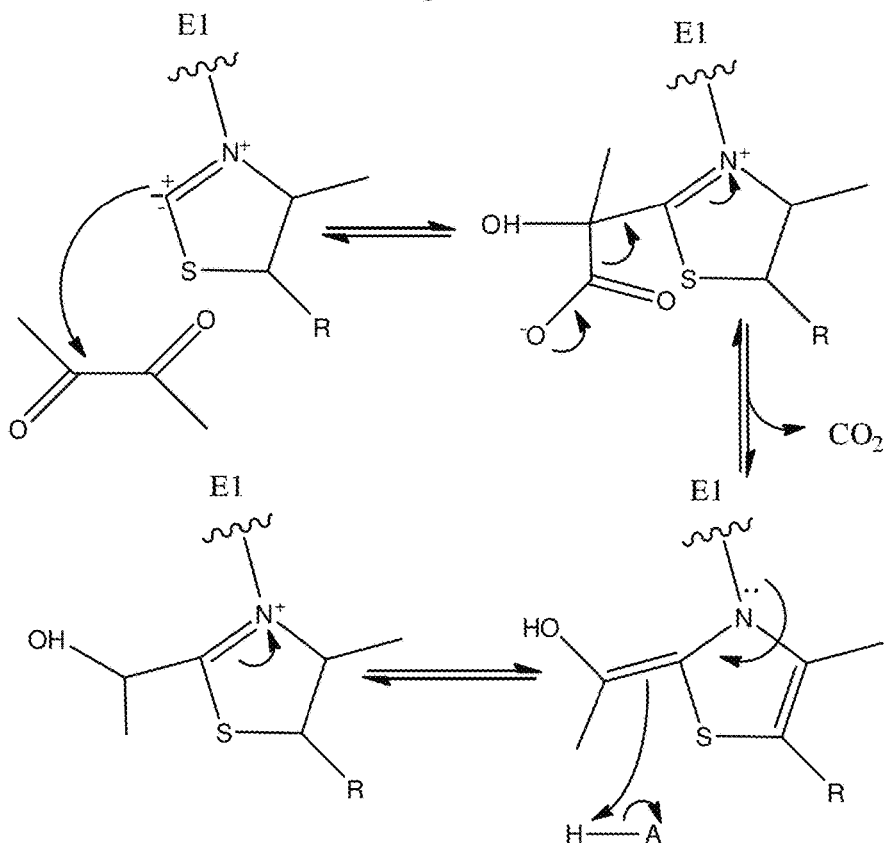
FIG. 20 shows the ylide resonance form of thiamine pyrophosphate (TPP).

FIGS. 17A and 17B shows reduction of biofilm burden in wounds. Second degree porcine burn wounds were infected with P. aeruginosa ATCC® 27312™. Wounds were either left untreated or exposed to pyruvate dehydrogenase (PDH, 200 mU, plus cofactors), silver sulfadiazine cream (SSD), or SSD plus PDH for 24 h. Then, bacterial cells were removed from the wounds and the number of viable cells, as shown in (CFU) per wound determined using viability counts. FIG. 17A shows the number of bacterial cells present in wounds. FIG. 17B shows the $Log_{10}$ reduction was determined relative to untreated biofilms (based on data shown in FIG. 17A). Experiments are representative data obtained using 3 wounds per treatment group (n=3). Error bars represent standard deviation. Pretreatment with PDH and SSD should have ability to prevent infection.

Encapsulated PDH demonstrates improved thermal stability. The specific depletion of pyruvate can be accomplished enzymatically using pyruvate dehydrogenase (PDH) or lactate dehydrogenase (LDH). PDH requires $NAD^+$ and CoA as cofactors to enzymatically convert pyruvate to acetyl-CoA while LDH requires NADH to convert pyruvate to lactate. PDH is preferred over LDH for three reasons: (i) $NAD^+$ is more stable than NADH, (ii) wound exudates have been reported to contain ≥10 mM lactate (but low pyruvate and no acetyl-CoA) with the presence of lactate likely resulting in LDH producing pyruvate in vivo, rather than depleting it (since LDH is reversible), and (iii) PDH is not inhibited by the presence of lactate (FIG. 15F). However, most if not all enzymes are relatively unstable and rapidly lose activity when exposed to temperatures relevant to in vivo applications (body temperature=37° C., FIG. 5A). Free PDH is no exception and is rendered inactive within less than 1 day when stored at 37° C. (FIG. 5A).

PLGA particles can be formulated with varying PLGA molecular weight, synthesis method, and the loading of PDH. The PLGA molecular weight affects the crystallinity, hydrophobicity, and degradation rate of the particles—factors likely to affect PDH stability over time. NPs may be synthesized using either a water-in-oil-in-water (W/O/W, FIG. 15C) double emulsion method or nanoprecipitation method.

W/O/W Synthesis: for a 1×batch, 400 µl of concentrated porcine PDH (Sigma Aldrich, 5.8 mU/µl) in phosphate buffered saline MOPS is rapidly mixed with 4 ml of acetone containing 100 mg PLGA (either 38 kDa or 60 kDa) and sonicated for 40 s. The solution is then added to 8 ml of 0.1% v/v polyvinyl alcohol solution with sonication. The emulsion is diluted, acetone is evaporated, and unencapsulated PDH is removed via centrifugation. Particles are frozen and freeze dried.

Nanoprecipitation Synthesis: In particle synthesis, the avoidance of solvents with potential effects on protein integrity is desirable and may increase the activity of encapsulated PDH. Formulations are created by by nanoprecipitation using glycofurol 67,68, which has low toxicity 69-74. PDH (100 µL) is added to 300 µL of 12% PLGA (38 kDa or 60 kDa) in glycofurol and mixed with 100 µL of ethanol and 1.5 mL of 1% Poloxamer 188. Particles are centrifuged, frozen, and freeze dried.

Chitosan NPs: While PLGA has been used extensively in drug delivery applications and has successfully delivered several proteins without substantial loss of activity and worked well in preliminary experiments, the breakdown of PLGA into its acidic constituents can potentially cause protein instability. As an alternative, chitosan is a natural, biodegradable polysaccharide with high biocompatibility and mucoadhesive properties. Chitosan NPs have been used for encapsulation of proteins and can be simply formed through ionic gelation. N-trimethyl chitosan chloride (TMC) particles may be prepared by ionic crosslinking with tripolyphosphate. Chitosan particles may be formulated with the following variables: chitosan molecular weight (low and medium, Sigma) and PDH loading.

PEGylation of particles: The widely used biocompatible polymer PEG may be incorporated to increase the hydrophilicity of the NP to preserve the biological activity of PDH38 and to render the particles less likely to be immunogenic. In order to avoid affecting the activity of already encapsulated PDH, PEG-5k may be be linked to the already-synthesized particles' surface. Carbodiimide chemistry (EDC/NHS) may then be used to create a bond between an amine group on PEG (mPEG5k-NH2) and PLGA-COOH 32. For chitosan particles, a carboxylic acid group on PEG (mPEG5k-COOH) bonds an amine on the chitosan that is present after reducing the C=N with $NaBH_4$.

Wound temperatures have been reported by Shorrock et al. to range from 32-41° C. Furthermore, wounds have been shown to be a proteolytic environment and to have an average pH of 7.1-7.5, with measurements taken at the wound center indicating an average pH of 7.6±0.6 and areas on the epitheliated wound borders showing physiological pH values of 5.9±0.4.

While free PDH activity decreases significantly upon storage, PLGA-encapsulated PDH remains active for 4 days (FIG. 15A).

PLGA-encapsulated PDH adheres to biofilm cells (FIG. 15D). This characteristic may be important for effective biofilm dispersion (FIG. 15E, compare 10 mU PDH to PDH-NP-induced dispersion response).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of inducing a dispersion of sessile organisms within a biofilm in an aqueous medium, comprising:
   enzymatically depleting pyruvate in the aqueous medium by supplying at least 5 mU/ml of an enzyme having a pyruvate substrate specificity, to a sufficient amount and for a sufficient time to induce hypoxic stress and a resulting dispersion response of the sessile organisms within the biofilm.

2. The method according to claim 1, wherein the enzymatically altering comprises decarboxylation.

3. The method according to claim 1, wherein the enzymatically altering comprises phosphorylation.

4. The method according to claim 1, further comprising adding at least cis-2-decenoic acid.

5. The method according to claim 1, further comprising adding at least nitric oxide.

6. The method according to claim 1, wherein the depleting comprises absorbing pyruvate to an insoluble matrix.

7. The method according to claim 1, wherein the depleting comprises chemically transforming the pyruvate to another chemical species.

8. The method according to claim 1, wherein the depleting comprises an imine-forming reaction.

9. The method according to claim 1, wherein the depleting comprises operation of pyruvate decarboxylase.

10. The method according to claim 1, wherein the depleting comprises use of a bioreactor comprising pyruvate fermentative organisms.

11. The method according to claim 1, wherein the depleting comprises selectively administering an enzyme preparation selected from the group consisting of pyruvate dehydrogenase; pyruvate oxidase; lactate dehydrogenase; and a transaminase.

12. The method according to claim 1, further comprising administering an antibiotic to the biofilm.

13. A method of treating a biofilm, comprising administering a formulation comprising an enzyme having a pyruvate substrate specificity to the biofilm at a level of at least 5 mU/ml, the enzyme being at least one of encapsulated and immobilized, under conditions effective for reducing pyruvate in an environment surrounding the biofilm, and causing a sufficient hypoxic stress of the cells associated with the biofilm to induce a dispersion response.

14. The method according to claim 13, further comprising administering a bacterial biofilm dispersion inducer to a subject having the biofilm.

15. The method according to claim 13, further comprising administering an antibiotic to the biofilm, wherein an antibacterial activity of the antibiotic is enhanced by the dispersion response.

16. The method according to claim 13, wherein the enzyme having the pyruvate specificity is pyruvate dehydrogenase, is stabilized with respect to a soluble form of pyruvate dehydrogenase by encapsulation.

17. The method according to claim 16, wherein the encapsulation comprises encapsulating the pyruvate dehydrogenase in chitosan nanoparticles.

18. A method of inducing a dispersion of sessile bacteria in a biofilm, comprising:
    enzymatically depleting pyruvate in an aqueous medium surrounding the biofilm, to induce hypoxic stress in the sessile bacteria and resulting is a dispersion response of the sessile organisms, with an enzyme that is encapsulated, which is stabilized with respect to a corresponding soluble form of the enzyme by the encapsulation to retain at least 50% of its initial activity for 48 hrs after hydration at 37° C. to a concentration of at least 5 mU/ml.

\* \* \* \* \*